(12) United States Patent
Kodek et al.

(10) Patent No.: US 11,760,935 B2
(45) Date of Patent: Sep. 19, 2023

(54) POLYMERIZABLE COMPOUNDS

(71) Applicant: MERCK PATENT GMBH, Darmstadt (DE)

(72) Inventors: Thorsten Kodek, Darmstadt (DE); Oliver Heppert, Darmstadt (DE); Timo Uebel, Darmstadt (DE); Rocco Fortte, Darmstadt (DE); Leo Weegels, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 3 days.

(21) Appl. No.: 17/215,873

(22) Filed: Mar. 29, 2021

(65) Prior Publication Data
US 2023/0045041 A1 Feb. 9, 2023

(30) Foreign Application Priority Data

Aug. 3, 2020 (EP) .................................. 20189130

(51) Int. Cl.
| | | |
|---|---|---|
| *C07C 323/20* | (2006.01) | |
| *C07C 323/62* | (2006.01) | |
| *C09K 19/54* | (2006.01) | |
| *C07C 323/18* | (2006.01) | |
| *C08F 222/20* | (2006.01) | |

(52) U.S. Cl.
CPC .......... *C09K 19/542* (2013.01); *C07C 323/18* (2013.01); *C07C 323/20* (2013.01); *C07C 323/62* (2013.01); *C08F 222/20* (2013.01)

(58) Field of Classification Search
CPC .... C07C 323/18; C07C 323/20; C07C 323/62
See application file for complete search history.

(56) References Cited

U.S. PATENT DOCUMENTS

| | | | | |
|---|---|---|---|---|
| 2008/0200582 | A1* | 8/2008 | Craciun | ........... B29D 11/00442 525/451 |
| 2015/0369982 | A1* | 12/2015 | Sargent | ................ C09K 19/322 264/1.32 |
| 2016/0137923 | A1* | 5/2016 | Yoon | ...................... C09K 19/04 252/299.61 |
| 2018/0203352 | A1* | 7/2018 | Ryu | ...................... G03F 7/0384 |

FOREIGN PATENT DOCUMENTS

| | | |
|---|---|---|
| CN | 106554280 B | 5/2019 |
| JP | 2059570 A | 2/1990 |

OTHER PUBLICATIONS

Extended Search report in corresponding EP21164214 .5 dated Sep. 23, 2021 (pp. 1-8).
Turos et al: "Antibiotic-conjugated polyacrylate nanoparticles: New opportunities for development of anti-MRSA agents", Bioorganic & Medicinal Chemistry Letters, Elsevier, Amsterdam, NL, vol. 17. No. 1. Dec. 22, 2006 (Dec. 22, 2006), pp. 53-56, XP005811211.

* cited by examiner

*Primary Examiner* — Rosalynd A Keys
(74) *Attorney, Agent, or Firm* — MILLEN WHITE ZELANO AND BRANIGAN, PC; Csaba Henter

(57) ABSTRACT

Polymerizable compounds, processes and intermediates for their preparation, compositions containing them, polymers made from the compounds or compositions, and uses of the polymerizable compounds, compositions and polymers.

12 Claims, No Drawings

POLYMERIZABLE COMPOUNDS

The present application relates to polymerizable compounds, processes and intermediates for their preparation, compositions containing them, polymers made from the compounds or compositions, and uses of the polymerizable compounds, compositions and polymers.

BACKGROUND OF THE INVENTION

Polymerizable compounds which can be advantageously polymerized by in-situ polymerization, for example UV-photopolymerization, compositions containing them and polymer particles or polymer films made therefrom, have been proposed in prior art for various applications, like for example protective, decorative or optoelectronic applications.

However, the polymerizable compounds known from prior art often show drawbacks such as a difficult synthesis with low yields, slow or incomplete polymerization, low stability, or low absorption in the desired UV wavelength range used for photopolymerization.

It is therefore an aim of the present invention to provide improved polymerizable compounds and compositions which do not have the drawbacks of the materials known from prior art, and show one or more advantages such as easy synthesis with high yield, quick and complete polymerization, high stability and high UV absorption. In particular there is a need for polymerizable compounds that can be polymerized effectively at longer UV wavelengths in the range >300 nm, which is for example often used in the manufacturing process of optoelectronic devices. Also, there is a need for polymerizable compounds which have good solubility in organic solvents and in liquid crystalline media.

The inventors have found that these aims can be achieved by providing polymerizable compounds as disclosed and claimed hereinafter.

SUMMARY OF THE INVENTION

The invention relates to a compound of formula I $$P\text{-}Sp\text{-}A^1\text{-}(Z^1\text{-}A^2)_z\text{-}R^b \qquad \qquad I$$

wherein the individual radicals, independently of each other and on each occurrence identically or differently, have the following meanings $R^b$ P-Sp- or R, R F, Cl, —CN, or straight chain, branched or cyclic alkyl having 1 to 25 C atoms, wherein one or more non-adjacent CH$_2$-groups are optionally replaced by —O—, —S—, —CO—, —CO—O—, —O—CO—, —O—CO—O—, CR$^0$=CR$^{00}$—, —C≡C—,

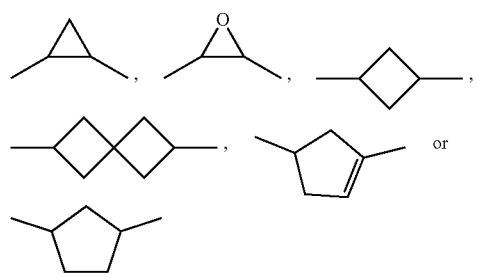

in such a manner that O- and/or S-atoms are not directly connected with each other, and wherein one or more H atoms are each optionally replaced by F or Cl or P-Sp-, P a polymerizable group, Sp a spacer group which is optionally substituted by P, or a single bond, $A^1$, $A^2$ an alicyclic, heterocyclic, aromatic or heteroaromatic group with 4 to 20 ring atoms, which is monocyclic or polycyclic and which is optionally substituted by one or more groups L, A or P-Sp-, $Z^1$ —O—, —S—, —CO—, —CO—O—, —O—CO—, —O—CO—O—, —OCH$_2$—, —CH$_2$O—, —SCH$_2$—, —CH$_2$S—, —CF$_2$O—, —OCF$_2$—, —CF$_2$S—, —SCF$_2$—, —(CH$_2$)$_{n1}$—, —CF$_2$CH$_2$—, —CH$_2$CF$_2$—, —(CF$_2$)$_{n1}$—, —CH=CH—, —CF=CF—, —CH=CF—, —CF=CH—, —C≡C—, —CH=CH—CO—O—, —O—CO—CH=CH—, —CH$_2$—CH$_2$—CO—O—, —O—CO—CH$_2$—CH$_2$—, —CR$^0$R$^{00}$—, or a single bond, $R^0$, $R^{00}$ H or alkyl having 1 to 12 C atoms, A alkyl with 2 to 12, preferably 2 to 8, C-atoms, wherein one or more, preferably non-terminal, CH$_2$ groups (i.e. the CH$_2$ group furthest away from $A^1$/$A^2$), are replaced by S, such that S atoms are not directly connected with each other, preferably thioalkyl with 1 to 7 C atoms, very preferably SCH$_3$, L F, Cl, —CN, P-Sp- or straight chain, branched or cyclic alkyl having 1 to 25 C atoms, wherein one or more non-adjacent CH$_2$-groups are optionally replaced by —O—, —S—, —CO—, —CO—O—, —O—CO—, —O—CO—O—, CR$^0$=CR$^{00}$—, —C≡C—,

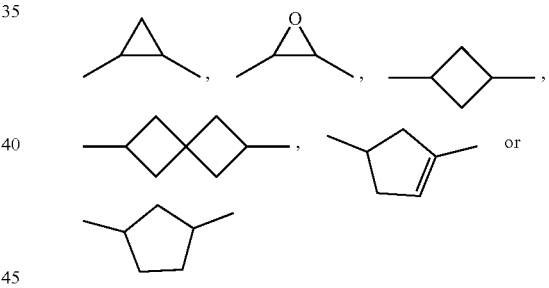

in such a manner that O- and/or S-atoms are not directly connected with each other, and wherein one or more H atoms are each optionally replaced by P-Sp-, F or Cl, z 0, 1, 2, 3 or 4, n1 1, 2, 3 or 4, characterized in that the compound contains at least one group $A^1$ or $A^2$ that is substituted by at least one group A.

The invention further relates to methods for preparing a compound of formula I, and to novel intermediates used or obtained in these methods.

The invention further relates to a polymerizable composition comprising one or more compounds of formula I.

The invention further relates to a polymer obtained by polymerizing a compound of formula I or a composition comprising it.

The invention furthermore relates to the use of a compound of formula I, a composition comprising it, or a polymer obtained by polymerizing the compound of formula I or a composition comprising it, for protective, decorative or optoelectronic applications or in liquid crystalline media.

The polymerizable compounds and compositions according to the present invention are preferably polymerized by photopolymerization, very preferably by UV photopolymerization.

The invention further relates to a compound of formula II $$Pg\text{-}Sp\text{-}A^1\text{-}(Z^1\text{-}A^2)_z\text{-}R^{b1} \qquad II$$

wherein Pg is OH, H, or protected or masked hydroxyl, $R^{b1}$ is R or Pg-Sp-, and Sp, $A^1$, $A^2$, R, Z and z have the meanings of formula I or of the preferred meanings above and below, and at least one of $A^1$ and $A^2$ is substituted by at least one group A as defined in formula I.

The invention furthermore relates to the use of compounds of formula as intermediates in the synthesis of polymerizable compounds, especially those of formula I.

The invention furthermore relates to a process for synthesizing compounds of formula I or its subformulae by esterification or etherification of a compound of formula II wherein Pg denotes OH, or protected or masked hydroxyl, using a corresponding acid, acid derivative or halogenated compound containing a polymerizable group P, optionally in the presence of a dehydrating reagent.

DETAILED DESCRIPTION OF THE INVENTION

The compounds of formula I show the following advantageous properties:
  fast polymerization with low amount of residual, unreacted monomer,
  good stability against heat,
  good solubility in organic solvents and in liquid crystalline media,
  good low temperature stability (LTS),
  quick and complete UV photopolymerization, in particular at longer UV wavelengths in the range from 300-380 nm and especially above 320 nm.

Unless stated otherwise, the compounds of formula I are preferably selected from achiral compounds.

Unless stated otherwise, the term "polymerizable compound" as used herein will be understood to mean a polymerizable monomeric compound.

Unless stated otherwise, the term "unpolymerizable compound" as used herein will be understood to mean a compound that does not contain a functional group that is suitable for polymerization under the conditions usually applied for the polymerization of the compounds of formula I.

Above and below,

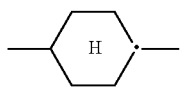

denotes a trans-1,4-cyclohexylene ring, and

denotes a 1,4-phenylene ring.

In a group

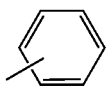

the single bond shown between the two ring atoms can be attached to any free position of the benzene ring.

If in formula I and its subformulae a group $R^b$, R or L denotes an alkyl radical and/or an alkoxy radical, this may be straight-chain or branched. It is preferably straight-chain, has 2, 3, 4, 5, 6 or 7 C atoms and accordingly preferably denotes ethyl, propyl, butyl, pentyl, hexyl, heptyl, ethoxy, propoxy, butoxy, pentoxy, hexyloxy or heptyloxy, furthermore methyl, octyl, nonyl, decyl, undecyl, dodecyl, tridecyl, tetradecyl, pentadecyl, methoxy, octyloxy, nonyloxy, decyloxy, undecyloxy, dodecyloxy, tridecyloxy or tetradecyloxy.

If in formula I and its subformulae a group $R^b$, R, L or A denotes an alkyl radical wherein one or more $CH_2$ groups are replaced by S, this may be straight-chain or branched. It is preferably straight-chain, has 1, 2, 3, 4, 5, 6 or 7 C atoms and accordingly preferably denotes thiomethyl, thioethyl, thiopropyl, thiobutyl, thiopentyl, thiohexyl or thioheptyl.

Oxaalkyl preferably denotes straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxa-decyl.

If in formula I and its subformulae a group $R^b$, R or L denotes an alkoxy or oxaalkyl group it may also contain one or more additional oxygen atoms, provided that oxygen atoms are not linked directly to one another.

In another preferred embodiment one or more of $R^b$, R or L are selected from the group consisting of

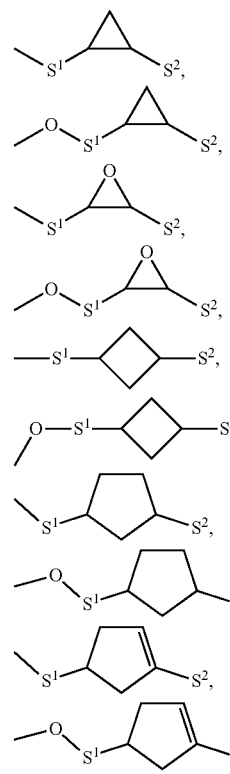

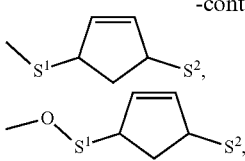

—S¹—F, —O—S¹—F, —O—S₁—O—S₂, wherein S¹ is $C_{1-12}$-alkylene or $C_{2-12}$-alkenylene and S² is H, $C_{1-12}$-alkyl or $C_{2-12}$-alkenyl and very preferably are selected from the group consisting of

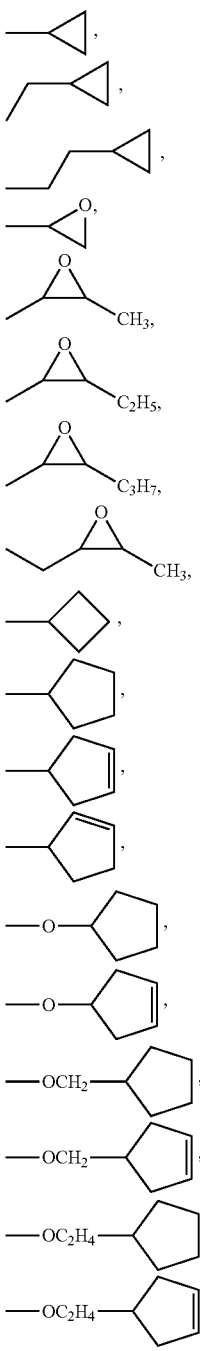

—OCH₂OCH₃, —O(CH₂)₂OCH₃, —O(CH₂)₃OCH₃, —O(CH₂)₄OCH₃, —O(CH₂)₂F, —O(CH₂)₃F, —O(CH₂)₄F.

If in formula I and its subformulae a group $R^b$, R or L denotes an alkyl radical in which one CH₂ group has been replaced by —CH=CH—, this may be straight-chain or branched. It is preferably straight-chain and has 2 to 10 C atoms. Accordingly, it denotes, in particular, vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3, -4-, -5-, -6-, -7- or -8-enyl, dec-1-, -2-, -3-, -4-, -5-, -6-, -7-, -8- or -9-enyl.

If in formula I and its subformulae a group $R^b$, R or L denotes an alkyl or alkenyl radical which is at least monosubstituted by halogen, this radical is preferably straight-chain, and halogen is preferably F or Cl. In the case of polysubstitution, halogen is preferably F. The resultant radicals also include perfluorinated radicals. In the case of monosubstitution, the fluorine or chlorine substituent may be in any desired position, but is preferably in the w-position.

Halogen is preferably F or Cl, very preferably F.

The group —CR⁰=CR⁰⁰— is preferably —CH=CH—.

In formula I and its subformulae, the aryl or heteroaryl groups A¹ and A² can be monocyclic, i.e. they can contain one ring (such as, for example, phenyl) or polycyclic, i.e. they contain two or more rings, which may also be fused (such as, for example, naphthyl) or covalently bonded (such as, for example, biphenyl), or contain a combination of fused and linked rings. Heteroaryl groups contain one or more heteroatoms, preferably selected from O, N, S and Se.

If in formula I and its subformulae a group A¹ or A² denotes a monocyclic or polycyclic aryl or heteroaryl group, this is preferably a mono-, bi- or tricyclic aryl group having 6 to 25 C atoms or a mono-, bi- or tricyclic heteroaryl group having 5 to 25 ring atoms, which optionally contains fused rings and is optionally substituted. Preference is furthermore given to 5-, 6- or 7-membered aryl and heteroaryl groups, in which, in addition, one or more CH groups may be replaced by N, S or O in such a way that O atoms and/or S atoms are not linked directly to one another.

Preferred aryl groups are, for example, phenyl, biphenyl, terphenyl, [1,1':3',1"]terphenyl-2'-yl, naphthyl, anthracene, binaphthyl, phenanthrene, 9,10-dihydro-phenanthrene, pyrene, dihydropyrene, chrysene, perylene, tetracene, pentacene, benzopyrene, fluorene, indene, indenofluorene, spirobifluorene, etc.

Preferred heteroaryl groups are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]thiophene, thieno[3,2b]thiophene, dithienothiophene, isobenzothiophene, dibenzothiophene, benzothiophene, benzothiadiazothiophene, or combinations of these groups.

The (non-aromatic) alicyclic and heterocyclic groups encompass both saturated rings, i.e. those containing exclusively single bonds, and also partially unsaturated rings, i.e. those which may also contain multiple bonds. Heterocyclic rings contain one or more heteroatoms, preferably selected from Si, O, N, S and Se.

The (non-aromatic) alicyclic and heterocyclic groups can be monocyclic, i.e. contain only one ring (such as, for example, cyclohexane), or polycyclic, i.e. contain a plurality of rings (such as, for example, decahydronaphthalene or bicyclooctane). Particular preference is given to saturated groups. Preference is furthermore given to mono-, bi- or tricyclic groups having 5 to 25 ring atoms, which optionally contain fused rings and are optionally substituted. Preference is furthermore given to 5-, 6-, 7- or 8-membered carbocyclic groups, in which, in addition, one or more C atoms may be replaced by Si and/or one or more CH groups may be replaced by N and/or one or more non-adjacent $CH_2$ groups may be replaced by —O— and/or —S—.

Preferred alicyclic and heterocyclic groups are, for example, 5-membered groups, such as cyclopentane, tetrahydrofuran, tetrahydrothiofuran, pyrrolidine, 6-membered groups, such as cyclohexane, silinane, cyclohexene, tetrahydropyran, tetrahydrothiopyran, 1,3-dioxane, 1,3-dithiane, piperidine, 7-membered groups, such as cycloheptane, and fused groups, such as tetrahydronaphthalene, decahydronaphthalene, indane, bicyclo[1.1.1]-pentane-1,3-diyl, bicyclo[2.2.2]octane-1,4-diyl, spiro[3.3]heptane-2,6-diyl, octahydro-4,7-methanoindane-2,5-diyl.

Further preferred are compounds of formula I comprising at least one group $A^1$ or $A^2$ that is an aryl or heteroaryl group, preferably selected from the preferred aryl and heteroaryl groups listed above, and at least one group $A^1$ or $A^2$ that is a non-aromatic, alicyclic or heterocyclic group, preferably selected from the preferred alicyclic and heterocyclic group groups listed above.

The aryl, heteroaryl, alicyclic and heterocyclic groups mentioned above and below may also be substituted by one or more groups L, P-Sp- or A.

Preferred substituents L are, for example, F, Cl, —CN, straight-chain or branched alkyl, alkoxy, alkylcarbonyl, alkoxycarbonyl, alkylcarbonyloxy or alkoxycarbonyloxy each having 1 to 25 C atoms, in which one or more H atoms may optionally be replaced by F, Cl or P-Sp-.

Particularly preferred substituents L are, for example, F, Cl, CN, $CH_3$, $C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F_5$.

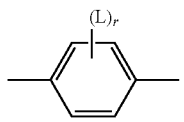

is preferably

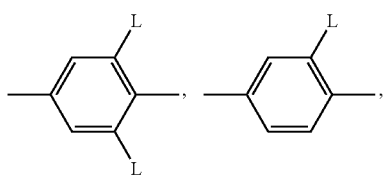

-continued

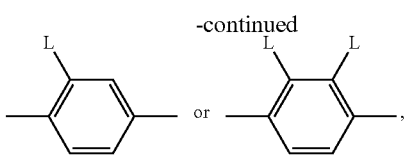

in which L has one of the meanings indicated above.

The polymerizable group P is a group which is suitable for a polymerization reaction, such as, for example, free-radical or ionic chain polymerization, polyaddition or polycondensation, or for a polymer-analogous reaction, for example addition or condensation onto a main polymer chain. Particular preference is given to groups for chain polymerization, in particular those containing a C=C double bond or —C≡C— triple bond, and groups which are suitable for polymerization with ring opening, such as, for example, oxetane or epoxide groups.

Preferred groups P are selected from the group consisting of $CH_2=CW^1—CO—O—$, $CH_2=CW^1—CO—$,

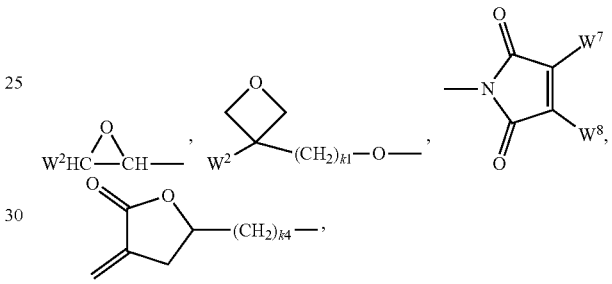

$CH_2=CW^2—(O)_{k3}—$, $CW^1=CH—CO—(O)_{k3}—$, $CW^1=CH—CO—NH—$, $CH_2=CW^1—CO—NH—$, $CH_3—CH=CH—O—$, $(CH_2=CH)_2CH—OCO—$, $(CH_2=CH—CH_2)_2CH—OCO—$, $(CH_2=CH)_2CH—O—$, $(CH_2=CH—CH_2)_2N—$, $(CH_2=CH—CH_2)_2N—CO—$, $HO—CW^2W^3—$, $HS—CW^2W^3—$, $HW^2N—$, $HO—CW^2W^3—NH—$, $CH_2=CW^1—CO—NH—$, $CH_2=CH—(COO)_{k1}$-Phe-$(O)_{k2}—$, $CH_2=CH—(CO)_{k1}$-Phe-$(O)_{k2}—$, Phe-CH=CH—, HOOC—, OCN— and $W^4W^5W^6Si—$, in which $W^1$ denotes H, F, C, CN, $CF_3$, phenyl or alkyl having 1 to 5 C atoms, in particular H, F, C or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote C, oxaalkyl or oxacarbonylalkyl having 1 to 5 C atoms, $W^7$ and $W^8$ each, independently of one another, denote H, C or alkyl having 1 to 5 C atoms, Phe denotes 1,4-phenylene, which is optionally substituted by one or more radicals L as defined above which are other than P-Sp-, $k_1$, $k_2$ and $k_3$ each, independently of one another, denote 0 or 1, $k_3$ preferably denotes 1, and $k_4$ denotes an integer from 1 to 10.

Very preferred groups P are selected from the group consisting of $CH_2=CW^1—CO—O—$, $CH_2=CW^1—CO—$,

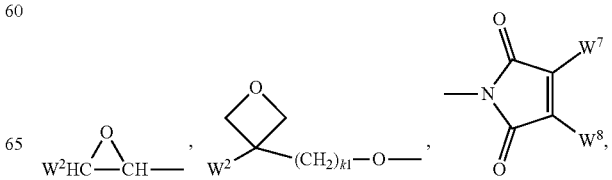

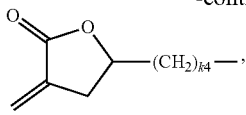

$CH_2=CW^2-O-$, $CH_2=CW^2-$, $CW^1=CH-CO-(O)_{k3}-$, $CW^1=CH-CO-NH-$, $CH_2=CW^1-CO-NH-$, $(CH_2=CH)_2CH-OCO-$, $(CH_2=CH-CH_2)_2CH-OCO-$, $(CH_2=CH)_2CH-O-$, $(CH_2=CH-CH_2)_2N-$, $(CH_2=CH-CH_2)_2N-CO-$, $CH_2=CW^1-CO-NH-$, $CH_2=CH-(COO)_{k1}$-Phe-$(O)_{k2}-$, $CH_2=CH-(CO)_{k1}$-Phe-$(O)_{k2}-$, Phe-$CH=CH-$ and $W^4W^5W^6Si-$, in which $W^1$ denotes H, F, Cl, CN, $CF_3$, phenyl or alkyl having 1 to 5 C atoms, in particular H, F, Cl or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote Cl, oxaalkyl or oxacarbonylalkyl having 1 to 5 C atoms, $W^7$ and $W^8$ each, independently of one another, denote H, Cl or alkyl having 1 to 5 C atoms, Phe denotes 1,4-phenylene, $k_1$, $k_2$ and $k_3$ each, independently of one another, denote 0 or 1, $k_3$ preferably denotes 1, and $k_4$ denotes an integer from 1 to 10.

Very particularly preferred groups P are selected from the group consisting of $CH_2=CW^1-CO-O-$, in particular $CH_2=CH-CO-O-$, $CH_2=C(CH_3)-CO-O-$ and $CH_2=CF-CO-O-$, furthermore $CH_2=CH-O-$ $(CH_2=CH)_2CH-O-CO-$, $(CH_2=CH)_2CH-O-$,

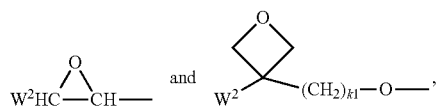

Further preferred polymerizable groups P are selected from the group consisting of vinyloxy, acrylate, methacrylate, fluoroacrylate, chloroacrylate, oxetane and epoxide, more preferably from acrylate and methacrylate, most preferably methacrylate.

If the spacer group Sp is different from a single bond, it is preferably of the formula Sp"-X", so that the respective radical P-Sp- conforms to the formula P-Sp"-X"—, wherein Sp" denotes linear or branched alkylene having 1 to 20, preferably 1 to 12, C atoms, which is optionally mono- or polysubstituted by F, Cl, Br, I or CN and in which, in addition, one or more non-adjacent $CH_2$ groups may each be replaced, independently of one another, by —O—, —S—, —NH—, —N($R^0$)—, —Si($R^0R^{00}$)—, —CO—, —CO—O—, —O—CO—, —O—CO—O—, —S—CO—, —CO—S—, —N($R^0$)—CO—O—, —O—CO—N($R^0$)—, —N($R^0$)—CO—N($R^{00}$)—, —CH=CH— or —C≡C— in such a way that O and/or S atoms are not linked directly to one another, X" denotes —O—, —S—, —CO—, —CO—O—, —O—CO—, —O—CO—O—, —CO—N($R^0$)—, —N($R^0$)—CO—, —N($R^0$)—CO—N($R^{00}$)—, —OCH_2—, —CH_2O—, —SCH_2—, —CH_2S—, —CF_2O—, —OCF_2—, —CF_2S—, —SCF_2—, —CF_2CH_2—, —CH_2CF_2—, —CF_2CF_2—, —CH=N—, —N=CH—, —N=N—, —CH=CR^0—, —CY^2=CY^3—, —C≡C—, —CH=CH—CO—O—, —O—CO—CH=CH— or a single bond, $R^0$ and $R^{00}$ each, independently of one another, denote H or alkyl having 1 to 20 C atoms, and $Y^2$ and $Y^3$ each, independently of one another, denote H, F, Cl or CN.

X" is preferably —O—, —S—, —CO—, —COO—, —OCO—, —O—COO—, —CO—NR$^0$—, —NR$^0$—CO—, —NR$^0$—CO—NR$^{00}$— or a single bond.

Typical spacer groups Sp and -Sp"-X"— are, for example, —(CH$_2$)$_{p1}$—, —(CH$_2$)$_{p1}$—O—, —(CH$_2$)$_{p1}$—O—CO—, —(CH$_2$)$_{p1}$—CO—O—, —(CH$_2$)$_{p1}$—O—CO—O—, —(CH$_2$CH$_2$O)$_{q1}$—CH$_2$CH$_2$—, —CH$_2$CH$_2$—S—CH$_2$CH$_2$—, —CH$_2$CH$_2$—NH—CH$_2$CH$_2$— or —(SiR$^0$R$^{00}$—O)$_{p1}$—, in which p1 is an integer from 1 to 12, q1 is an integer from 1 to 3, and $R^0$ and $R^{00}$ have the meanings indicated above.

Particularly preferred groups Sp and -Sp"-X"— are —(CH$_2$)$_{p1}$—, —(CH$_2$)$_{p1}$—O—, —(CH$_2$)$_{p1}$—O—CO—, —(CH$_2$)$_{p1}$—CO—O—, —(CH$_2$)$_{p1}$—O—CO—O—, in which p1 and q1 have the meanings indicated above.

Particularly preferred groups Sp" are, in each case straight-chain, ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methylimino-ethylene, 1-methylalkylene, ethenylene, propenylene and butenylene.

In a preferred embodiment of the invention the compounds of formula I and its subformulae contain a spacer group Sp that is substituted by one or more polymerizable groups P, so that the group Sp-P corresponds to Sp(P)$_s$, with s being ≥2 (branched polymerizable groups).

Preferred compounds of formula I according to this preferred embodiment are those wherein s is 2, i.e. compounds which contain a group Sp(P)$_2$. Very preferred compounds of formula I according to this preferred embodiment contain a group selected from the following formulae:

| | |
|---|---|
| —X-alkyl-CHPP | Sp1 |
| —X-alkyl-CH((CH$_2$)$_{aa}$P)((CH$_2$)$_{bb}$P) | Sp2 |
| —X—N((CH$_2$)$_{aa}$P)((CH$_2$)$_{bb}$P) | Sp3 |
| —X-alkyl-CHP—CH$_2$—CH$_2$P | Sp4 |
| —X-alkyl-C(CH$_2$P)(CH$_2$P)—C$_{aa}$H$_{2aa+1}$ | Sp5 |
| —X-alkyl-CHP—CH$_2$P | Sp6 |
| —X-alkyl-CPP—C$_{aa}$H$_{2aa+1}$ | Sp7 |
| —X-alkyl-CHPCHP—C$_{aa}$H$_{2aa+1}$ | Sp8 | in which P is as defined in formula I, alkyl denotes a single bond or straight-chain or branched alkylene having 1 to 12 C atoms which is unsubstituted or mono- or polysubstituted by F, Cl or CN and in which one or more non-adjacent CH$_2$ groups may each, independently of one another, be replaced by —C($R^0$)=C($R^0$)—, —C≡C—, —N($R^0$)—, —O—, —S—, —CO—, —CO—O—, —O—CO—, —O—CO—O— in such a way that O and/or S atoms are not linked directly to one another, where $R^0$ has the meaning indicated above, aa and bb each, independently of one another, denote 0, 1, 2, 3, 4, 5 or 6, X has one of the meanings indicated for X", and is preferably O, CO, SO$_2$, O—CO—, CO—0 or a single bond.

Preferred spacer groups Sp(P)$_2$ are selected from formulae Sp1, Sp2 and Sp3.

Very preferred spacer groups Sp(P)$_2$ are selected from the following subformulae:

| | |
|---|---|
| —CHPP | Sp1a |
| —O—CHPP | Sp1b |
| —CH$_2$—CHPP | Sp1c |
| —OCH$_2$—CHPP | Sp1d |
| —CH(CH$_2$—P)(CH$_2$—P) | Sp2a |
| —OCH(CH$_2$—P)(CH$_2$—P) | Sp2b |
| —CH$_2$—CH(CH$_2$—P)(CH$_2$—P) | Sp2c |
| —OCH$_2$—CH(CH$_2$—P)(CH$_2$—P) | Sp2d |
| —CO—NH((CH$_2$)$_2$P)((CH$_2$)$_2$P) | Sp3a |

In the compounds of formula I and its subformulae as described above and below, P is preferably selected from the group consisting of vinyloxy, acrylate, methacrylate, fluoroacrylate, chloroacrylate, oxetane and epoxide, very preferably from acrylate and methacrylate, most preferably methacrylate.

Further preferred are compounds of formula I and its subformulae as described above and below, wherein all polymerizable groups P that are present in the compound have the same meaning, and very preferably denote acrylate or methacrylate, most preferably methacrylate.

Further preferred are compounds of formula I and its subformulae as described above and below, which contain one, two, three or four groups P-Sp, very preferably two or three groups P-Sp.

Further preferred are compounds of formula I and its subformulae as described above and below, wherein $R^b$ is P-Sp-.

Further preferred are compounds of formula I and its subformulae as described above and below, wherein Sp denotes a single bond or —(CH$_2$)$_{p1}$—, —O—(CH$_2$)$_{p1}$—, —O—CO—(CH$_2$)$_{p1}$, or —CO—O—(CH$_2$)$_{p1}$, wherein p1 is 2, 3, 4, 5 or 6, and, if Sp is —O—(CH$_2$)$_{p1}$—, —O—CO—(CH$_2$)$_{p1}$ or —CO—O—(CH$_2$)$_{p1}$ the O-atom or CO-group, respectively, is linked to the benzene ring.

Further preferred are compounds of formula I and its subformulae as described above and below, wherein at least one group Sp is a single bond.

Further preferred are compounds of formula I and its subformulae as described above and below, wherein at least one group Sp is different from a single bond, and is selected from —(CH$_2$)$_{p1}$—, —O—(CH$_2$)$_{p1}$—, —O—CO—(CH$_2$)$_{p1}$, or —CO—O—(CH$_2$)$_{p1}$, wherein p1 is 2, 3, 4, 5 or 6, and, if Sp is —O—(CH$_2$)$_{p1}$—, —O—CO—(CH$_2$)$_{p1}$ or —CO—O—(CH$_2$)$_{p1}$ the O-atom or CO-group, respectively, is linked to the benzene ring.

Very preferred are compounds of formula I and its subformulae as described above and below, wherein at least one group Sp is different from a single bond, and is selected from —(CH$_2$)$_2$—, —(CH$_2$)$_3$—, —(CH$_2$)$_4$—, —O—(CH$_2$)$_2$—, —O—(CH$_2$)$_3$—, —O—CO—(CH$_2$)$_2$ and —CO—O—(CH)$_2$—, wherein the O atom or the CO group is attached to the benzene ring.

Preferably A in formula I and its subformulae denotes thioalkyl with 1 to 7 C atoms which is preferably straight-chain or branched, most preferably straight-chain, and is preferably selected from —SCH$_3$, —SC$_2$H$_5$ and —SC$_3$H$_7$, very preferably —SCH$_3$ or —SC$_2$H$_5$, most preferably —SCH$_3$. Further preferably A is selected from —CH$_2$—S—CH$_3$ or —CH$_2$—S—C$_2$H$_5$.

Preferably $A^1$ and $A^2$ in formula I are selected from the group consisting of 1,4-phenylene, 1,3-phenylene, naphthalene-1,4-diyl, naphthalene-2,6-diyl, phenanthrene-2,7-diyl, 9,10-dihydro-phenanthrene-2,7-diyl, anthracene-2,7-diyl, fluorene-2,7-diyl, coumarine, flavone, where, in addition, one or more CH groups in these groups may be replaced by N, cyclohexane-1,4-diyl, in which, in addition, one or more non-adjacent CH$_2$ groups may be replaced by O and/or S, 1,4-cyclohexenylene, bicycle[1.1.1]pentane-1,3-diyl, bicyclo[2.2.2]octane-1,4-diyl, spiro[3.3]heptane-2,6-diyl, piperidine-1,4-diyl, decahydronaphthalene-2,6-diyl, 1,2,3,4-tetrahydronaphthalene-2,6-diyl, indane-2,5-diyl or octahydro-4,7-methanoindane-2,5-diyl, all of which are optionally substituted by one or more groups A, L or P-Sp-, and wherein at least one group $A^1$ or $A^2$, preferably at least one aryl or heteroaryl group $A^1$ or $A^2$, is substituted by at least one group A.

Very preferably $A^1$ and $A^2$ in formula I are selected from the group consisting of benzene, naphthalene, phenanthrene, anthracene, dibenzofuran or dibenzothiophene, all of which are optionally substituted by one or more groups A, L or P-Sp-, and wherein at least one group $A^1$ or $A^2$ is substituted by at least one group A.

Preferably z in formula I is 0, 1 or 2, very preferably 1 or 2.

Preferably -$A^1$-($Z^1$-$A^2$)$_z$- in formula I denotes benzene, biphenylene, p-terphenylene (1,4-diphenylbenzene), m-terphenylene (1,3-diphenylbenzene), naphthylene, 2-phenylnaphthylene, phenanthrene or anthracene, dibenzofuran or dibenzothiophene, all of which are optionally substituted by one or more groups A, L or P-Sp- and are at least mono-substituted by A.

Further preferred are compounds of formula I and its subformulae that contain at least one group $A^1$ or $A^2$ that is not substituted by L or A.

Further preferred are compounds of formula I and its subformulae as described above and below, wherein -$A^1$-(Z-$A^2$)$_z$- is selected from the following formulae

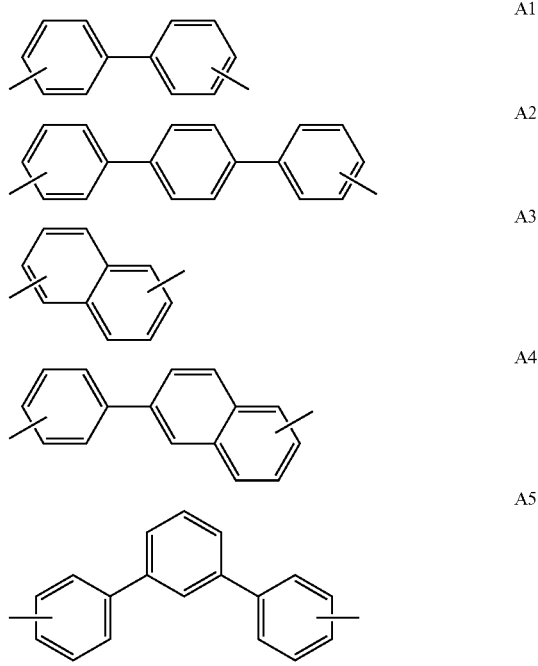

-continued

A6 wherein the single bonds depict the linkages to the groups P-Sp and $R^b$ in formula I, and wherein benzene rings are optionally further substituted by one or more groups A, L or P-Sp- as defined in formula I, and at least one benzene ring is substituted by at least one group A, and preferably at least one benzene ring does not carry any substituents A or L.

Preferred are formulae A1, A2 and A5, more preferred are formulae A1 and A2, most preferred is formula A1.

Preferred compounds of formula I are selected from the following subformulae

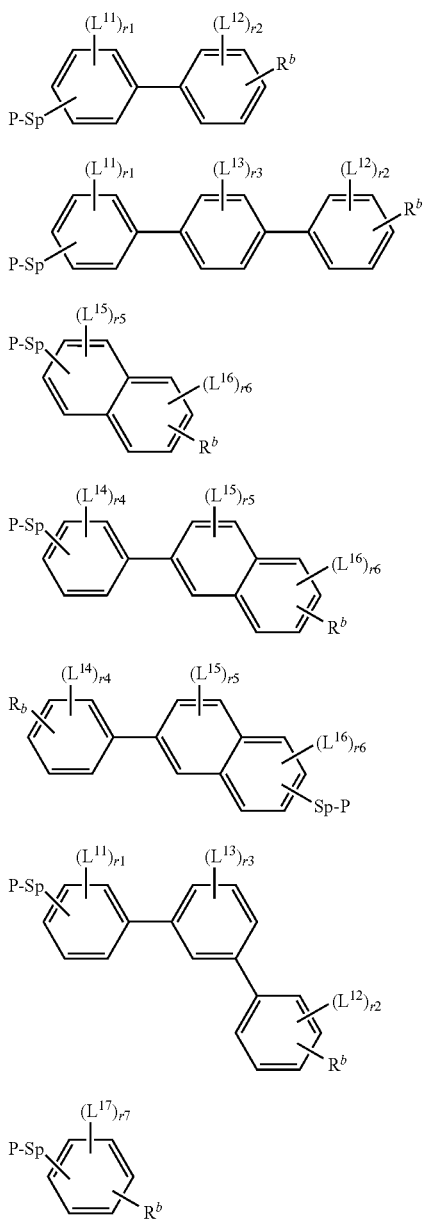

wherein the individual radicals, independently of each other, and on each occurrence identically or differently, have the following meanings A, P, Sp, $R^b$ one of the meanings given in formula I or one of the preferred meanings as given above and below, $L^{11}$ to $L^{17}$ L or A, preferably F, Cl, $OCH_3$, $OCF_3$, CN, P-Sp or A, r1, r2, r3, r4 0, 1, 2, 3 or 4, preferably 0, 1 or 2, very preferably 0 or 1, wherein in formula I1, I2 and I5 r1+r2+r3≥1, r5, r6, 0, 1, 2 or 3, preferably 0, 1 or 2, very preferably 0 or 1, wherein in formula I3 r5+r6≥1 and in formula I4a and I4b r4+r5+r6≥1, r7 1, 2, 3 or 4, preferably 1 or 2, very preferably 1, wherein the compounds contain at least one group $L^{11}$ to $L^{17}$ that is A.

Preferred are compounds of formula I1, I2 and I5, very preferred are compounds of formulae I1 and I2, most preferred are compounds of formula I1.

Further preferred are compounds of formula I12

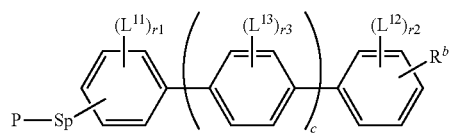
I12 wherein P, Sp, $R^b$, $L^{11}$, $L^{12}$, $L^{13}$, r1, r2 and r3 have the meanings given above and below, r1+r2+r3≥, and c is 0, 1 or 2, preferably 0 or 1.

Preferred subformulae of formula I12 include the preferred subformulae of formulae I1 and I2 as listed below.

Further preferred are compounds of formula I, I1-I6 and I12 wherein $R^b$ denotes P-Sp.

Further preferred are compounds of formula I, I1-I6 and I12 wherein $R^b$ is different from P-Sp, and preferably denotes F, Cl, CN or straight chain, branched or cyclic alkyl having 1 to 25 C atoms, wherein one or more non-adjacent $CH_2$-groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by F or Cl.

Further preferred are compounds of formula I1, I2, I5 wherein at least one of r1, r2 and r3 is 0, compounds of formula I3 wherein at least one of r4 and r5 is 0, compounds of formula I4a and I4b wherein at least one of r4, r5 and r6 is 0, and compounds of formula I12 wherein, if c is 0 then one of r1 and r2 is 0, and if c is 1 or 2 then at least one of r1, r2 and r3 is 0.

Preferred compounds of formula I, I1 to I6 and I12 are selected from the following subformulae:

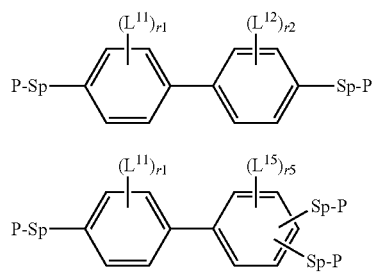

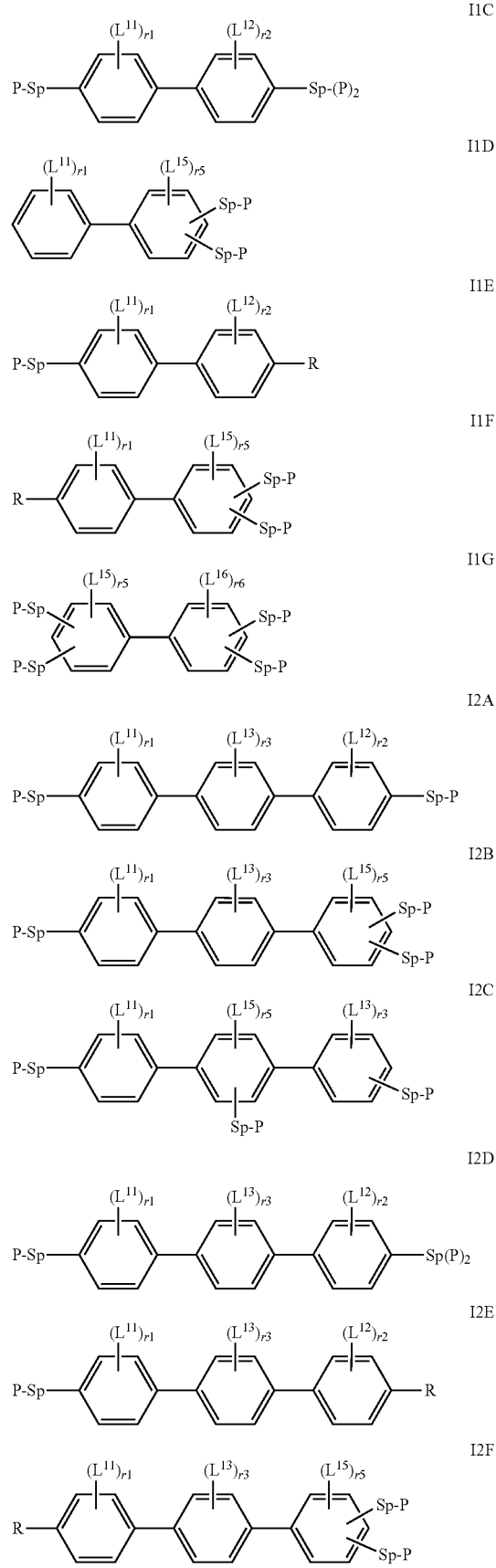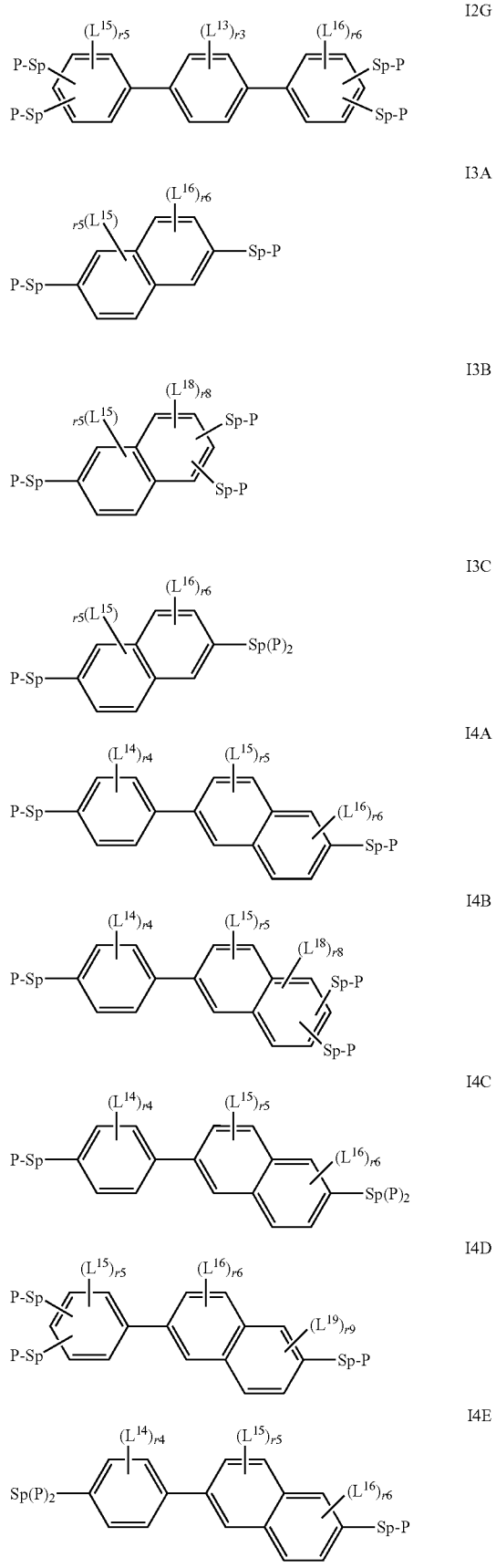

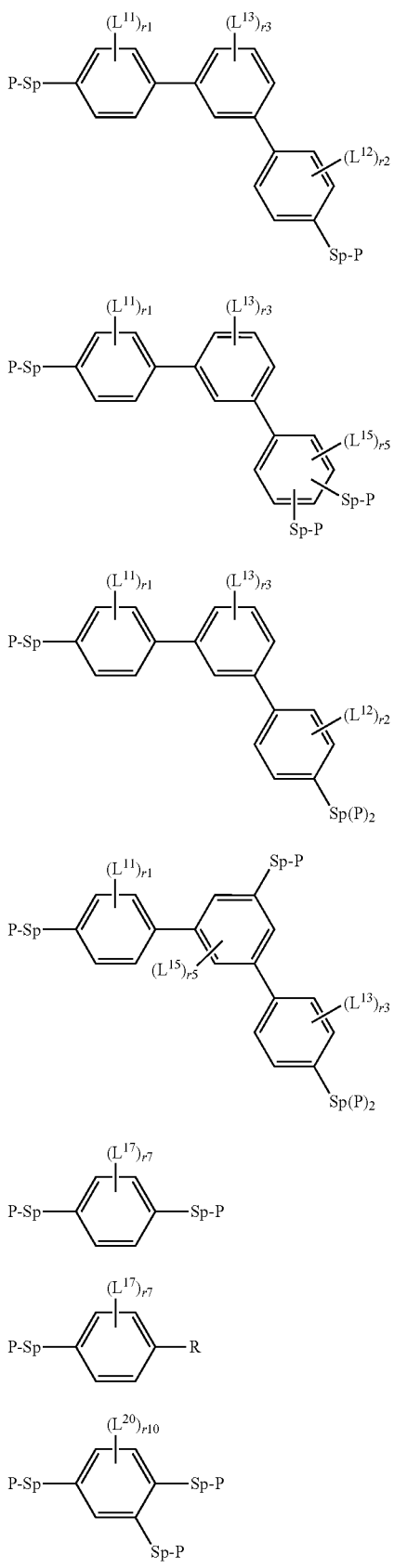

wherein
R, P, Sp, $L^{11}$-$^{17}$ and r1-r7 have the meanings given in formula I or one of the preferred meanings as given above and below,
$L^{18}$, $L^{19}$ and $L^{20}$ have one of the meanings given for $L^{11}$,
r8 is 0, 1 or 2, preferably 0 or 1,
r9 is 0, 1, 2 or 3, preferably 0, 1 or 2, very preferably 0 or 1,
r10 is 1, 2 or 3, preferably 1 or 2, very preferably 1,
Sp(P)$_2$ denotes a spacer group Sp that is substituted by two polymerizable groups P at identical or different positions, and wherein
in formulae I1A, I1C and I1E r1+r2≥1,
in formula I1B, I1D and I1F r1+r5≥1,
in formula I1G, I3A and I3C r5+r6≥1,
in formulae I2A, I2D, I2E, I5A and I5C r1+r2+r3≥1,
in formulae I2B, I2C, I2F, I5B and I5D r1+r3+r5≥1,
in formula I2G r3+r5+r6≥1,
in formula I4A, I4C and I4E r4+r5+r6≥1,
in formula I4D r5+r6+r9≥1,
in formula I3B r5+r8≥1,
in formula I4B r4+r5+r8≥1,
and wherein the compounds contain at least one group $L^{11}$ to $L^{20}$ that denotes A.

Further preferred compounds of formula I and I12 are selected from the following subformulae

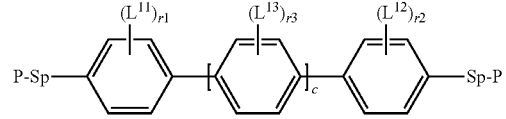

I12A

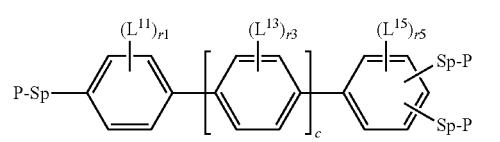

I12B

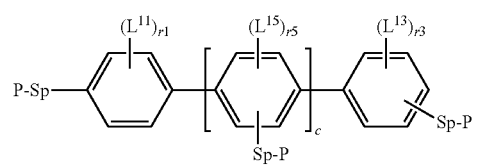

I12C

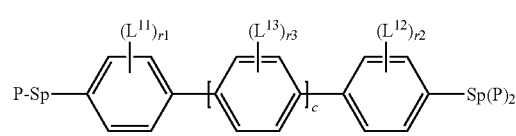

I12D

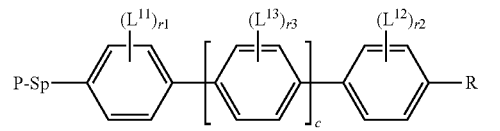

I12E

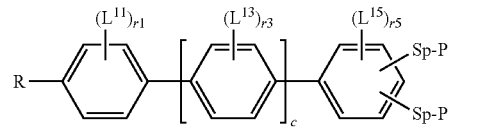

I12F

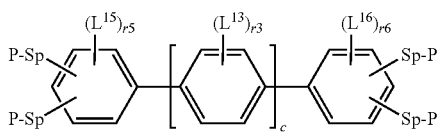
I12G wherein

R, P, Sp, Sp(P)$_2$, L$^{11-16}$ and r1-r6 have the meanings given in formula I2D or one of the preferred meanings as given above and below, c is 0, 1 or 2, in formulae I12A, I12D and I12E r1+r2+r3≥1, in formulae I12B, I12C and I12F r1+r3+r5≥1, in formula I12G r3+r5+r6≥1, and the compounds contain at least one group L$^{11}$ to L$^{16}$ that is A.

Preferably, in the compounds of formulae I12A to I12G, if c is 0 then one of r1 and r2 is 0, and if c is 1 or 2 then at least one of r1, r2 and r3 is 0.

Very preferred are compounds of formula I12A.

Further preferred compounds of formulae I, I1 to I6, I12, I1A-I6C and I12A-I12G are selected from the following subformulae:

I1A-1

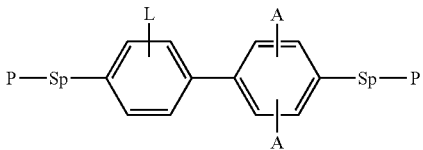

I1A-2

I1A-3

I1A-4

I1A-5

I1A-6

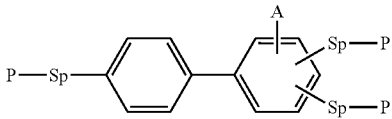
I1A-7

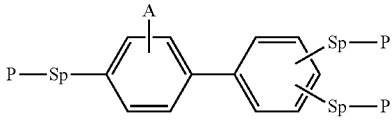
I1B-1

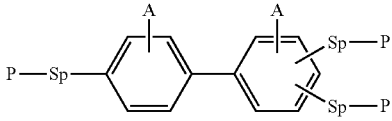
I1B-2

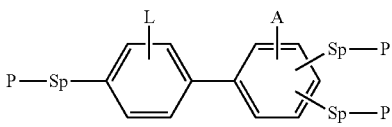
I1B-3

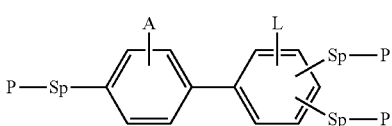
I1B-4

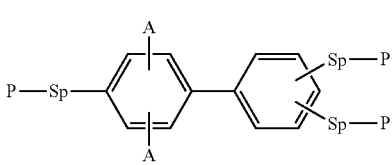
I1B-5

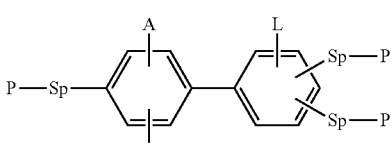
I1B-6

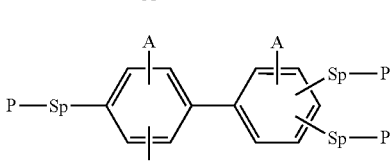
I1B-7

I1B-8

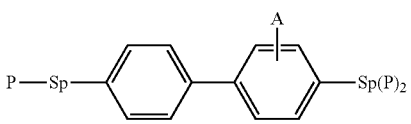
IC1-1

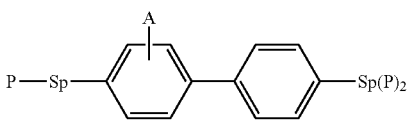
IC1-2

-continued
IC1-3
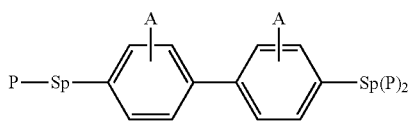
IC1-4
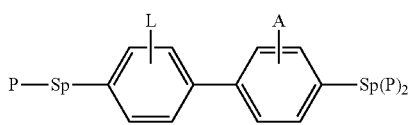
IC1-5
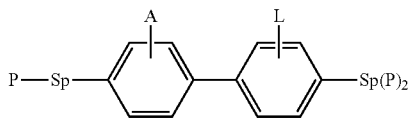
IC1-6
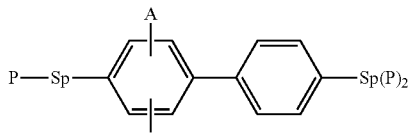
I1C-7
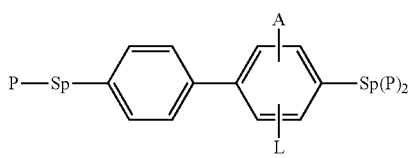
I1C-8
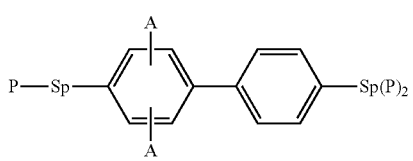
I1C-9
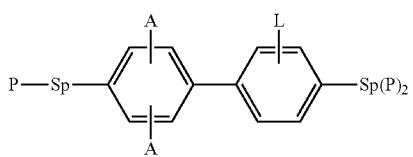
I1C-10
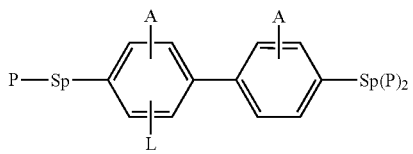
I1C-11
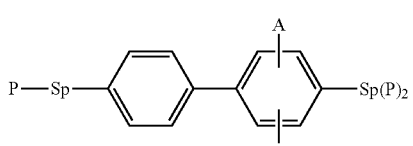
I1C-12
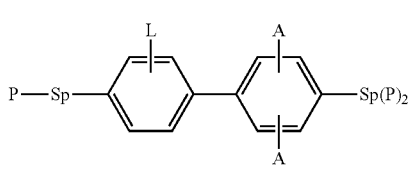
-continued
I1C-13
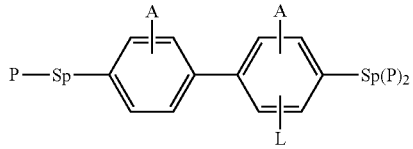
I1D-1
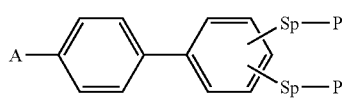
I1D-2
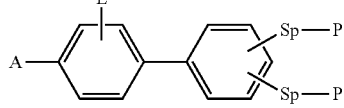
I1D-3
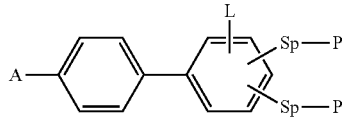
I1D-4
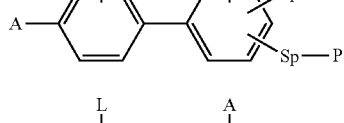
I1D-5
I1E-1
I1E-2
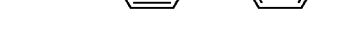
I1E-3
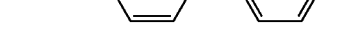
I1E-4
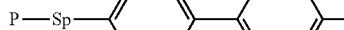
I1F-1
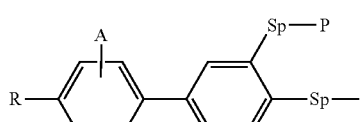
I1F-2
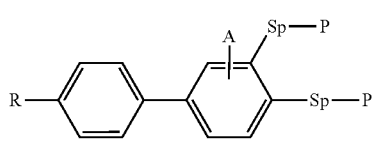

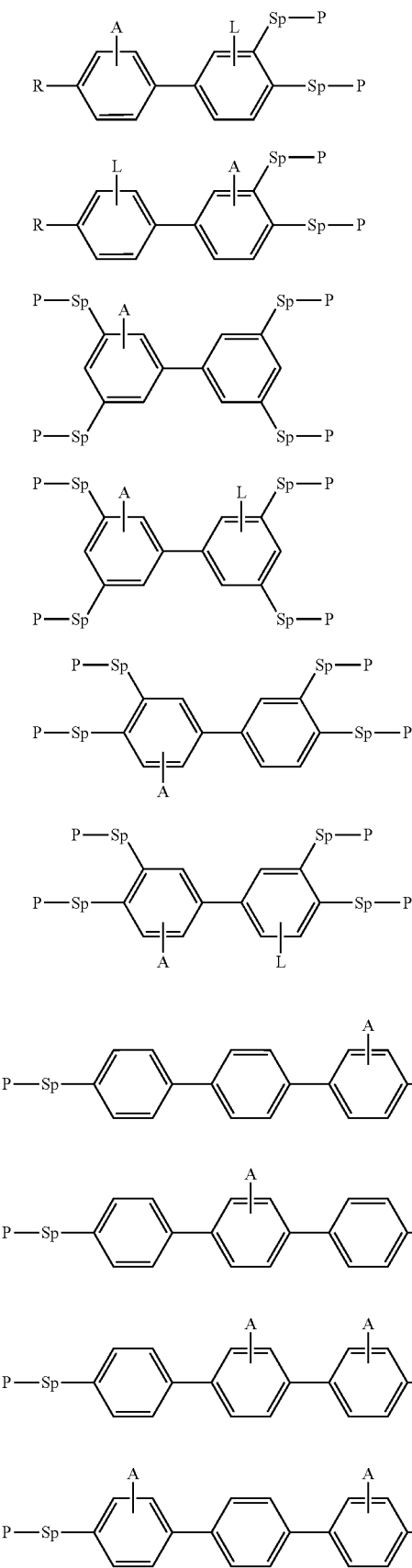
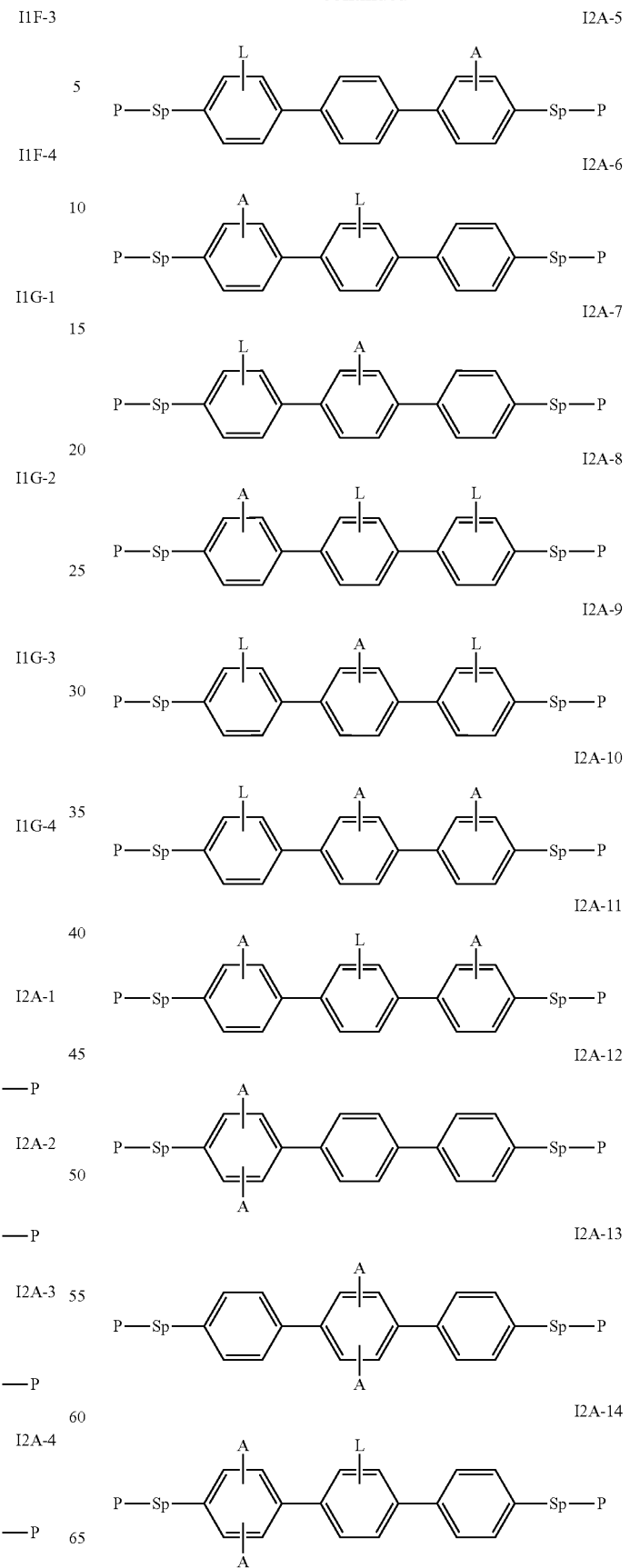

I2A-15
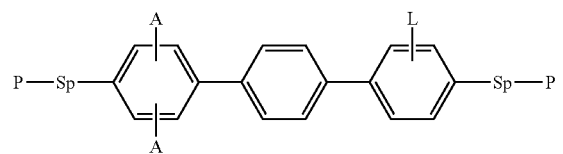
I2A-16
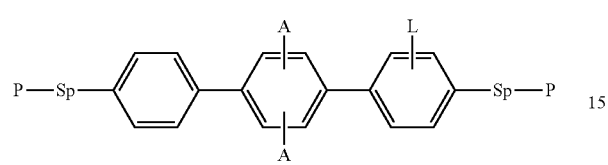
I2A-17
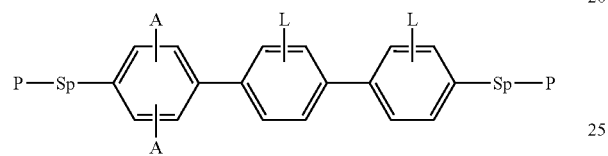
I2A-18
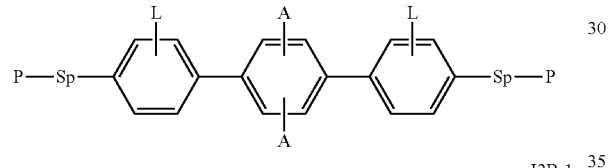
I2B-1
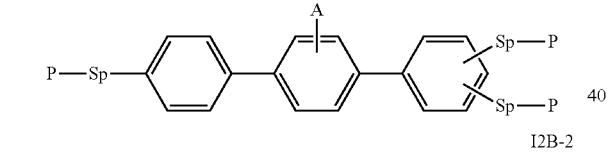
I2B-2
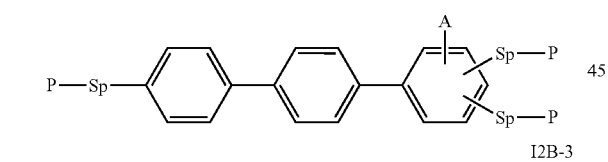
I2B-3
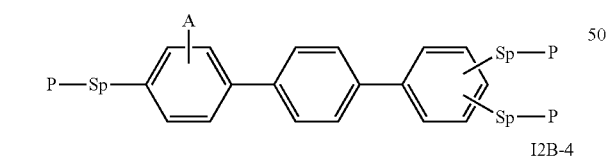
I2B-4
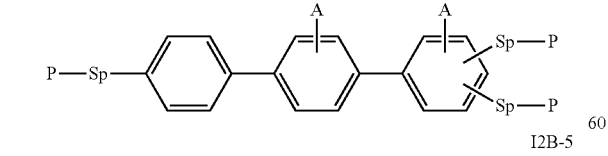
I2B-5
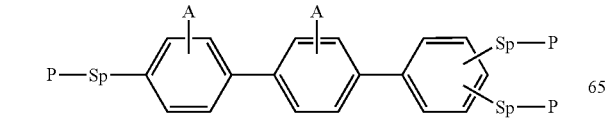
I2B-6
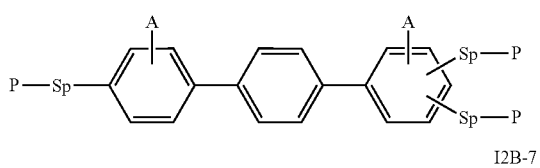
I2B-7
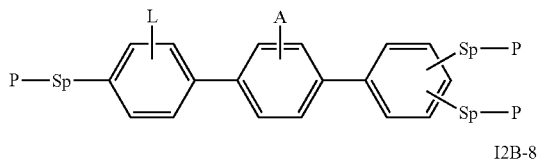
I2B-8
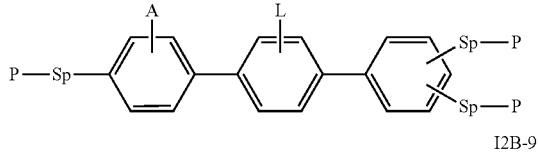
I2B-9
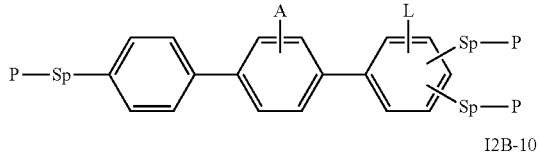
I2B-10
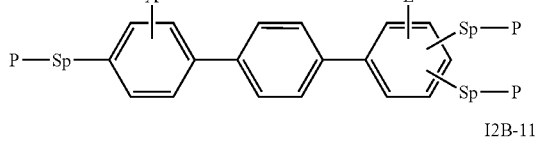
I2B-11
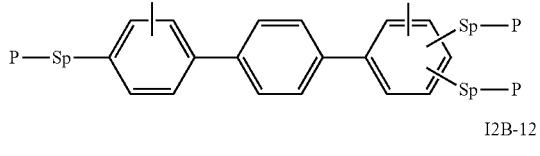
I2B-12
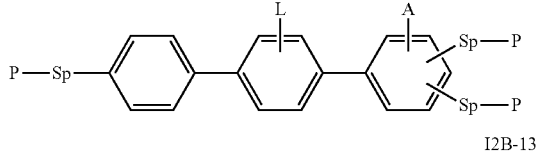
I2B-13
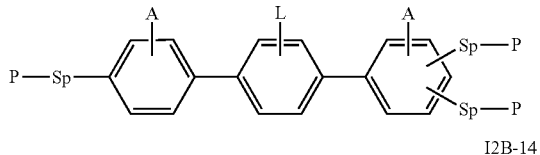
I2B-14
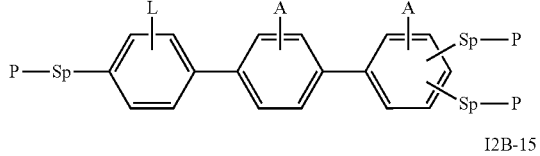
I2B-15
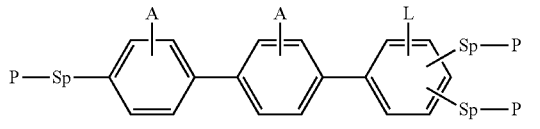

I2C-9
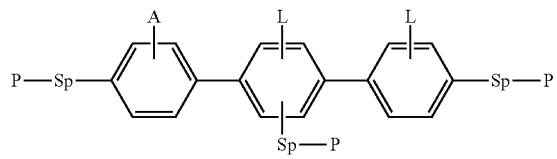
I2C-10
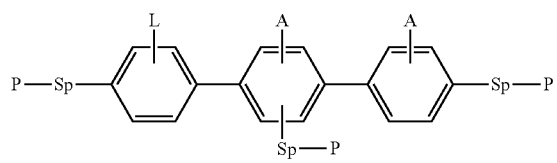
I2C-11
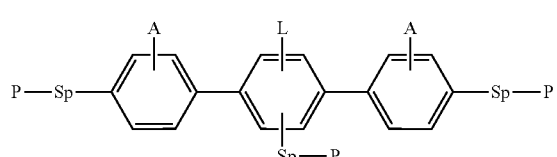
I2C-12
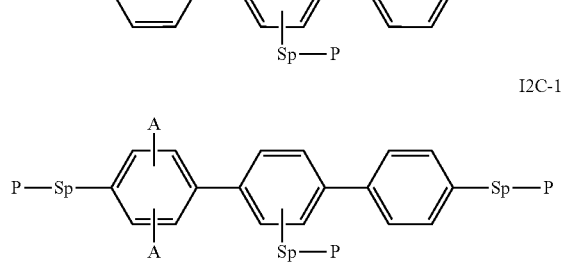
I2C-13
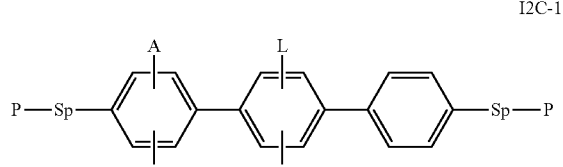
I2C-14
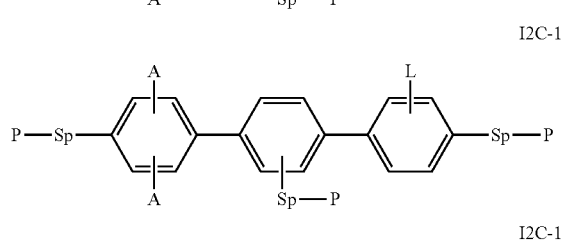
I2C-15
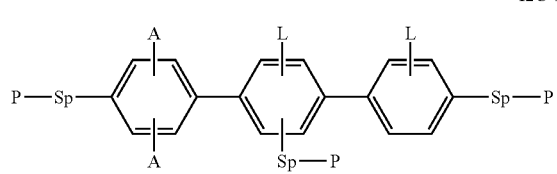
I2D-1
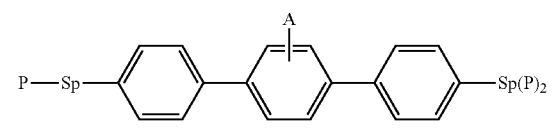
I2D-2
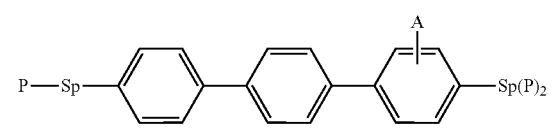
I2D-3
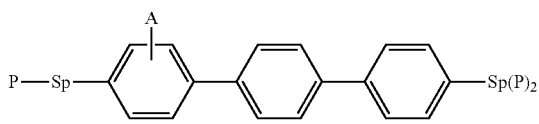
I2D-4
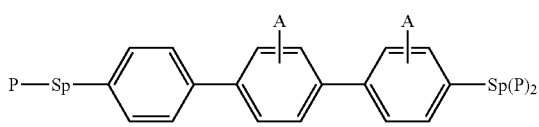
I2D-5
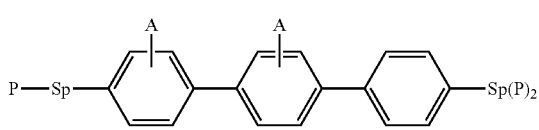
I2D-6
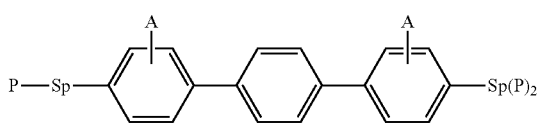
I2D-7
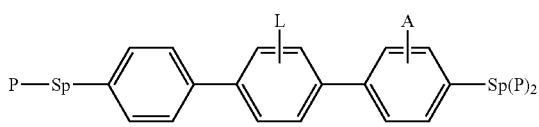
I2D-8
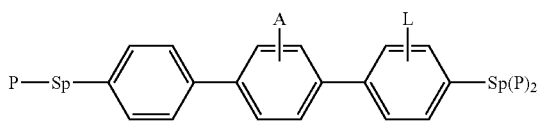
I2D-9
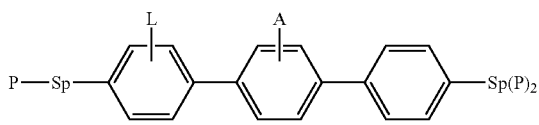
I2D-10
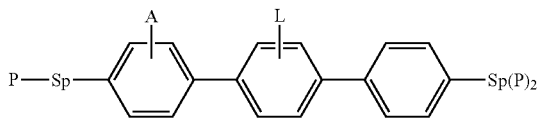
I2D-11
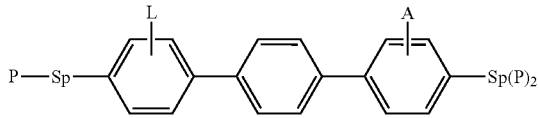
I2D-12
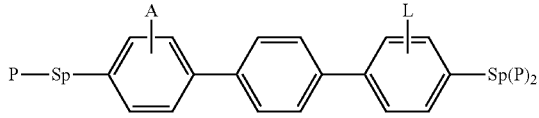

I2D-13
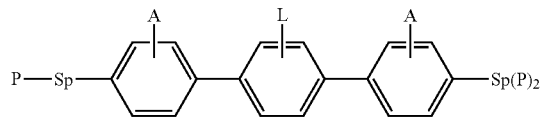
I2D-14
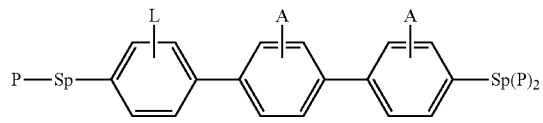
I2D-15
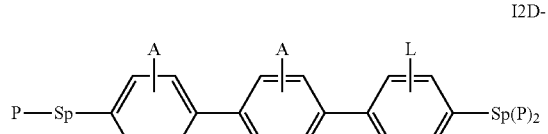
I2D-16
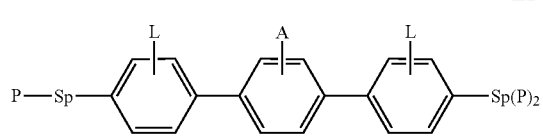
I2D-17
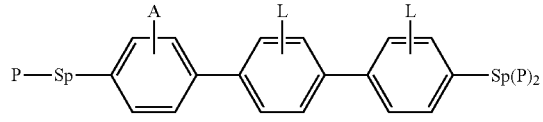
I2D-18
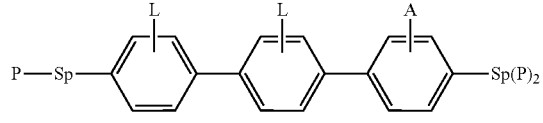
I2D-19
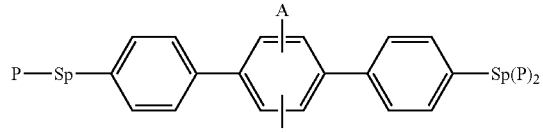
I2D-20
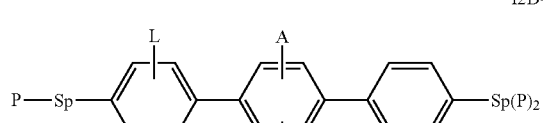
I2D-21
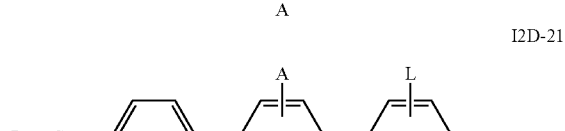
I2D-22
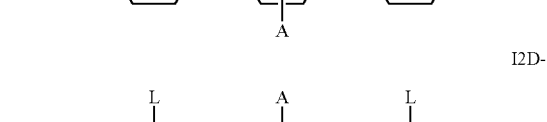
I2D-23
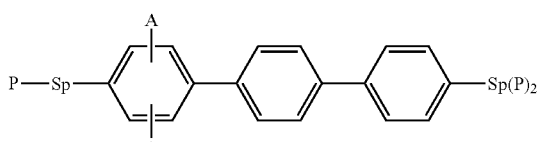
I2D-24
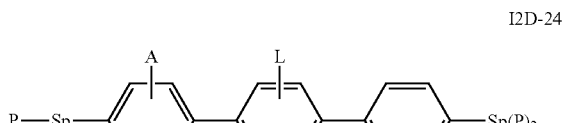
I2D-25
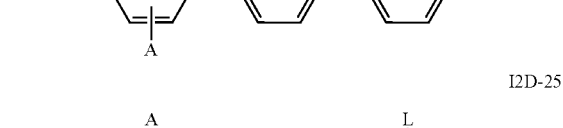
I2D-26
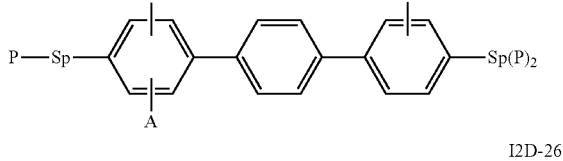
I2D-27
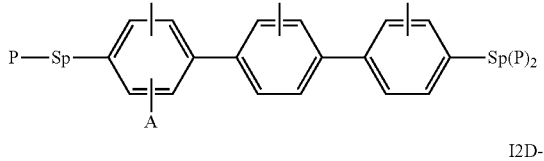
I2D-28
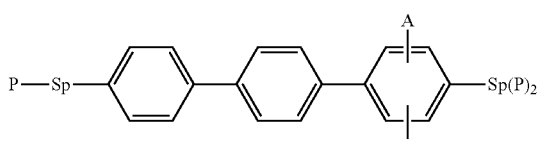
I2D-29
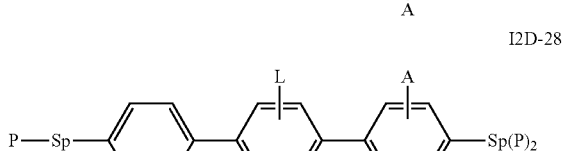
I2D-30
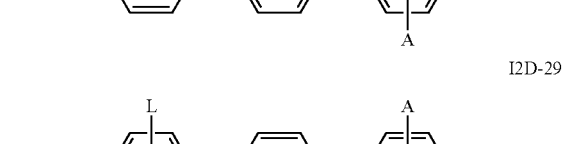
I2E-1
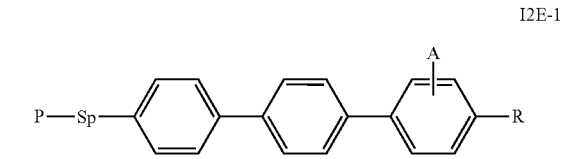

I2E-2
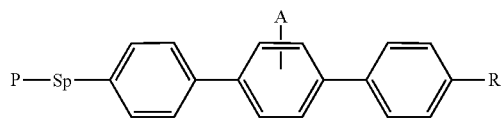
I2E-3
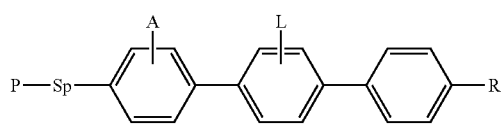
I2E-4
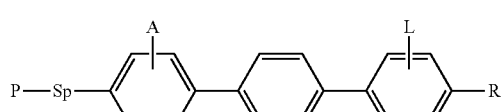
I2F-1
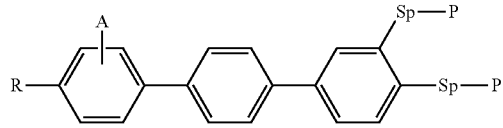
I2F-2
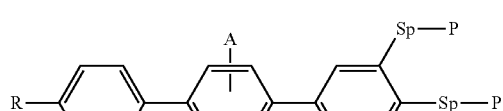
I2F-3
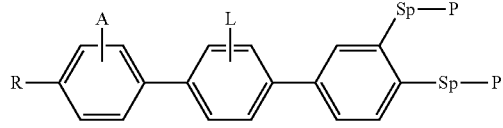
I2F-4
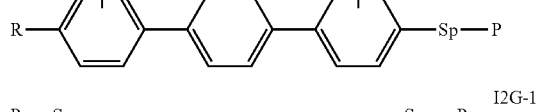
I2G-1
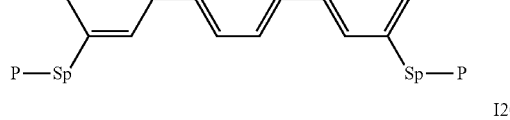
I2G-2
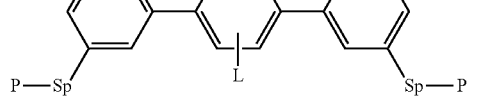
I2G-3
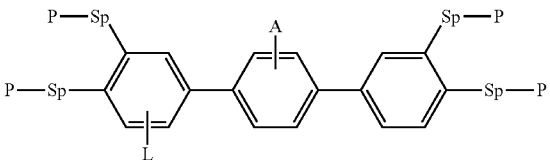
I2G-4
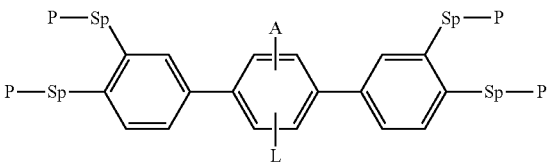
I3A-1
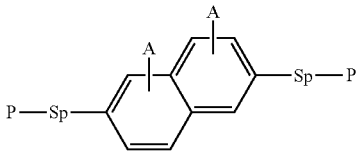
I3A-2
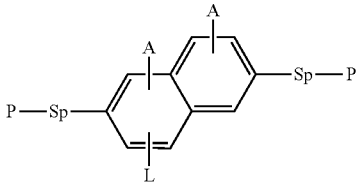
I3B-1
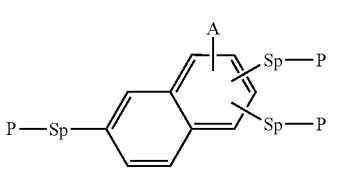
I3B-2
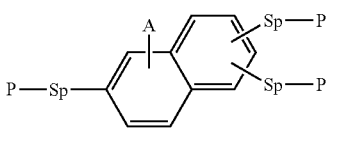
I3B-3
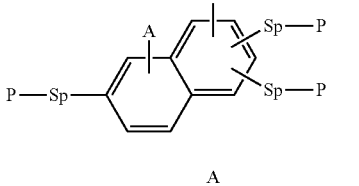
I3B-4
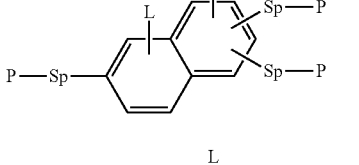
I3B-5

I3C-1
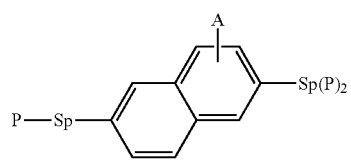
I3C-2
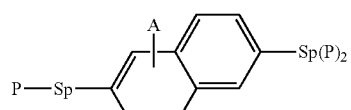
I3C-3
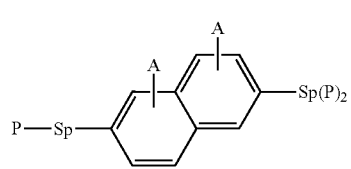
I3C-4
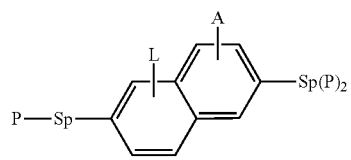
I3C-5
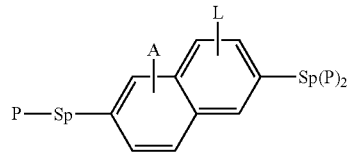
I4A-1
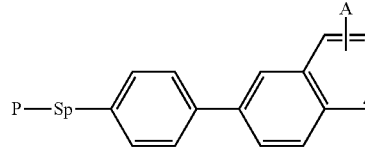
I4A-2
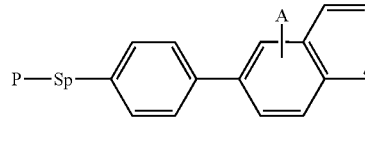
I4A-3
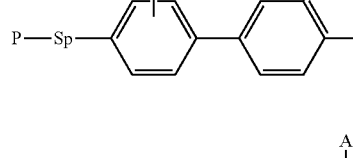
I4A-4
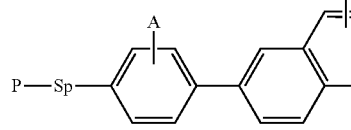
I4A-5
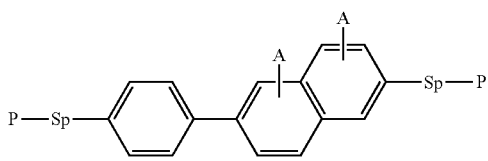
I4A-6
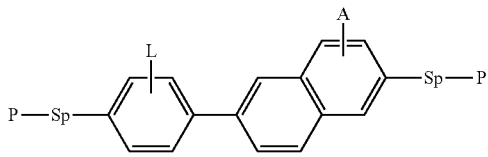
I4A-7
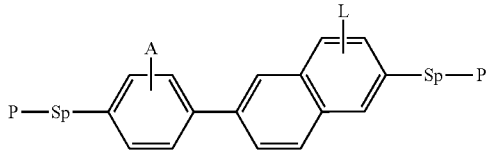
I4A-8
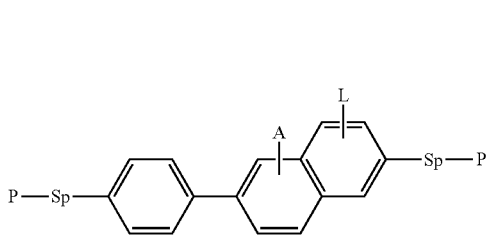
I4A-9
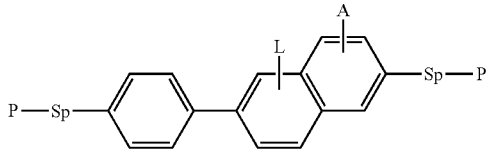
I4A-10
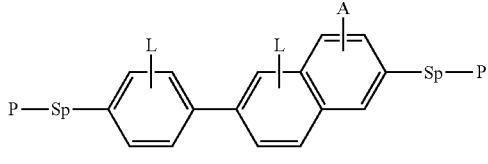
I4A-11
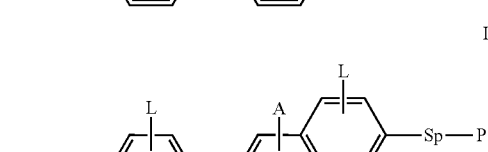
I4A-12
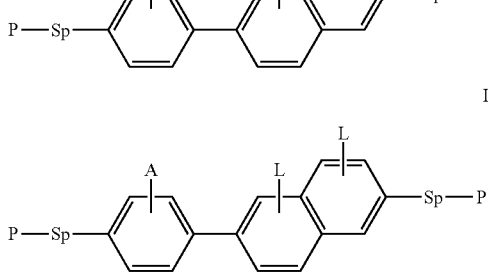

-continued
I4A-13
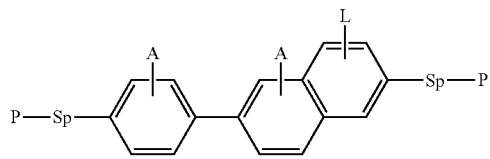
I4A-14
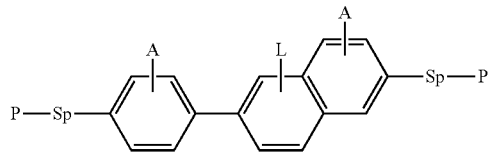
I4A-15
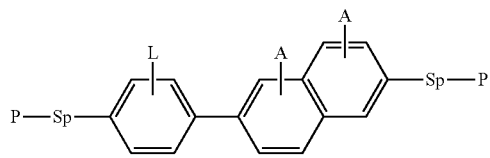
I4A-16
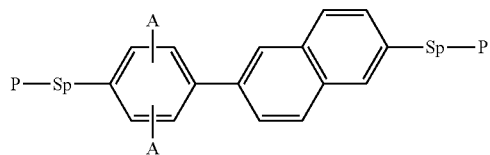
I4A-17
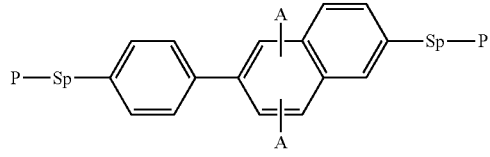
I4A-18
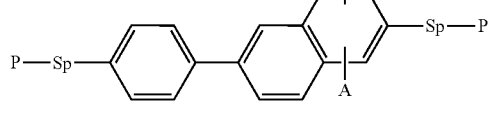
I4A-19
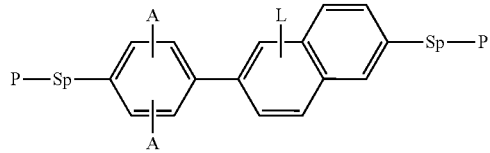
I4A-20
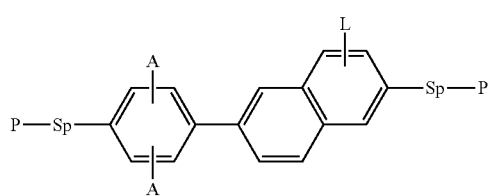
-continued
I4A-21
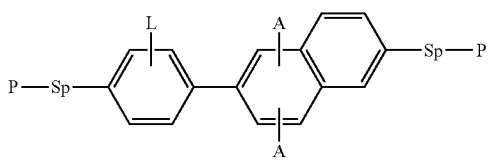
I4A-22
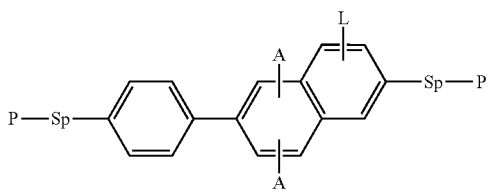
I4A-23
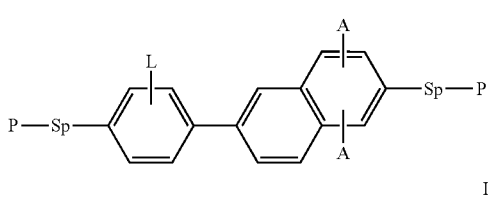
I4A-24
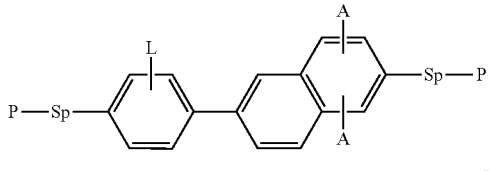
I4A-25
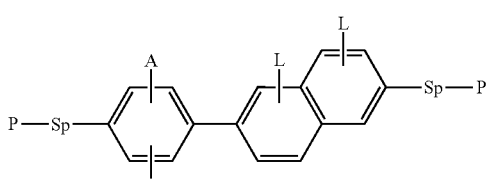
I4A-26
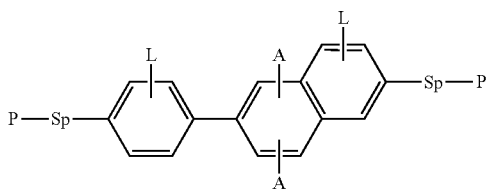
I4A-27
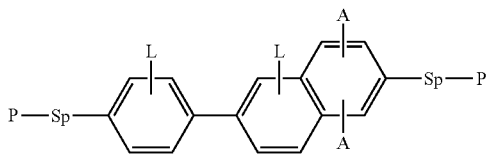
I4B-1
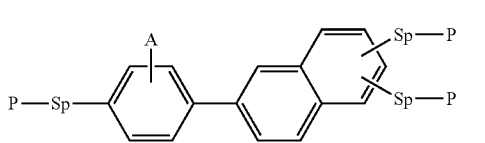

I4B-2
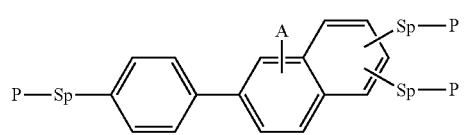
I4B-3
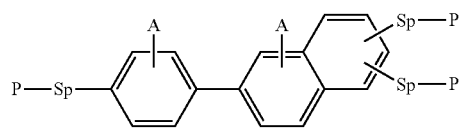
I4B-4
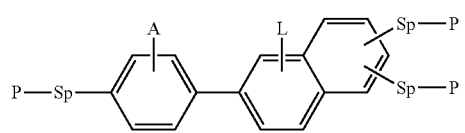
I4B-5
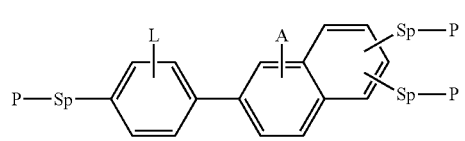
I4B-6
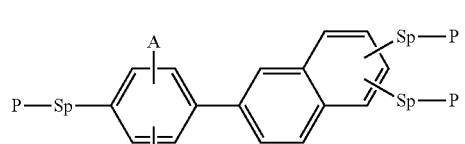
I4B-7
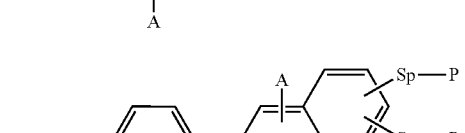
I4B-8
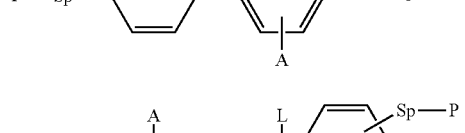
I4B-9
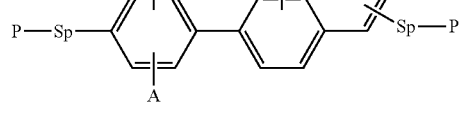
I4C-1
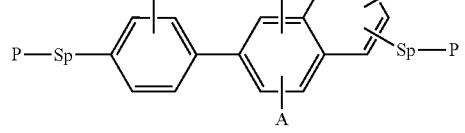
I4C-2
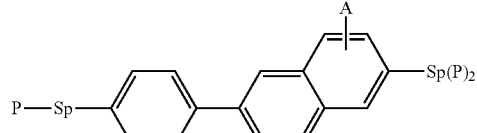
I4C-3
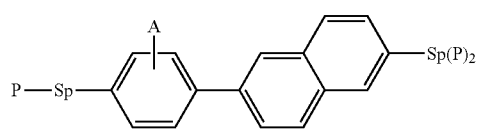
I4C-4
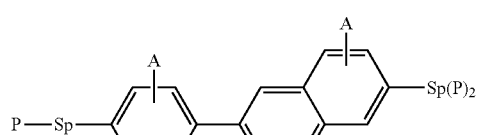
I4C-5
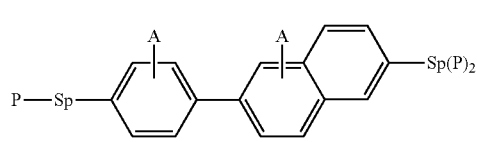
I4C-6
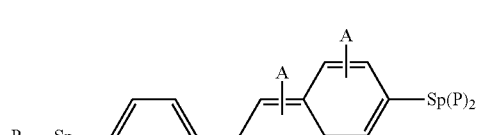
I4C-7
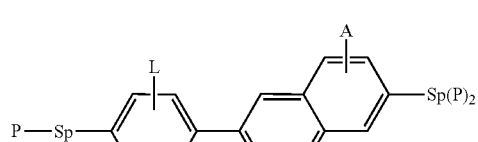
I4C-8
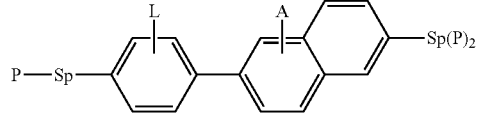
I4C-9
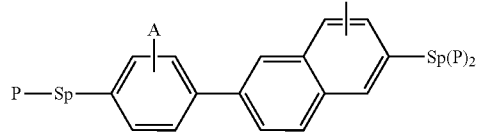
I4C-10
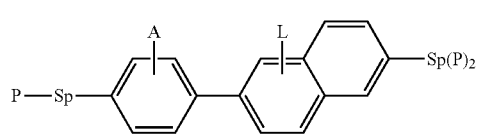
I4C-11
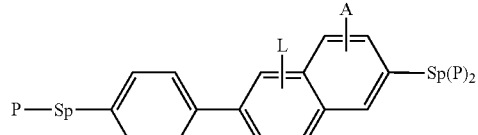
I4C-12
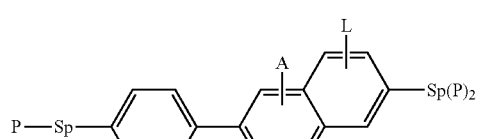

-continued
I4C-13
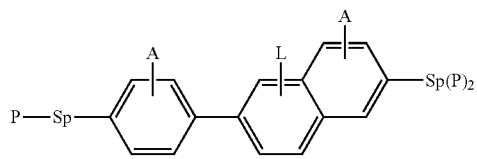
I4C-14
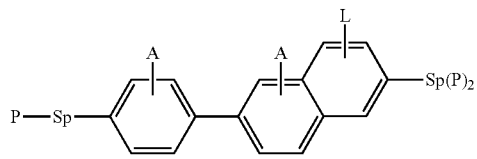
I4C-15
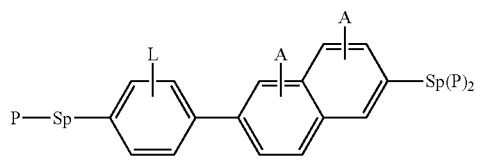
I4C-16
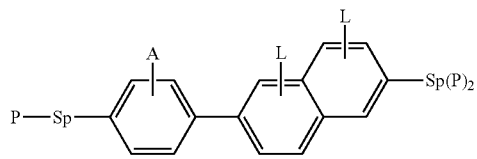
I4C-17
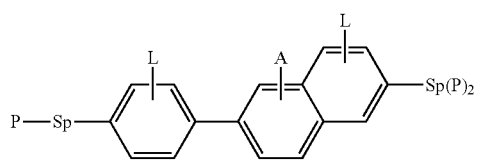
I4C-18
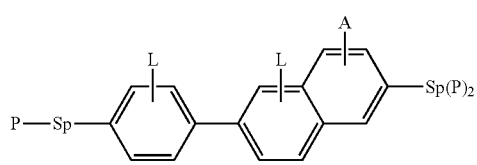
I4C-19
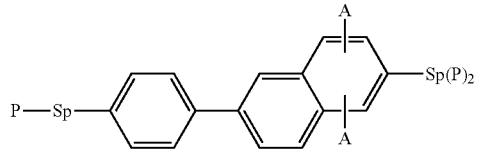
I4C-20
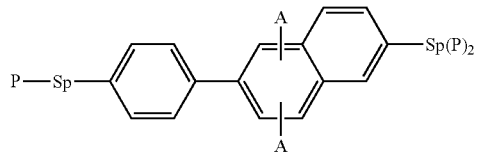
-continued
I4C-21
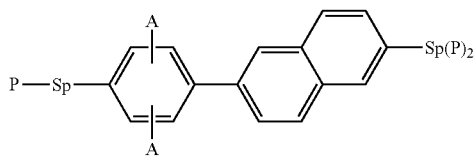
I4C-22
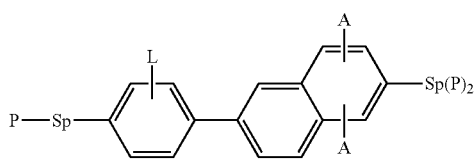
I4C-23
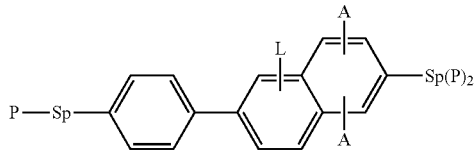
I4C-24
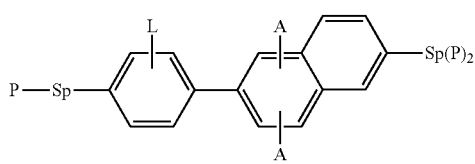
I4C-25
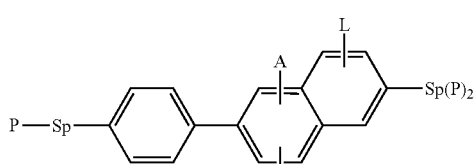
I4C-26
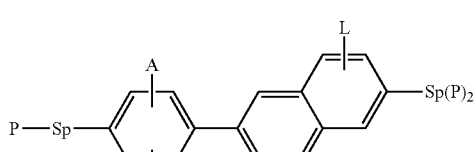
I4C-27
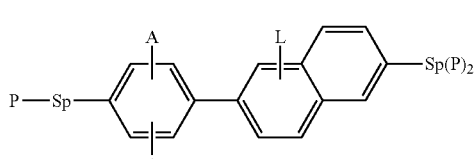
I4C-28
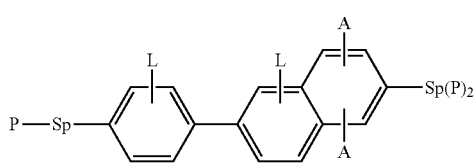

I4C-29
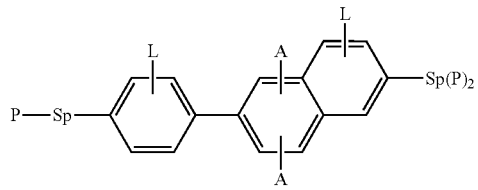
I4C-30
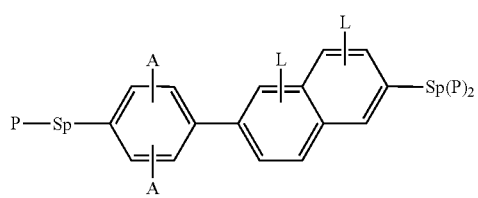
I4D-1
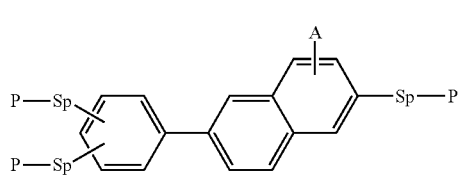
I4D-2
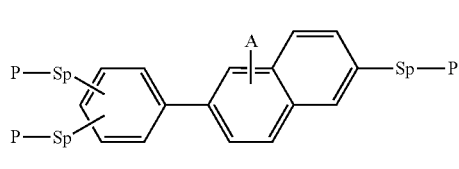
I4D-3
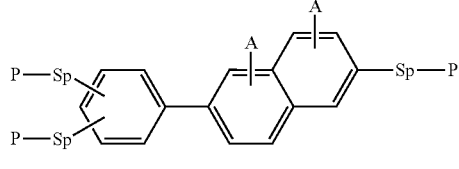
I4D-4
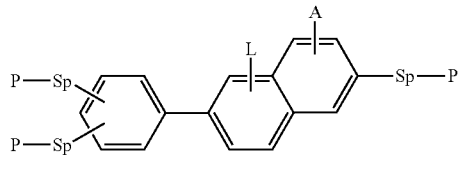
I4D-5
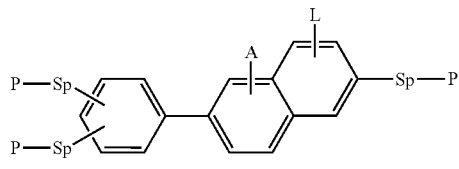
I4D-6
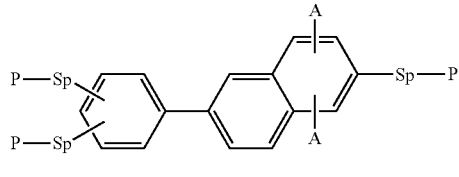
I4D-7
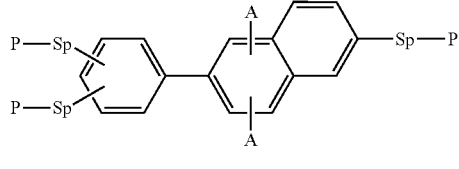
I4D-8
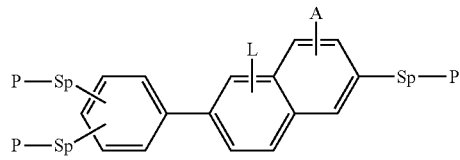
I4D-9
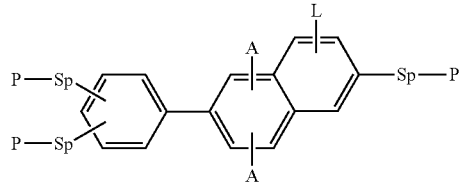
I4E-1
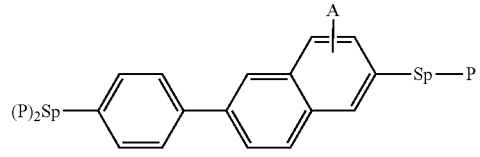
I4E-2
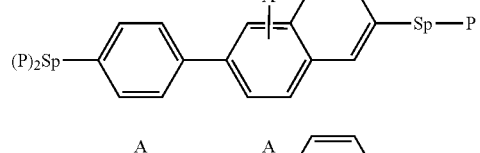
I4E-3
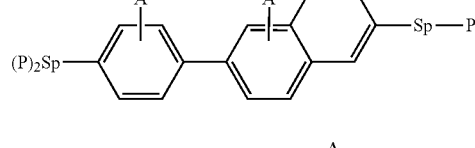
I4E-4
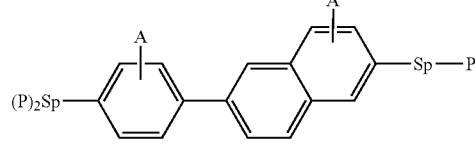
I4E-5
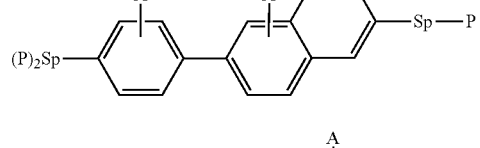
I4E-6
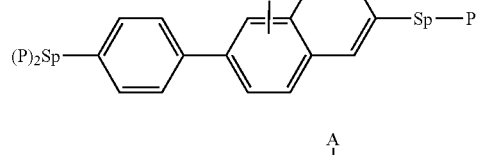
I4E-7
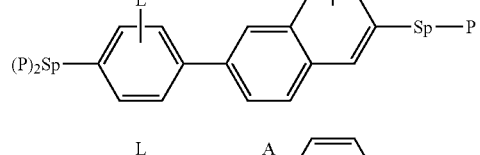
I4E-8

I4E-9
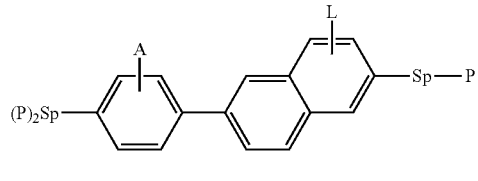
I4E-10
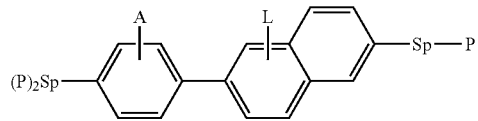
I4E-11
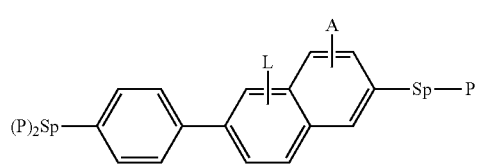
I4E-12
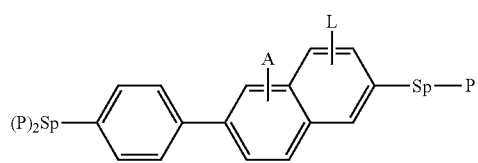
I4E-13
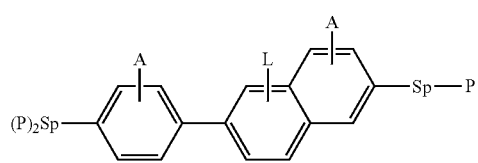
I4E-14
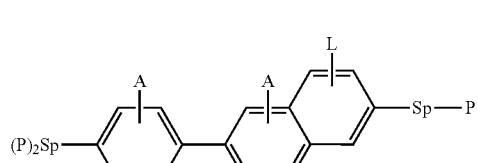
I4E-15
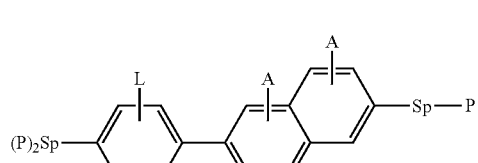
I4E-16
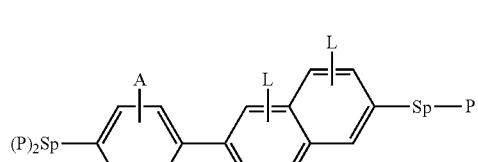
I4E-17
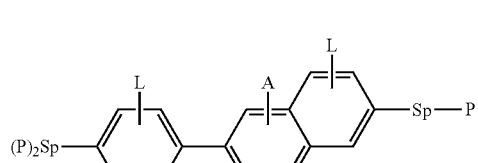
I4E-18
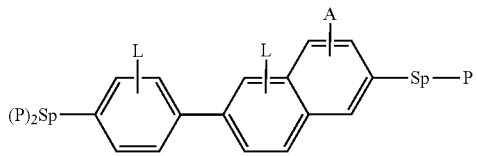
I4E-19
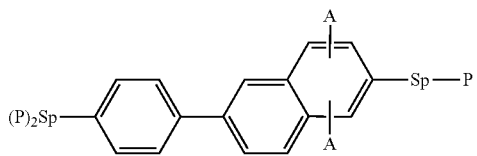
I4E-20
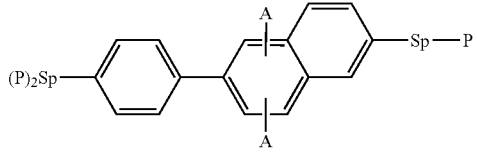
I4E-21
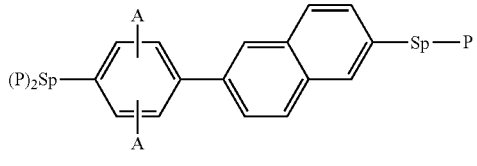
I4E-22
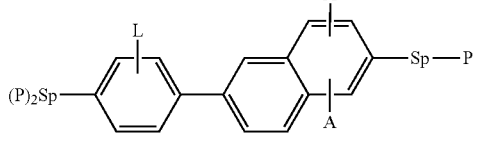
I4E-23
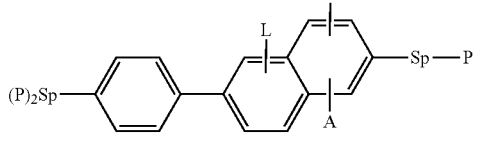
I4E-24
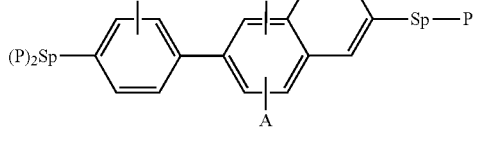
I4E-25
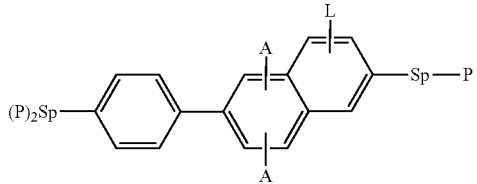

I4E-26
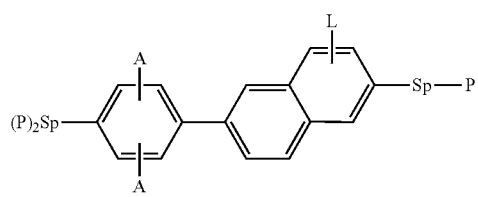
I4E-27
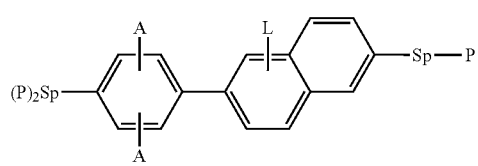
I4E-28
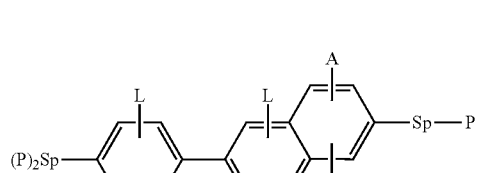
I4E-29
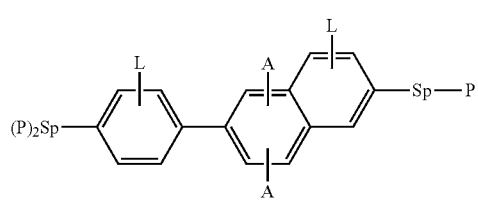
I4E-30
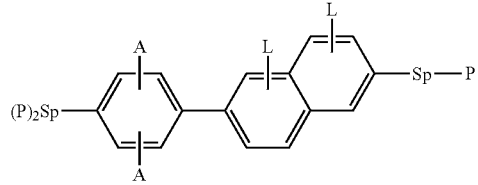
I5A-1
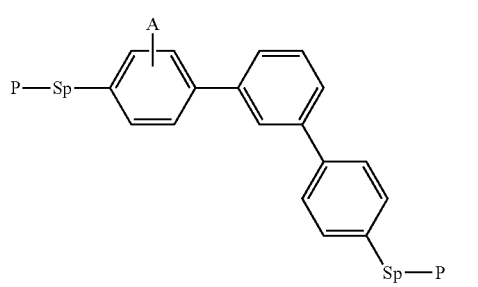
I5A-2
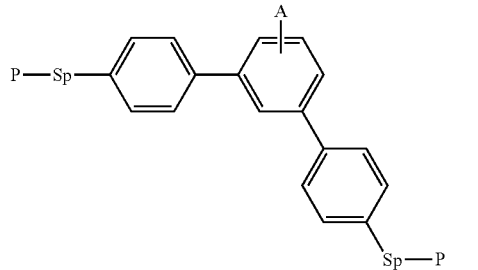
I5A-3
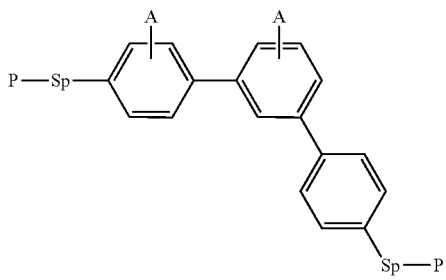
I5A-4
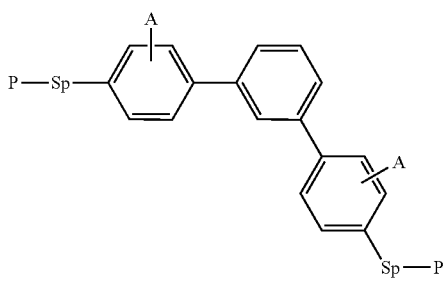
I5A-5
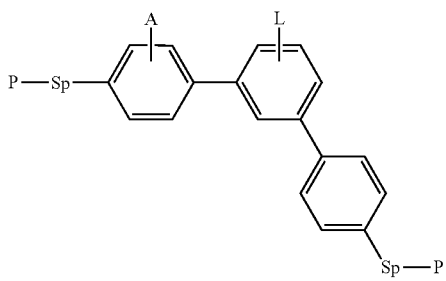
I5A-6
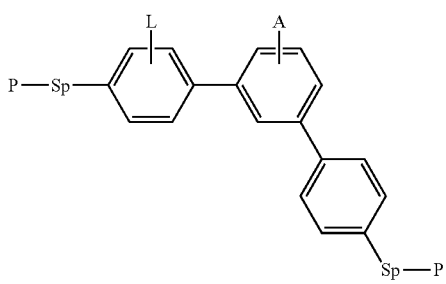
I5A-7
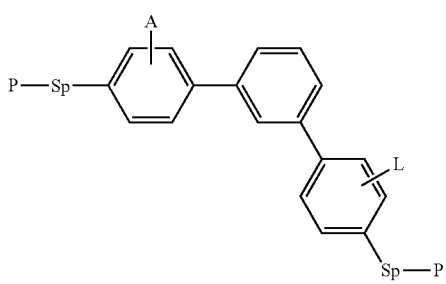

I5A-8
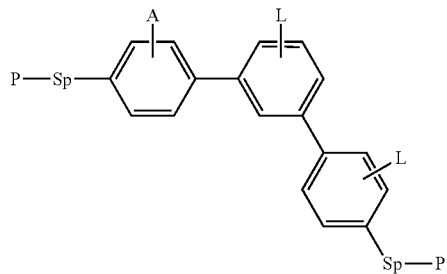
I5A-13
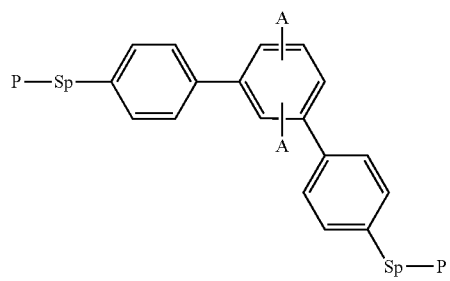
I5A-9
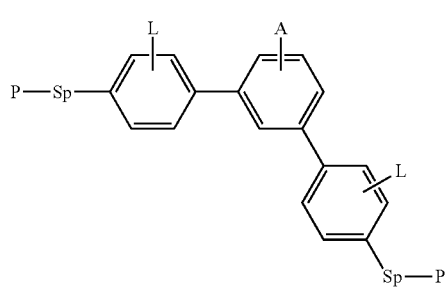
I5A-14
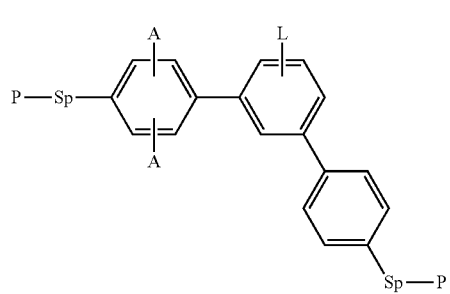
I5A-10
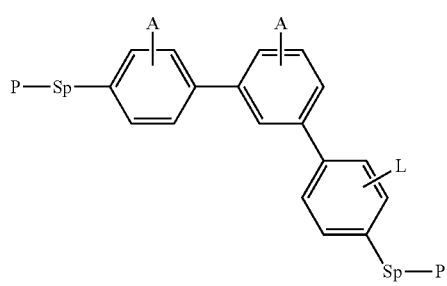
I5A-15
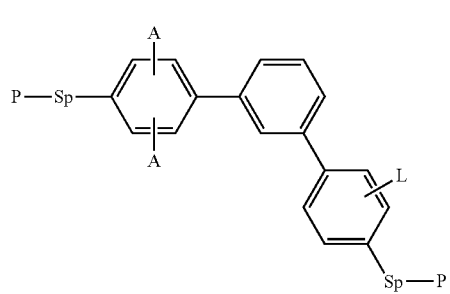
I5A-11
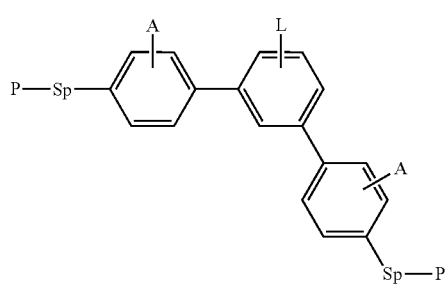
I5A-16
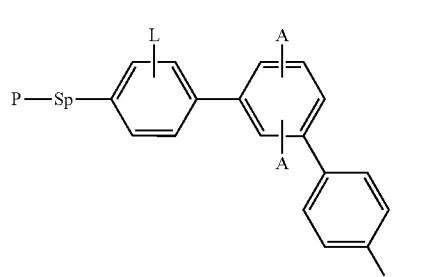
I5A-12
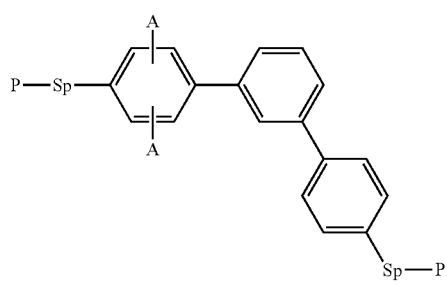
I5A-17
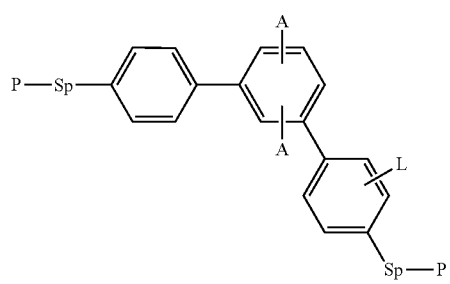

I5A-18
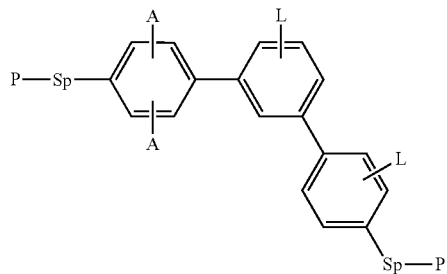
I5A-19
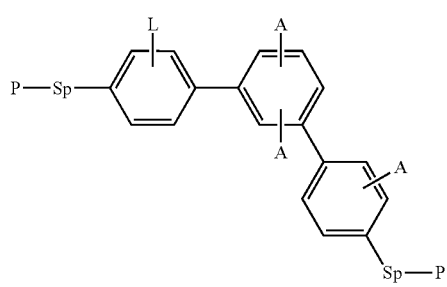
I5B-1
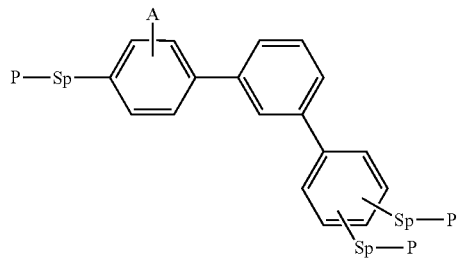
I5B-2
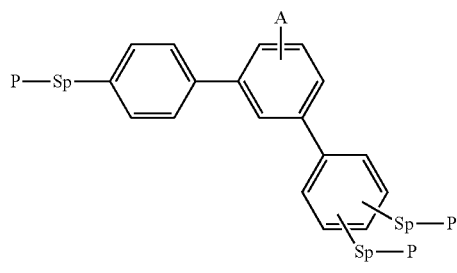
I5B-3
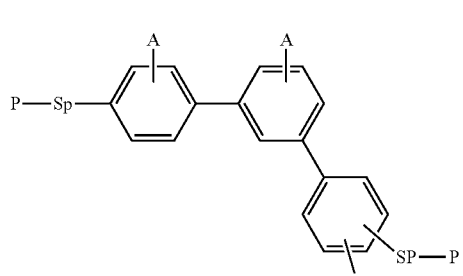
I5B-4
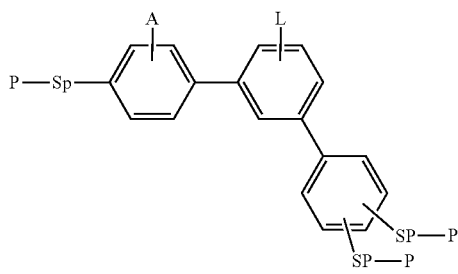
I5B-5
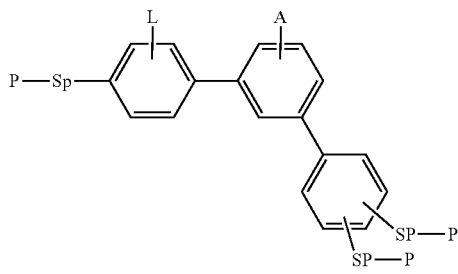
I5B-6
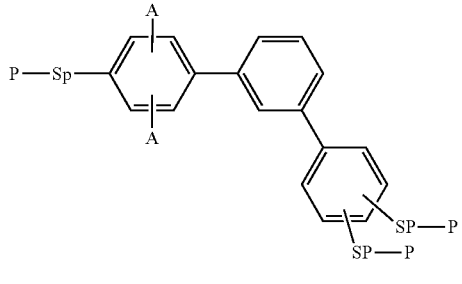
I5B-7
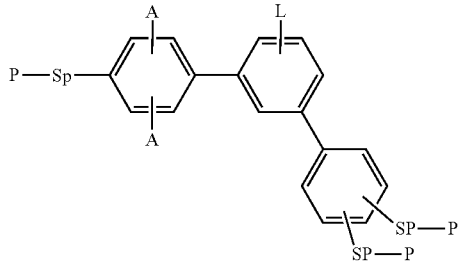
I5B-8
I5B-9
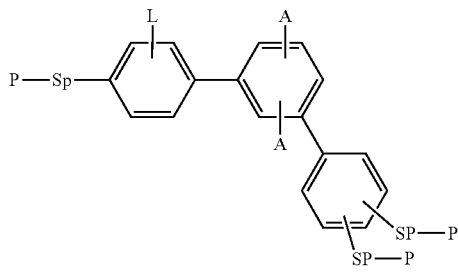

-continued
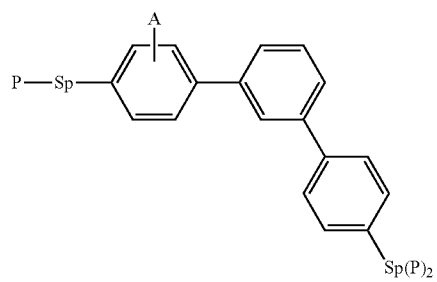
I5C-1
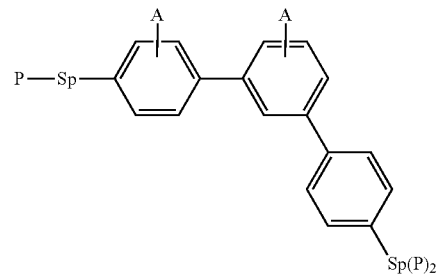
I5C-6
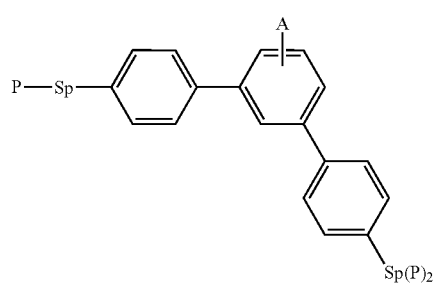
I5C-2
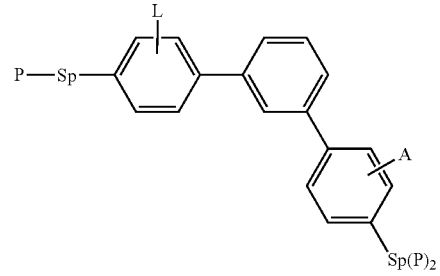
I5C-7
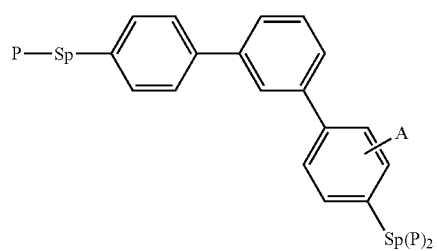
I5C-3
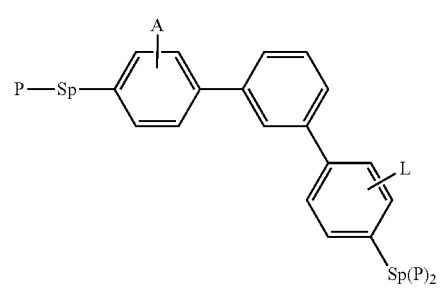
I5C-8
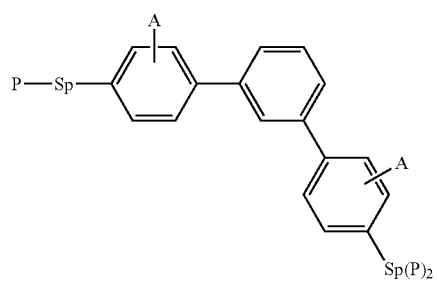
I5C-4
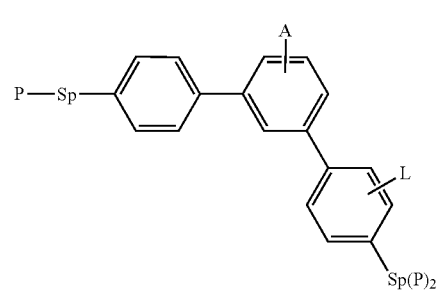
I5C-9
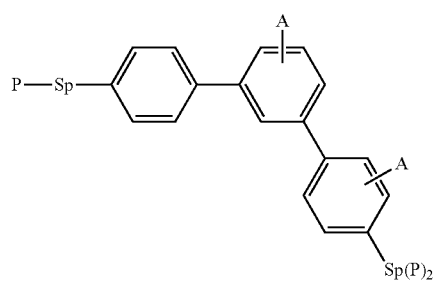
I5C-5
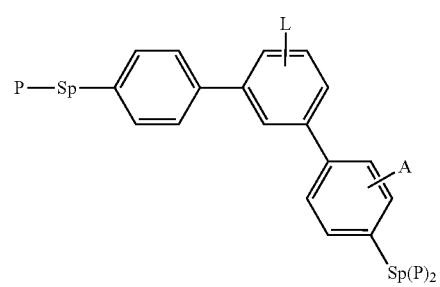
I5C-10

I5C-11
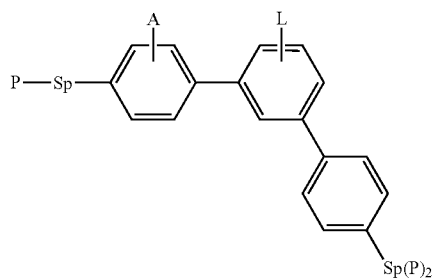
I5C-12
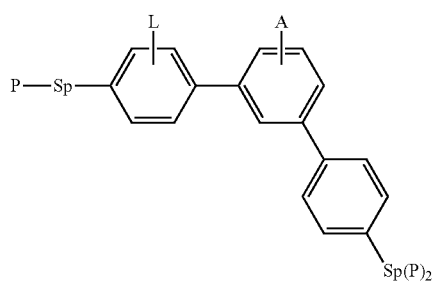
I5C-13
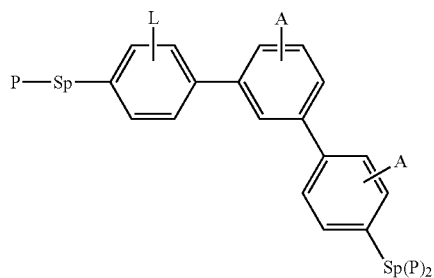
I5C-14
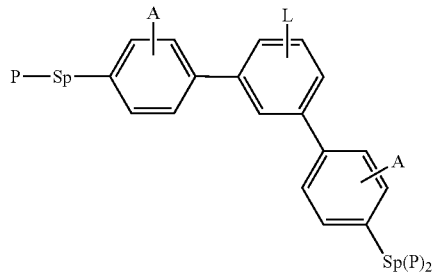
I5C-15
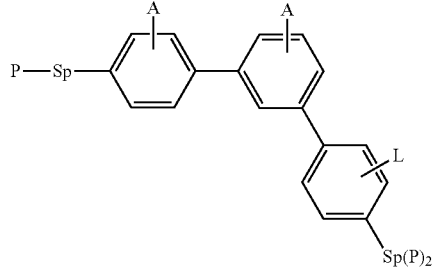
I5C-16
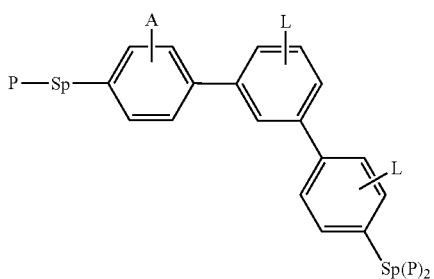
I5C-17
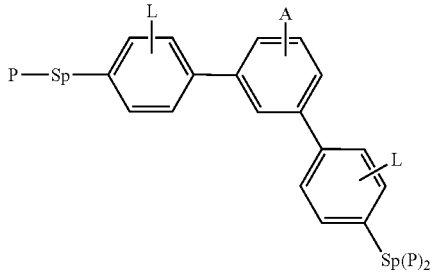
I5C-18
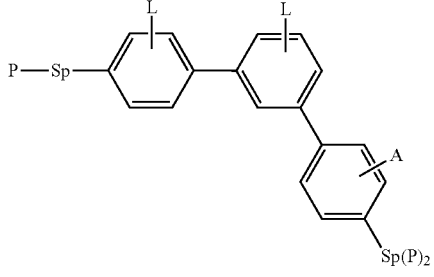
I5C-19
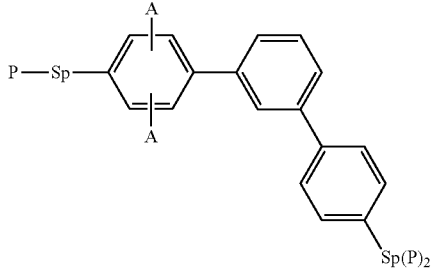
I5C-20
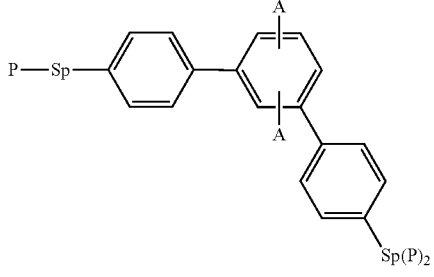

I5C-21
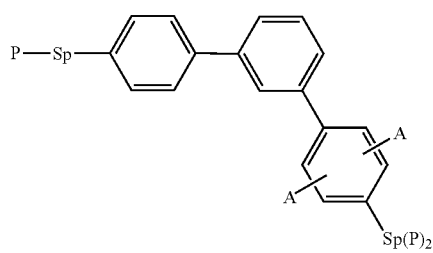
I5C-22
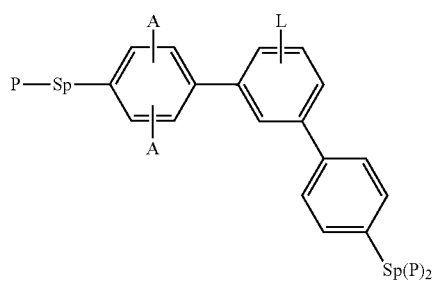
I5C-23
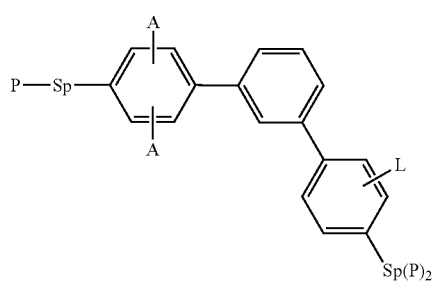
I5C-24
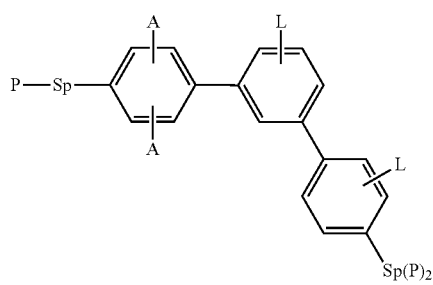
I5C-25
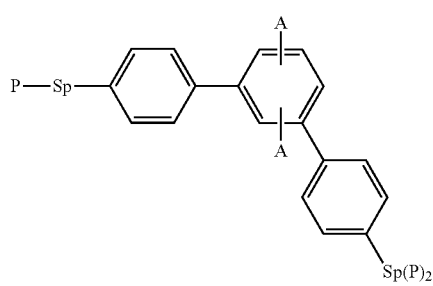
I5C-26
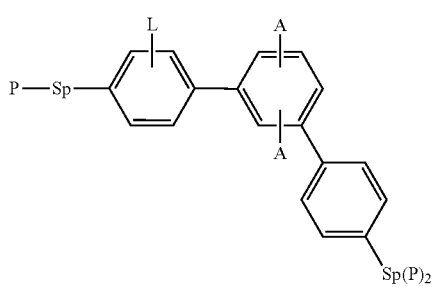
I5C-27
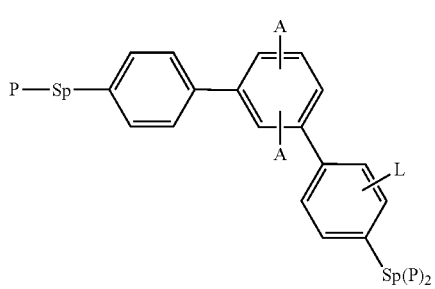
I5C-28
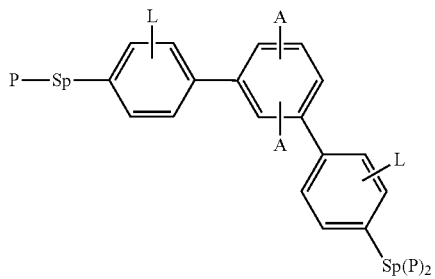
I5D-1
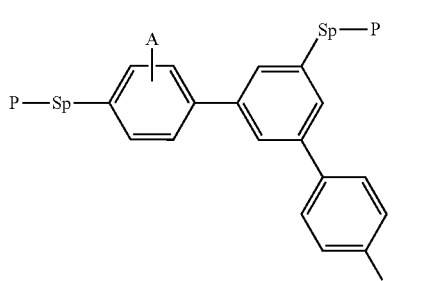
I5D-2
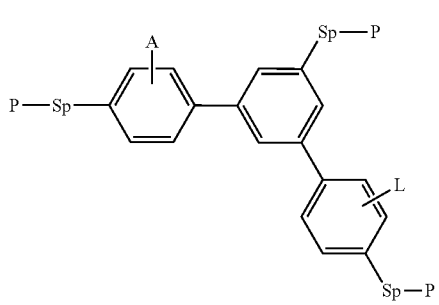

I5D-3 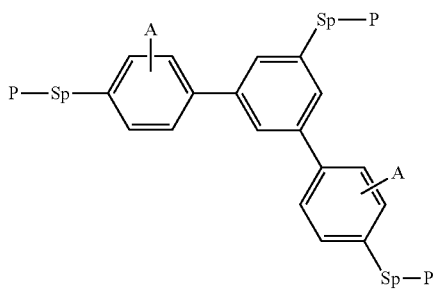

I5D-4 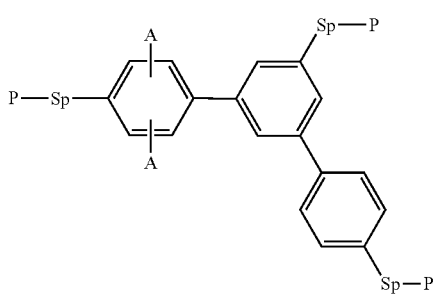

I5D-5 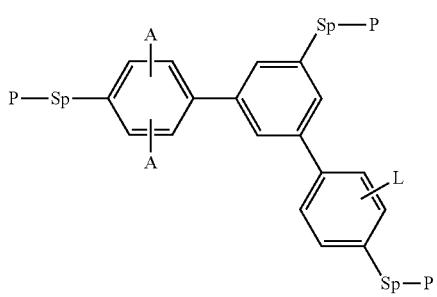

I6A-1 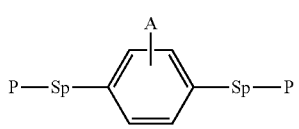

I6A-2 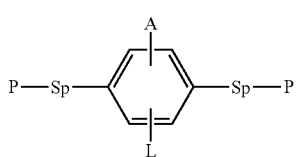

I6B-1 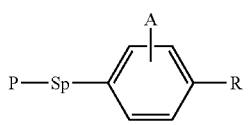

I6B-2 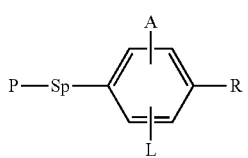

I6C-1 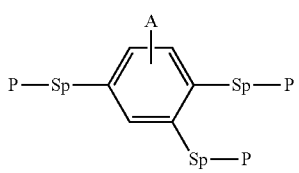

wherein R, P, Sp, Sp(P)$_2$, A and L have the meanings given in formula I or one of the preferred meanings as given above and below, L is preferably F, Cl or CN, A is preferably thioalkyl with 1 to 7 C atoms which is preferably straight-chain, more preferably —SCH$_3$, —SC$_2$H$_5$ or —SC$_3$H$_7$, very preferably —SCH$_3$, further preferably —CH$_2$S—CH$_3$ or —CH$_2$—S—C$_2$H$_5$.

Especially preferred are compounds selected from the group consisting of formulae I1A-1 to I2G-4.

Further preferred compounds of formula I, I1 to I6, I12, I1A-I5D, I12A-I12G and I1A-1 to I6C-1 are selected from the following subformulae:

I1A-1-1 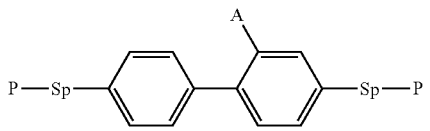

I1A-1-2 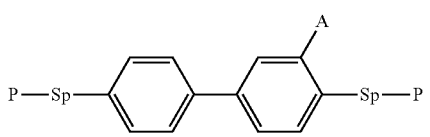

I1A-2-1 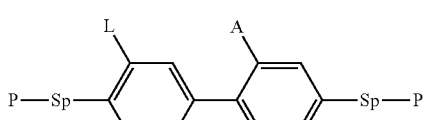

I1A-2-2 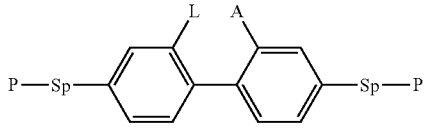

I1A-2-3 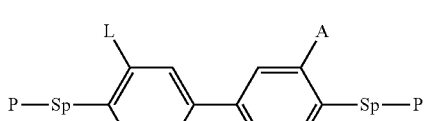

I1A-2-4 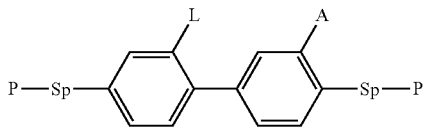

I1A-3-1 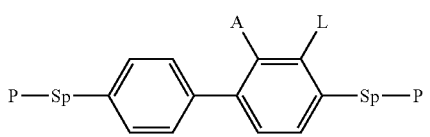

I1A-3-2
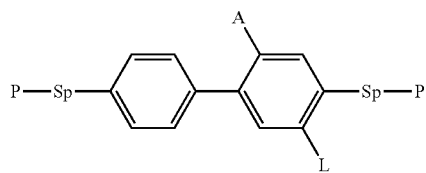
I1A-3-3
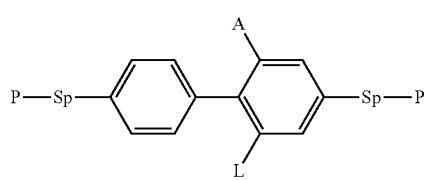
I1A-3-4
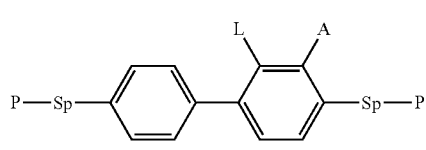
I1A-3-5
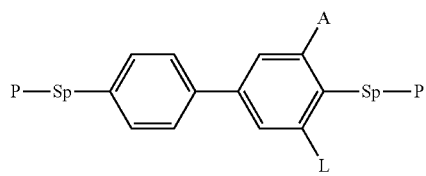
I1A-3-6
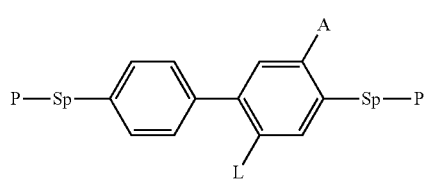
I1A-4-1
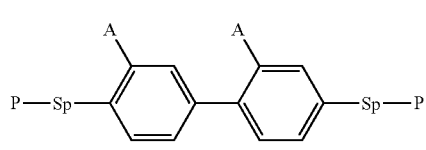
I1A-4-2
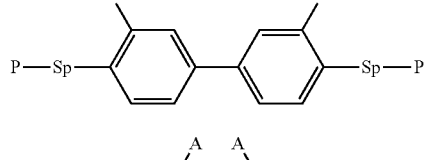
I1A-4-3
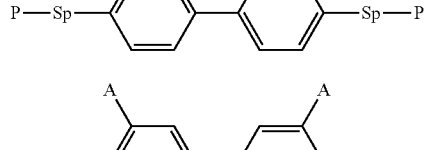
I1A-5-1
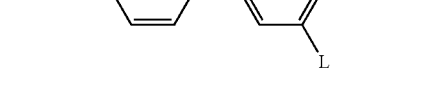
I1A-5-2
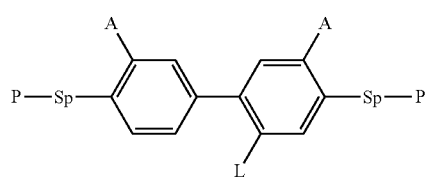
I1A-5-3
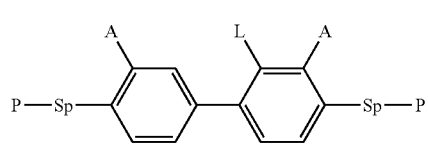
I1A-6-1
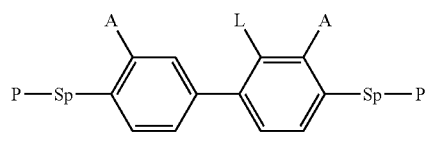
I1A-6-2
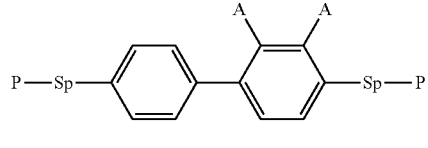
I1A-6-3
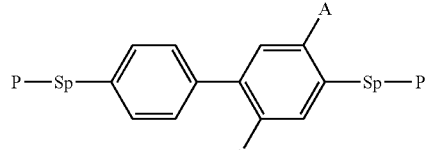
I1A-7-1
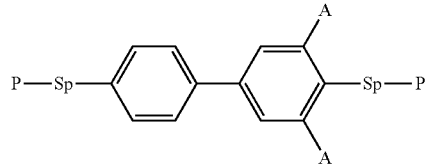
I1A-7-2
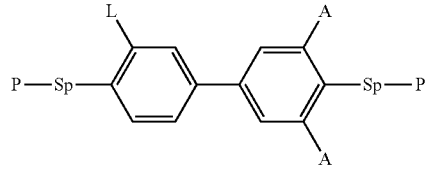
I1A-7-3
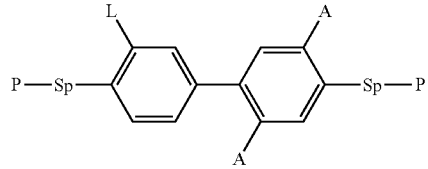
I1B-1-1
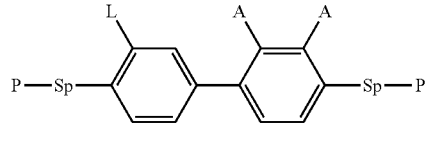

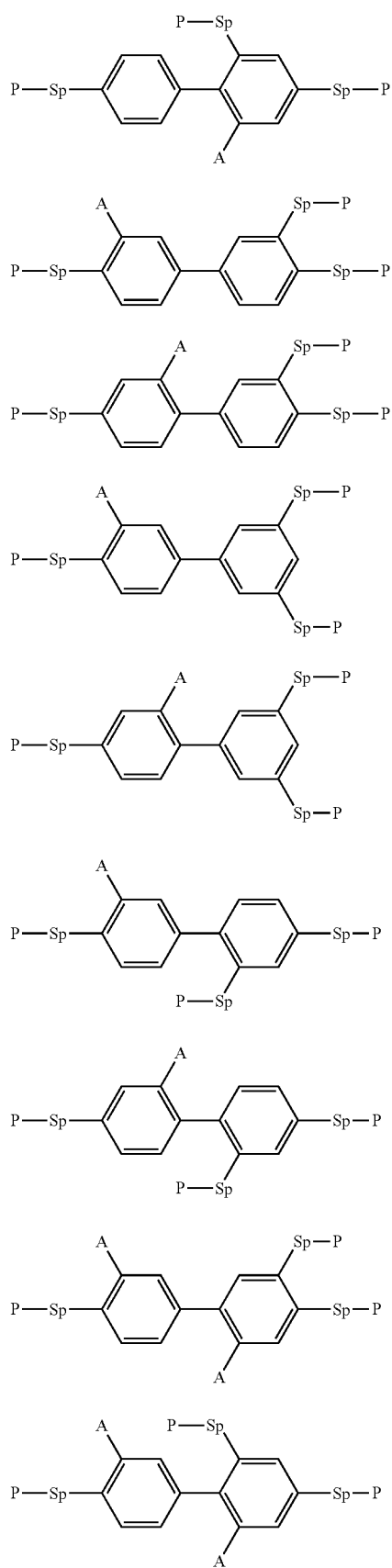
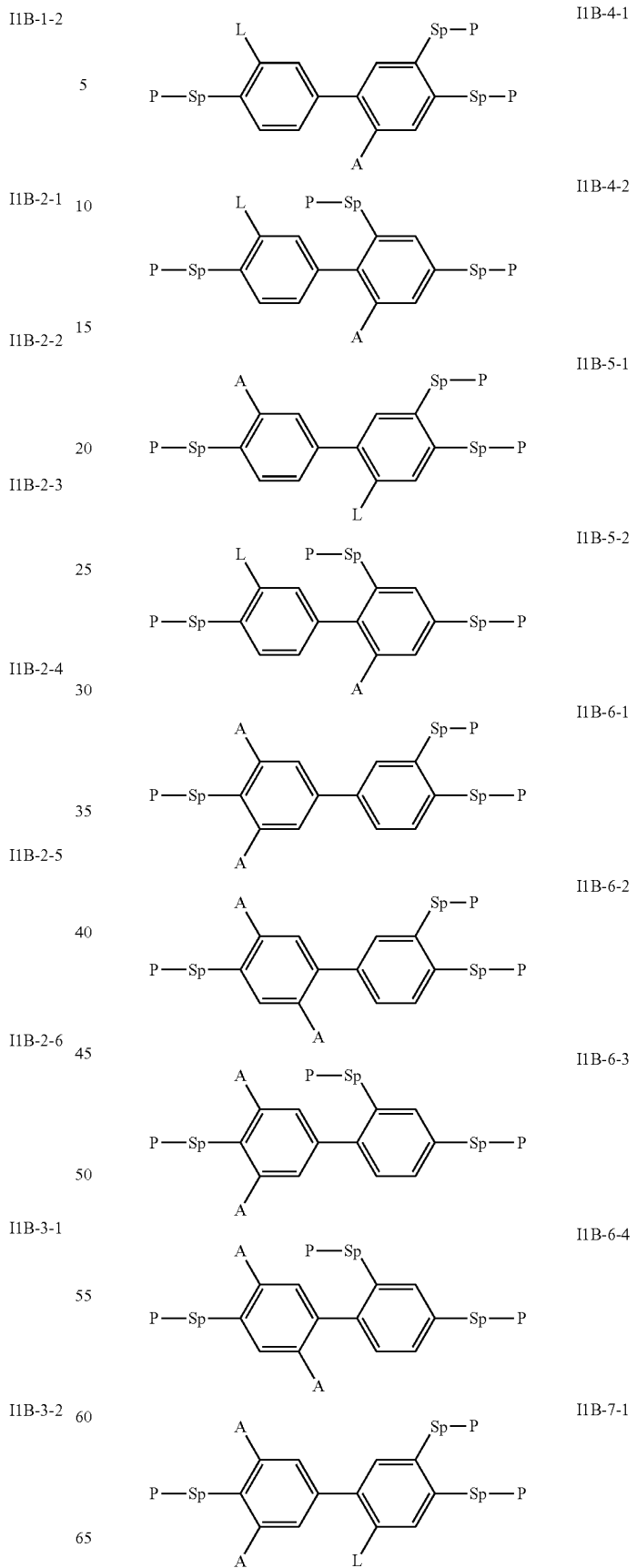

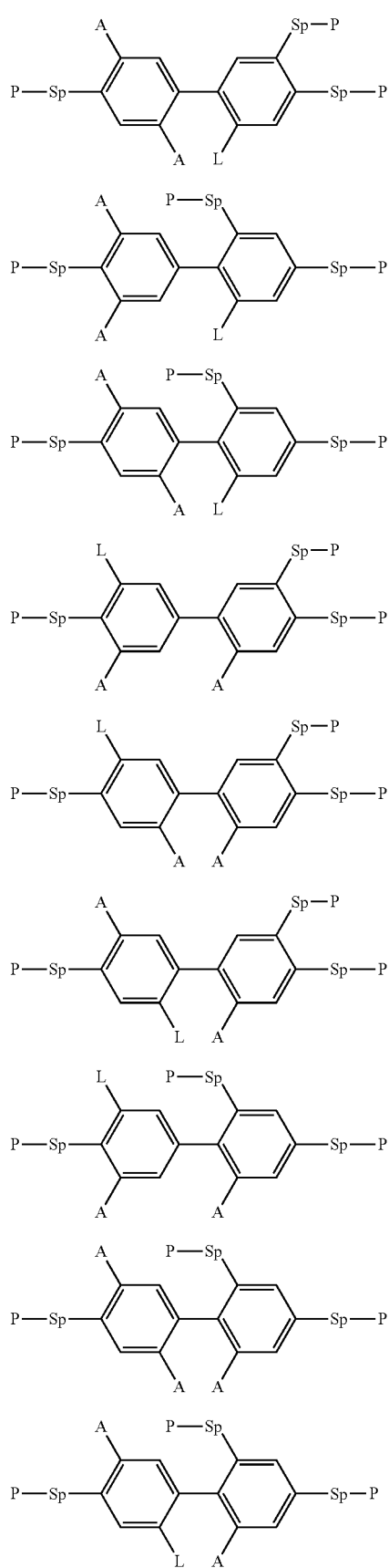
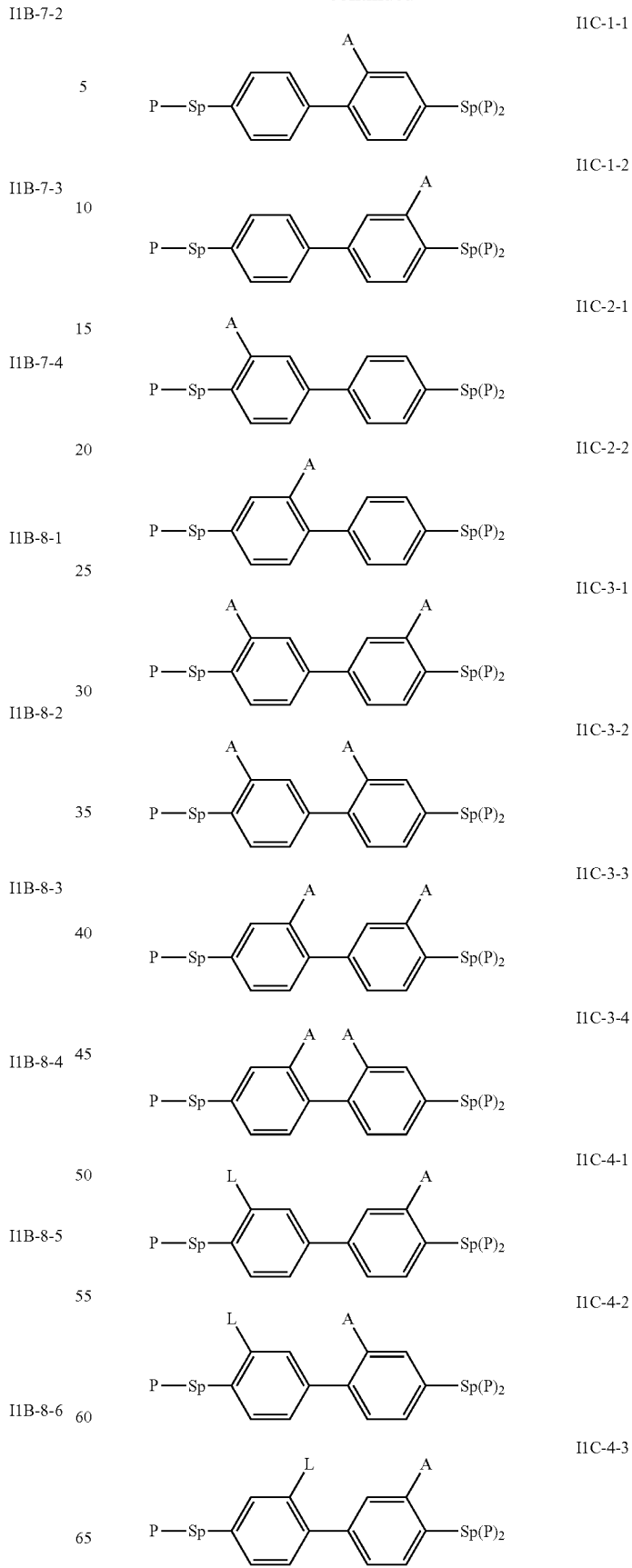

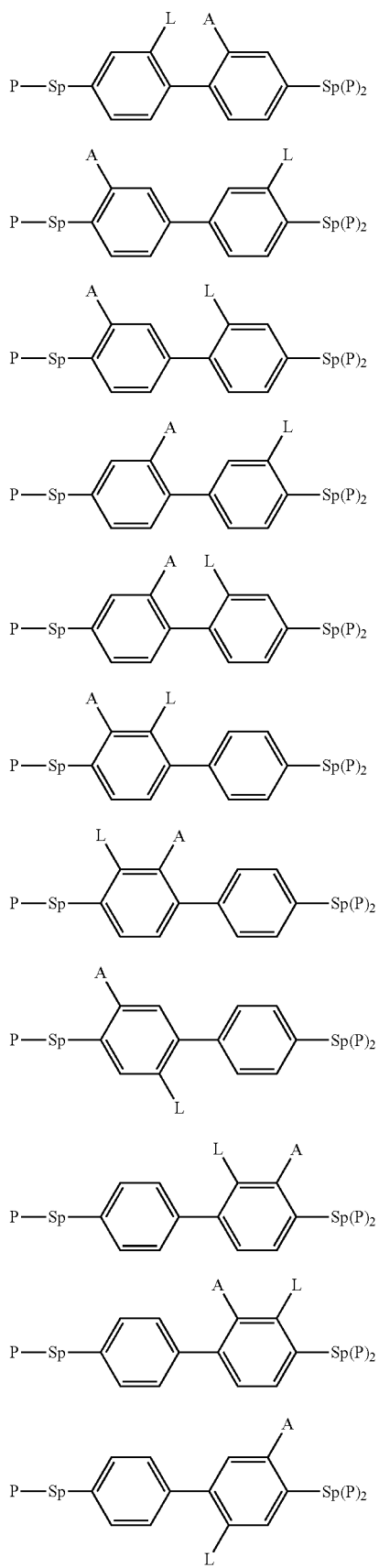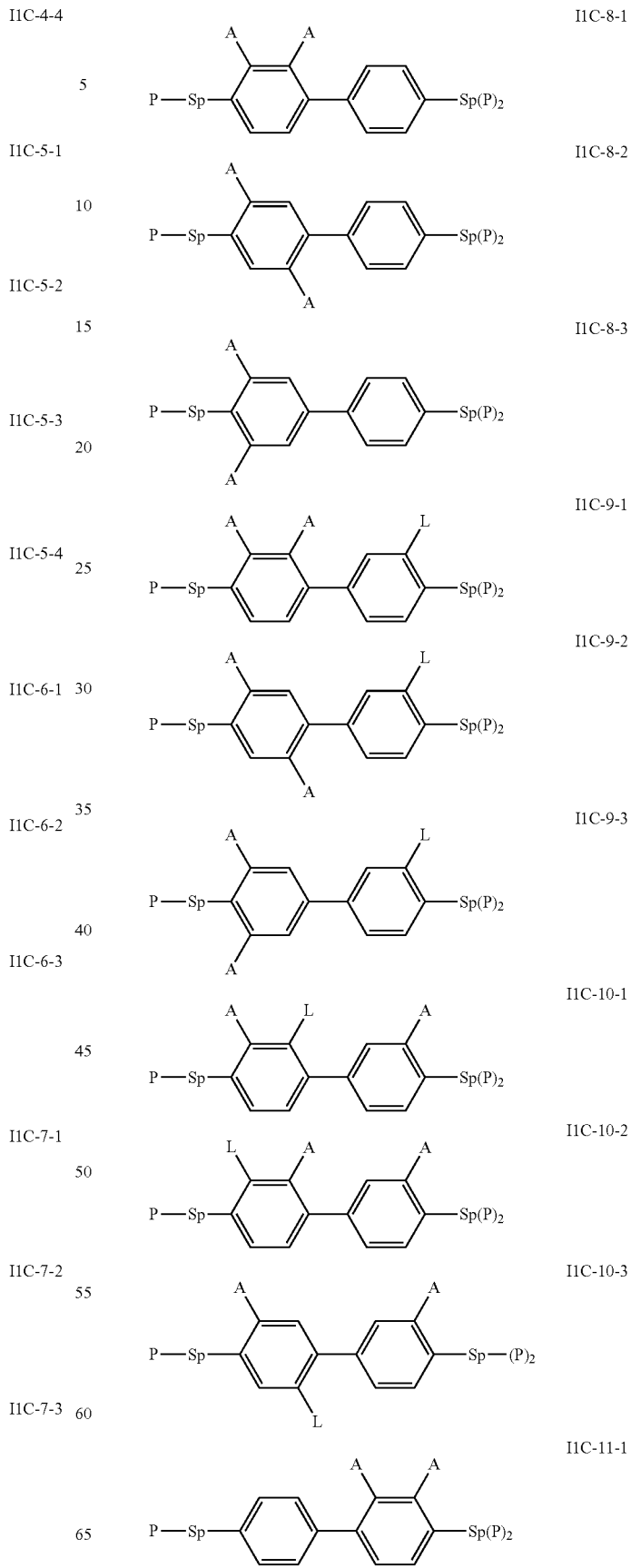

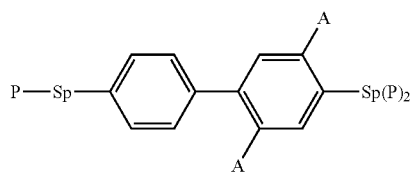 I1C-11-2
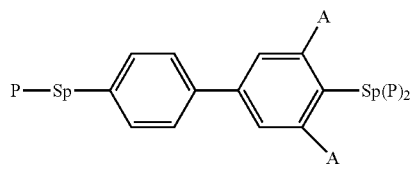 I1C-11-3
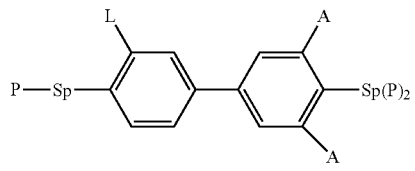 I1C-12-1
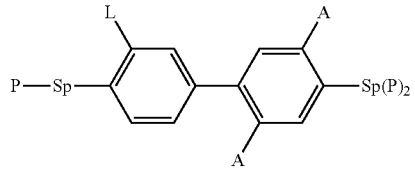 I1C-12-2
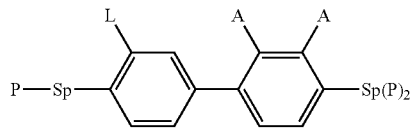 I1C-12-3
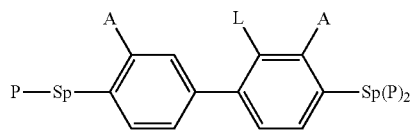 I1C-13-1
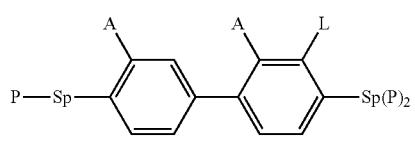 I1C-13-2
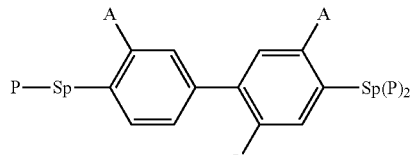 I1C-13-3
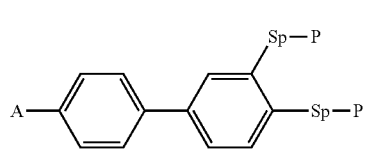 I1D-1-1
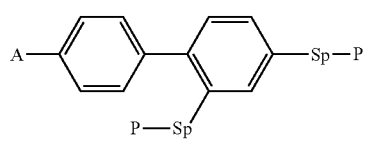 I1D-1-2
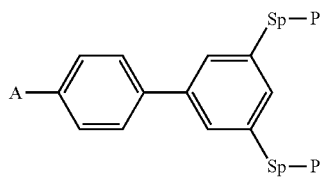 I1D-1-3
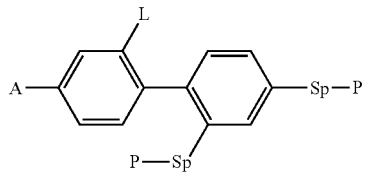 I1D-2-1
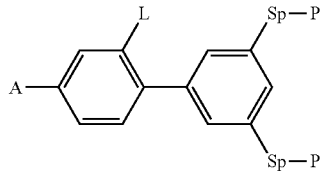 I1D-2-2
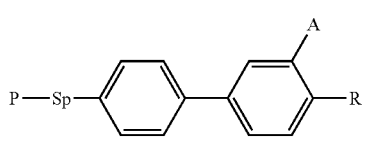 I1D-2-3
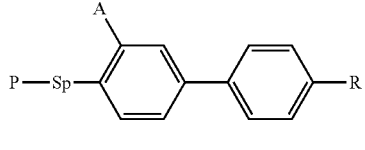 I1E-1-1
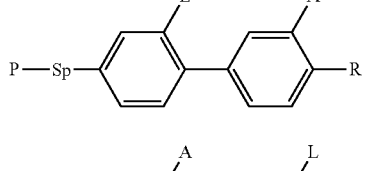 I1E-2-1
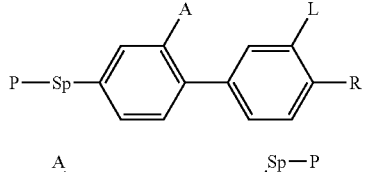 I1E-3-1
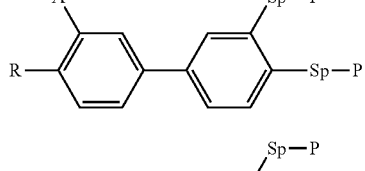 I1E-4-1
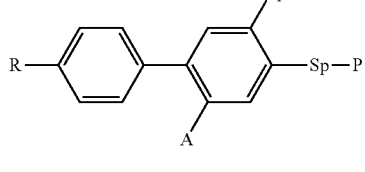 I1F-1-1
I1F-2-1

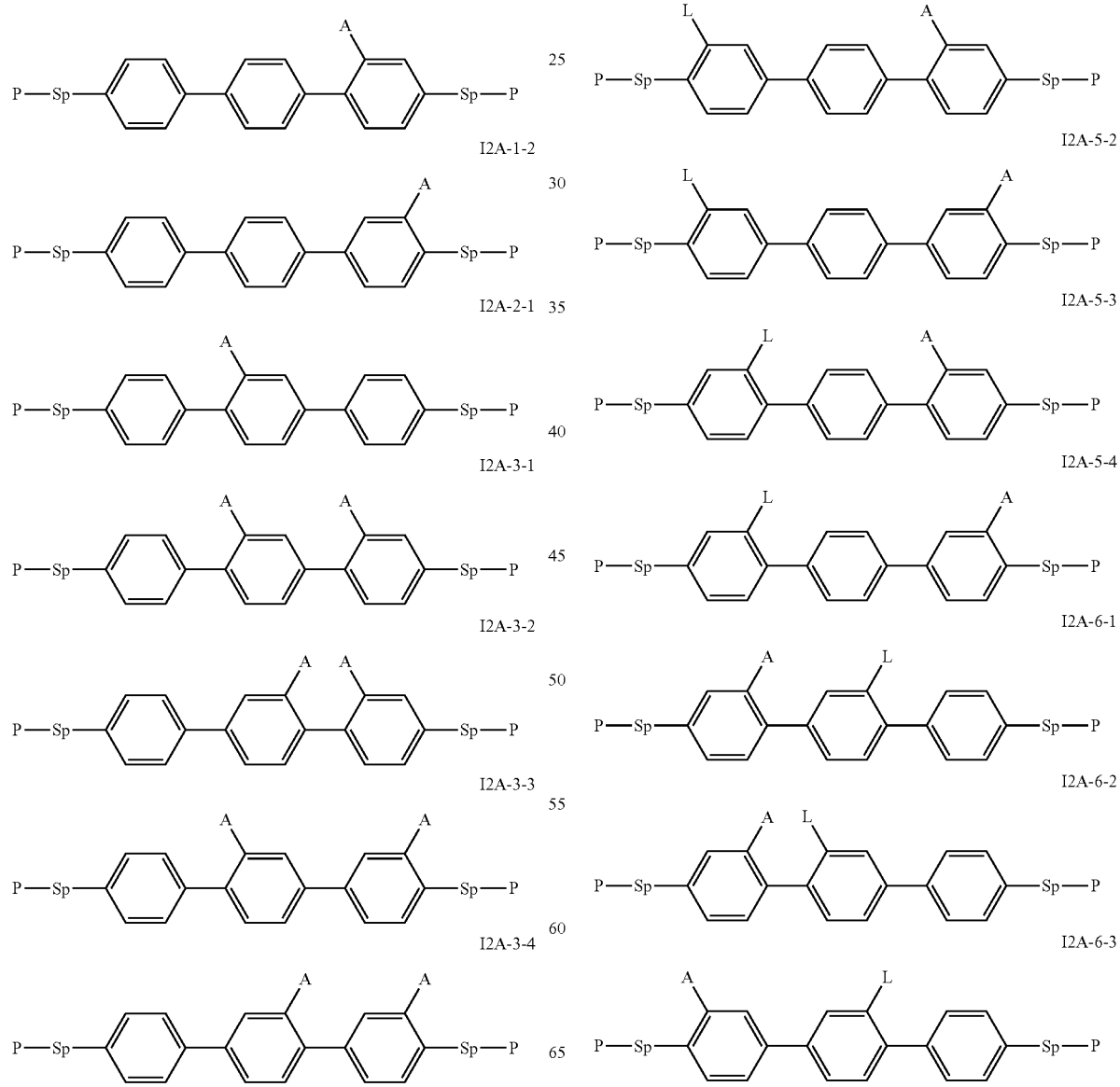

I2A-6-4
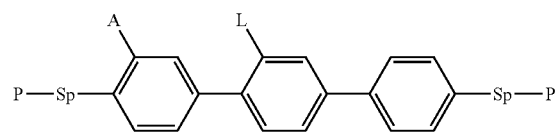
I2A-7-1
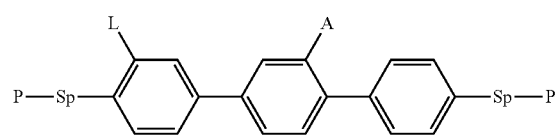
I2A-7-2
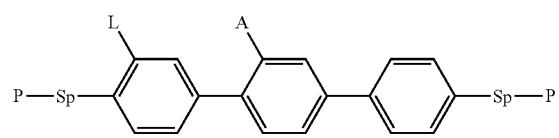
I2A-7-3
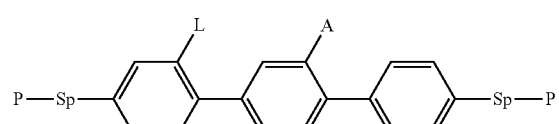
I2A-7-4
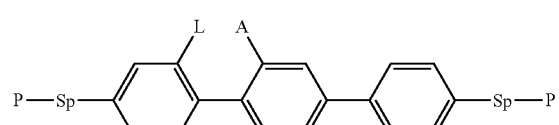
I2A-8-1
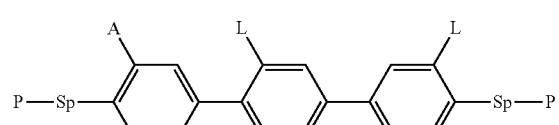
I2A-8-2
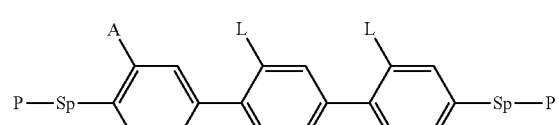
I2A-9-1
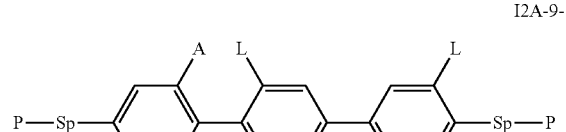
I2A-9-2
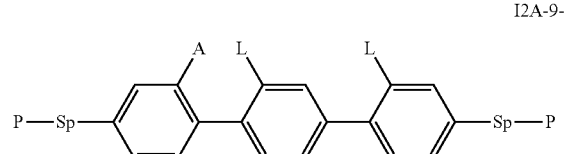
I2A-9-3
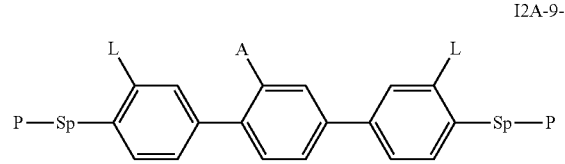
I2A-9-4
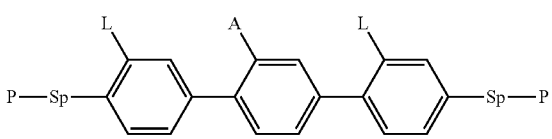
I2A-10-1
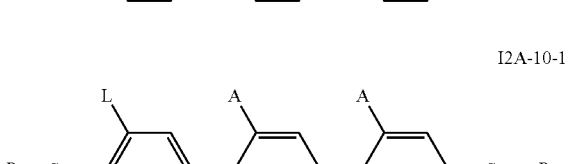
I2A-10-2
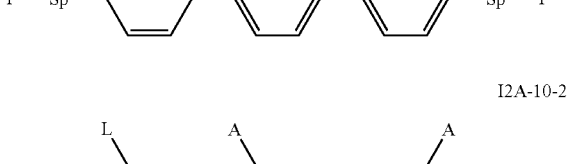
I2A-10-3
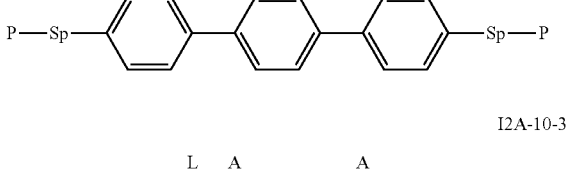
I2A-10-4
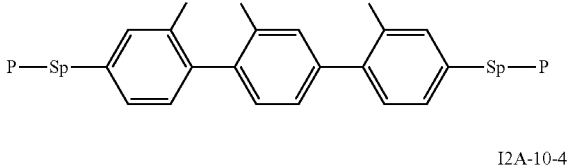
I2A-11-1
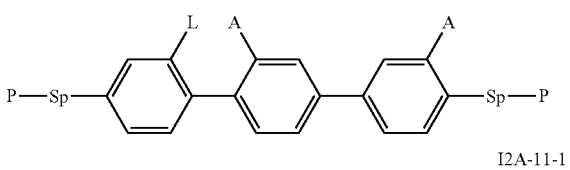
I2A-11-2
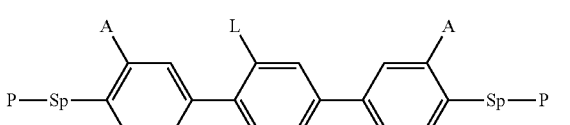
I2A-12-1
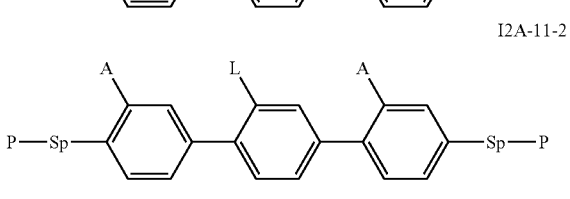
I2A-12-2
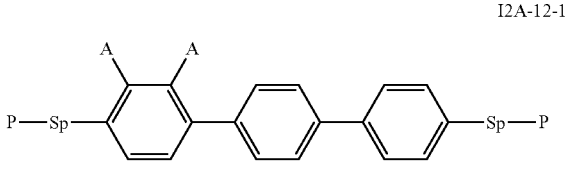

I2A-12-3
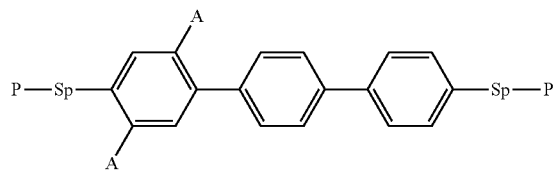
I2A-13-1
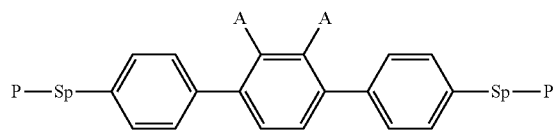
I2A-13-2
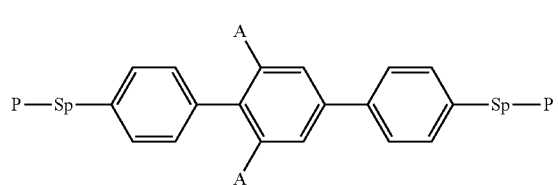
I2A-13-3
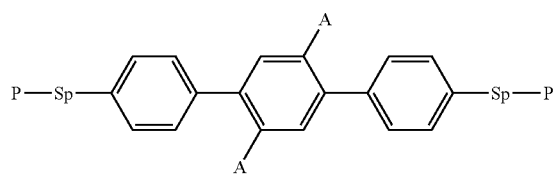
I2A-14-1
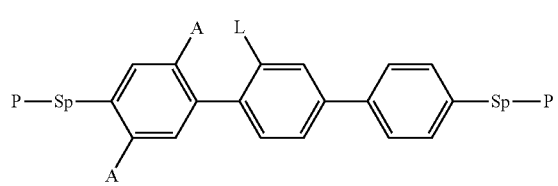
I2A-14-2
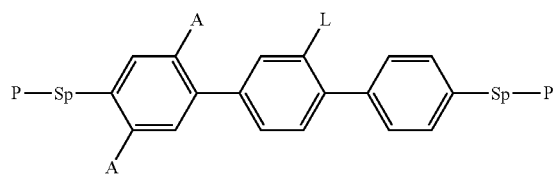
I2A-14-3
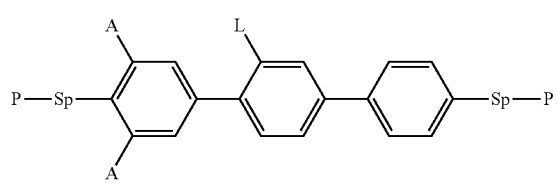
I2A-14-4
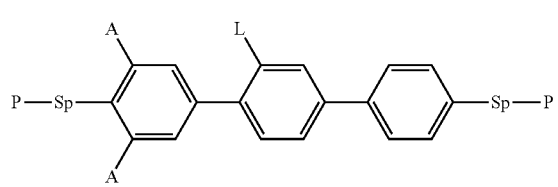
I2A-15-1
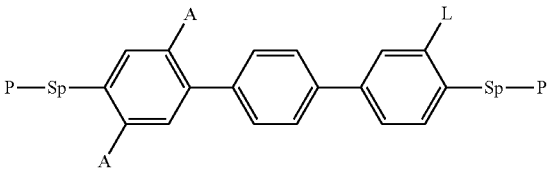
I2A-15-2
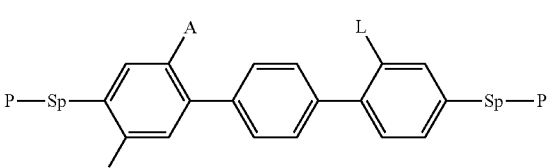
I2A-15-3
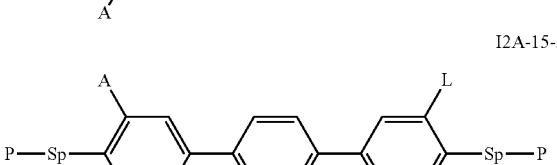
I2A-15-4
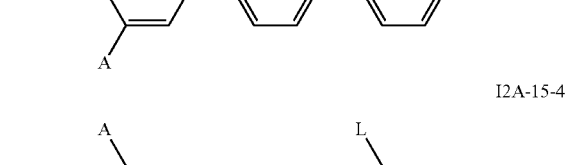
I2A-16-1
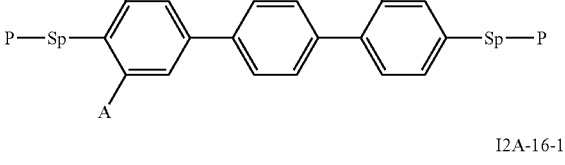
I2A-16-2
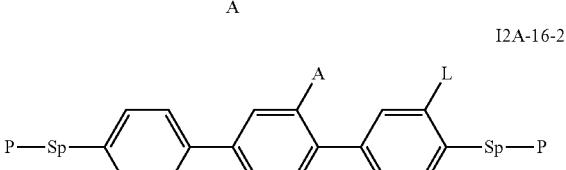
I2A-16-3
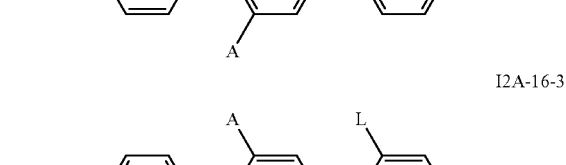
I2A-16-4
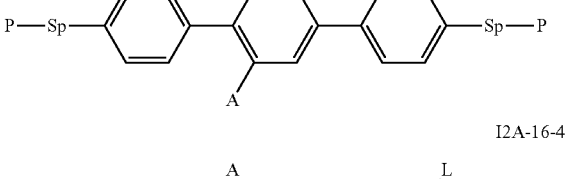

-continued
I2A-17-1
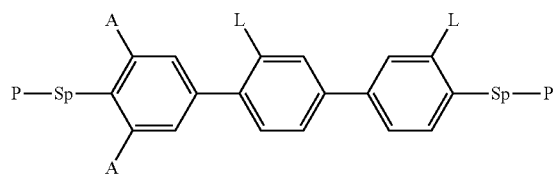
I2A-17-2
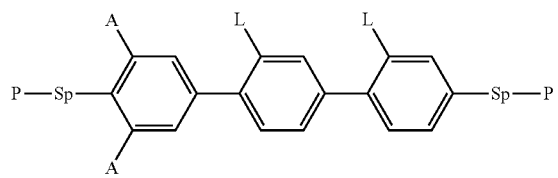
I2A-17-3
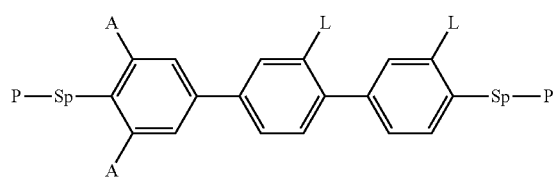
I2A-17-4
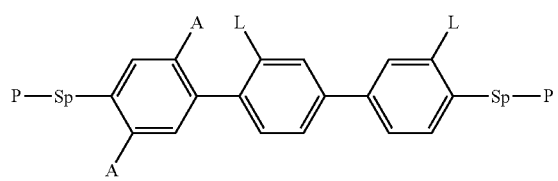
I2A-17-5
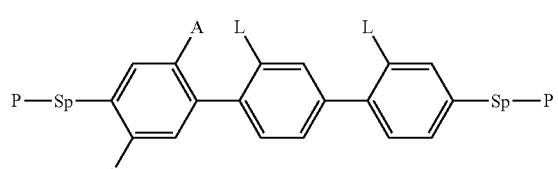
I2A-17-6
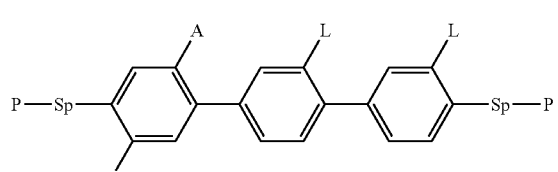
I2A-18-1
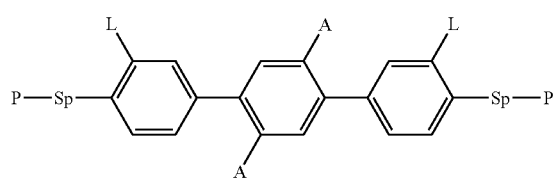
I2A-18-2
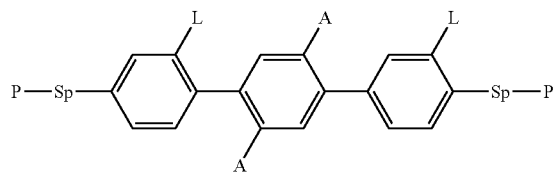
-continued
I2B-1-1
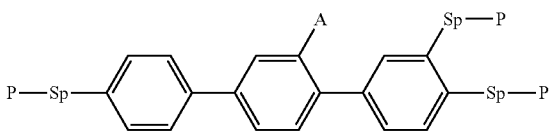
I2B-1-2
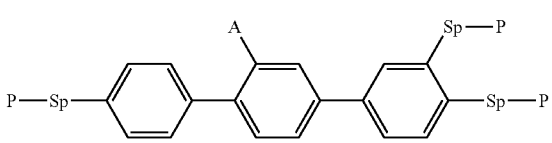
I2B-1-3
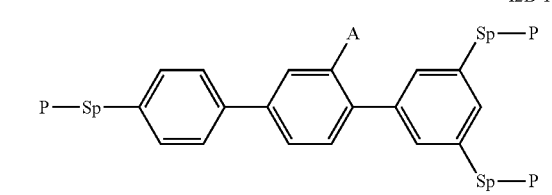
I2B-1-4
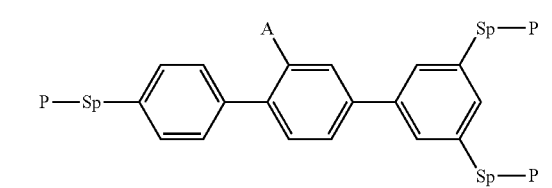
I2B-1-5
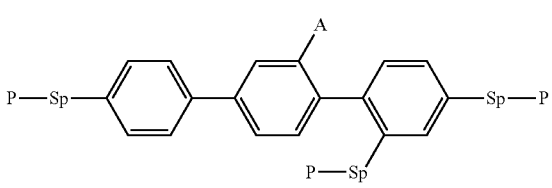
I2B-1-6
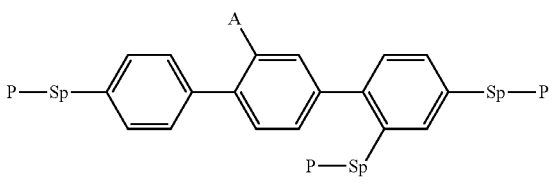
I2B-3-1
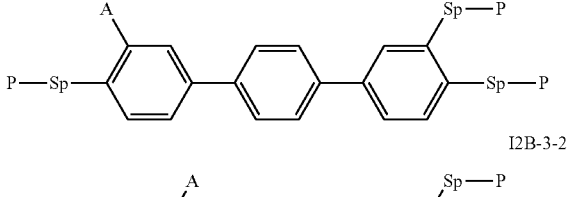
I2B-3-2

I2B-3-3
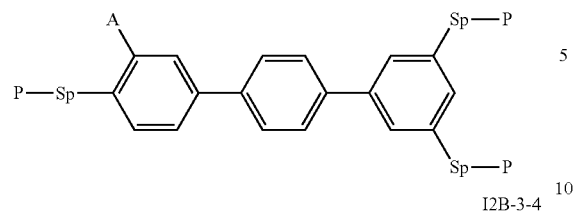
I2B-3-4
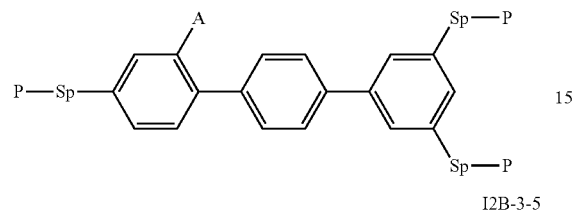
I2B-3-5
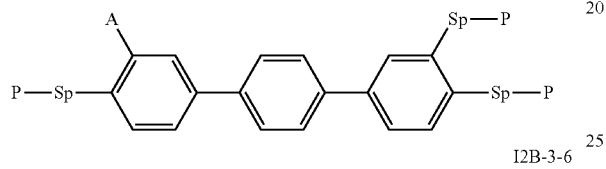
I2B-3-6
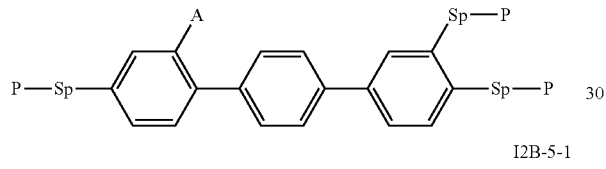
I2B-5-1
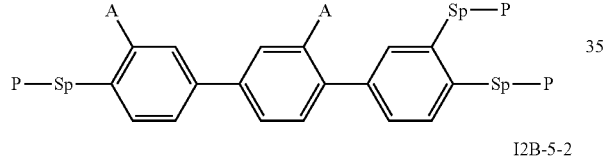
I2B-5-2
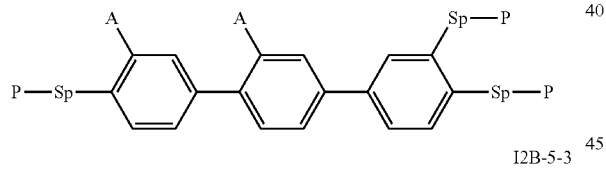
I2B-5-3
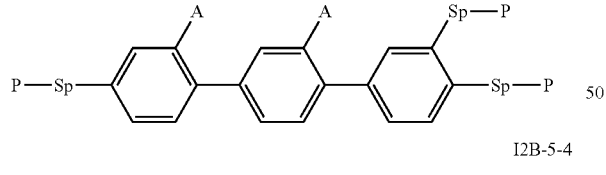
I2B-5-4
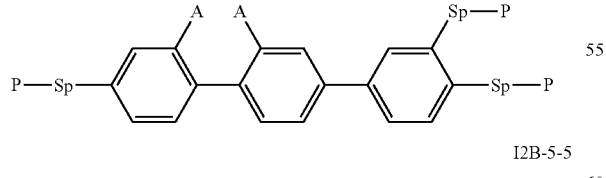
I2B-5-5
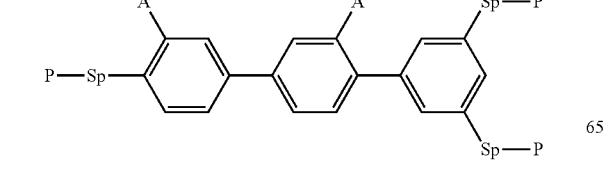
I2B-5-6
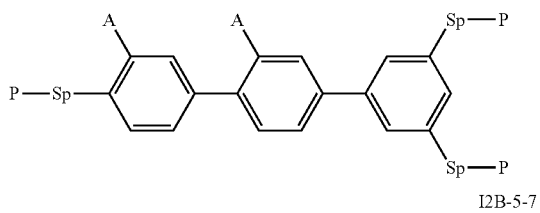
I2B-5-7
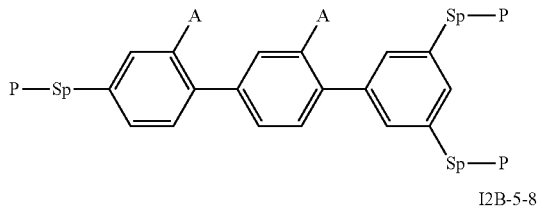
I2B-5-8
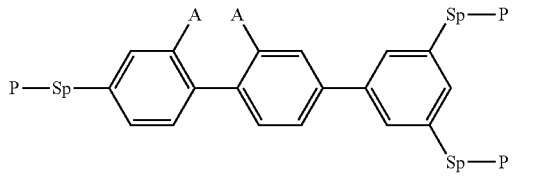
I2B-5-9
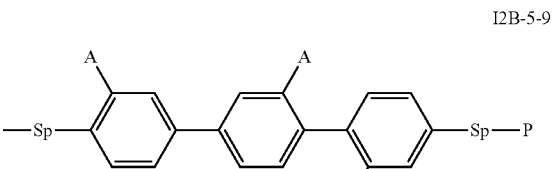
I2B-5-10
I2B-5-11
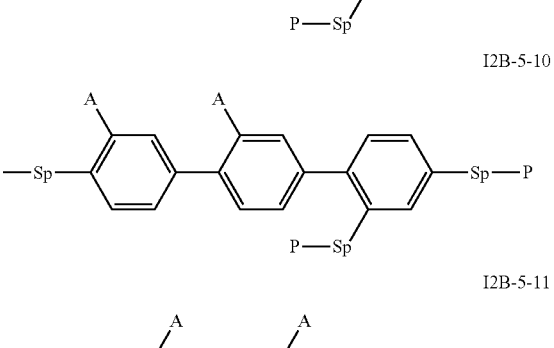
I2B-5-12
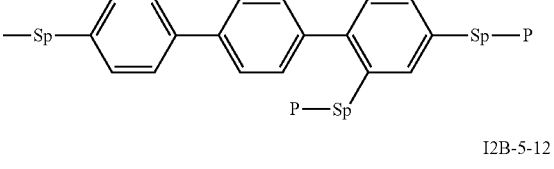
I2B-7-1
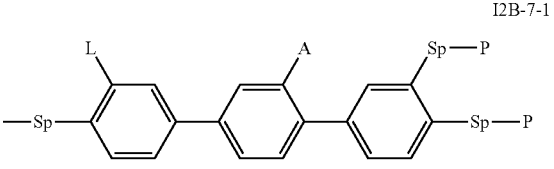

I2B-7-2
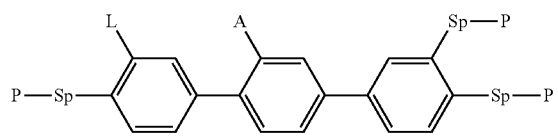
I2B-7-3
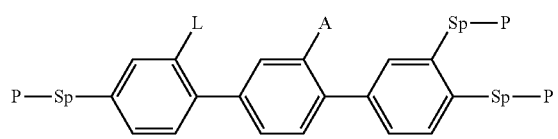
I2B-7-4
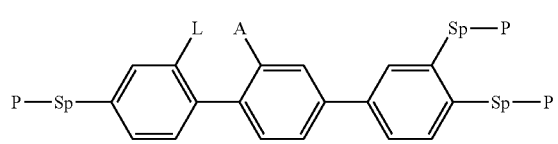
I2B-7-5
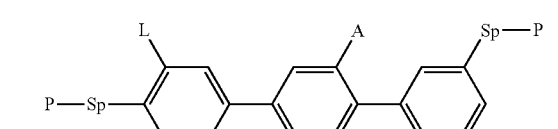
I2B-7-6
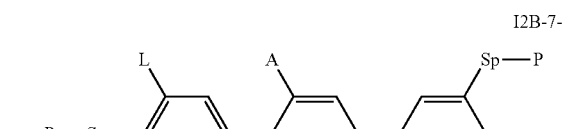
I2B-7-7
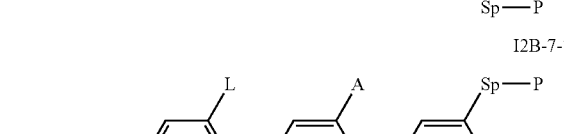
I2B-7-8
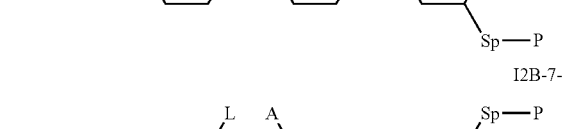
I2B-7-9
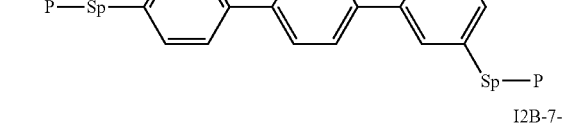
I2B-7-10
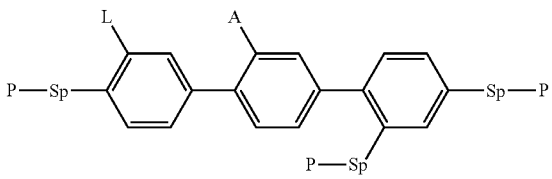
I2B-7-11
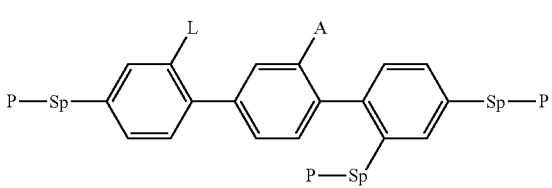
I2B-7-12
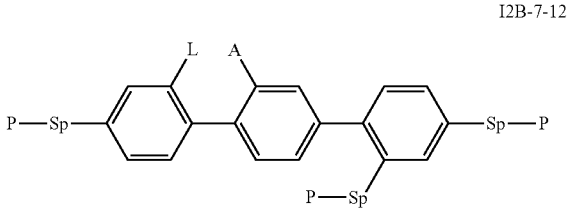
I2B-8-1
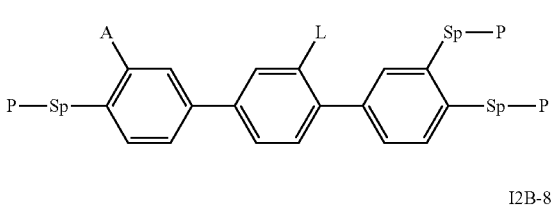
I2B-8-2
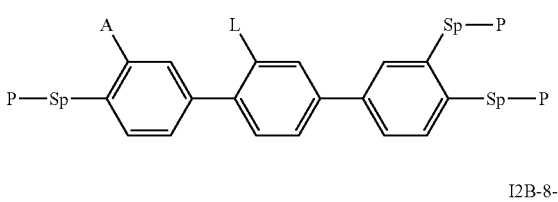
I2B-8-3
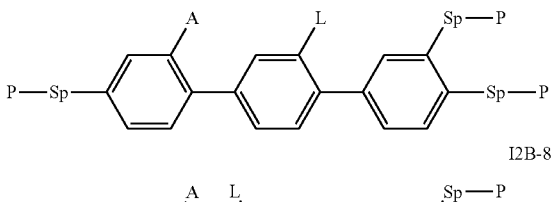
I2B-8-4
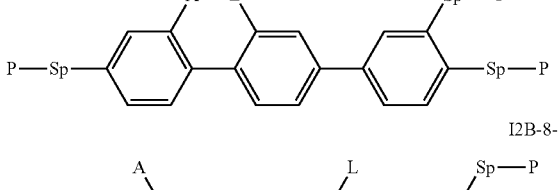
I2B-8-5
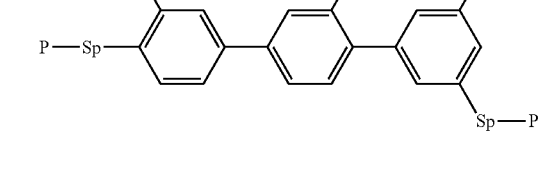

I2B-8-6
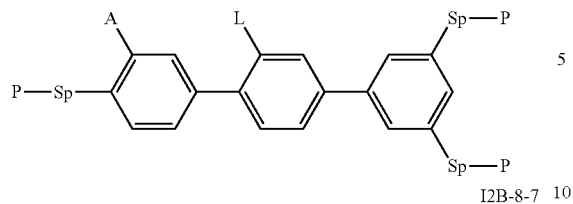
I2B-8-7
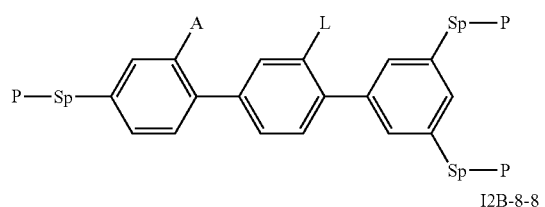
I2B-8-8
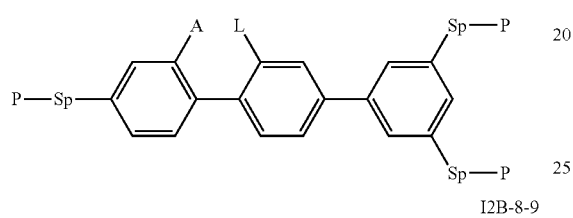
I2B-8-9
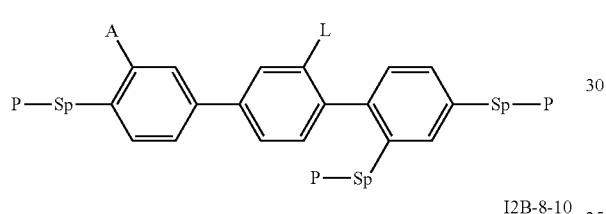
I2B-8-10
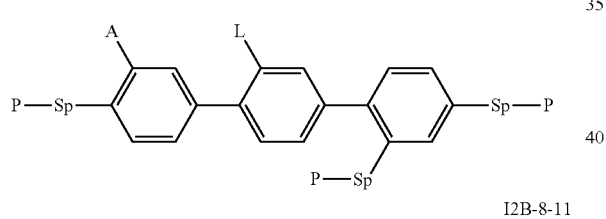
I2B-8-11
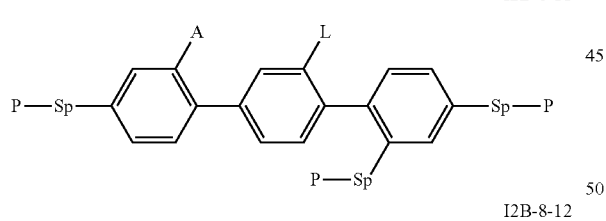
I2B-8-12
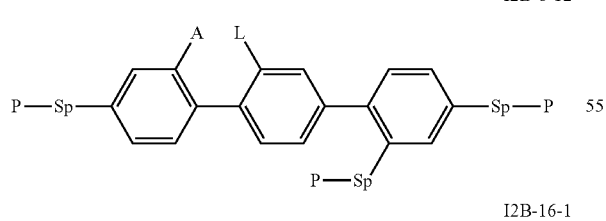
I2B-16-1
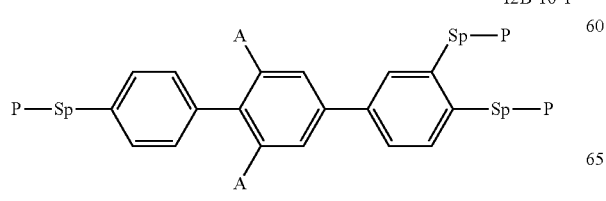
I2B-16-2
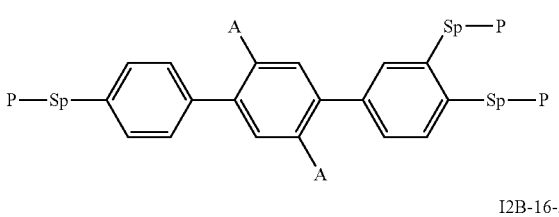
I2B-16-3
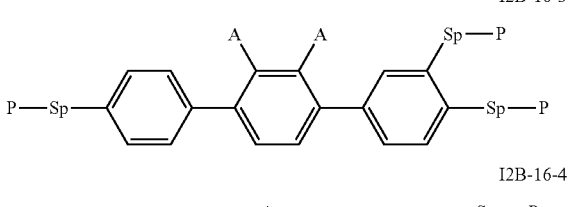
I2B-16-4
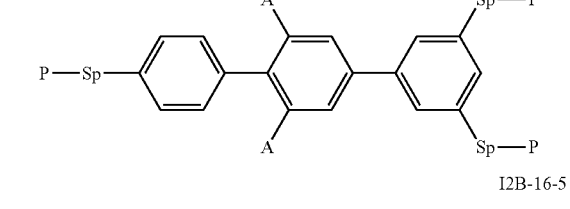
I2B-16-5
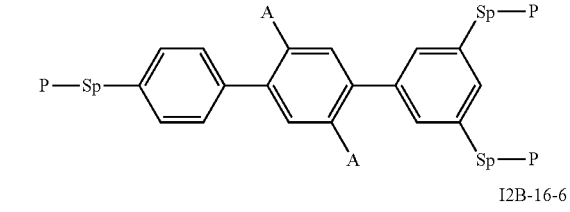
I2B-16-6
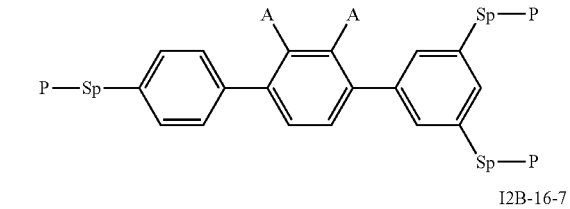
I2B-16-7
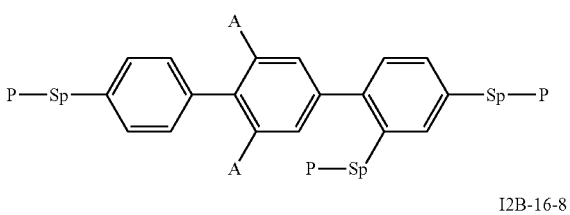
I2B-16-8
I2B-17-1
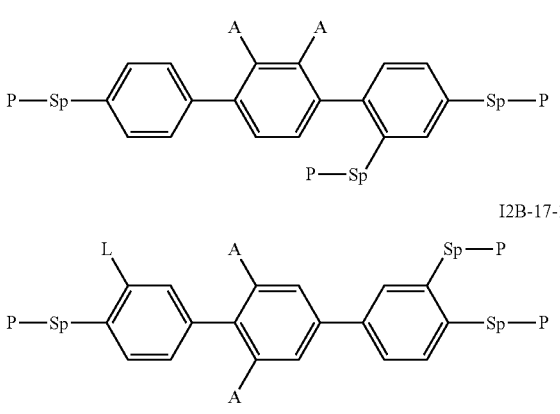

I2B-17-2
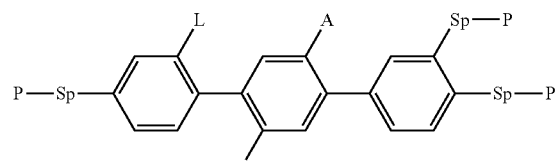
I2B-17-3
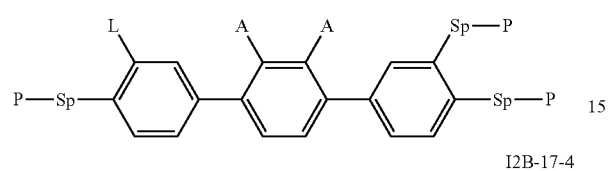
I2B-17-4
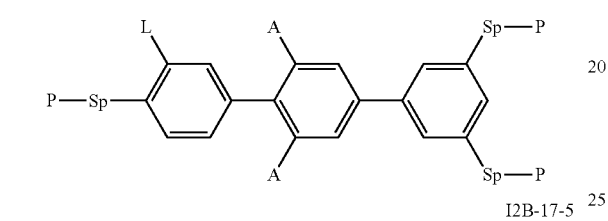
I2B-17-5
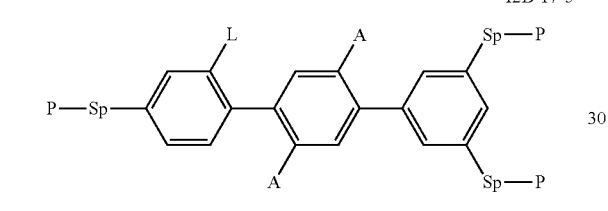
I2B-17-6
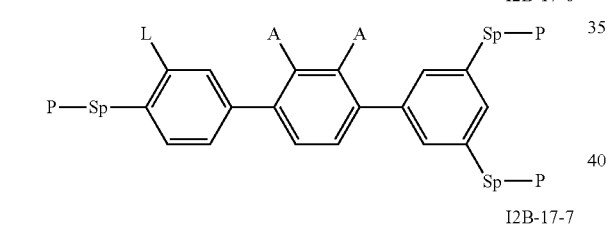
I2B-17-7
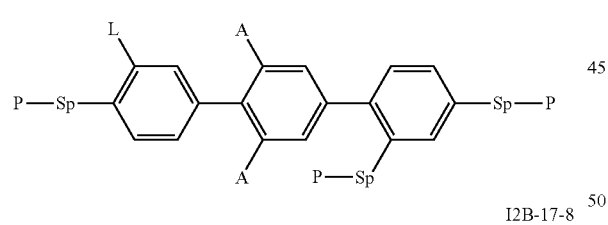
I2B-17-8
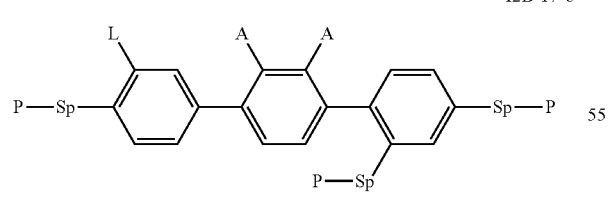
I2B-20-1
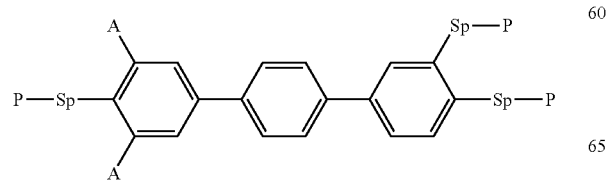
I2B-20-2
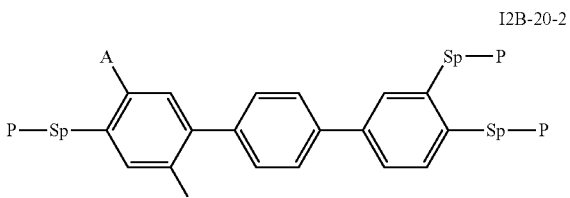
I2B-20-3
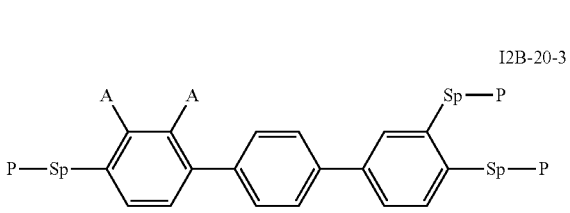
I2B-20-4
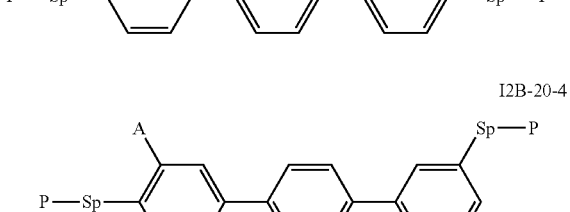
I2B-20-5
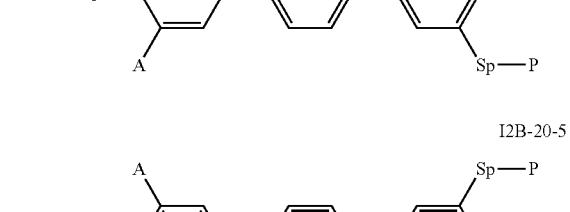
I2B-20-6
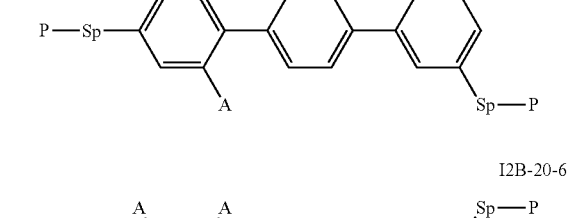
I2B-20-7
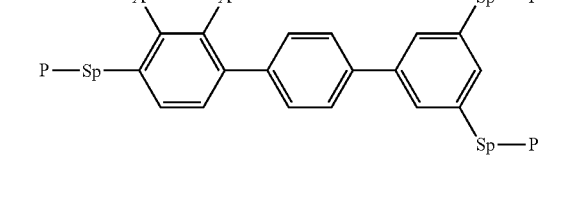
I2B-20-8
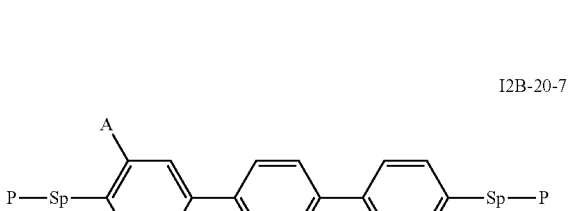

I2B-20-9
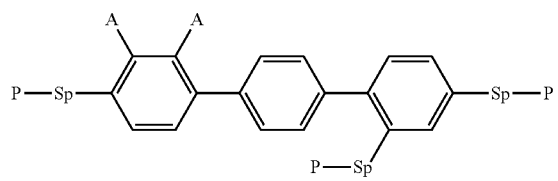
I2B-21-1
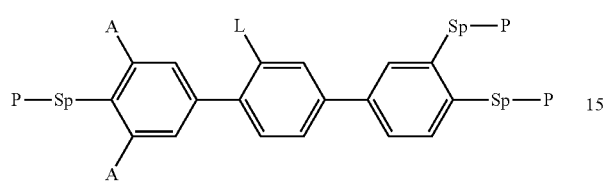
I2B-21-2
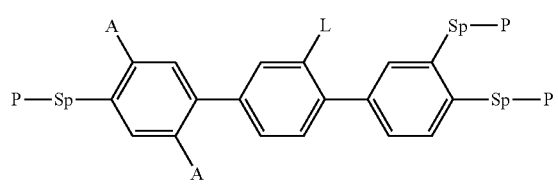
I2B-21-3
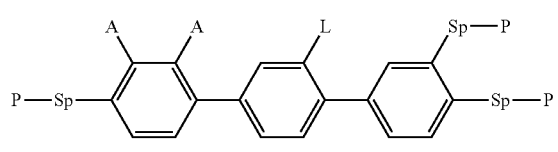
I2B-21-4
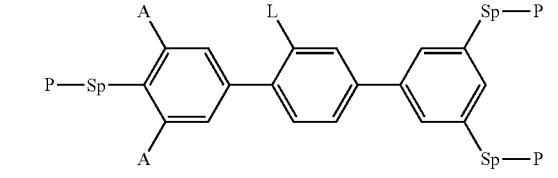
I2B-21-5
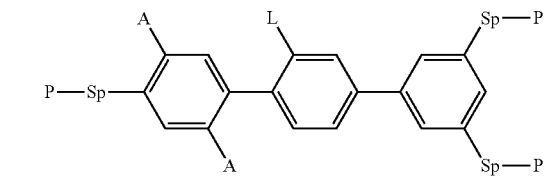
I2B-21-6
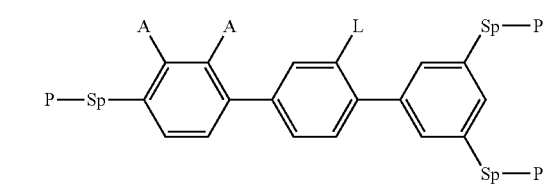
I2B-21-7
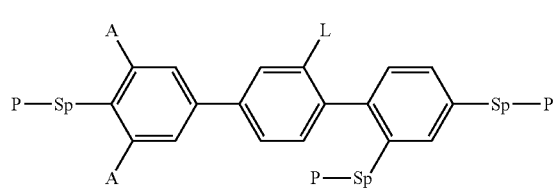
I2B-21-8
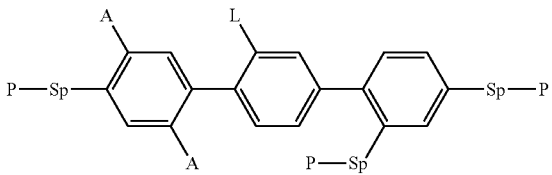
I2B-21-9
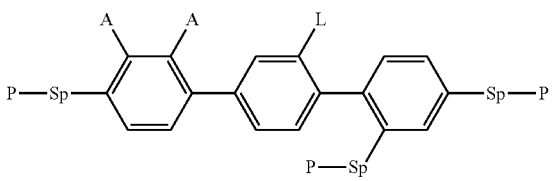
I2C-1-1
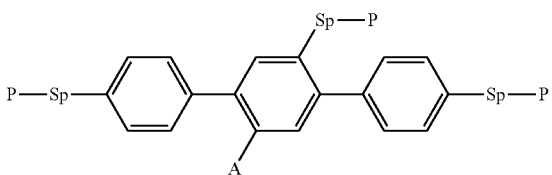
I2C-1-2
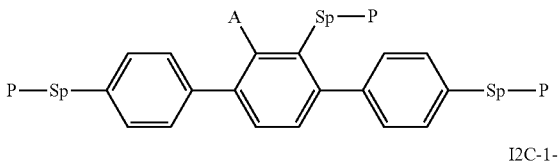
I2C-1-3
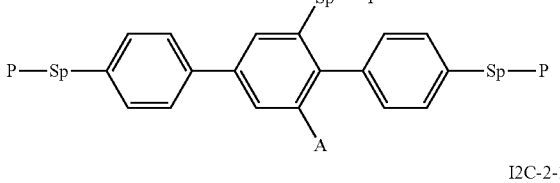
I2C-2-1
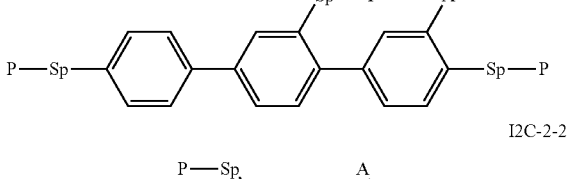
I2C-2-2
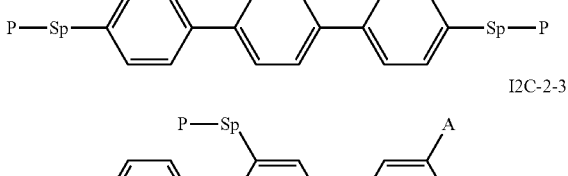
I2C-2-3
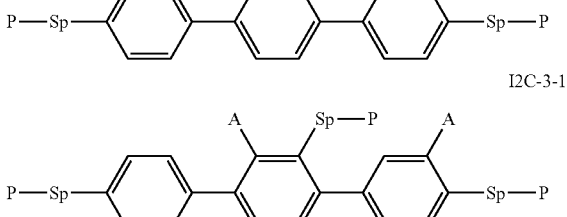
I2C-3-1

I2C-3-2
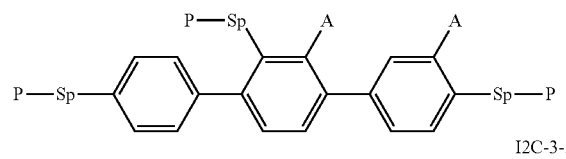
I2C-3-3
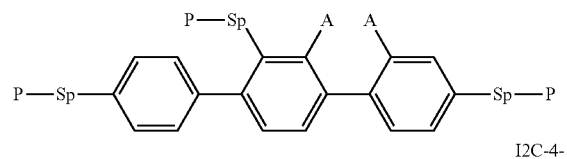
I2C-4-1
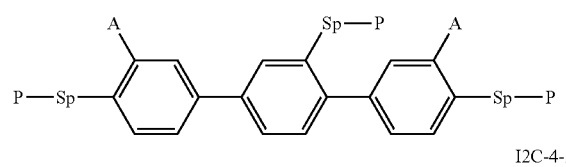
I2C-4-2
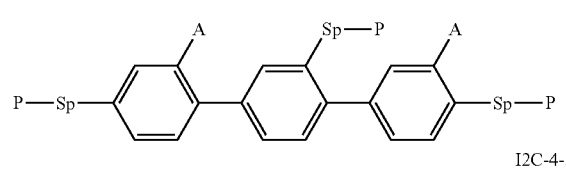
I2C-4-3
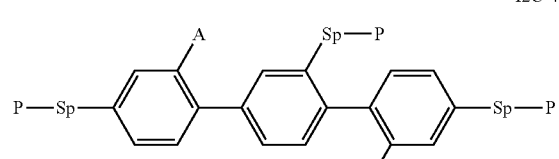
I2C-5-1
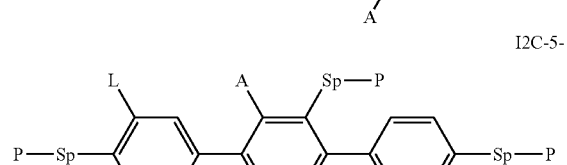
I2C-5-2
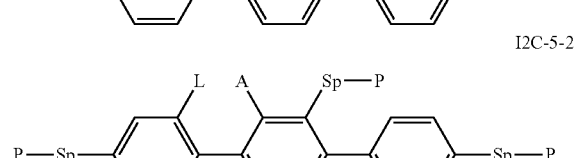
I2C-5-3
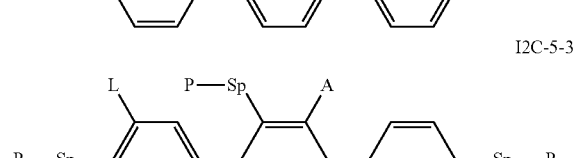
I2C-6-1
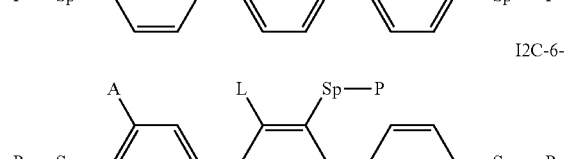
I2C-6-2
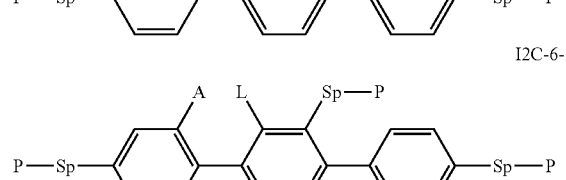
I2C-6-3
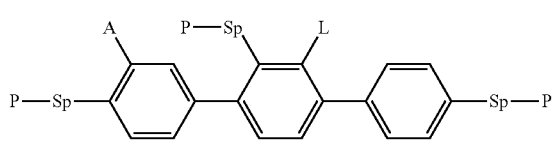
I2C-7-1
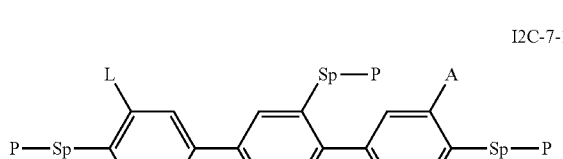
I2C-7-2
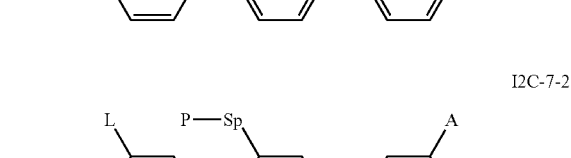
I2C-7-3
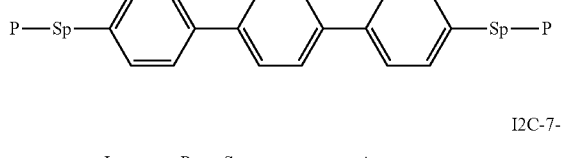
I2C-8-1
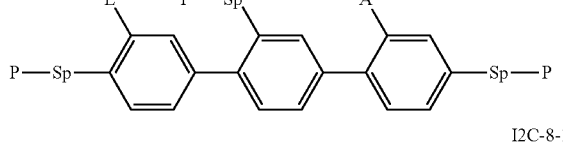
I2C-8-2
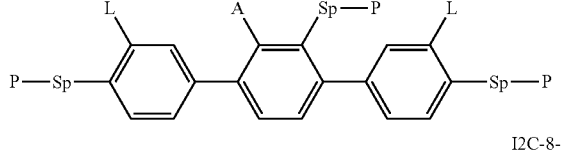
I2C-8-3
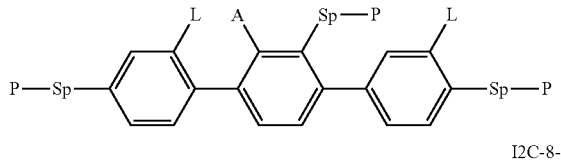
I2C-9-1
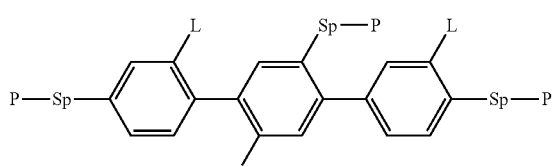
I2C-9-2
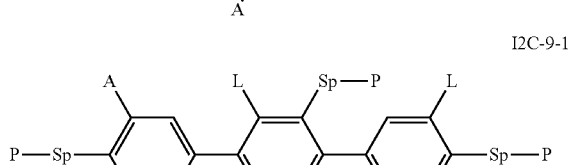

I2C-9-3
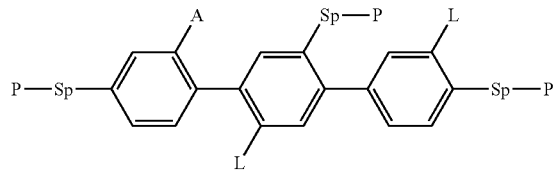
I2C-10-1
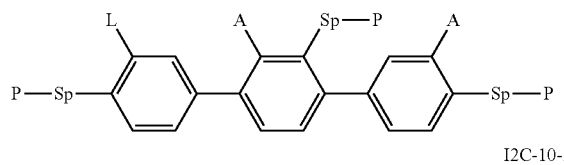
I2C-10-2
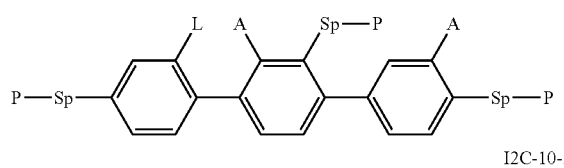
I2C-10-3
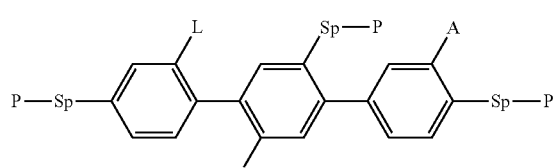
I2C-11-1
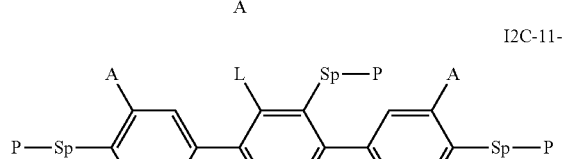
I2C-11-2
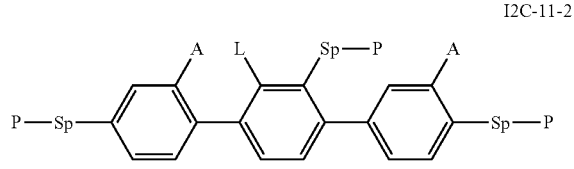
I2C-11-3
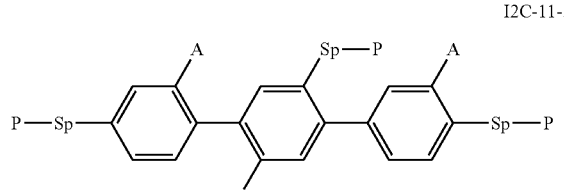
I2C-12-1
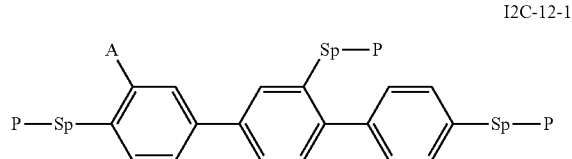
I2C-12-2
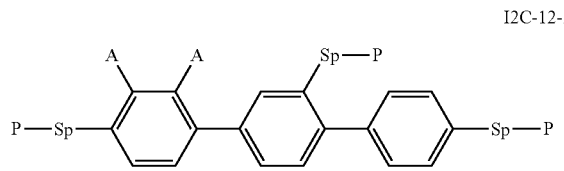
I2C-12-3
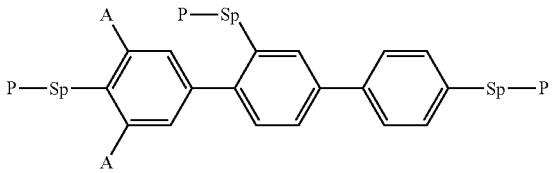
I2C-12-4
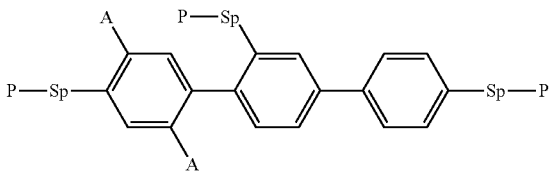
I2C-13-1
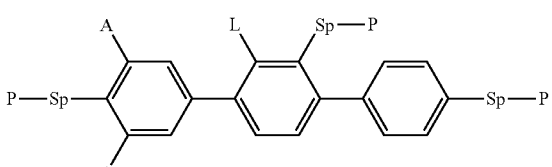
I2C-13-2
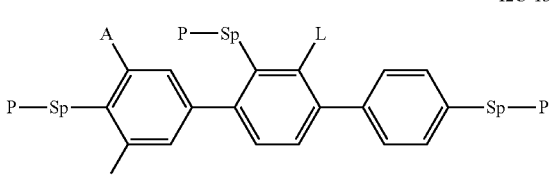
I2C-13-3
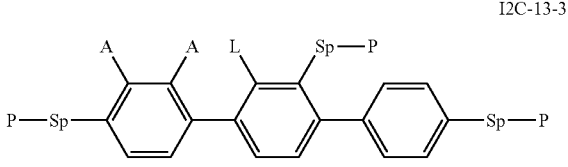
I2C-13-4
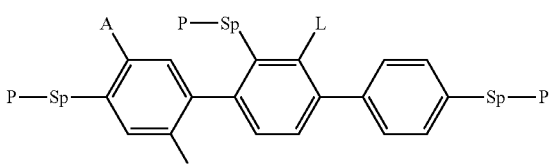
I2C-14-1
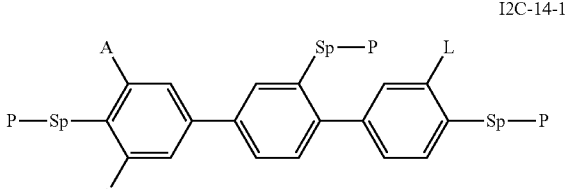
I2C-14-2
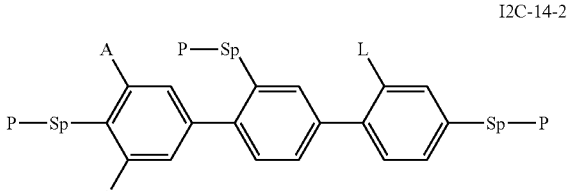

I2C-14-3
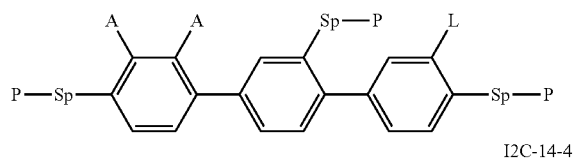
I2C-14-4
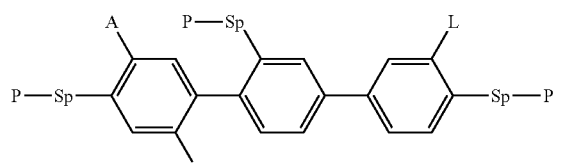
I2C-15-1
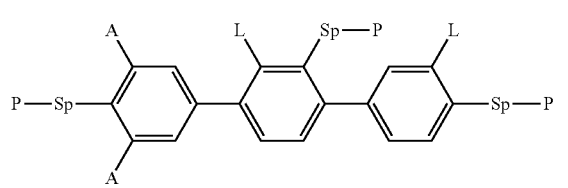
I2C-15-2
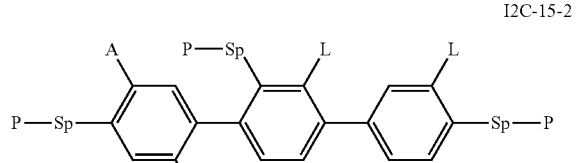
I2C-15-3
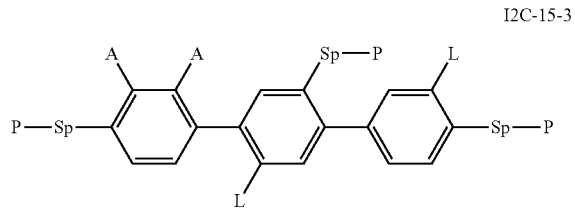
I2C-15-4
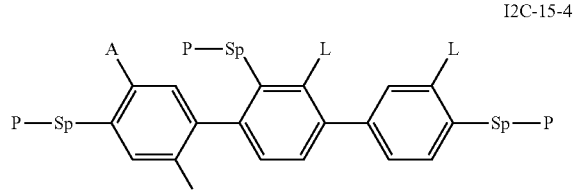
I2D-1-1
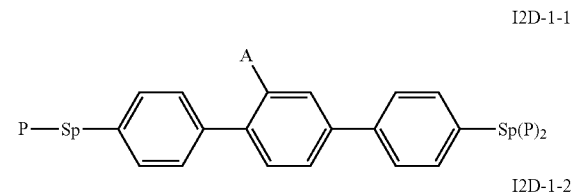
I2D-1-2
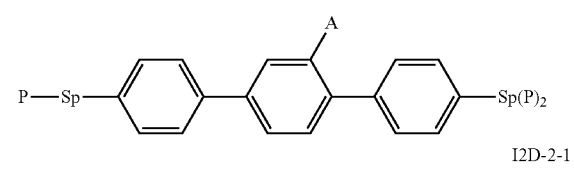
I2D-2-1
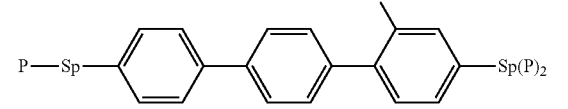
I2D-2-2
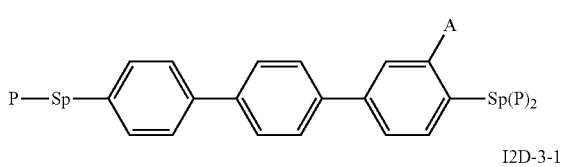
I2D-3-1
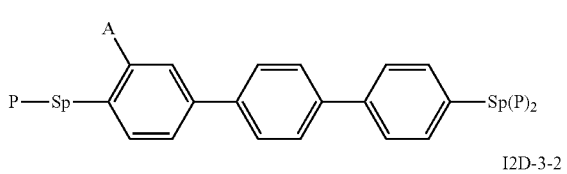
I2D-3-2
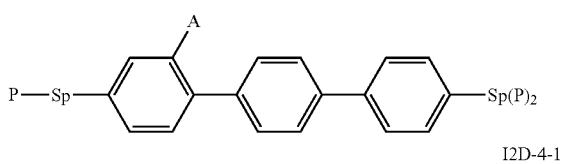
I2D-4-1
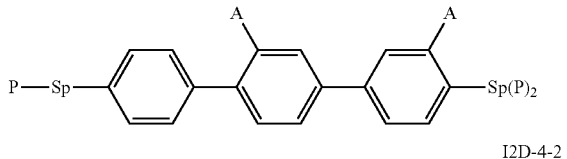
I2D-4-2
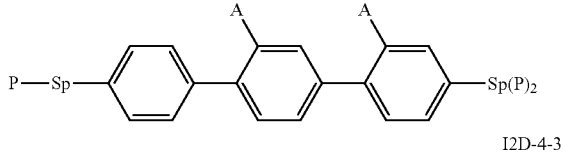
I2D-4-3
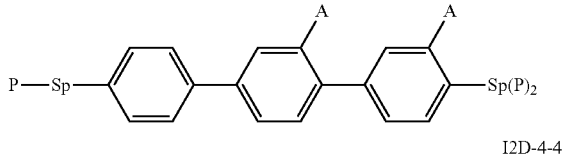
I2D-4-4
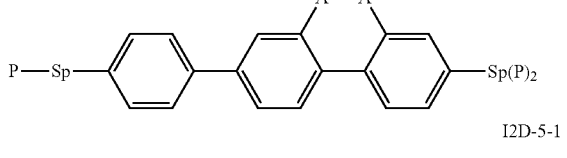
I2D-5-1
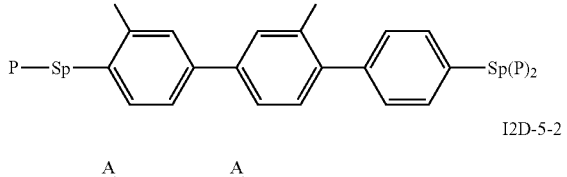
I2D-5-2
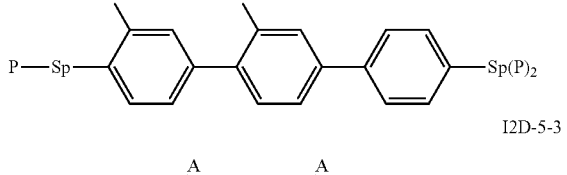
I2D-5-3
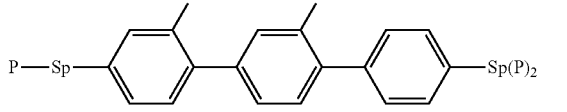

I2D-5-4
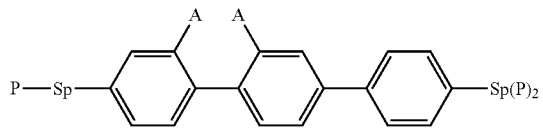
I2D-6-1
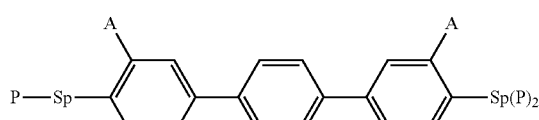
I2D-6-2
I2D-6-3
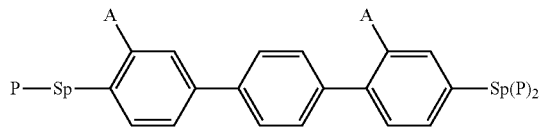
I2D-6-4
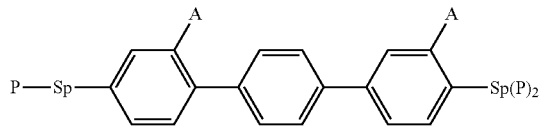
I2D-7-1
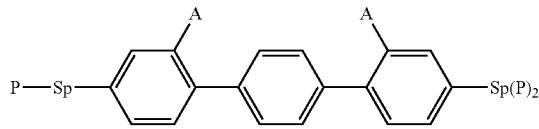
I2D-7-2
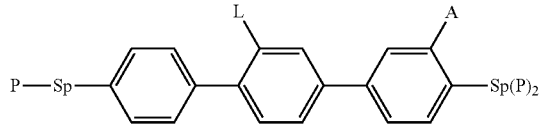
I2D-7-3
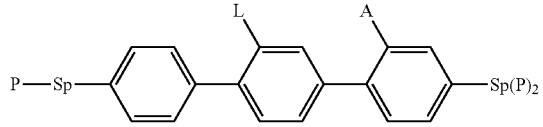
I2D-7-4
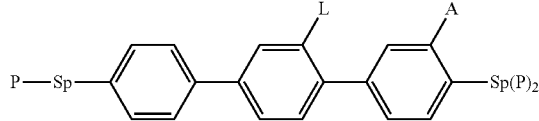
I2D-8-1
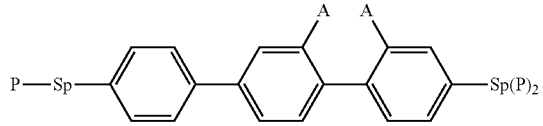
I2D-8-2
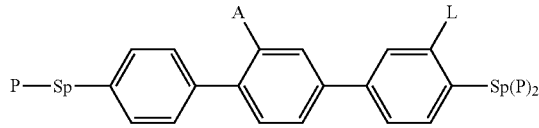
I2D-8-3
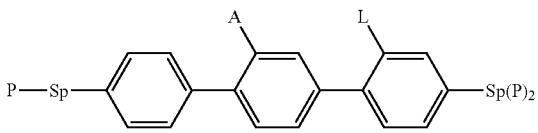
I2D-8-4
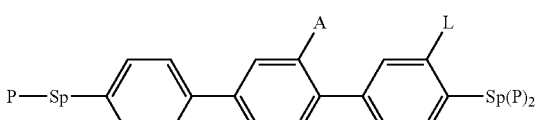
I2D-9-1
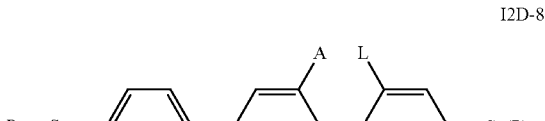
I2D-9-2
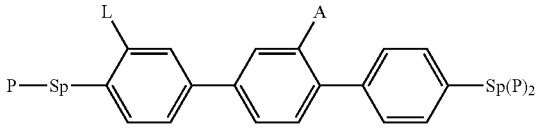
I2D-9-3
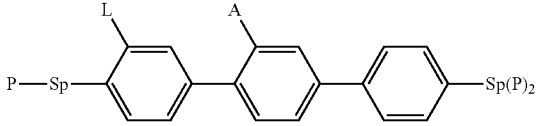
I2D-9-4
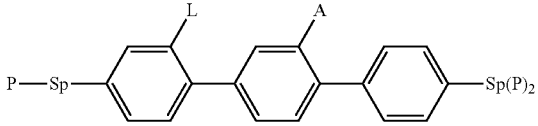
I2D-10-1
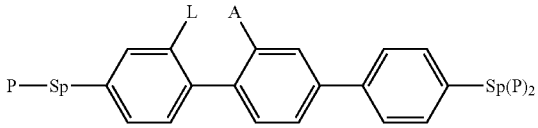
I2D-10-2
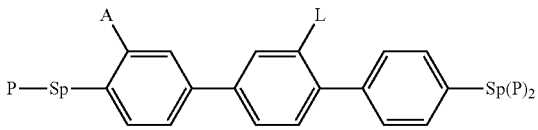
I2D-10-3
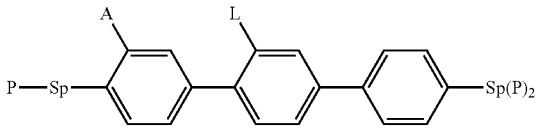
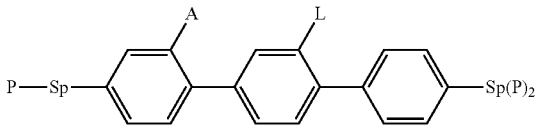

I2D-10-4
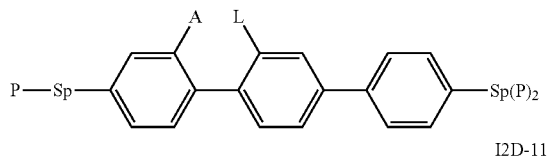
I2D-11-1
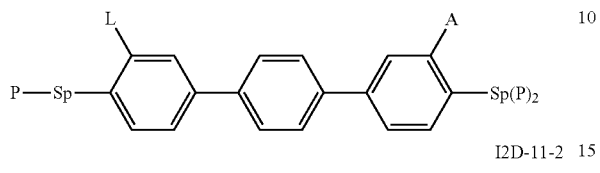
I2D-11-2
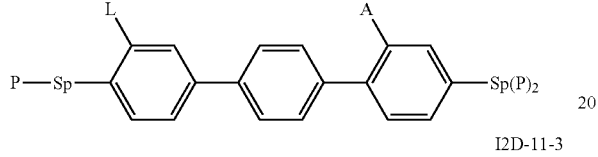
I2D-11-3
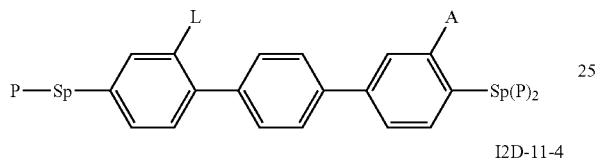
I2D-11-4
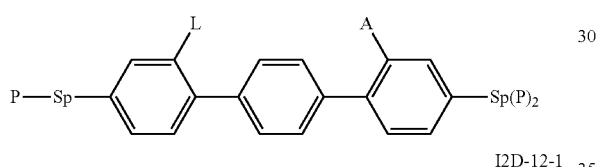
I2D-12-1
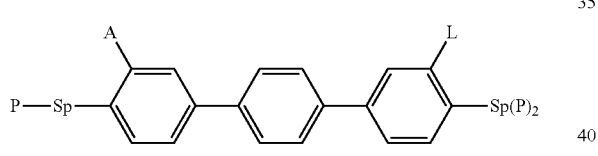
I2D-12-2
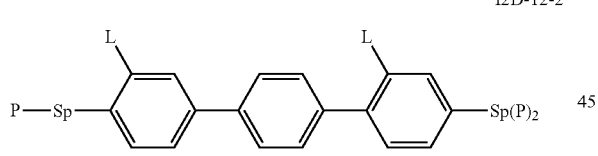
I2D-12-3
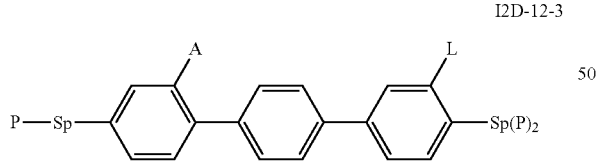
I2D-12-4
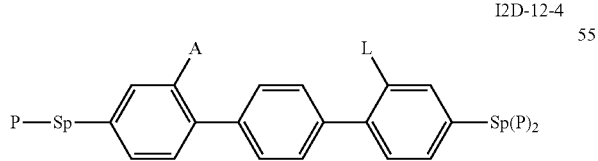
I2D-13-1
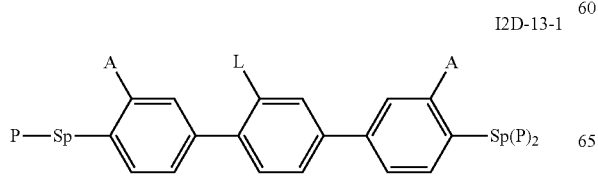
I2D-13-2
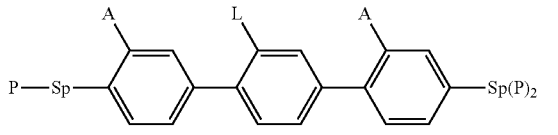
I2D-13-3
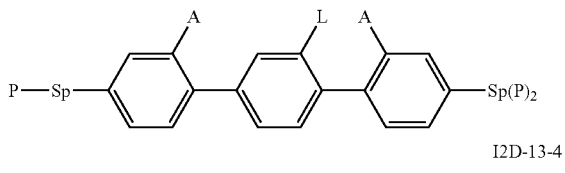
I2D-13-4
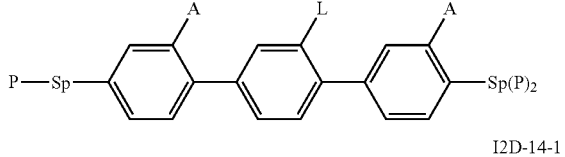
I2D-14-1
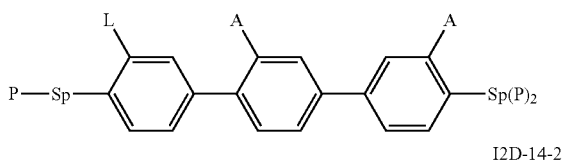
I2D-14-2
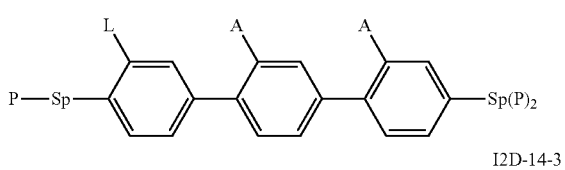
I2D-14-3
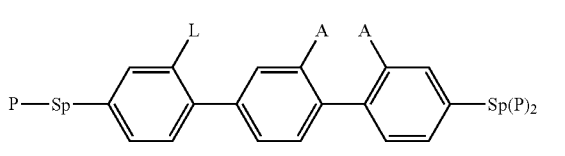
I2D-14-4
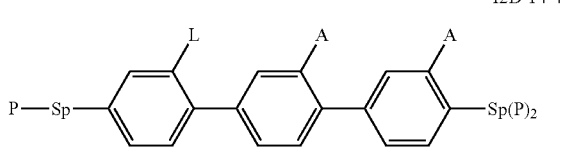
I2D-15-1
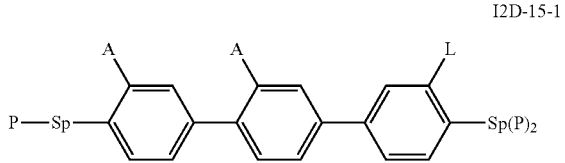
I2D-15-2
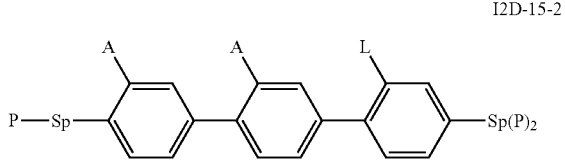
I2D-15-3
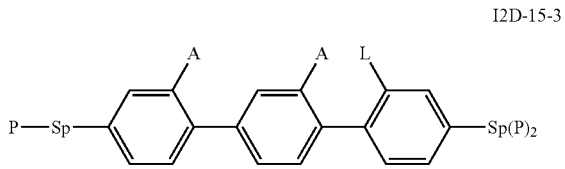

I2D-15-4
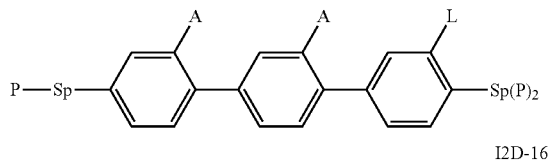
I2D-16-1
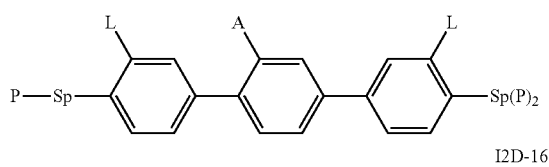
I2D-16-2
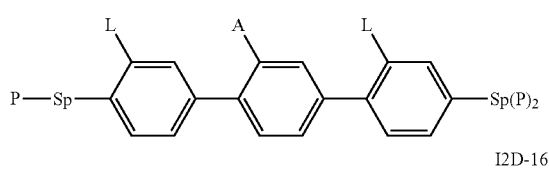
I2D-16-3
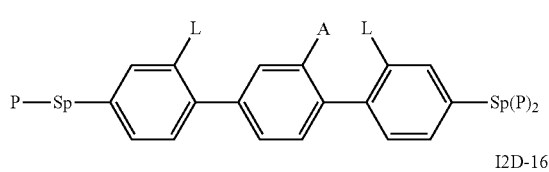
I2D-16-4
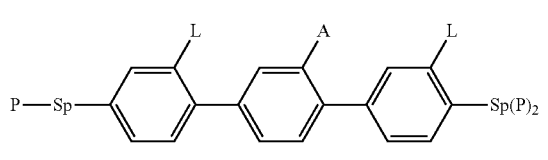
I2D-17-1
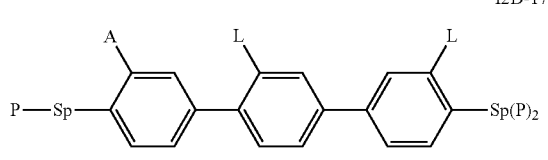
I2D-17-2
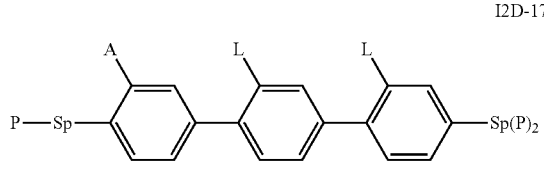
I2D-17-3
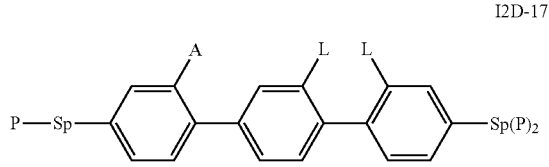
I2D-17-4
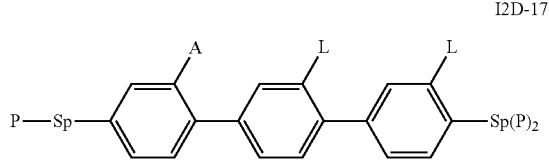
I2D-19-1
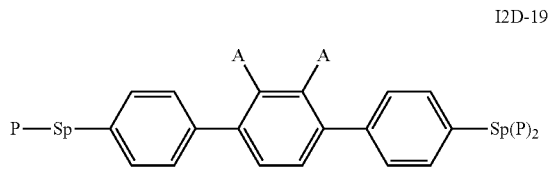
I2D-19-2
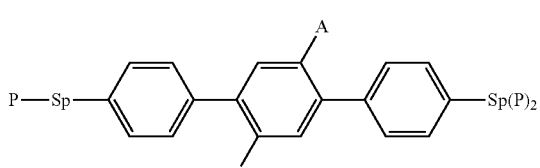
I2D-19-3
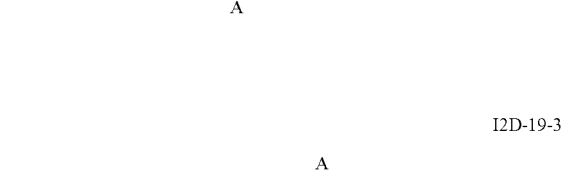
I2D-20-1
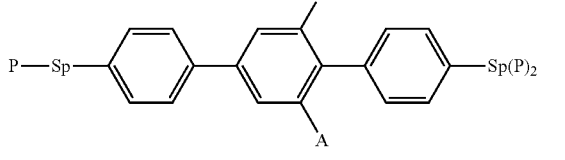
I2D-20-2
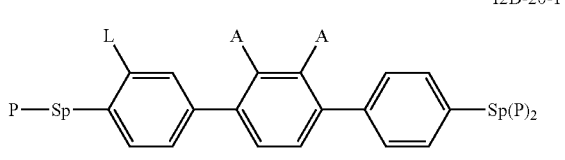
I2D-20-3
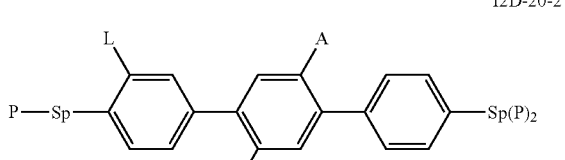
I2D-21-1
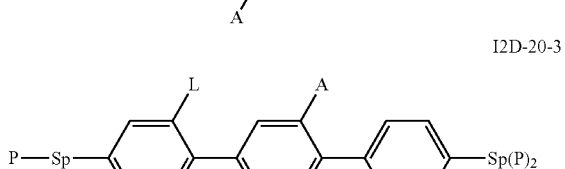
I2D-21-2
I2D-21-3

I2D-22-1
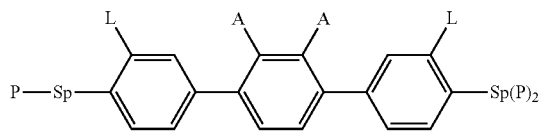
I2D-22-2
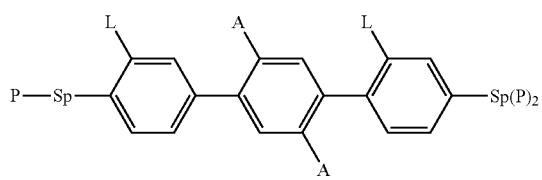
I2D-22-3
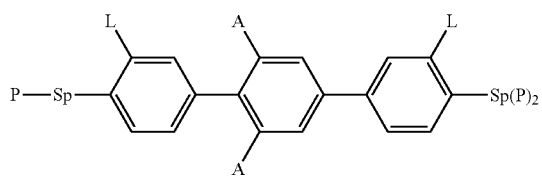
I2D-22-4
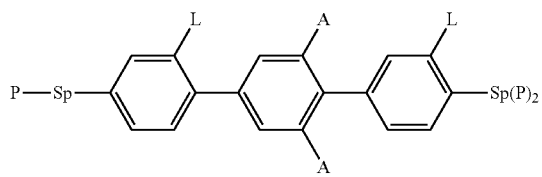
I2D-23-1
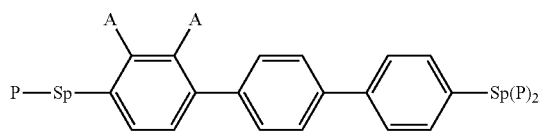
I2D-23-2
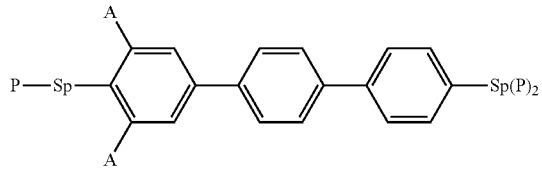
I2D-23-3
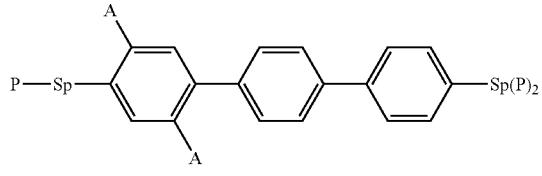
I2D-24-1
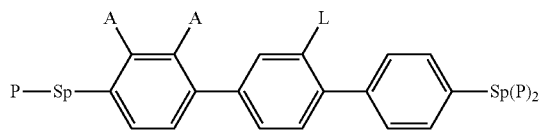
I2D-24-2
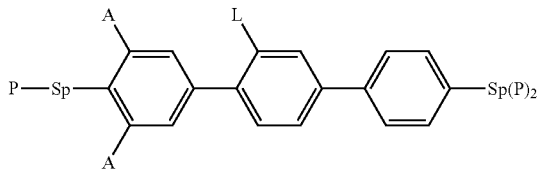
I2D-24-3
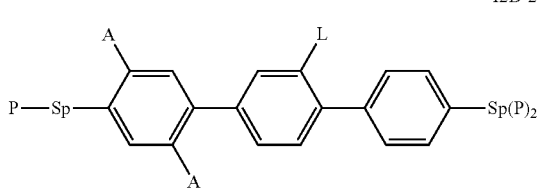
I2D-25-1
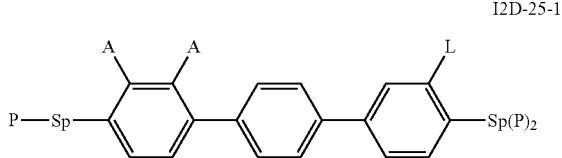
I2D-25-2
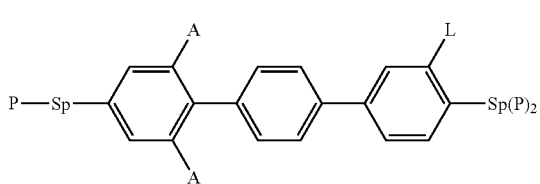
I2D-25-3
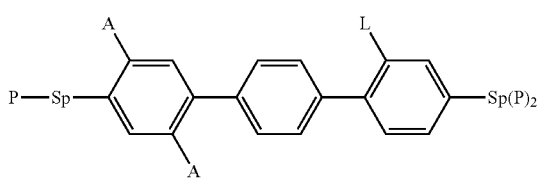
I2D-26-1
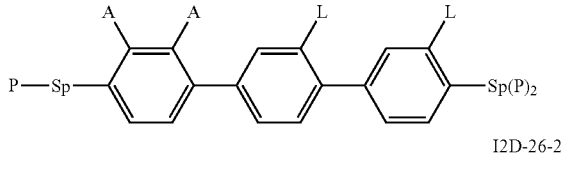
I2D-26-2
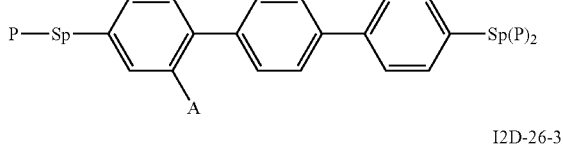
I2D-26-3
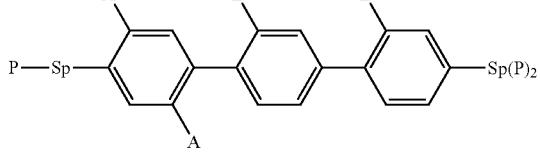

I2D-26-4
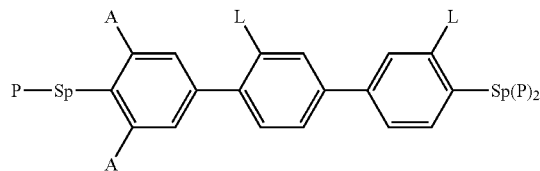
I2D-27-1
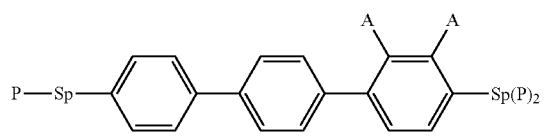
I2D-27-2
I2D-27-3
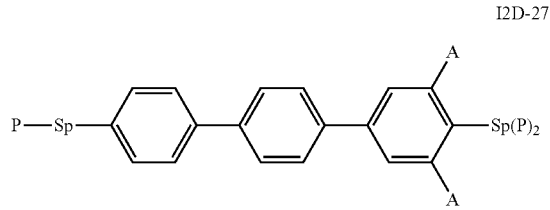
I2D-28-1
I2D-28-2
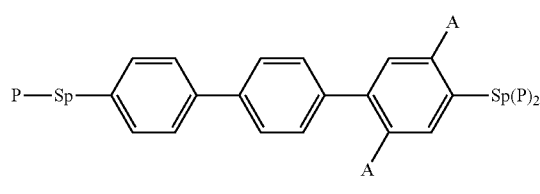
I2D-28-3
I2D-29-1
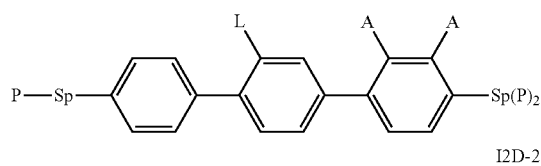
I2D-29-2
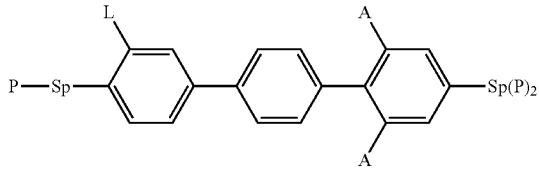
I2D-29-3
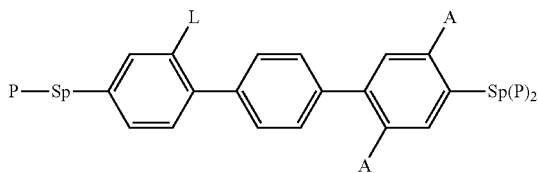
I2D-30-1
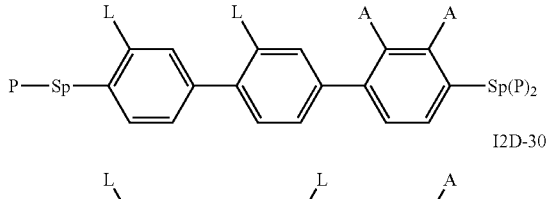
I2D-30-2
I2D-30-3
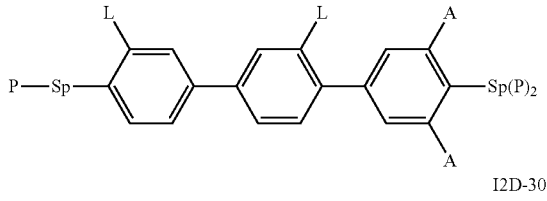
I2D-30-4
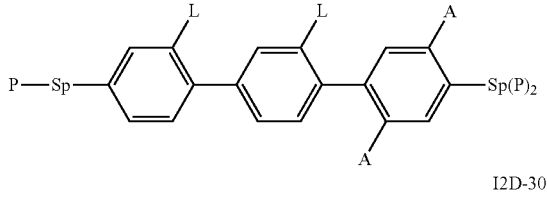
I2E-1-1
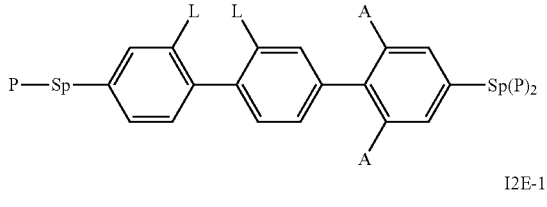
I2E-1-2
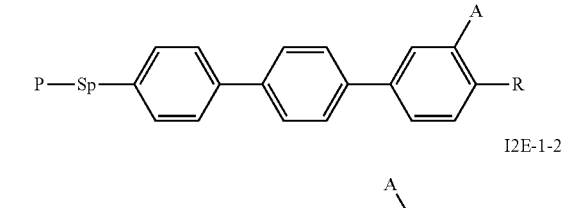
I2E-2-1
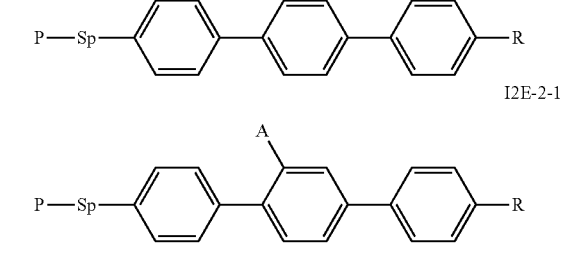

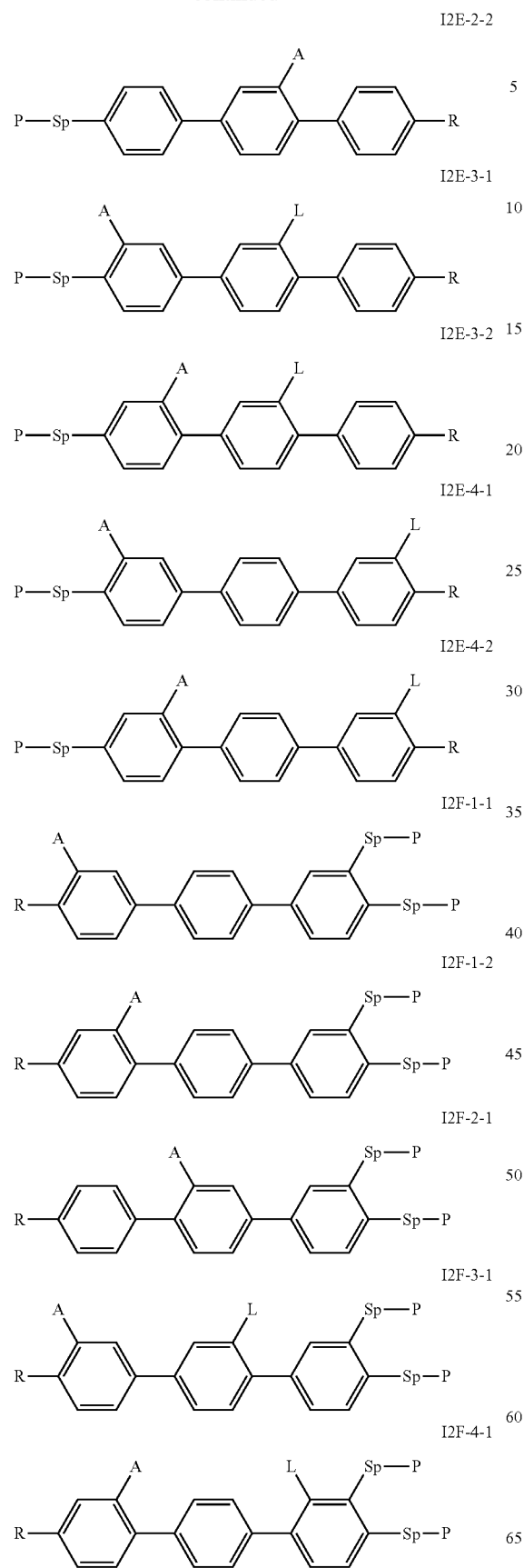

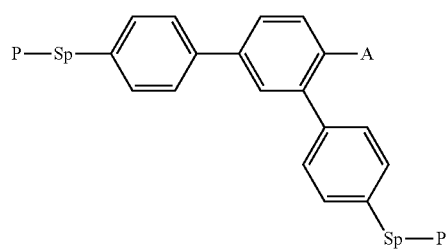
I5A-2-2
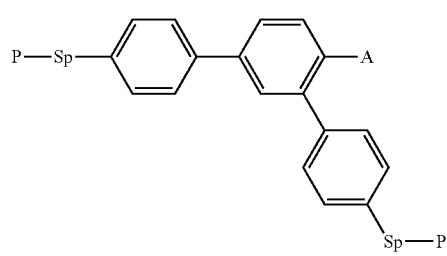 
I5A-2-3
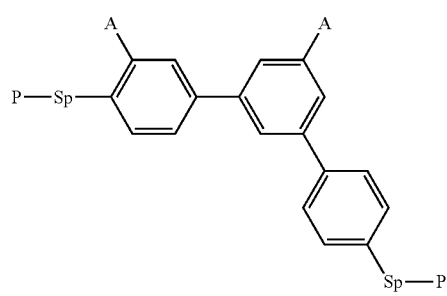
I5A-3-1
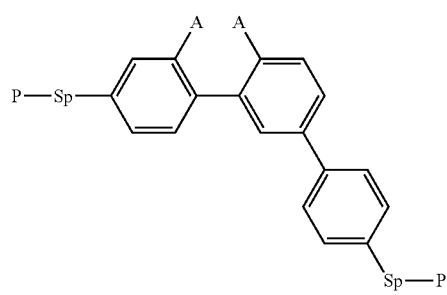
I5A-3-2
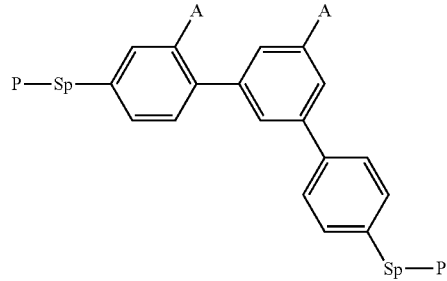
I5A-3-3
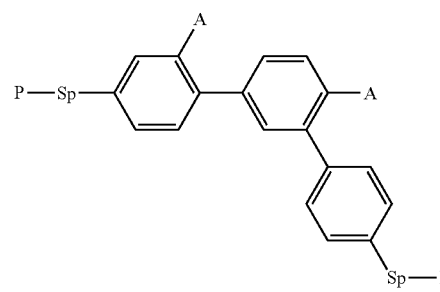
I5A-3-4
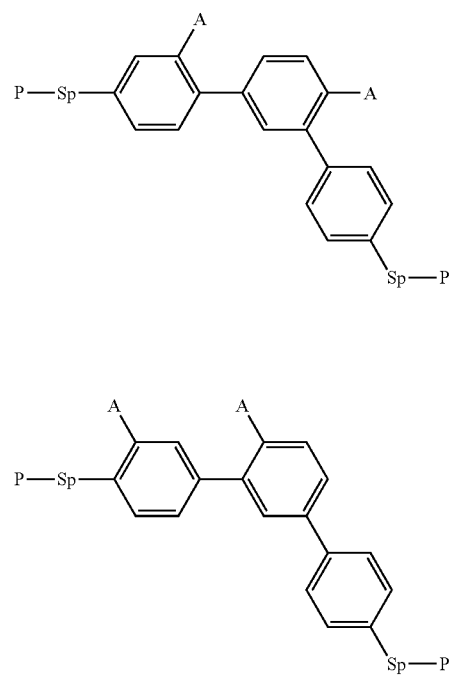
I5A-3-5
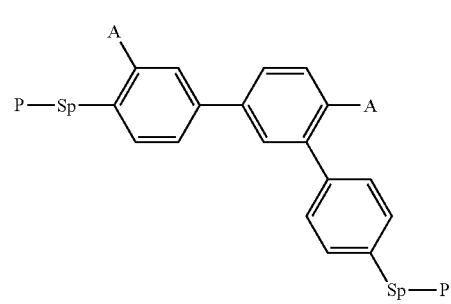
I5A-3-6
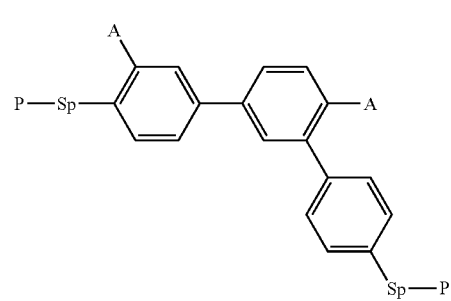
I5A-3-7
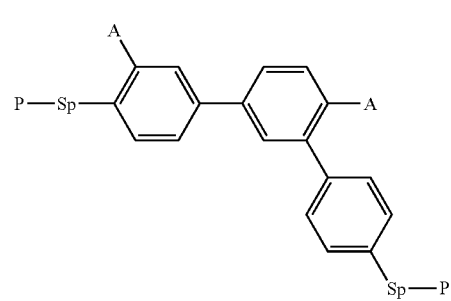
I5A-4-1

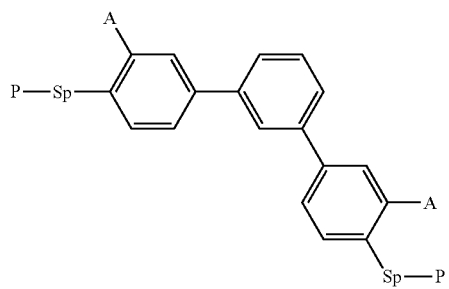
I5A-4-2
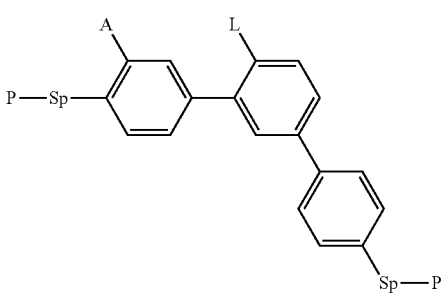
I5A-5-4
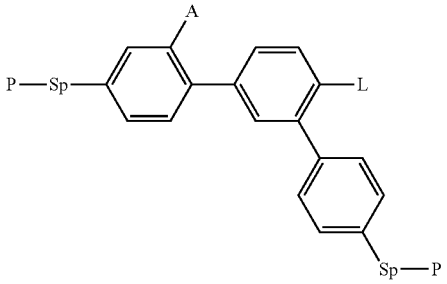
I5A-5-5
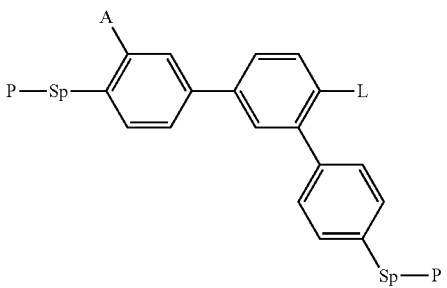
I5A-5-6
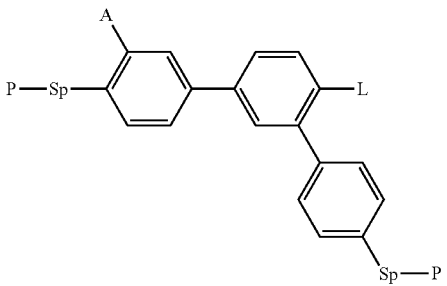
I5A-5-7
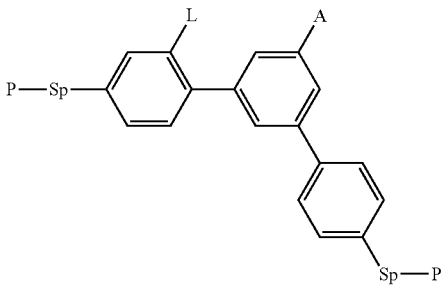
I5A-6-1

-continued

I5A-6-2

I5A-6-3

I5A-6-4

I5A-6-5

I5A-6-6

-continued

I5A-7-1

I5A-7-2

I5A-7-3

I5A-7-4

I5A-8-1

I5A-8-2
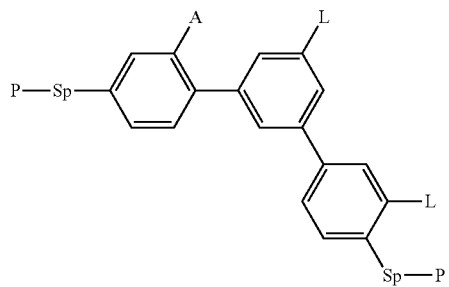
I5A-8-3
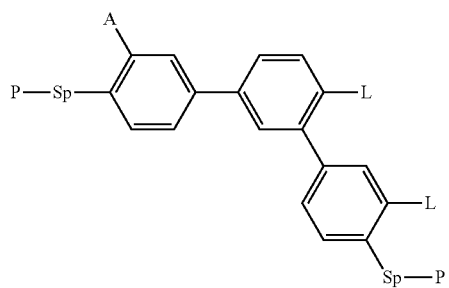
I5A-8-4
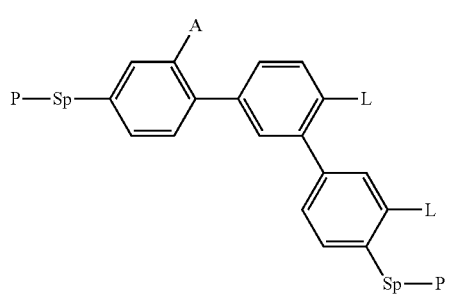
I5A-9-1
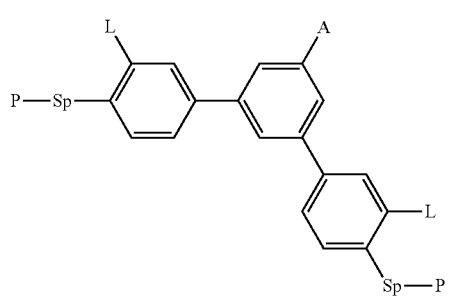
I5A-9-2
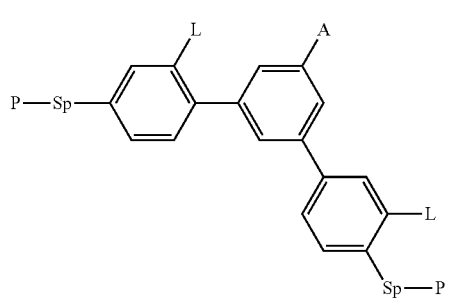
I5A-9-3
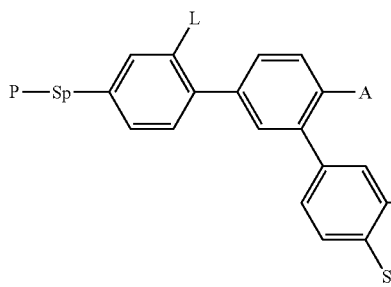
I5A-9-4
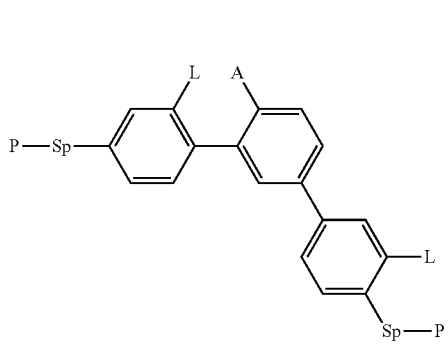
I5A-9-5
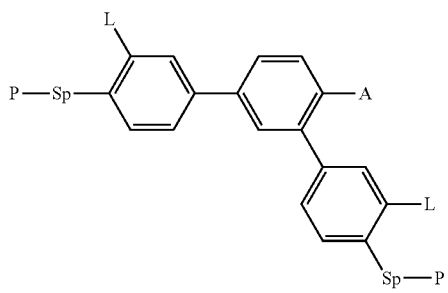
I5A-10-1
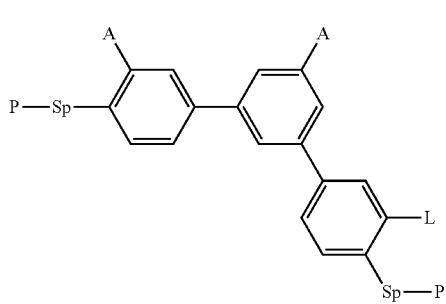
I5A-10-2
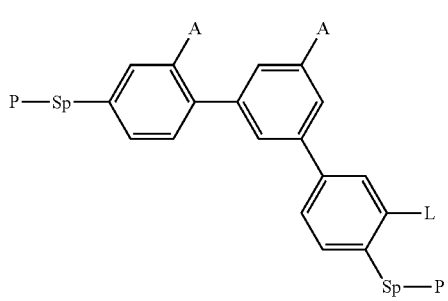

I5A-10-3
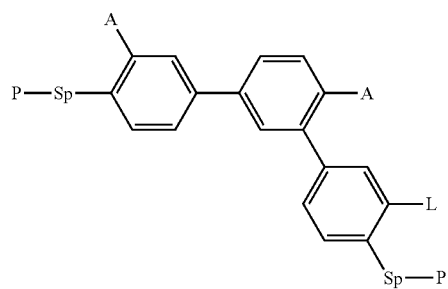
I5A-10-4
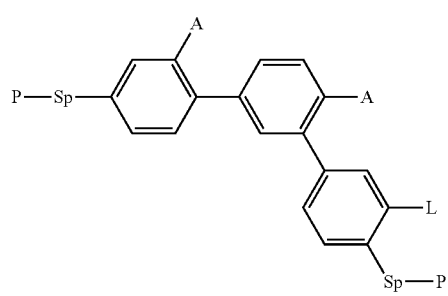
I5A-11-1
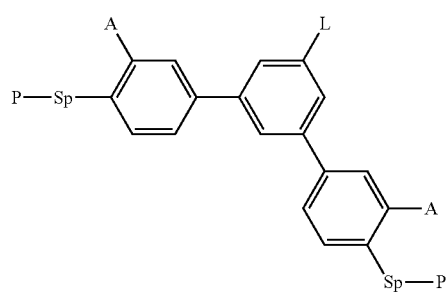
I5A-11-2
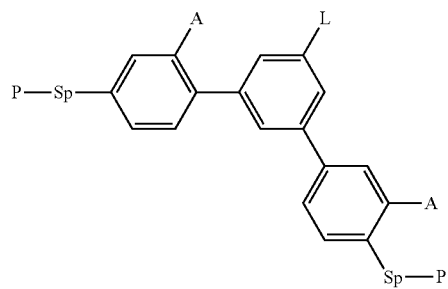
I5A-11-3
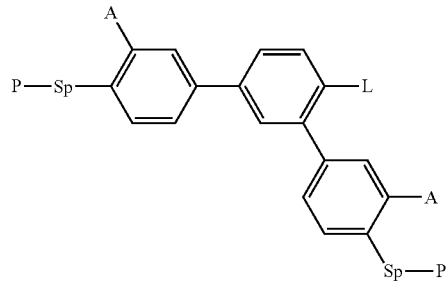
I5A-11-4
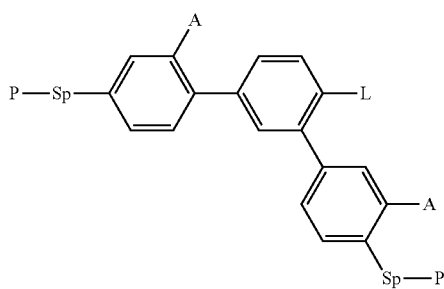
I5A-12-1
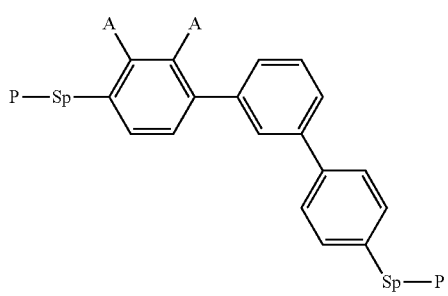
I5A-12-2
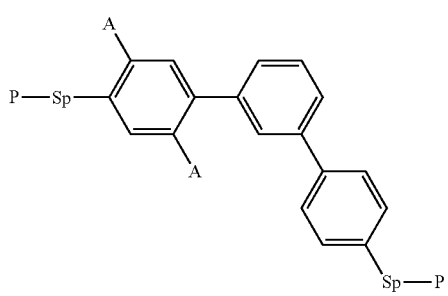
I5A-12-3
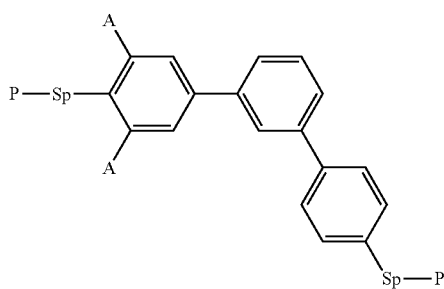
I5A-12-4
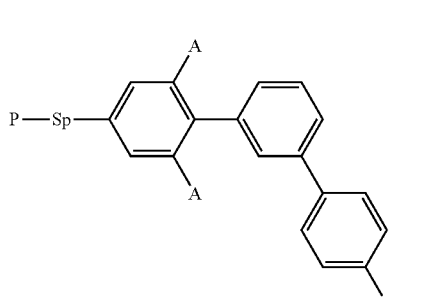

-continued
I5A-13-1
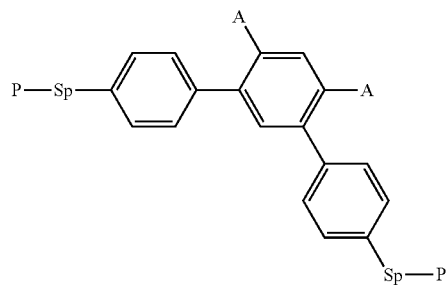
I5A-14-3
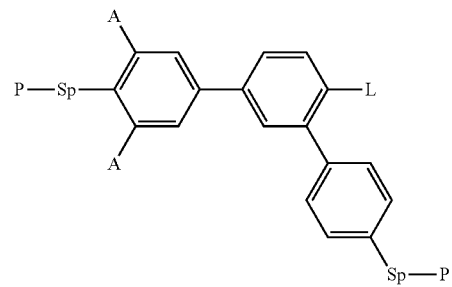
I5A-13-2
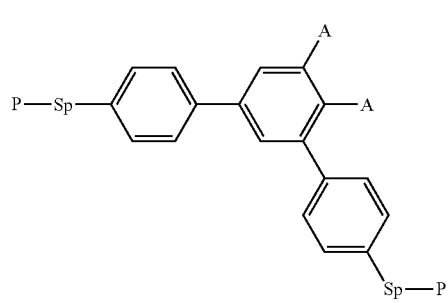
I5A-15-1
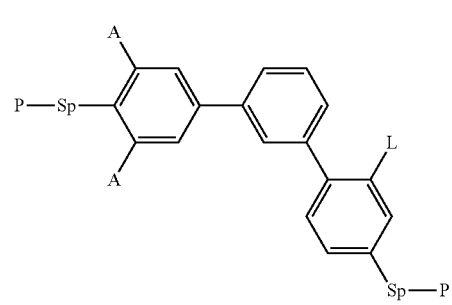
I5A-13-3
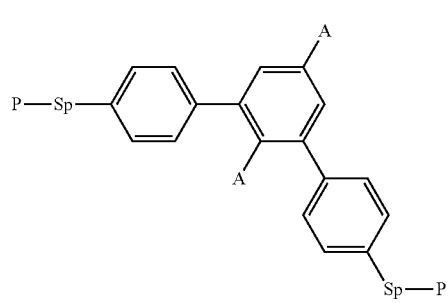
I5A-15-2
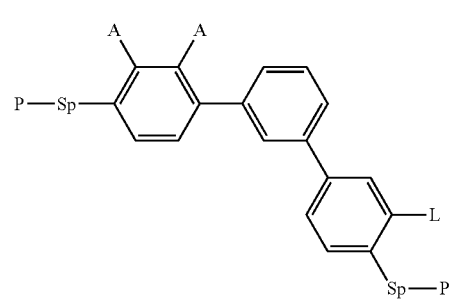
I5A-14-1
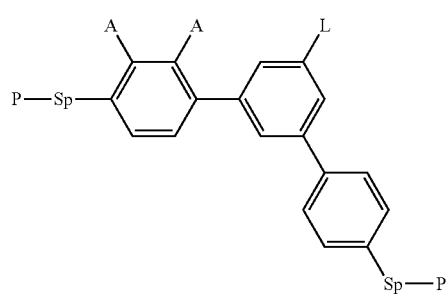
I5A-16-1
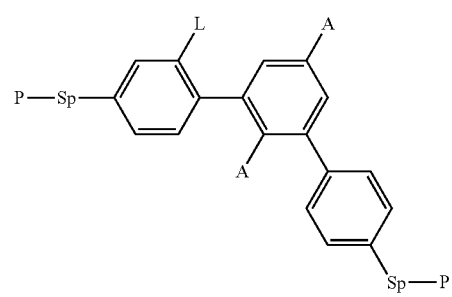
I5A-14-2
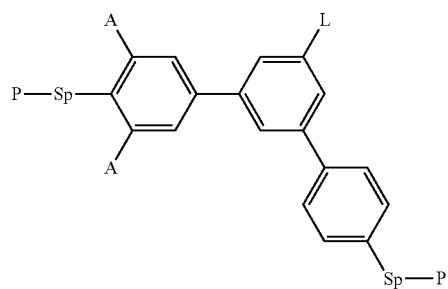
I5A-16-2
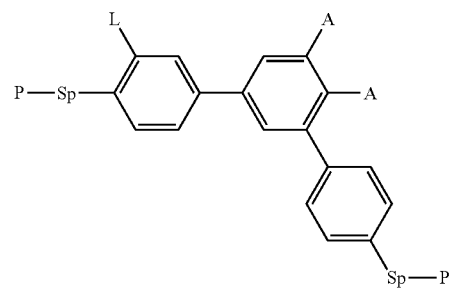

-continued
I5A-18-1
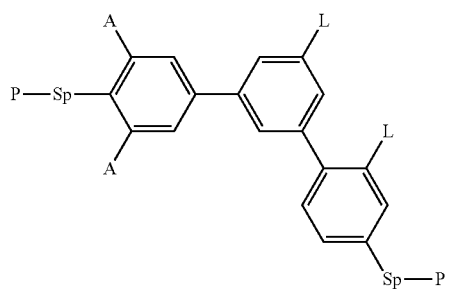
I5A-18-2
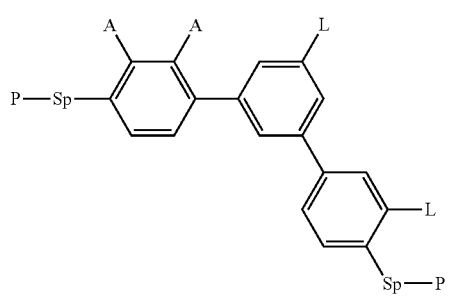
I5A-19-1
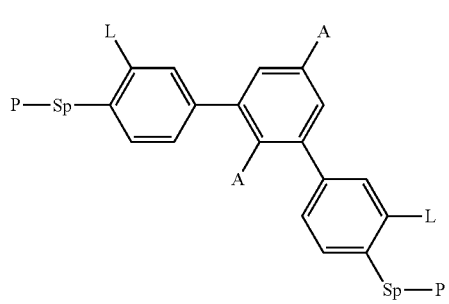
I5A-19-2
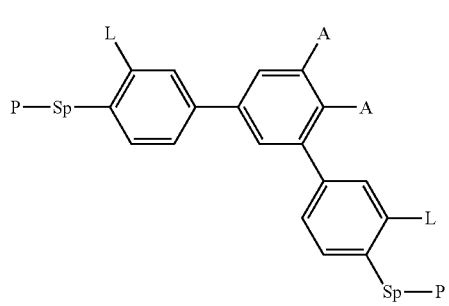
I5A-19-3
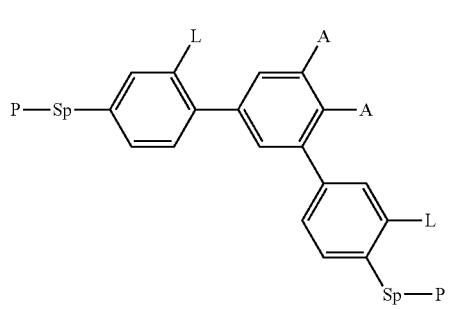
-continued
I5B-1-1
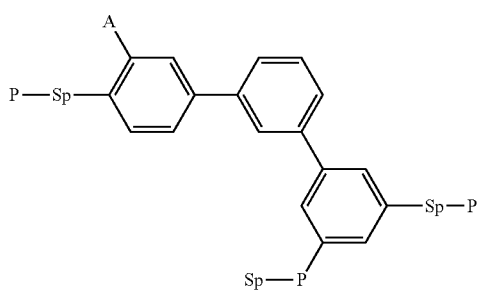
I5B-1-2
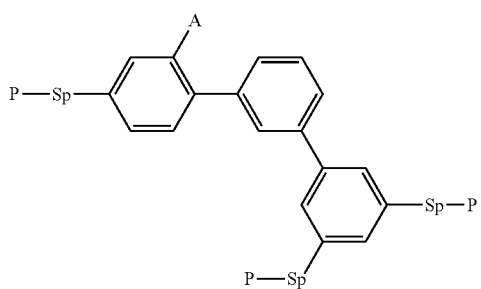
I5B-1-3
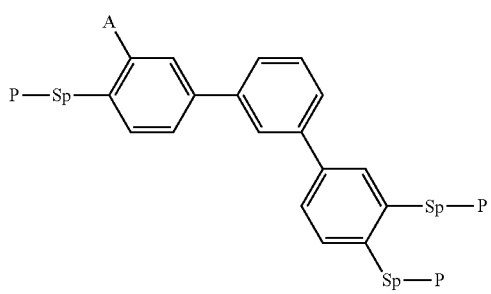
I5B-1-4
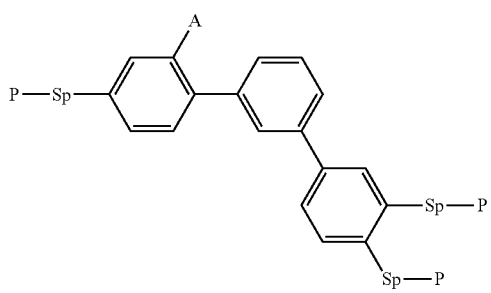
I5B-2-1
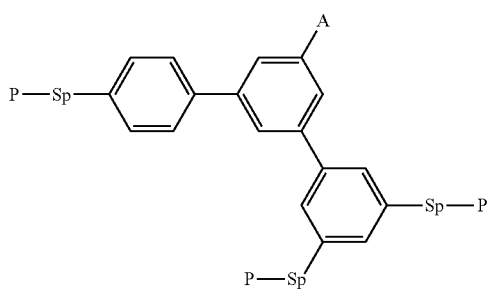

I5B-2-2
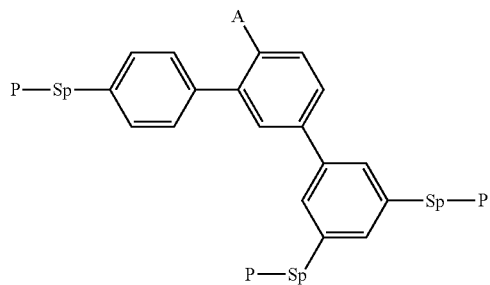
I5B-2-3
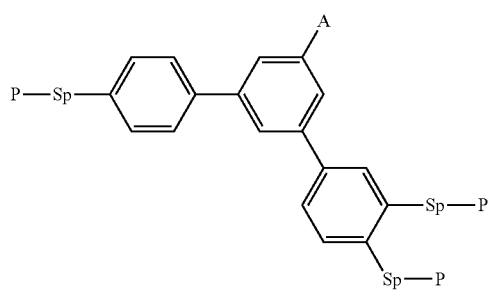
I5B-2-4
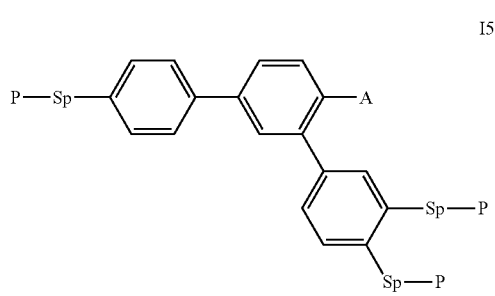
I5B-3-1
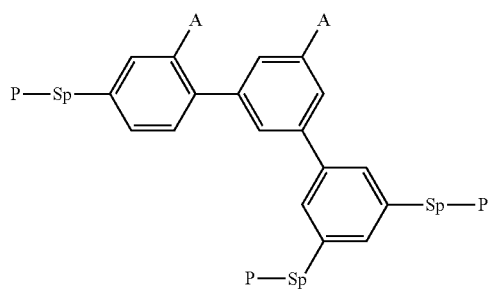
I5B-3-2
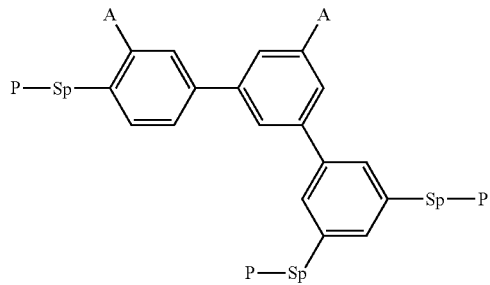
I5B-3-3
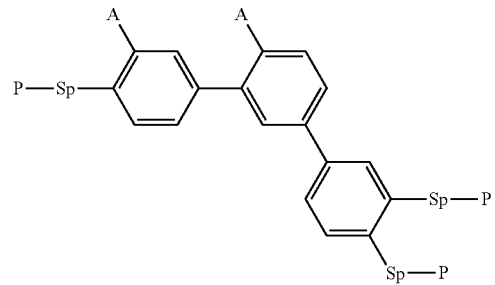
I5B-3-4
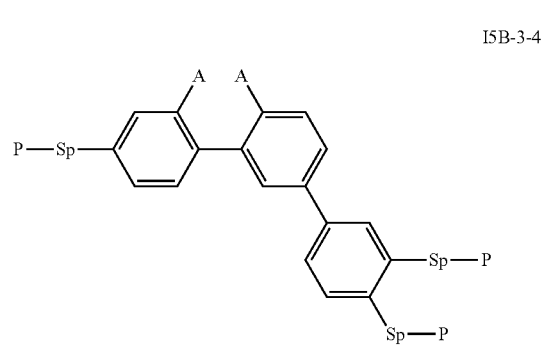
I5B-4-1
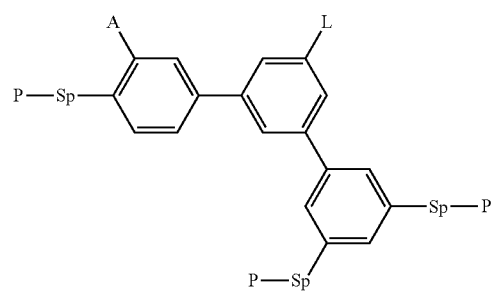
I5B-4-2
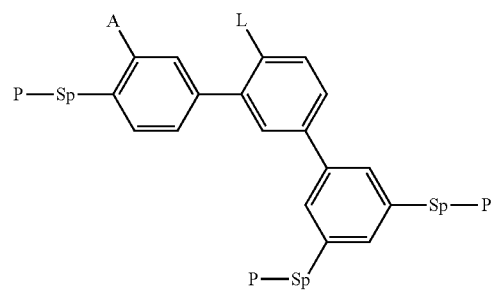
I5B-4-3
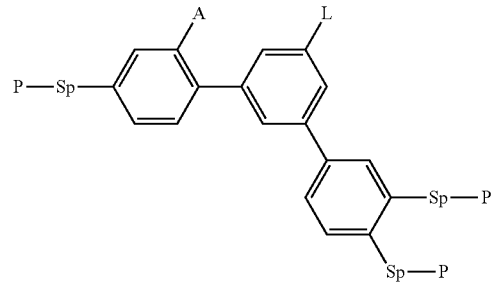

I5B-4-4
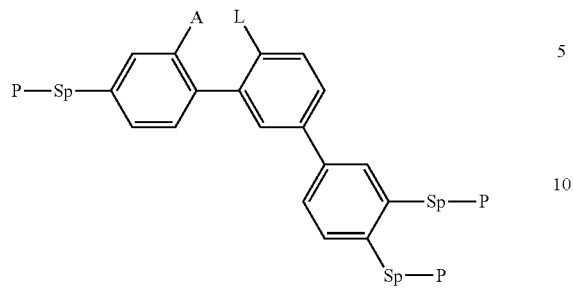
I5B-6-1
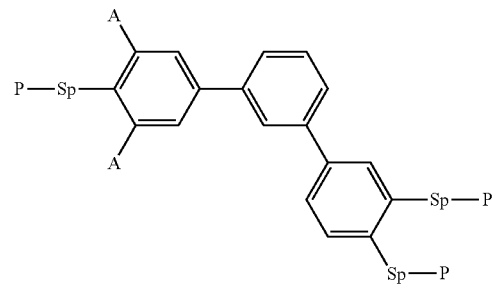
I5B-5-1
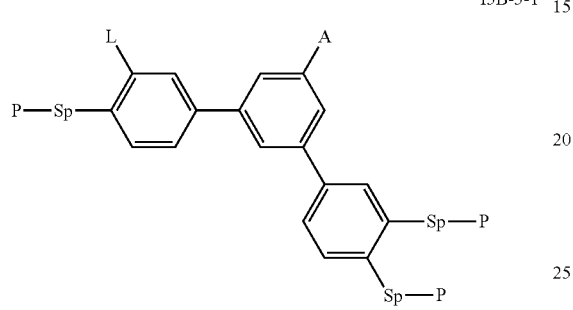
I5B-6-2
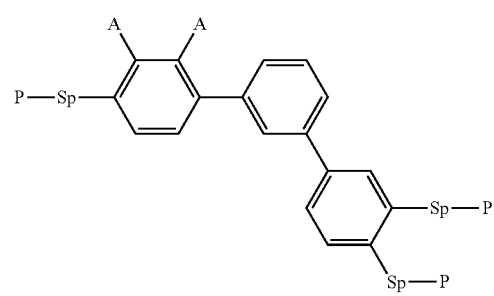
I5B-5-2
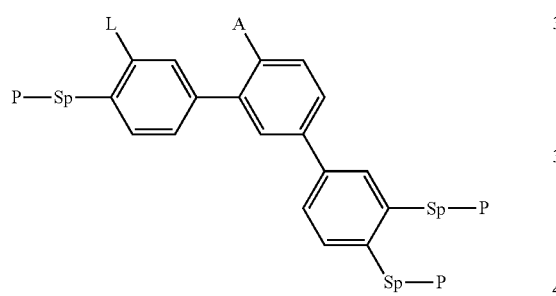
I5B-6-3
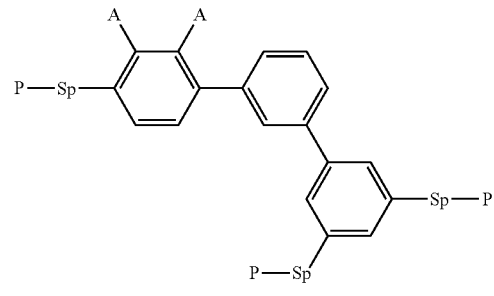
I5B-5-3
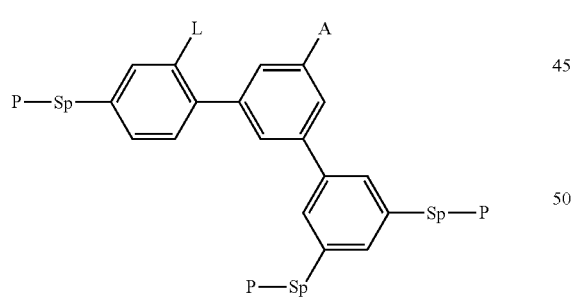
I5B-6-4
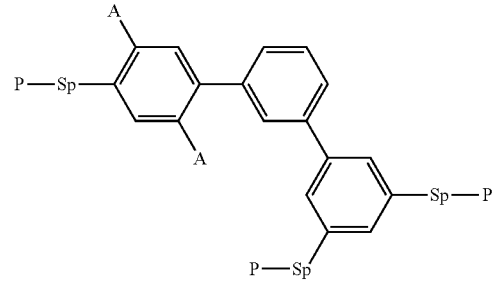
I5B-5-4
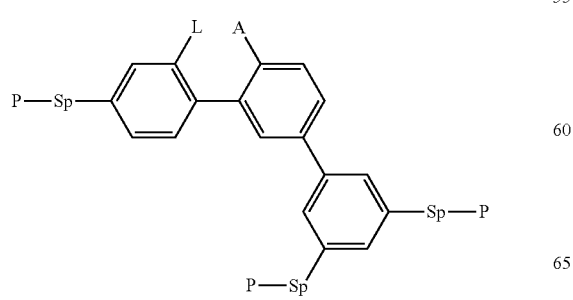
I5B-7-1
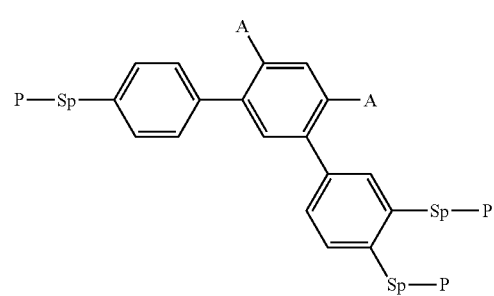

I5B-7-2
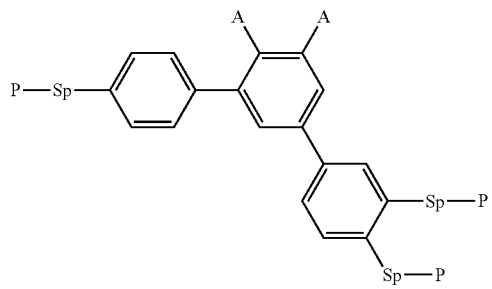
I5B-7-3
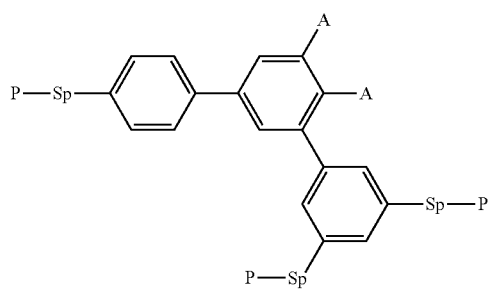
I5B-7-4
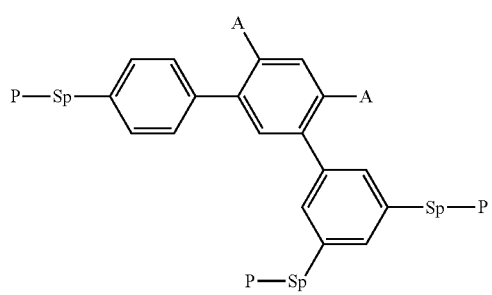
I5B-8-1
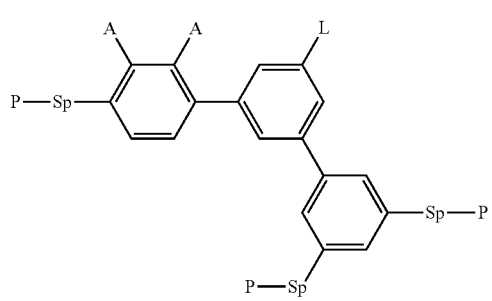
I5B-8-2
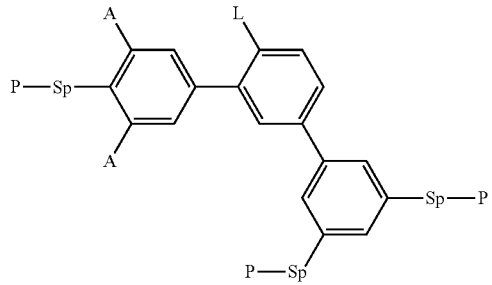
I5B-8-3
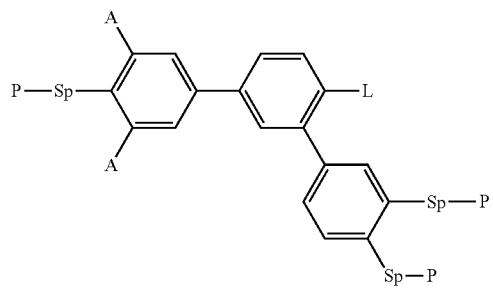
I5B-8-4
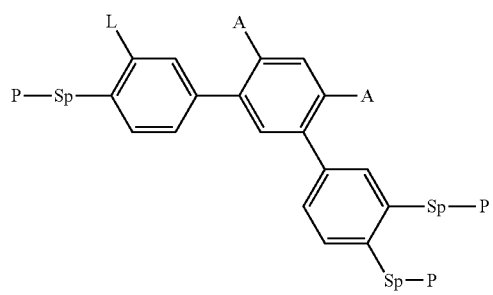
I5B-9-1
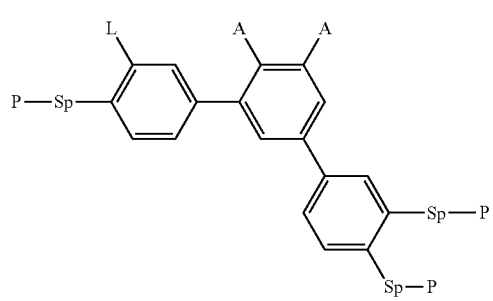
I5B-9-2
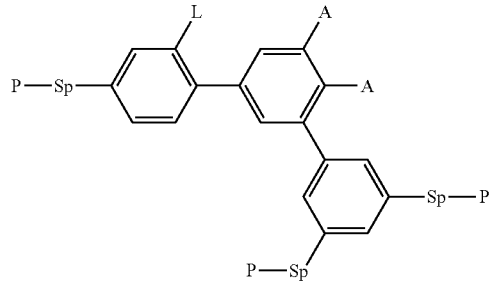
I5B-9-3
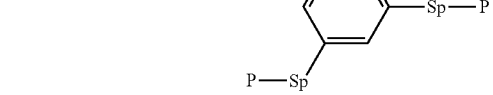

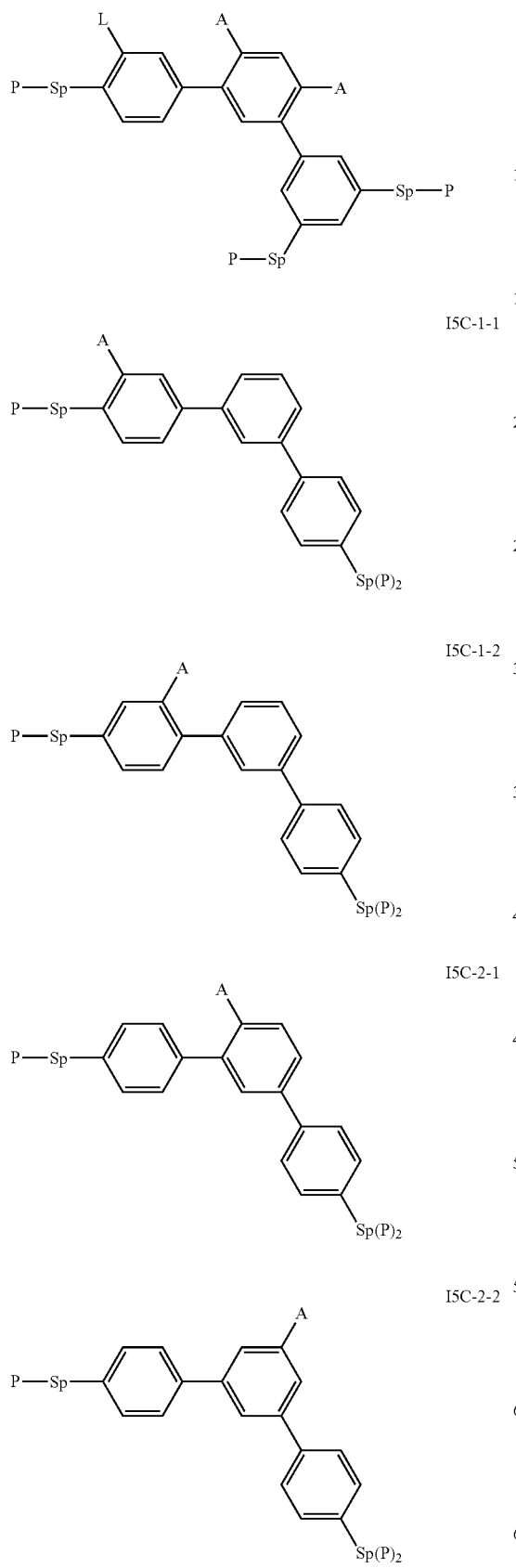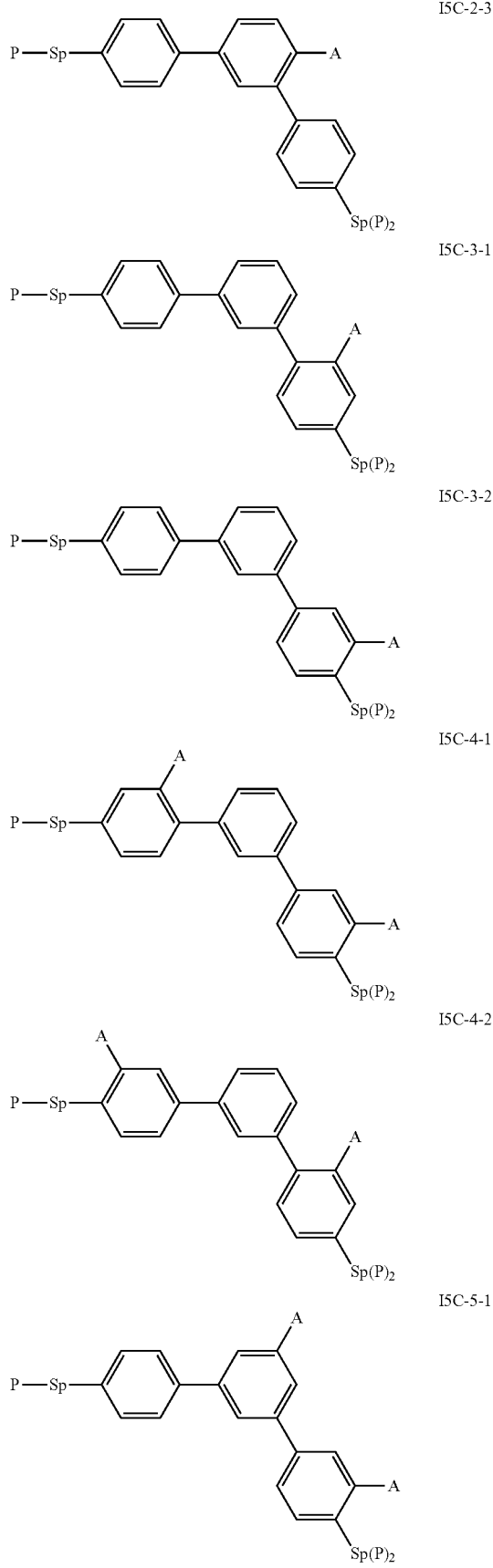

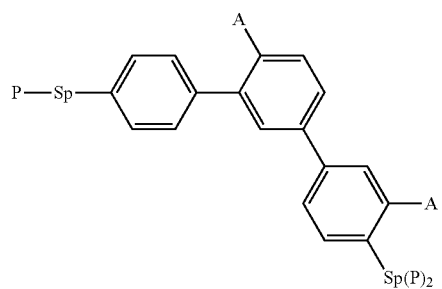
I5C-5-2
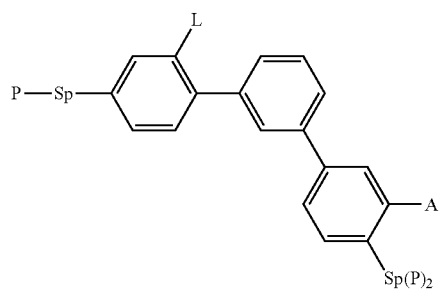
I5C-7-3
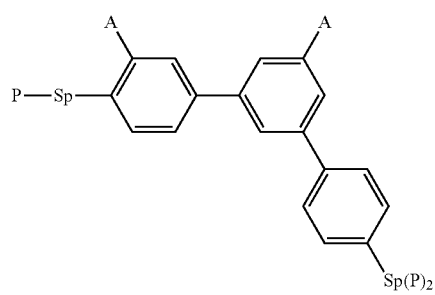
I5C-6-1
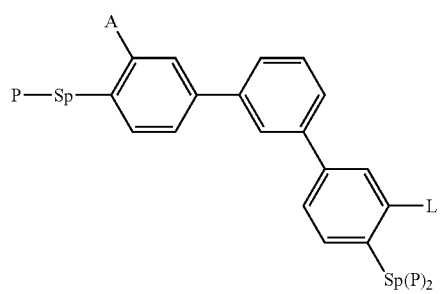
I5C-8-1
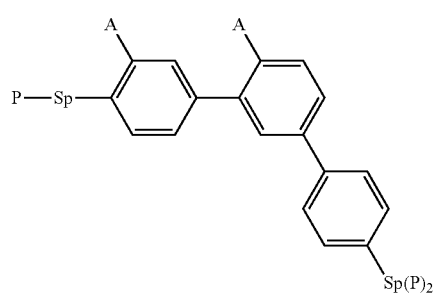
I5C-6-2
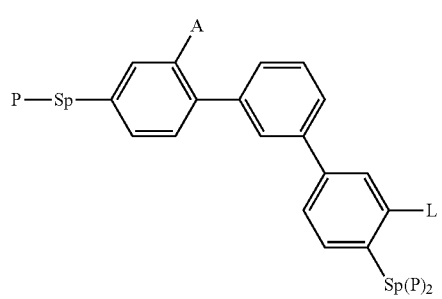
I5C-8-2
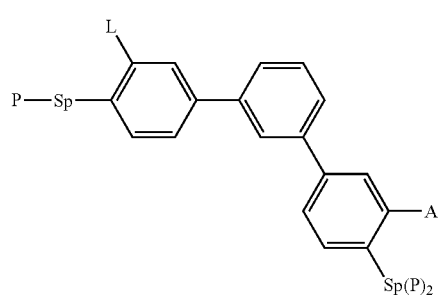
I5C-7-1
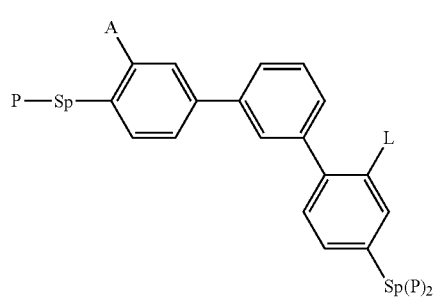
I5C-8-3
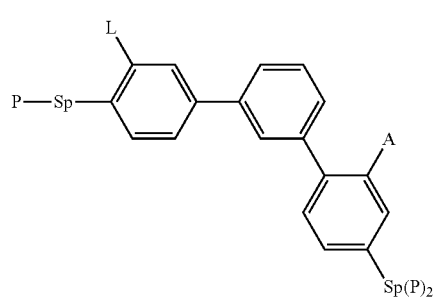
I5C-7-2
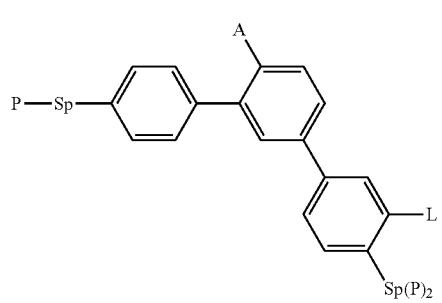
I5C-9-1

-continued

-continued
I5C-12-1
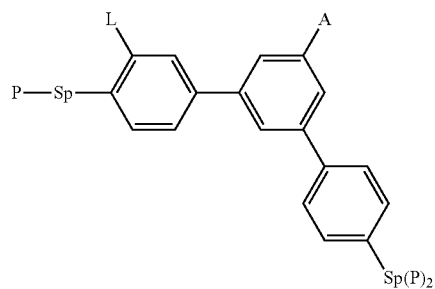
I5C-12-2
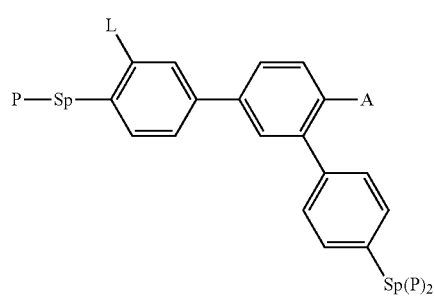
I5C-12-3
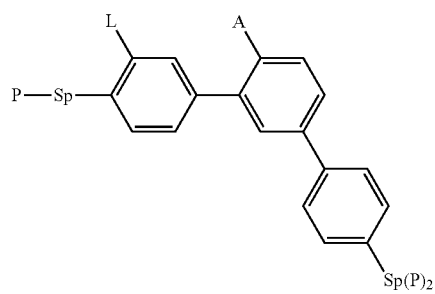
I5C-12-4
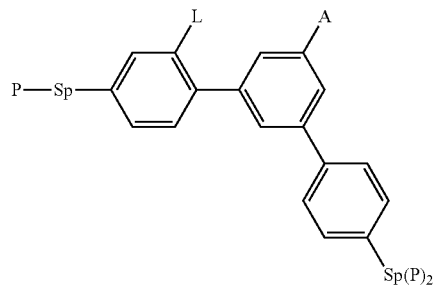
I5C-13-1
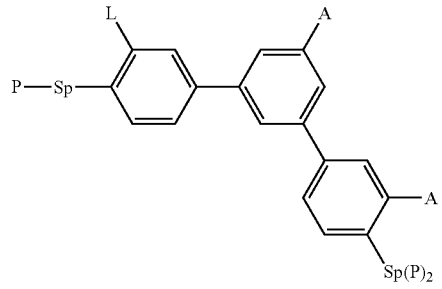
-continued
I5C-13-2
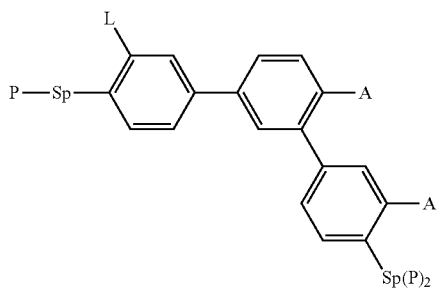
I5C-13-3
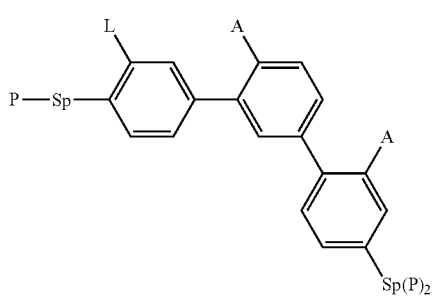
I5C-13-4
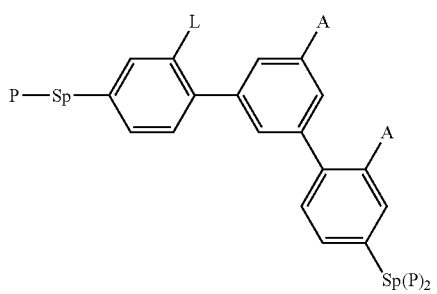
I5C-14-1
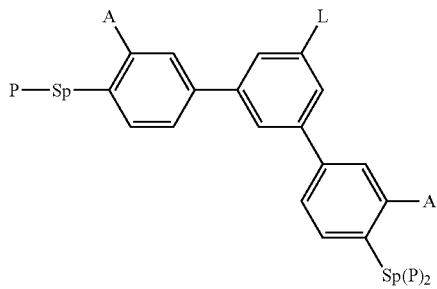
I5C-14-2
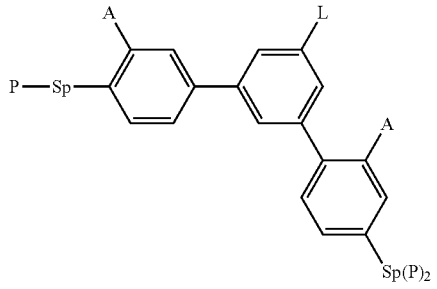

I5C-14-3
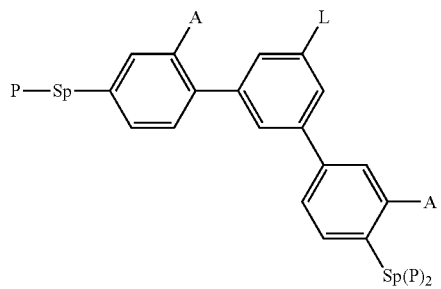
I5C-14-4
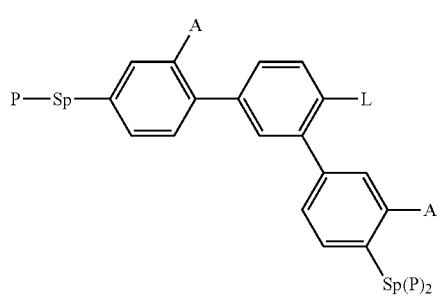
I5C-15-1
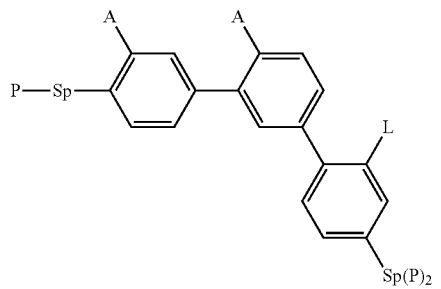
I5C-15-2
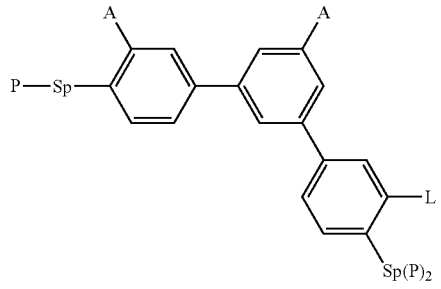
I5C-15-3
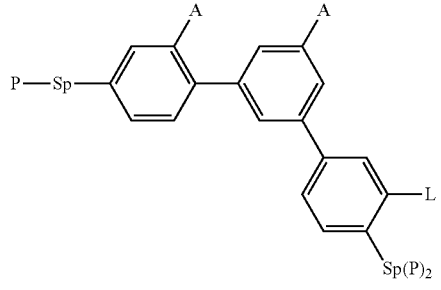
I5C-15-4
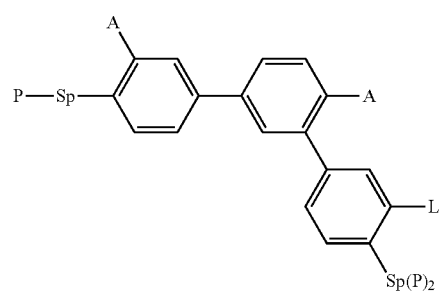
I5C-16-1
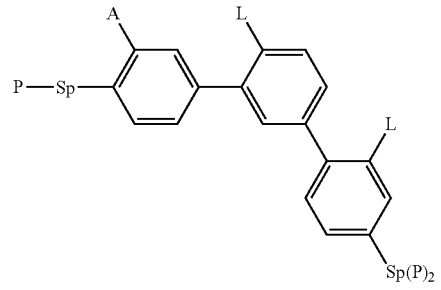
I5C-16-2
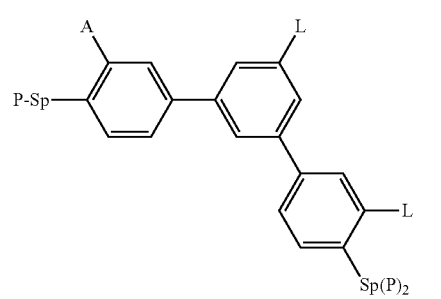
I5C-16-3
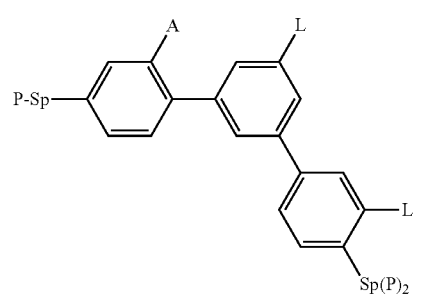
I5C-16-4
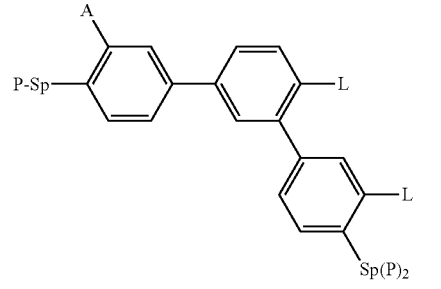

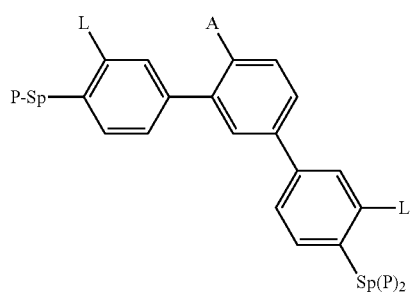
l5C-17-1
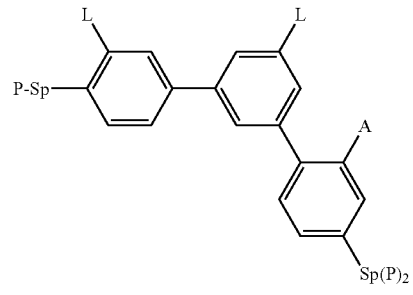
l5C-18-2
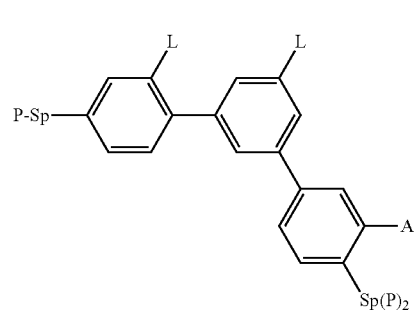
l5C-18-3
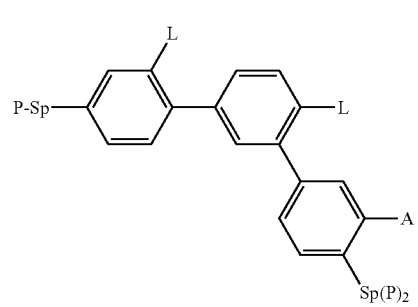
l5C-18-4
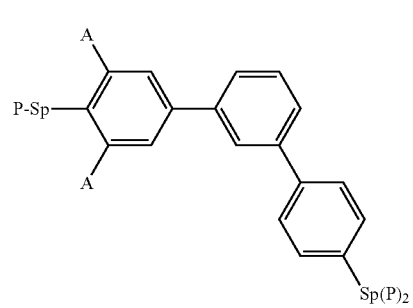
l5C-19-1
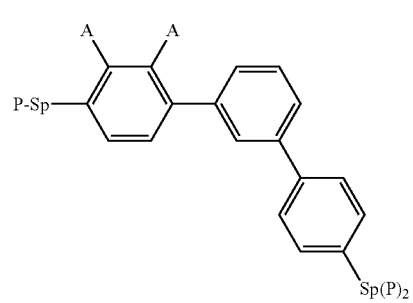
l5C-19-2

-continued
l5C-20-1
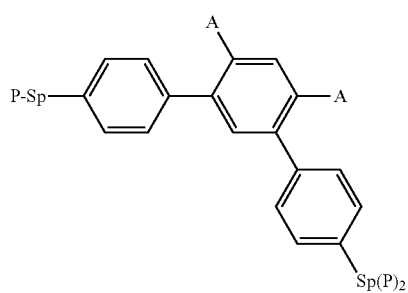
l5C-20-2
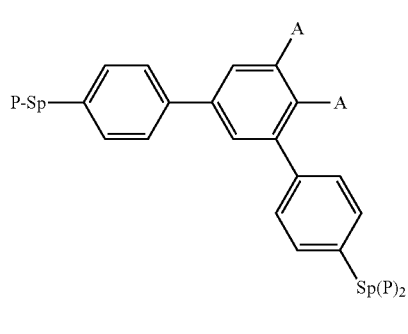
l5C-20-3
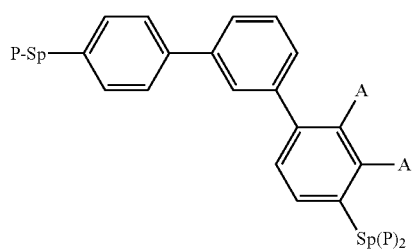
l5C-21-1
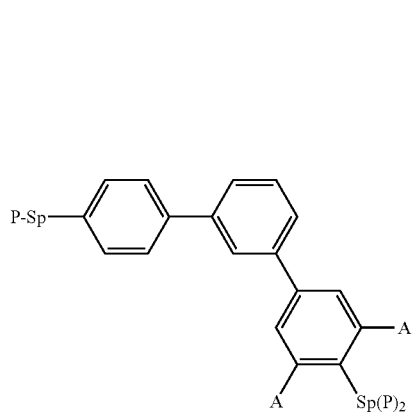
l5C-21-2
l5C-22-1
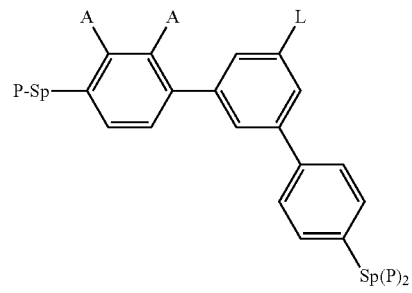
l5C-22-2
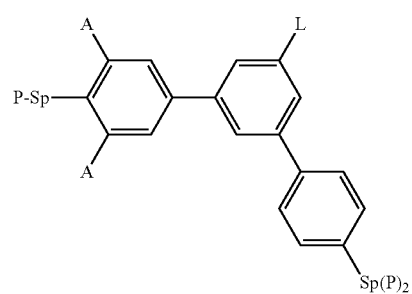
l5C-22-3
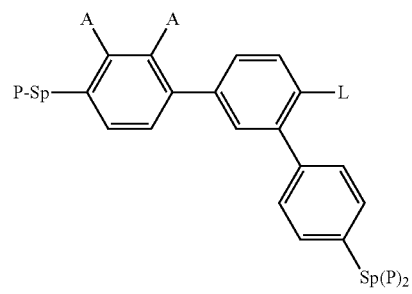
l5C-23-1
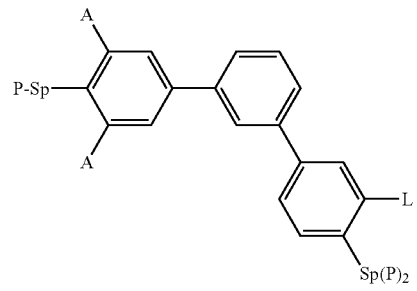
l5C-23-2
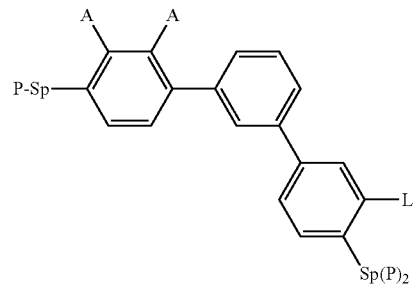

l5C-23-3
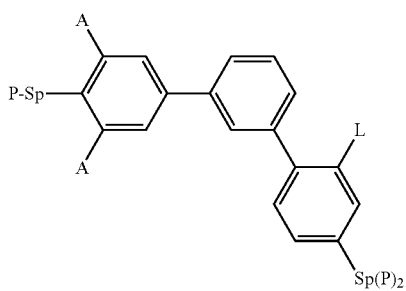
l5C-24-1
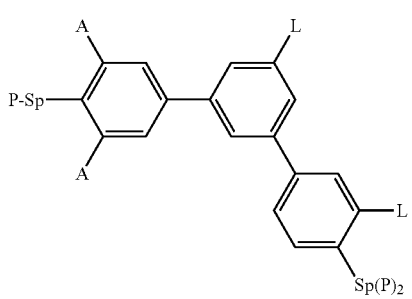
l5C-24-2
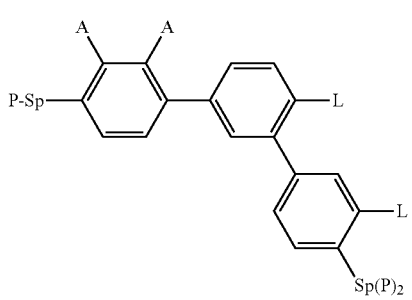
l5C-24-3
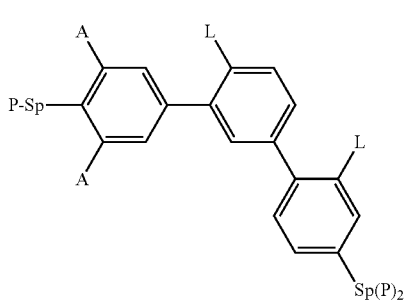
l5C-24-4
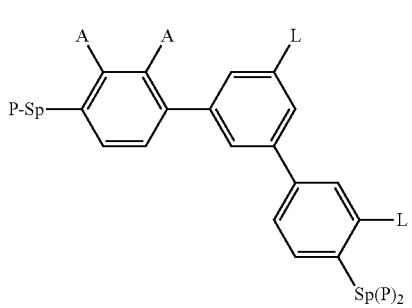
l5C-26-1
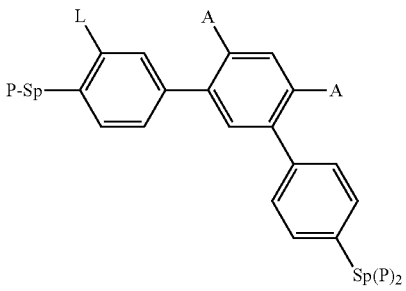
l5C-26-2
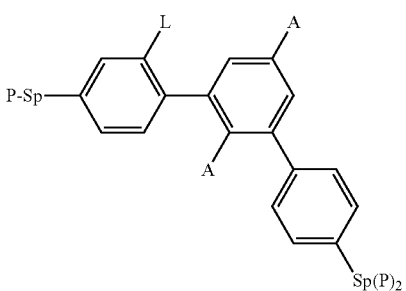
l5C-26-3
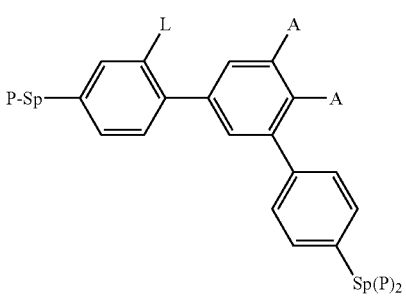
l5C-27-1
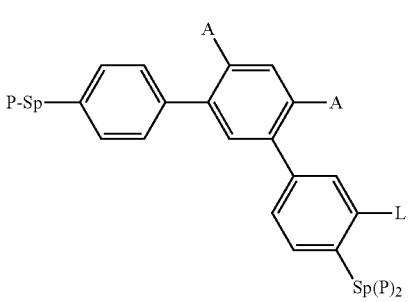
l5C-27-2
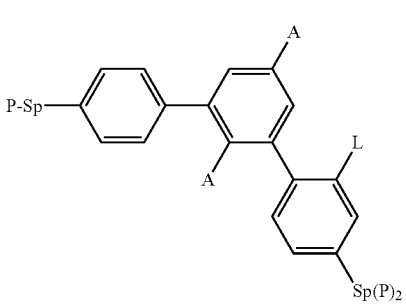

-continued
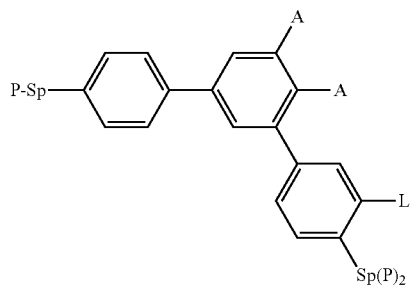 l5C-27-3
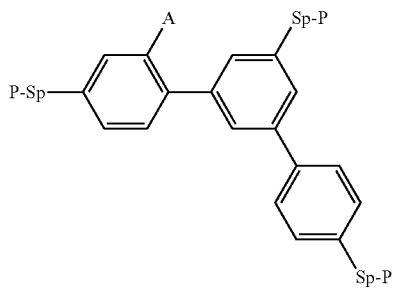 l5D-1-2
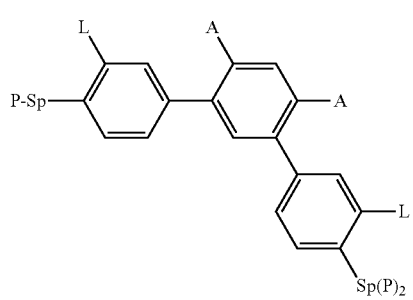 l5C-28-1
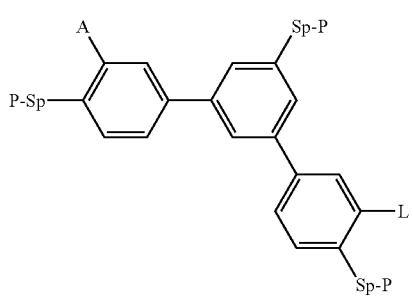 l5D-2-1
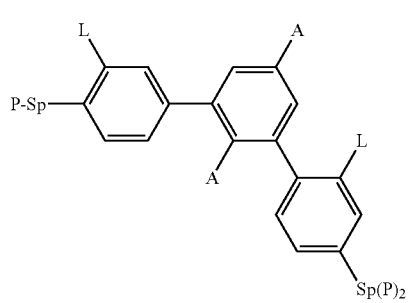 l5C-28-2
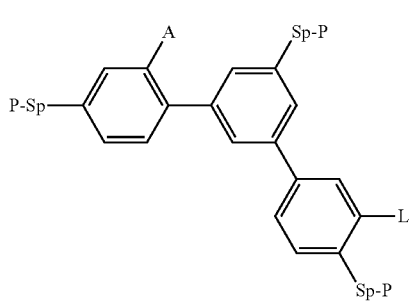 l5D-2-2
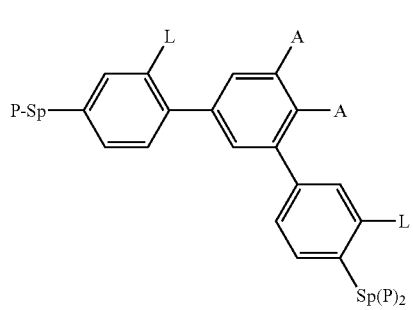 l5C-28-3
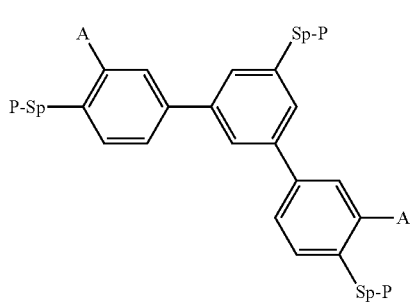 l5D-3-1
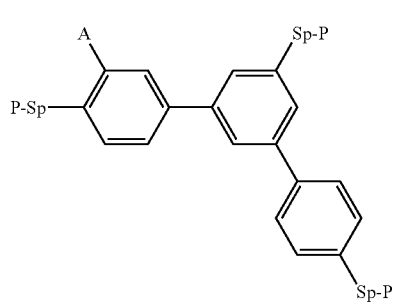 l5D-1-1
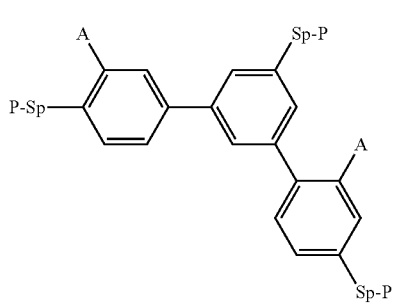 l5D-3-2 l5D-3-3

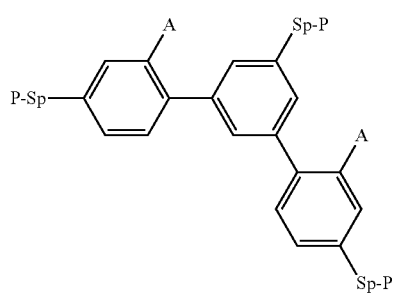

l5D-4-1

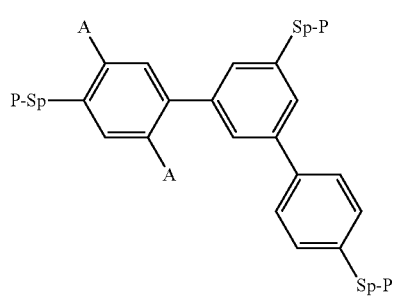

l5D-4-2

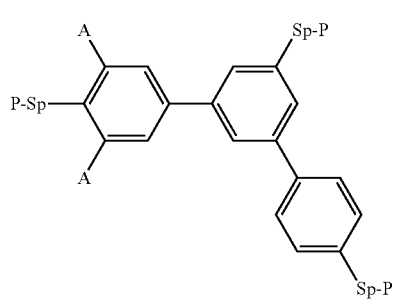

l5D-4-3

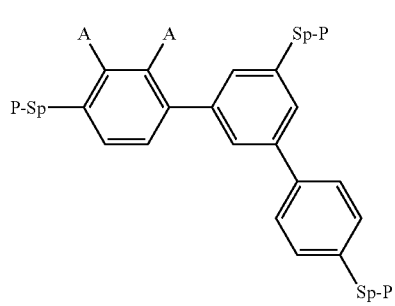

l5D-5-1

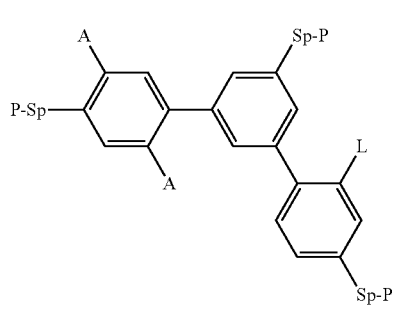

l5D-5-2

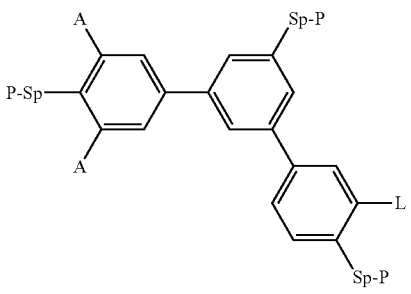

l5D-5-3

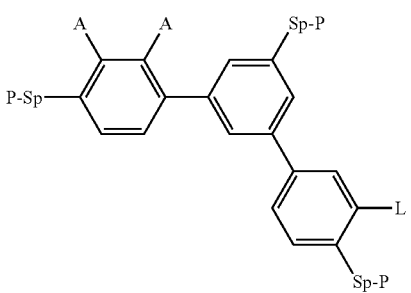

I6A-1-1

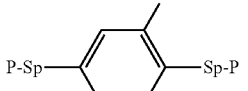

I6A-2-1

I6B-1-1

I6B-2-1

I6C-1-1

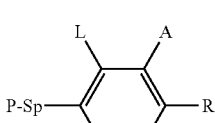

wherein A, L, R, P, Sp and Sp(P)$_2$ have the meanings given in formula I or one of the preferred meanings given above and below, and A is preferably thioalkyl with 1 to 7 C atoms which is preferably straight-chain, more preferably —SCH$_3$, —SC$_2$H$_5$ or —SC$_3$H$_7$, very preferably —SCH$_3$, further preferably —CH$_2$S—CH$_3$ or —CH$_2$—S—C$_2$H$_5$.

Very preferred are compounds selected from the group consisting of formulae I1A-1-1 to I2D-30-4.

Preferred are compounds of the formulae I1A-1-1 to I1B-8-6, I1D-1-1 to I2C-15-4, I2E-1-1 to I5B-9-4 and I5D-1-1 to I5D-5-3.

Further preferred are compounds of the formulae I1A-1-1 to I1A-7-3, I2A-1-1 to I2A-18-12, I5A-1-1 to I5A-19-3 and I6A-1-1 to I6B-2-1 wherein all groups Sp are a single bond. Further preferred are compounds of the formulae I1A-1-1 to I1A-7-3, I2A-1-1 to I2A-18-2, I5A-1-1 to I5A-19-3 and I6A-1-1 to I6B-2-1 wherein one of the groups Sp denotes a single bond and the other group Sp is different from a single bond.

Further preferred are compounds of the formulae I1B-1-1 to I1B-8-6, I1D-1-1 to I1G-3-1, I2B-1-1 to I2C-15-4, I2E-1-1 to I2G-4-1, I5B-1-1 to I5B-9-4, I5D-1-1 to I5D-5-3 and I6C-1-1 wherein all groups Sp are a single bond. Further preferred are compounds of the formulae I1B-1-1 to I1B-8-6, I1D-1-1 to I1G-3-1, I2B-1-1 to I2C-15-4, I2E-1-1 to I2G-4-1, I5B-1-1 to I5B-9-4, I5D-1-1 to I5D-5-3 and I6C-1-1 wherein one or two of the groups Sp denote a single bond and the other groups Sp are different from a single bond. Further preferred are compounds of the formulae I1B-1-1 to I1B-8-6, I1D-1-1 to I1G-3-1, I2B-1-1 to I2C-15-4, I2E-1-1 to I2G-4-1, I5B-1-1 to I5B-9-4, I5D-1-1 to I5D-5-3 and I6C-1-1 wherein one or two of the groups Sp are different from a single bond and the other groups Sp denote a single bond.

Further preferred are compounds of the formulae I1C-1-1 to I1C-13-3, I2D-1-1 to I2D-30-4 and I5C-1-1 to I5C-28-3 wherein in the radical P-Sp the group Sp is a single bond. Further preferred are compounds of the formulae I1C-1-1 to I1C-13-3, I2D-1-1 to I2D-30-4 and I5C-1-1 to I5C-28-3 wherein all groups Sp are different from a single bond Further preferred are compounds of the formulae I1A-1-1 to I6C-1-1 are those wherein A denotes thioalkyl with 1 to 7 C atoms which is preferably straight-chain, more preferably —$SCH_3$, —$SC_2H_5$ or —$SC_3H_7$, most preferably —$SCH_3$, further preferably —$CH_2S$—$CH_3$ or —$CH_2$—S—$C_2H_5$.

Further preferred are compounds of the formulae I1A-1-1 to I6C-1-1 wherein L denotes F, Cl, CN or $OCH_3$, very preferably F.

Further preferred are compounds of the formulae I1A-1-1 to I6C-1-1 wherein P denotes acrylate or methacrylate, very preferably methacrylate.

Further preferred are compounds of the formulae I1A-1-1 to I6C-1-1 wherein Sp, when being different from a single bond, denotes alkylene with 2 to 6 C atoms.

Further preferred are compounds of the formulae I1A-1-1 to I6C-1-1 where all groups Sp denote a single bond, all groups P denote methacrylate, all groups A denote S—$CH_3$, and all groups L denote F.

Preferred compounds of formula I and II and their subformulae are selected from the following preferred embodiments, including any combination thereof:

the compounds contain one group A,
the compounds contain two or more groups A,
the compounds contain one or more groups A and one or more groups L,
the compounds contain two unfused or fused, preferably unfused, benzene rings,
the compounds contain three or more, preferably three or four unfused or fused benzene rings,
the compounds contain at least one benzene ring that is not substituted by A or L,
A is thioalkyl with 1 to 7 C atoms which is preferably straight-chain, more preferably —$SCH_3$, —$SC_2H_5$ or —$SC_3H_7$, very preferably —$SCH_3$,
A is —$CH_2S$—$CH_3$ or —$CH_2$—S—$C_2H_5$,
the compounds contain exactly one polymerizable group (represented by the group P),
the compounds contain exactly two polymerizable groups (represented by the groups P),
the compounds contain exactly three polymerizable groups (represented by the groups P),
the compounds contain exactly four polymerizable groups (represented by the groups P),
P is selected from the group consisting of acrylate, methacrylate and oxetane, very preferably acrylate or methacrylate,
P is methacrylate,
Pg is a hydroxyl group,
each of the groups Sp denotes a single bond,
at least one of the groups Sp is different from a single bond,
at least one of the groups Sp is a single bond and at least one of the groups Sp is different from a single bond,
Sp, when being different from a single bond, is selected from —$(CH_2)_{p2}$—, —$(CH_2)_{p2}$—O—, —$(CH_2)_{p2}$—CO—O—, —$(CH_2)_{p2}$—O—CO—, wherein p2 is 2, 3, 4, 5 or 6, and the O-atom or the CO-group, respectively, is connected to the benzene ring,
Sp, when being different from a single bond, is selected from —$(CH_2)_2$—, —$(CH_2)_3$—, —$(CH_2)_4$—, —O—$(CH_2)_2$—, —O—$(CH_2)_3$—, —O—CO—$(CH_2)_2$ and —CO—O—$(CH_2)_2$—, wherein the O atom or the CO group is attached to the benzene ring
Sp is a single bond or denotes —$(CH_2)_{p2}$—, —$(CH_2)_{p2}$—O—, —$(CH_2)_{p2}$—CO—O—, —$(CH_2)_{p2}$—O—CO—, wherein p2 is 2, 3, 4, 5 or 6, and the O-atom or the CO-group, respectively, is connected to the benzene ring,
$Sp(P)_2$ is selected from subformulae Sp1a-Sp3a,
$R^b$ denotes P-Sp-,
$R^b$ does not denote or contain a polymerizable group,
$R^b$ denotes denotes F, Cl, CN or straight chain, branched or cyclic alkyl having 1 to 25 C atoms, wherein one or more non-adjacent $CH_2$-groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by F or Cl,
R denotes F, Cl, CN or straight chain, branched or cyclic alkyl having 1 to 25 C atoms, wherein one or more non-adjacent $CH_2$-groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by F or Cl,
$Z^1$ is a single bond,
z is 0, 1, 2 or 3, very preferably 0 or 1,
L is selected from the group consisting of F, Cl, CN, alkyl, alkoxy, alkylcarbonyl, alkoxycarbonyl, alkylcarbonyloxy or alkoxycarbonyloxy each having 1 to 6 C atoms, in which one or more H atoms may optionally be replaced by F or Cl, preferably F, Cl, CN or $OCH_3$, very preferably F.

Very preferred compounds of formula I and its subformulae are selected from the following subformulae:

149 150
I1A-1-1a
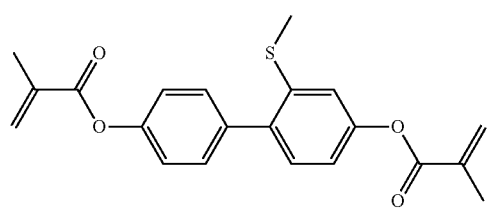
I1A-1-1b
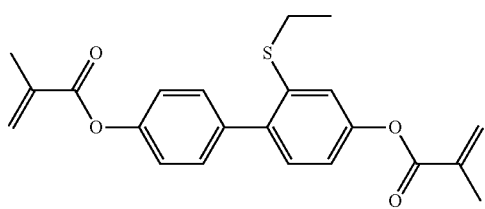
I1A-1-1c
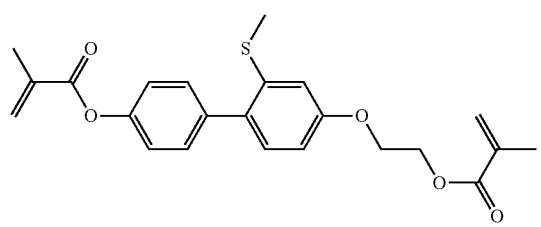
I1A-1-1d
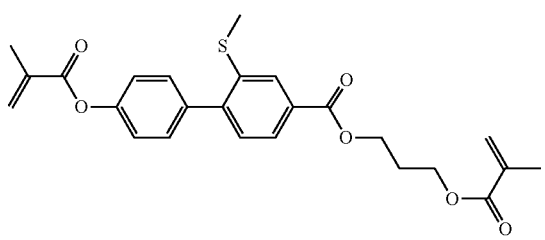
I1A-1-2a
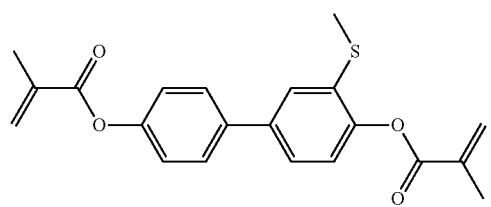
I1A-1-2b
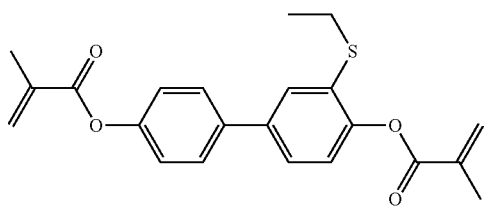
I1A-1-2c
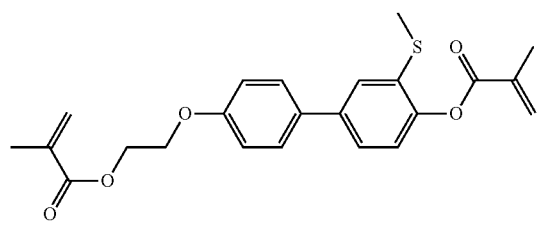
I1A-1-2d
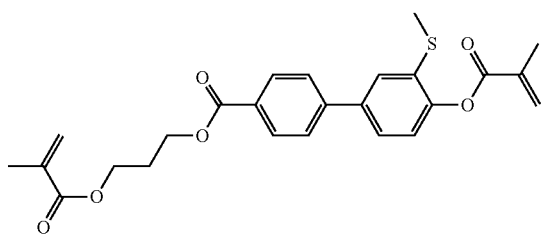
I1A-1-2e
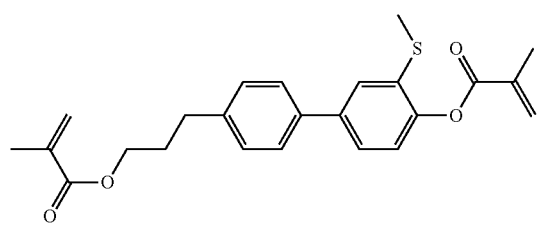
I1A-2-1a
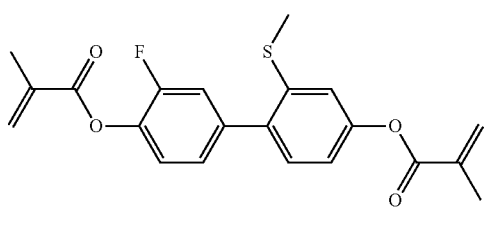
I1A-2-1b
I1A-2-2a
I1A-2-2b
I1A-2-3a
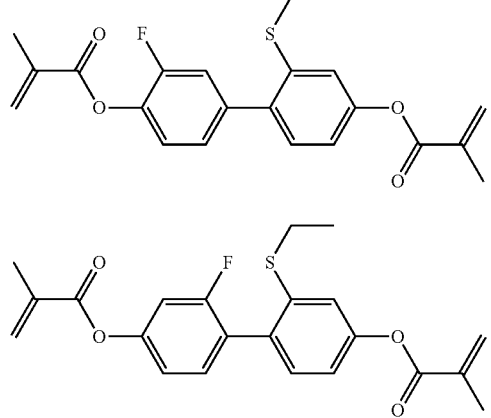
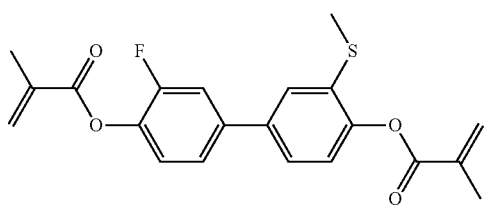

-continued
I1A-2-3b
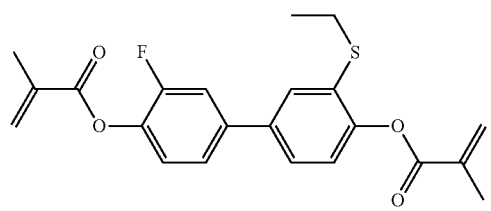
I1A-2-4a
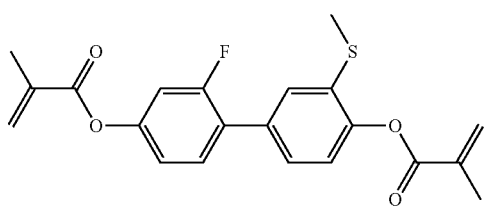
I1A-2-4b
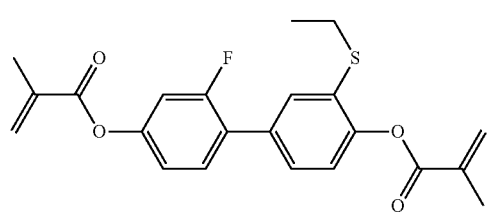
I1A-4-1a
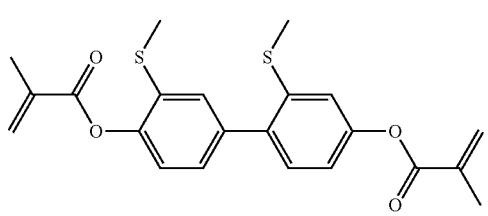
I1A-4-1b
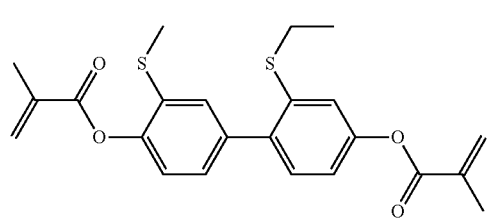
I1A-4-1c
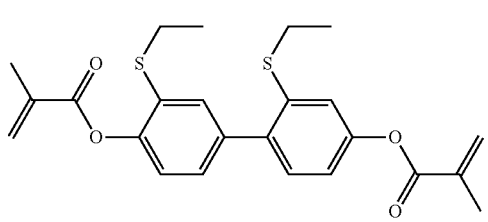
I1A-4-2a
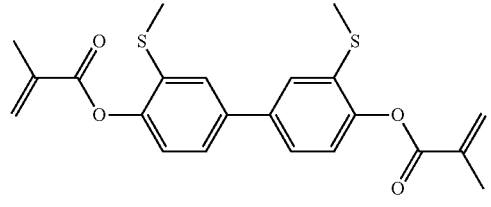
I1A-4-2b
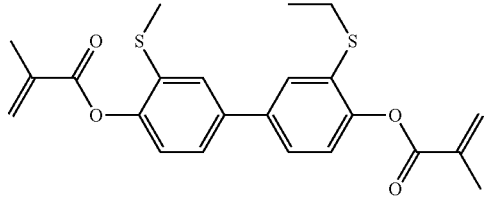
I1A-4-2c
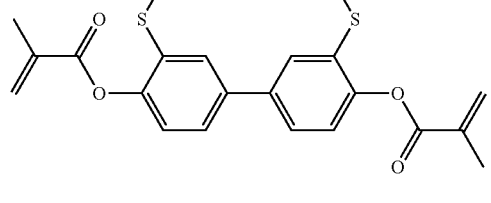
I1A-4-3a
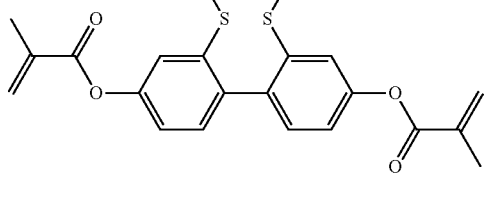
I1A-4-3b
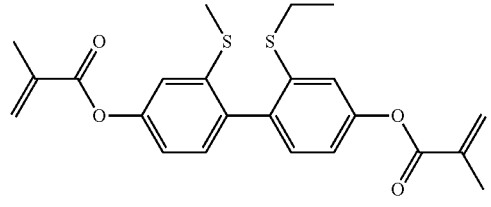
I1A-4-3c
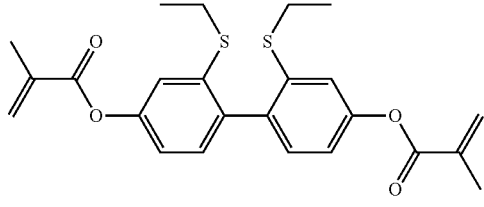
I1B-1-1a
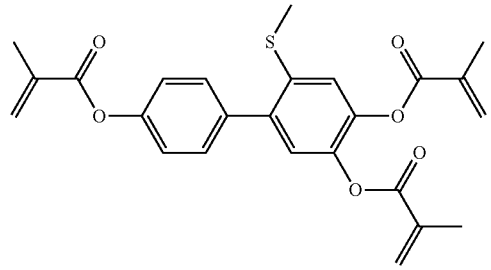
I1B-2-1a
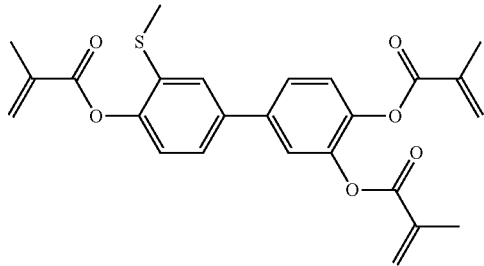

-continued
I1B-2-1b
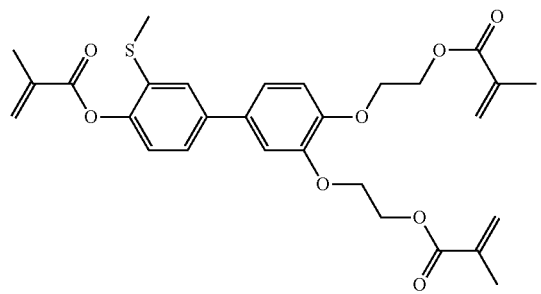
I1B-2-1c
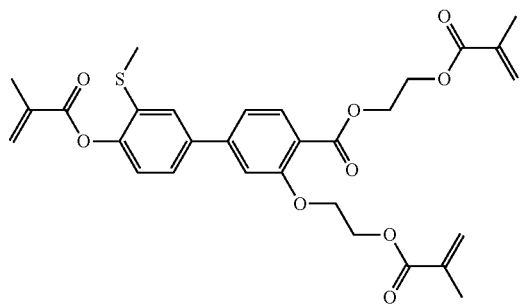
I1B-2-2a
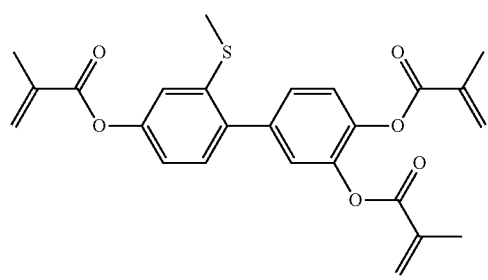
I1B-2-3a
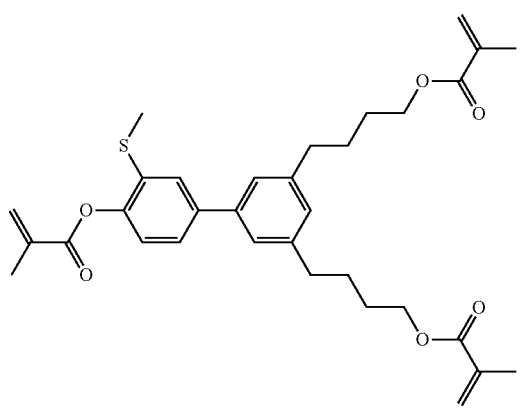
I1B-2-3b
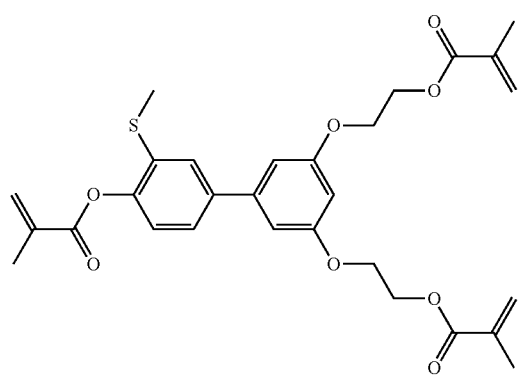
I1B-2-5a
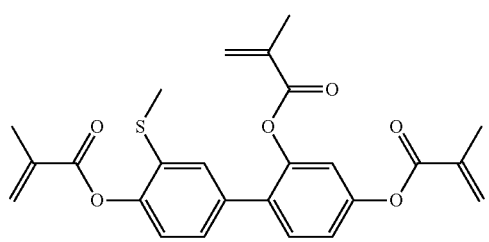
I1B-2-5b
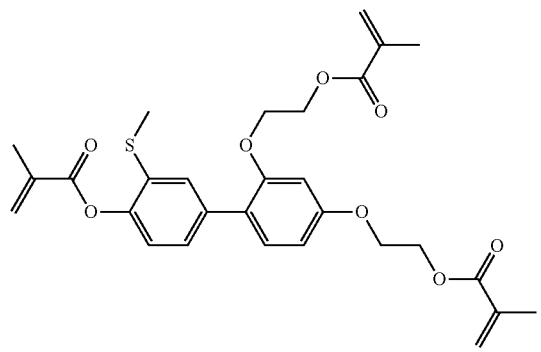
I2A-1-1a
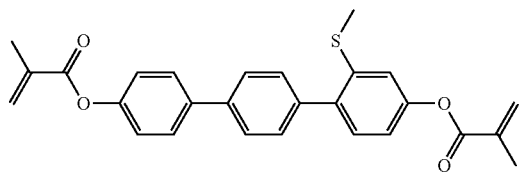

-continued
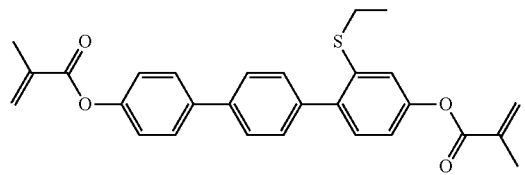
I2A-1-1b
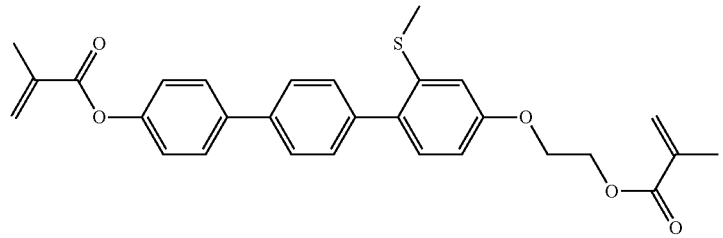
I2A-1-1c
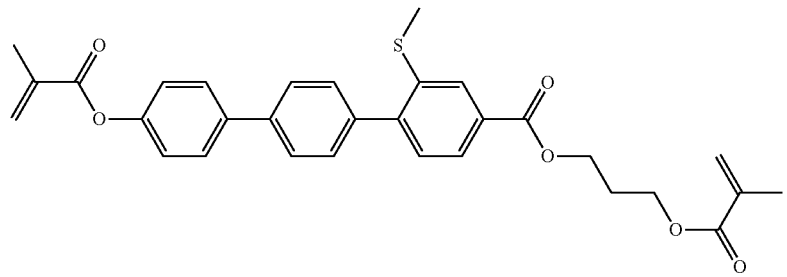
I2A-1-1d
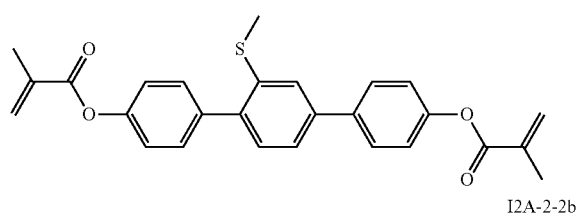
I2A-2-1a
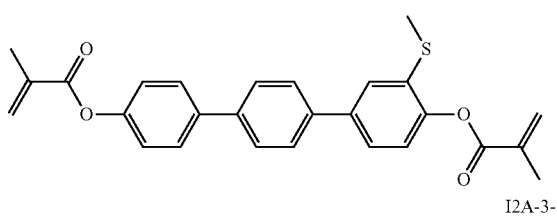
I2A-2-2a
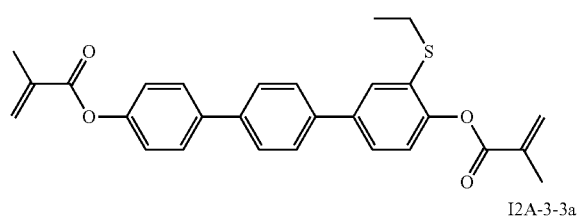
I2A-2-2b
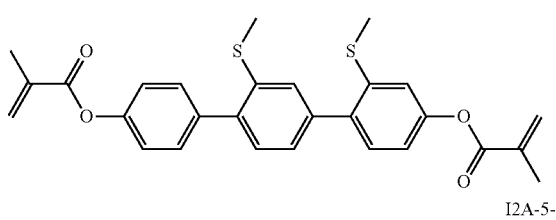
I2A-3-1a
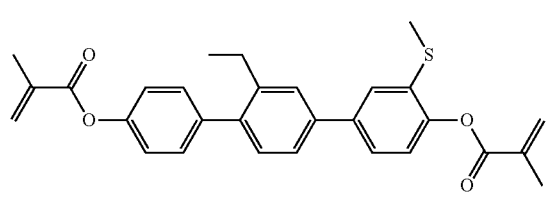
I2A-3-3a
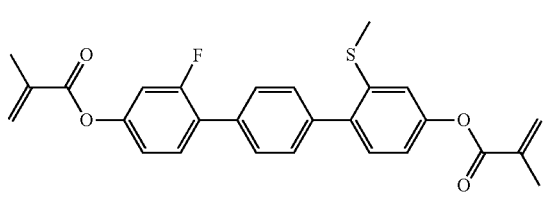
I2A-5-3a
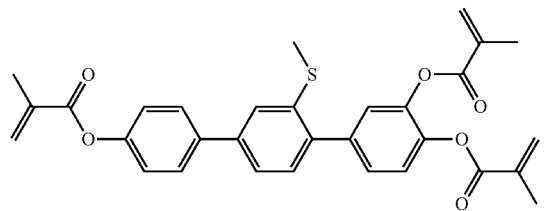
I2B-1-1a

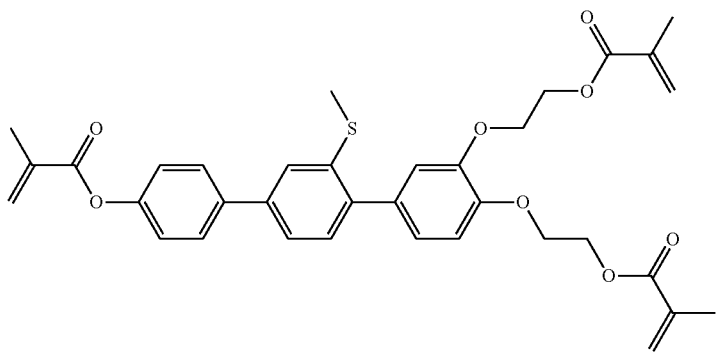

I2B-1-1b

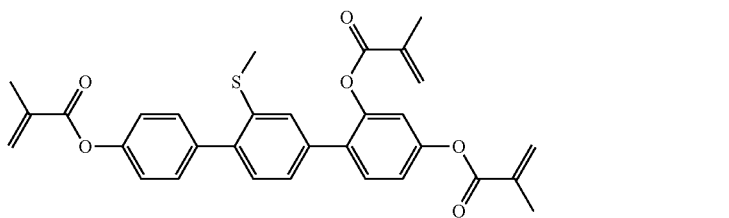

I2B-1-6a

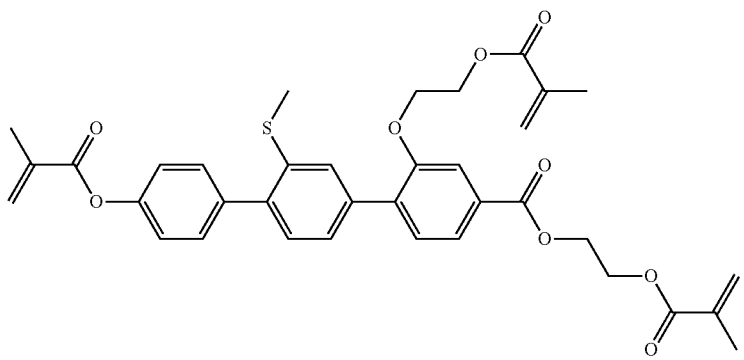

I2B-1-6b

Further preferred are compounds of formula I1A-1-1a to I2B-1-6b wherein one, two or three of the methacrylate groups are replaced by acrylate groups.

Very preferred compounds of formula are those selected from the above subformulae I1 to I6, I12, I1A to I6C, I12A to I12G, I1A-1 to I6C-1 and I1A-1-1 to I6C-1-1 wherein each group P is replaced by a group Pg as defined in formula II, and those selected from the above subformulae I1A-1-1a to I2B-1-6b wherein each methacrylate group is replaced by a group Pg as defined in formula II.

Suitable protected hydroxyl groups Pg for use in compounds of formula II and its subformulae are known to the person skilled in the art. Preferred protecting groups for hydroxyl groups are alkyl, alkoxyalkyl, acyl, alkylsilyl, arylsilyl and arylmethyl groups, especially 2-tetrahydropyranyl, methoxymethyl, methoxyethoxymethyl, acetyl, triisopropylsilyl, tert-butyl-dimethylsilyl or benzyl.

The term "masked hydroxyl group" is understood to mean any functional group that can be chemically converted into a hydroxyl group. Suitable masked hydroxyl groups Pg are known to the person skilled in the art.

The compounds of formula II are suitable as intermediates for the preparation of compounds of the formula I and its subformulae.

The invention further relates to the use of the compounds of formula II as intermediates for the preparation of compounds of the formula I and its subformulae.

The compounds and intermediates of the formulae I and II and sub-formulae thereof can be prepared analogously to processes known to the person skilled in the art and described in standard works of organic chemistry, such as, for example, in Houben-Weyl, Methoden der organischen Chemie [Methods of Organic Chemistry], Thieme-Verlag, Stuttgart.

For example, compounds of formula I can be synthesized by esterification or etherification of the intermediates of formula II, wherein Pg denotes OH, H, or protected or masked hydroxyl, using corresponding acids, acid derivatives, or halogenated compounds containing a polymerizable group P, optionally in the presence of a dehydrating reagent.

For example, acrylic or methacrylic esters can be prepared by esterification of the corresponding alcohols with acid derivatives like, for example, (meth)acryloyl chloride or (meth)acrylic anhydride in the presence of a base like pyridine or triethyl amine, and 4-(N,N-dimethylamino)pyridine (DMAP). Alternatively the esters can be prepared by esterification of the alcohols with (meth)acrylic acid in the presence of a dehydrating reagent, for example according to Steglich with dicyclohexylcarbodiimide (DCC), N-(3-dimethylaminopropyl)-N'-ethylcarbodiimide (EDC) or N-(3-dimethylaminopropyl)-N'-ethylcarbodiimide hydrochloride and DMAP.

A further suitable and preferred general synthesis methods for the compounds of formula I and II is shown below in Scheme 1.

Scheme 1

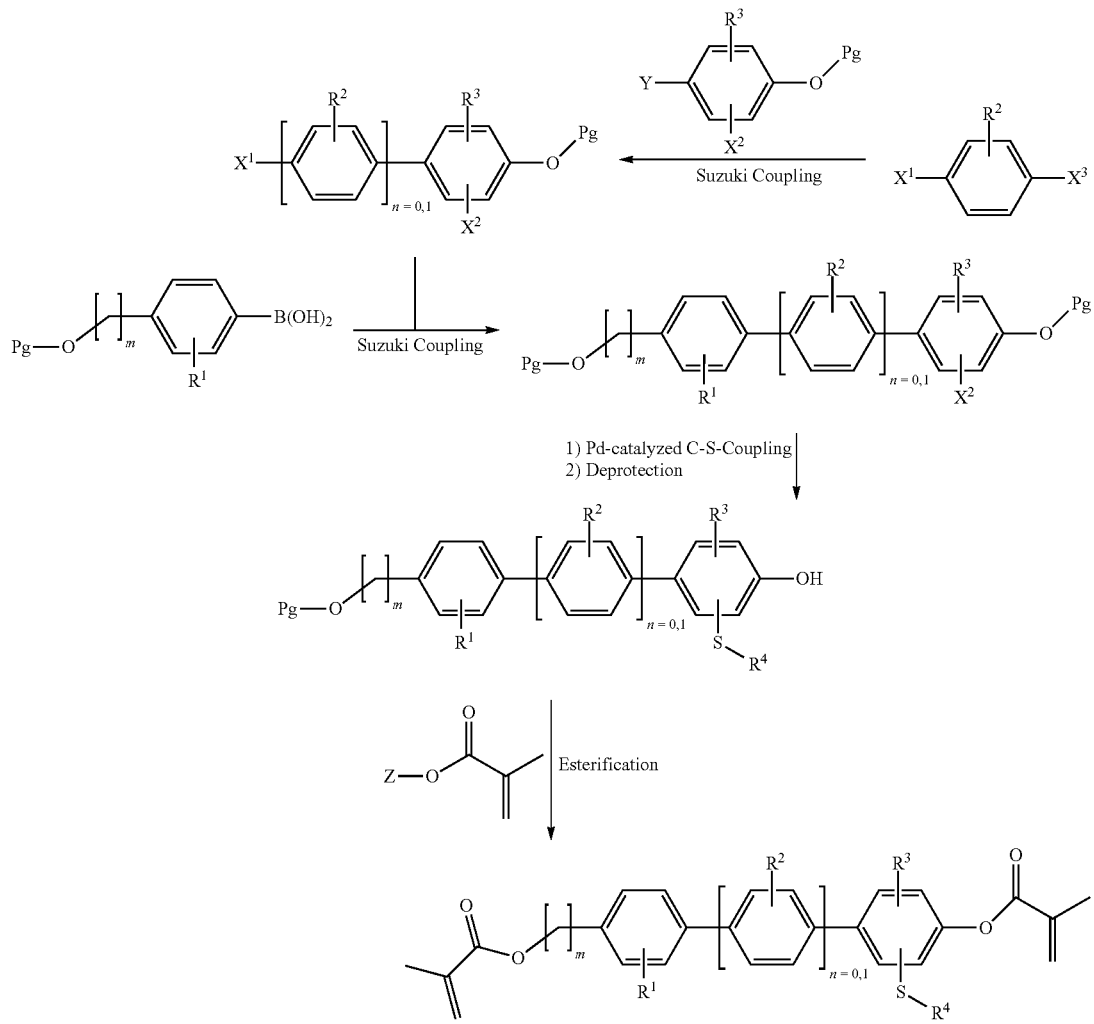

Wherein Z denote H or —R—OH, Y denote boronic ester, boronic acid or halogen, $X^{1,2,3}$ denote halogen, preferably Br or Cl, $R^{1,2,3,4}$ denote substituents, Pg denote protecting groups or H, m is ≥0, m=0 denotes a single bond.

Compounds of formula I and II or their subformulae with different substitution pattern or with different mesogenic groups can be prepared in analogy to Scheme 1.

Further suitable methods are shown in the examples below.

The invention furthermore relates to a composition comprising one or more compounds of formula I or its subformulae. Another preferred embodiment relates to a composition comprising at least two polymerizable compounds, at least one of which is a compound of formula I or its subformulae.

The invention furthermore relates to a polymer obtained polymerizing a compound of formula I or its subformulae or a composition comprising it.

Suitable and preferred polymerization methods are, for example, thermal or photopolymerization, preferably photopolymerization, in particular UV induced photopolymerization, which can be achieved by exposure of the polymerizable compounds to UV radiation.

Optionally one or more polymerization initiators are added to the compound of formula I or the composition comprising it. Suitable conditions for the polymerization and suitable types and amounts of initiators are known to the person skilled in the art and are described in the literature. Suitable for free-radical polymerization are, for example, the commercially available photoinitiators Irgacure651®, Irgacure184®, Irgacure907®, Irgacure369® or Darocure1173® (Ciba AG). If a polymerization initiator is employed, its proportion is preferably 0.001 to 5% by weight, particularly preferably 0.001 to 1% by weight.

The polymerizable compounds according to the invention are also suitable for polymerization without an initiator, which is accompanied by considerable advantages, such, for example, lower material costs and in particular less contamination of the polymer or the composition by possible residual amounts of the initiator or degradation products thereof. The polymerization can thus also be carried out without the addition of an initiator. In a preferred embodiment, the polymerizable compound or composition according to the present invention does not contain a polymerization initiator.

The polymerizable compound or composition according to the present invention may also comprise one or more stabilizers in order to prevent undesired spontaneous polymerization of the compounds, for example during storage or transport. Suitable types and amounts of stabilizers are known to the person skilled in the art and are described in the literature. Particularly suitable are, for example, the commercially available stabilizers from the Irganox® series (Ciba AG), such as, for example, Irganox® 1076. If stabilizers are employed, their proportion, based on the total amount of polymerizable compounds, is preferably 10-50,000 ppm, particularly preferably 50-5,000 ppm.

In a preferred embodiment the polymerizable compound or composition according to the present invention contains one or more chiral dopants, preferably in a concentration from 0.01 to 1% by weight, very preferably from 0.05 to 0.5% by weight. It is also possible to use a racemate of one or more chiral dopants.

The polymerizable compound or composition according to the present invention may additionally comprise one or more further components or additives, preferably selected from the list including but not limited to co-monomers, chiral dopants, polymerization initiators, inhibitors, stabilizers, surfactants, wetting agents, lubricating agents, dispersing agents, hydrophobing agents, adhesive agents, flow improvers, defoaming agents, deaerators, diluents, reactive diluents, auxiliaries, colourants, dyes, pigments and nanoparticles.

Particular preference is given to compositions comprising one, two or three polymerizable compounds of formula I.

Preference is furthermore given to compositions in which the polymerizable compounds are exclusively selected from polymerizable compounds of formula I.

Preference is furthermore given to achiral compounds of formula I, and to compositions in which all components are selected exclusively from the group consisting of achiral compounds.

The following examples explain the present invention without restricting it. However, they show the person skilled in the art preferred mixture concepts with compounds preferably to be employed and the respective concentrations thereof and combinations thereof with one another. In addition, the examples illustrate which properties and property combinations are accessible.

Unless explicitly noted otherwise, all temperature values indicated in the present application are quoted in degrees Celsius (° C.) and all percentages mean percent by weight. The following abbreviations are used: M.p. or m.p.=melting point (in ° C.), DCM=dichloromethane.

Example 1

Compound 1 is prepared as follows.

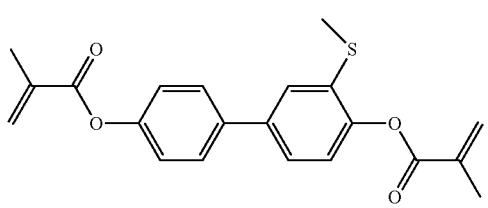

1.1 Synthesis of Bromide A

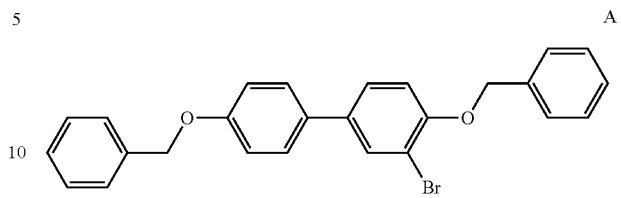

13.51 g (127.42 mmol) $Na_2CO_3$ are dissolved in 100.0 mL water and 56.74 mL ethanol. A solution of 18.3 g (46.3 mmol) of 1-Benzyloxy-2-bromo-4-iodo-benzene and 10.36 g (45.41 mmol) 4-Benzyloxyphenylboronic-acid in 220.8 mL toluene and 1.921 g (1.662 mmol) Tetrakis(triphenylphosphine)-palladium(0) is added. The reaction mixture is refluxed for 14 h and cooled to room temperature, acetic acid ethylester (EE) is added and the organic layer is separated. The water layer was extracted several times with EE and the combined organic layers are washed with saturated NaCl-solution (Brine), filtered, dried over $MgSO_4$ and evaporated under vacuum. The reaction product is purified by column chromatography (Heptane/EE 1:1) to yield the product as a slightly brownish crystalline solid.

1.2 Synthesis of Thiol B

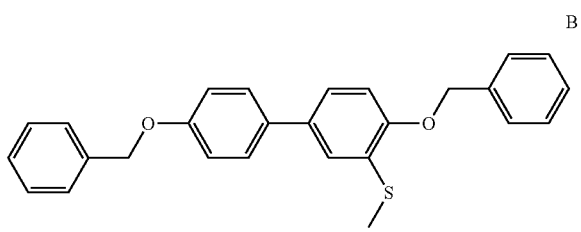 [SMILES: CSc1cc(-c2ccc(OCc3ccccc3)cc2)ccc1OCc1ccccc1]

7.00 g (15.72 mmol) bromide A, N,N-diisopropylethylamine are dissolved in toluene (50 mL) and filled in an autoclave vessel. 148.39 mg (0.16 mmol) $Pd_2dba_3$ and 206.27 mg Xanthphos are being added and 0.849 g (17.290 mmol) methane thiol is transferred into the autoclave at <6° C. (special caution in handling this reagent is needed). The reaction mixture is stirred for 14 h at 110-112° C., cooled to room temperature, washed with NaOH— and $Na_2CO_3$— and NaCl-solution. The organic layer is separated and dried over $Na_2SO_4$ and evaporated under vacuum. The reaction product is purified by column chromatography (Toluene/EE 1:1) to yield the product as a white solid.

1.3 Synthesis of Phenol C

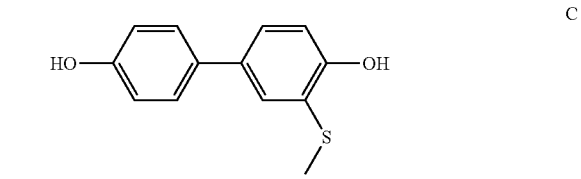 [SMILES: CSc1cc(-c2ccc(O)cc2)ccc1O]

4.00 g (9.70 mmol) of diol C are dissolved in dochloromethane (DCM) (160 mL) and cooled to +3° C., stirred for 30 min and 24.24 mL (24.24 mmol, 1 M in dichloro methane) BBr$_3$ is added dropwise and stirred at 3° C. for 30 min. The reaction is quenched by pouring the mixture carefully in 100 mL ice water. The organic layer is separated and the water layer is extracted with DCM. The combined organic layers are washed with brine, dried over Na$_2$SO$_4$, filtered and evaporated under vacuum. The product is purified via column chromatography (DCM/EE 4:1) to yield the product as a yellow oil.

$^1$H NMR (500 MHz, DMSO-d$_6$) δ 9.79 (s, 1H), 9.40 (s, 1H), 7.44-7.35 (m, 2H), 7.22 (d, J=2.2 Hz, 1H), 7.17 (dd, J=8.2, 2.2 Hz, 1H), 6.85-6.77 (m, 3H), 2.42 (s, 3H).

1.4 Synthesis of Compound 1

100.00 mg (0.43 mmol) of Diol C are dissolved in DCM (5 mL), 0.084 mL (0.990 mmol) methacrylic acid are added and the mixture is cooled to 0° C. and 1-(3-Dimethlyaminopropyl)-3-ethylcarbodiimide (0.160 g, 1.033 mmol) dissolved in DCM (5 mL) is added dropwise. The reaction mixture is stirred for 14 h at room temperature and filtered directly over silica gel with DCM/EE 9:1. The product fractions are combined and after evaporation crystallized with heptane (5 mL) to yield the product as a white solid.

M.p.=76° C., MS (EI)=368 (M$^+$)

$^1$H NMR (500 MHz, Chloroform-d) δ 7.63-7.56 (m, 2H), 7.45 (d, J=2.1 Hz, 1H), 7.39 (dd, J=8.2, 2.2 Hz, 1H), 7.25-7.16 (m, 3H), 6.44 (dt, J=30.7, 1.1 Hz, 2H), 5.82 (dq, J=9.9, 1.6 Hz, 2H), 2.51 (s, 3H), 2.13 (dt, J=13.2, 1.2 Hz, 6H).

The absorption wavelength λ of compound 1 at an extinction coefficient of E=0.5 is measured as 336 nm for a solution in DCM at a concentration of 3 g/L.

Examples 2 to 15

Compounds 2 to 15 are prepared by the method as described in Example 1 or in analogy thereto.

2

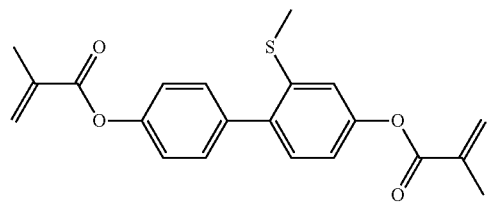

MS (EI) = 368 (M+)
M.p. = 113° C.

$^1$H NMR (500 MHz, DMSO) δ 7.50-7.37 (m, 2H), 7.26 (dd, J=8.3, 5.8 Hz, 3H), 7.15 (d, J=2.3 Hz, 1H), 7.04 (dd, J=8.2, 2.3 Hz, 1H), 6.32 (d, J=1.6 Hz, 2H), 5.93 (q, J=1.9 Hz, 2H), 2.40 (s, 3H), 2.03 (d, J=1.6 Hz, 6H).

3

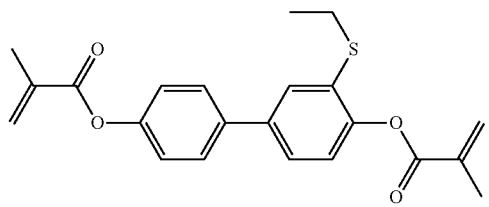

MS (EI) = 382 (M$^+$)

4

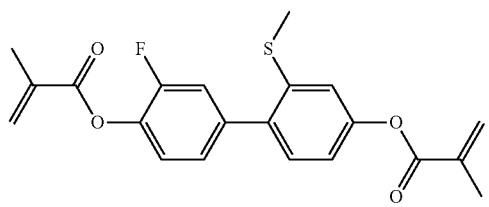

MS (EI) = 386 (M$^+$)

5

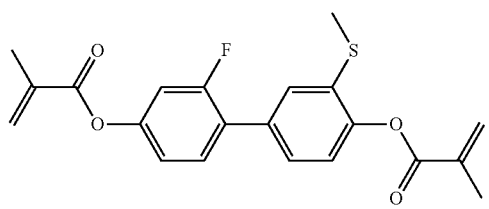

MS (EI) = 386 (M$^+$)

6

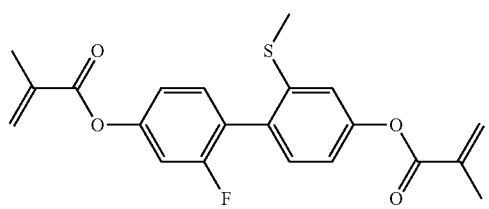

MS (EI) = 386 (M$^+$)

7

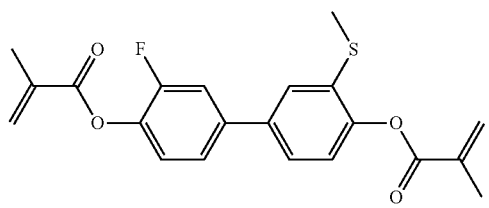

MS (EI) = 386 (M$^+$)

8

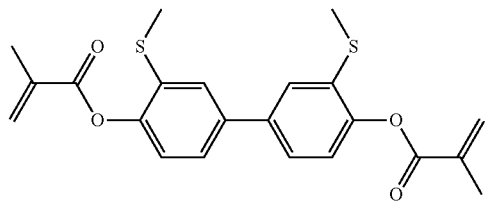

MS (EI) = 414 (M$^+$)
M.p. = 94° C.

$^1$H NMR (500 MHz, DMSO) δ 7.58 (d, J=2.2 Hz, 1H), 7.54 (dd, J=8.3, 2.1 Hz, 1H), 7.28 (d, J=8.3 Hz, 1H), 6.34 (t, J=1.3 Hz, 1H), 5.95 (t, J=1.6 Hz, 1H), 2.54 (s, 3H), 2.04 (t, J=1.2 Hz, 3H).

9

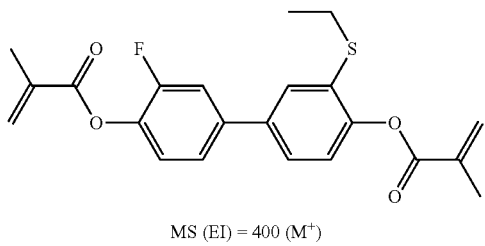

MS (EI) = 400 (M⁺)

10

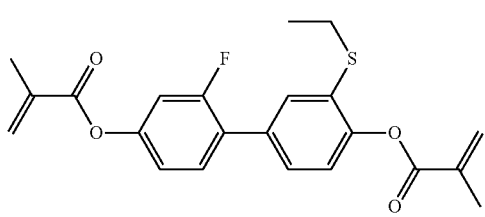

MS (EI) = 400 (M⁺)

11

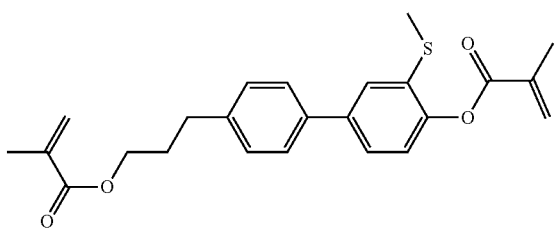

MS (EI) = 410 (M⁺)

12

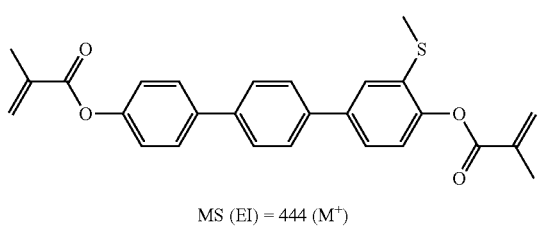

MS (EI) = 444 (M⁺)

13

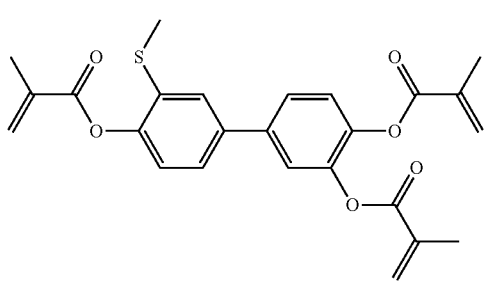

MS (EI) = 452 (M⁺)

-continued

14

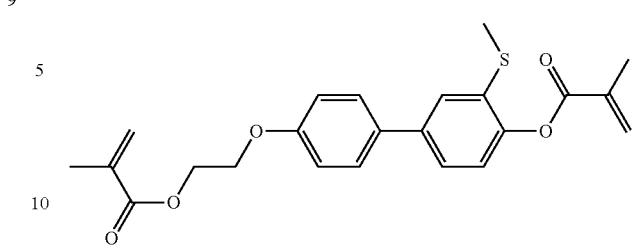

MS (EI) = 412 (M⁺)

15

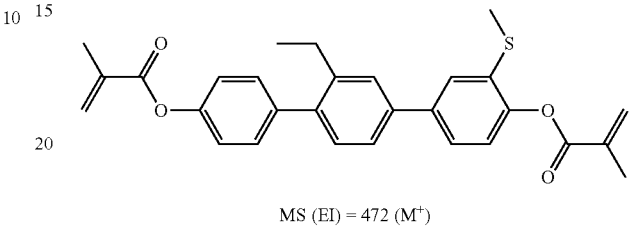

MS (EI) = 472 (M⁺)

Compounds 2 to 15 show UV absorption at a wavelength >300 nm.

Use Example A—Comparison of Physical Properties

The absorption wavelength λ at an extinction coefficient of E=0.5 is determined for compounds C1 and C2 of prior art by the method as described in Example 1. This wavelength is useful to characterize the wavelength dependence of the UV photopolymerization of the compound.

C1

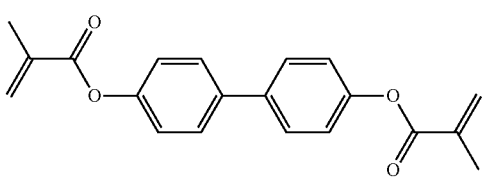

C2

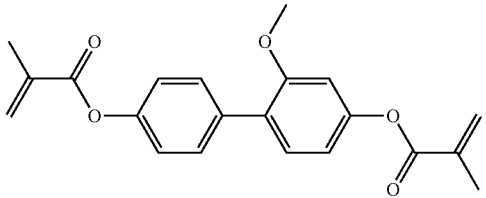

The melting point and UV absorption wavelength of compound 1 according to the invention are compared with those of compounds C1 and C2 of prior art. The results are shown in Table 1.

TABLE 1

| Melting point and UV Absorption | | | |
|---|---|---|---|
| | C1 | C2 | 1 |
| Melting point (° C.) | 152 | 105 | 76 |
| UV absorption wavelength λ (nm) at E = 0.5 | 320 | 329 | 336 |

From Table 1 it can be seen that compound 1 according to the invention has the lowest melting point, which is especially advantageous as it indicates that the monomer dissolves faster, leading to shorter production cycles, and has higher solubility in the LC medium compared with C1 and C2.

From Table 1 it can also be seen that compound 1 according to the invention has the longest absorption wavelength, and is thus especially suitable for UV photopolymerization at longer wavelengths or faster polymerization at shorter wavelengths.

Use Example B—UV Photopolymerization

Each of compounds 1, C1 and C2 is dissolved in a nematic LC host mixture (MDA-10-1077, Merck KGaA) at a concentration of approx. 0.3 wt. % and then polymerized by exposure to UV radiation using a 320 nm long pass filter and a light intensity of 100 mW/cm$^2$.

The amount of the residual unreacted monomer in the LC host mixture is determined by HPLC after various UV exposure times. The results are shown in Table 2.

TABLE 2

Residual monomer concentration (relative to initial amount)

| UV Exp. Time/min | Residual monomer (%) | | |
|---|---|---|---|
| | C1 | C2 | 1 |
| 0 | 100% | 100% | 100% |
| 2 | 62% | 45% | 38% |
| 6 | 22% | 11% | 7% |

From Table 2 it can be seen that monomer 1 according to the invention shows the quickest polymerization and the lowest residual monomer amount and is thus especially suitable for polymerization at longer UV wavelengths.

The invention claimed is:
1. A compound selected from compounds of the following formulae:

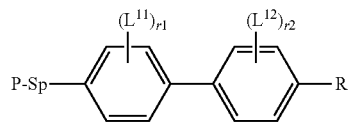
I1A

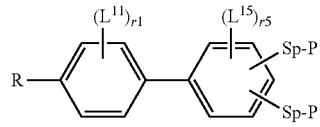
I1B

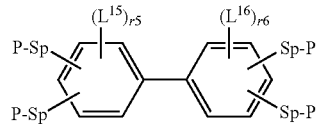
I1C

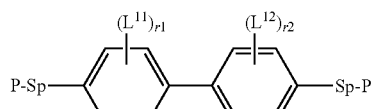
I1D

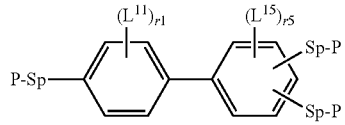
I1E

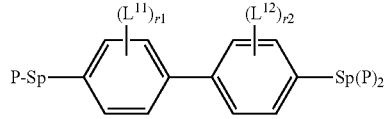
I1F

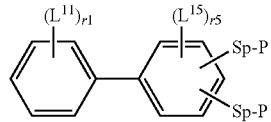
I1G

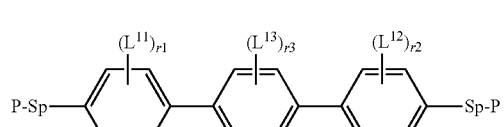
I2A

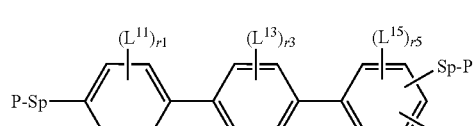
I2B

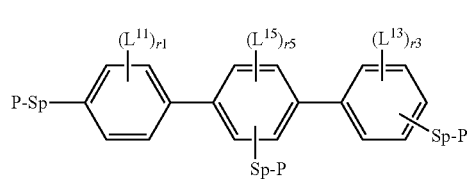
I2C

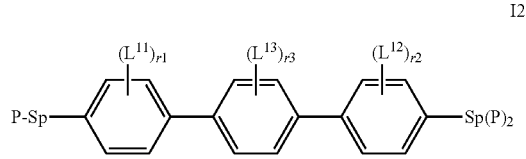
I2D

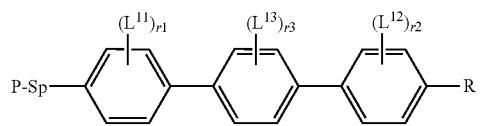
I2E

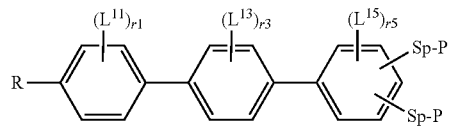
I2F

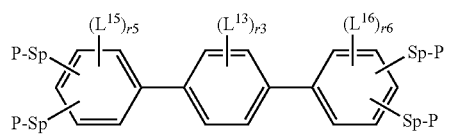
I2G

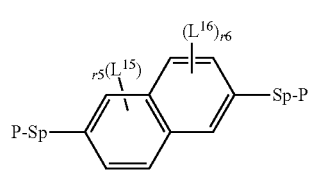
I3A

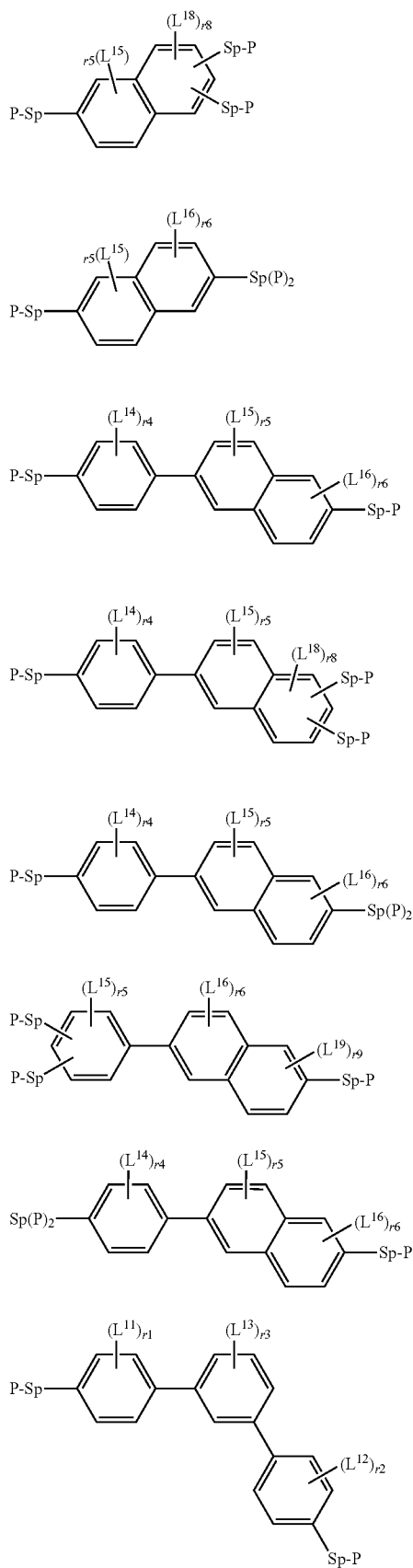
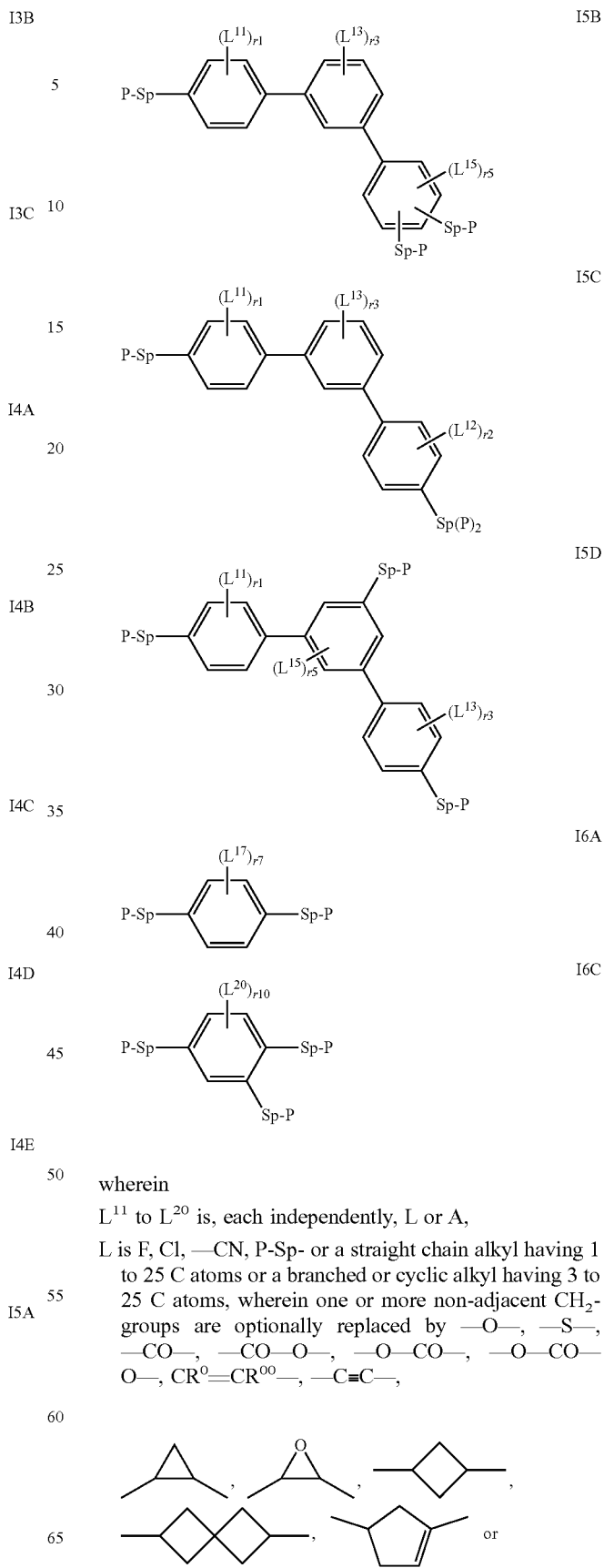
wherein
$L^{11}$ to $L^{20}$ is, each independently, L or A,
L is F, Cl, —CN, P-Sp- or a straight chain alkyl having 1 to 25 C atoms or a branched or cyclic alkyl having 3 to 25 C atoms, wherein one or more non-adjacent $CH_2$- groups are optionally replaced by —O—, —S—, —CO—, —CO—O—, —O—CO—, —O—CO—O—, $CR^o{=}CR^{oo}$—, —C≡C—,
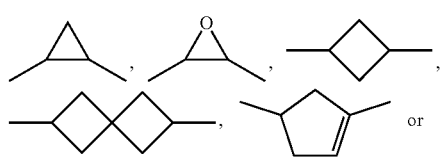

-continued

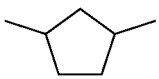

in such a manner that O- and/or S-atoms are not directly connected with each other, and wherein one or more H atoms are each optionally replaced by P-Sp-, F or Cl, $R^0$, $R^{00}$ is, each independently, H or alkyl having 1 to 12 C atoms, r1, r2, r3, r4 is, each independently, 0, 1, 2, 3 or 4,
r5, r6, is, each independently, 0, 1, 2 or 3,
r7 is 1, 2, 3 or 4,
r8 is 0, 1 or 2,
r9 is 0, 1, 2 or 3,
r10 is 1, 2 or 3,
P is a polymerizable group,
Sp is a spacer group or a single bond,
A is —SCH$_3$, —SC$_2$H$_5$ or —SC$_3$H$_7$, and
R is F, Cl, —CN, or a straight chain alkyl having 1 to 25 C atoms or a branched or cyclic alkyl having 3 to 25 C atoms, wherein one or more non-adjacent CH$_2$-groups are optionally replaced by —O—, —S—, —CO—, —CO—O—, —O—CO—, —O—CO—O—, $CR^0$=$CR^{00}$—, —C≡C—, in such a manner that O- and/or S-atoms are not directly connected with each other, and wherein one or more H atoms are each optionally replaced by F or Cl or P-Sp-, wherein
in formulae I1A, I1C and I1E, r1+r2≥1,
in formula I1B, I1D and I1F, r1+r5≥1,
in formula I1G, I3A and I3C, r5+r6≥1,
in formulae I2A, I2D, I2E, I5A and I5C, r1+r2+r3≥1,
in formulae I2B, I2C, I2F, I5B and I5D, r1+r3+r5≥1,
in formula I2G, r3+r5+r6≥1,
in formula I4A, I4C and I4E, r4+r5+r6≥1,
in formula I4D, r5+r6+r9≥1,
in formula I3B, r5+r8≥1,
and in formula, I4B r4+r5+r8≥1,
wherein the compound contains at least one group $L^{11}$ to $L^{20}$ that denotes A.

2. A compound selected from compounds of the following formulae:

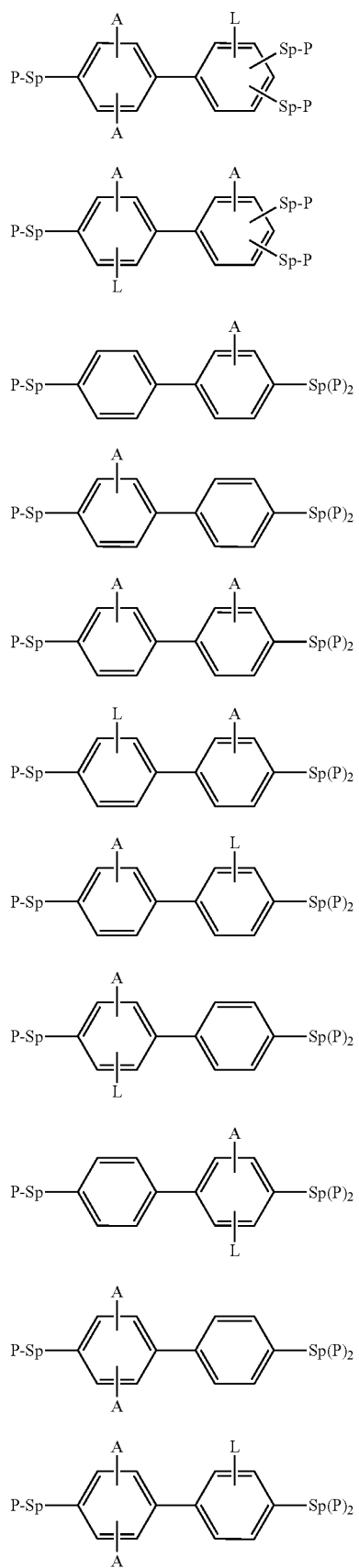
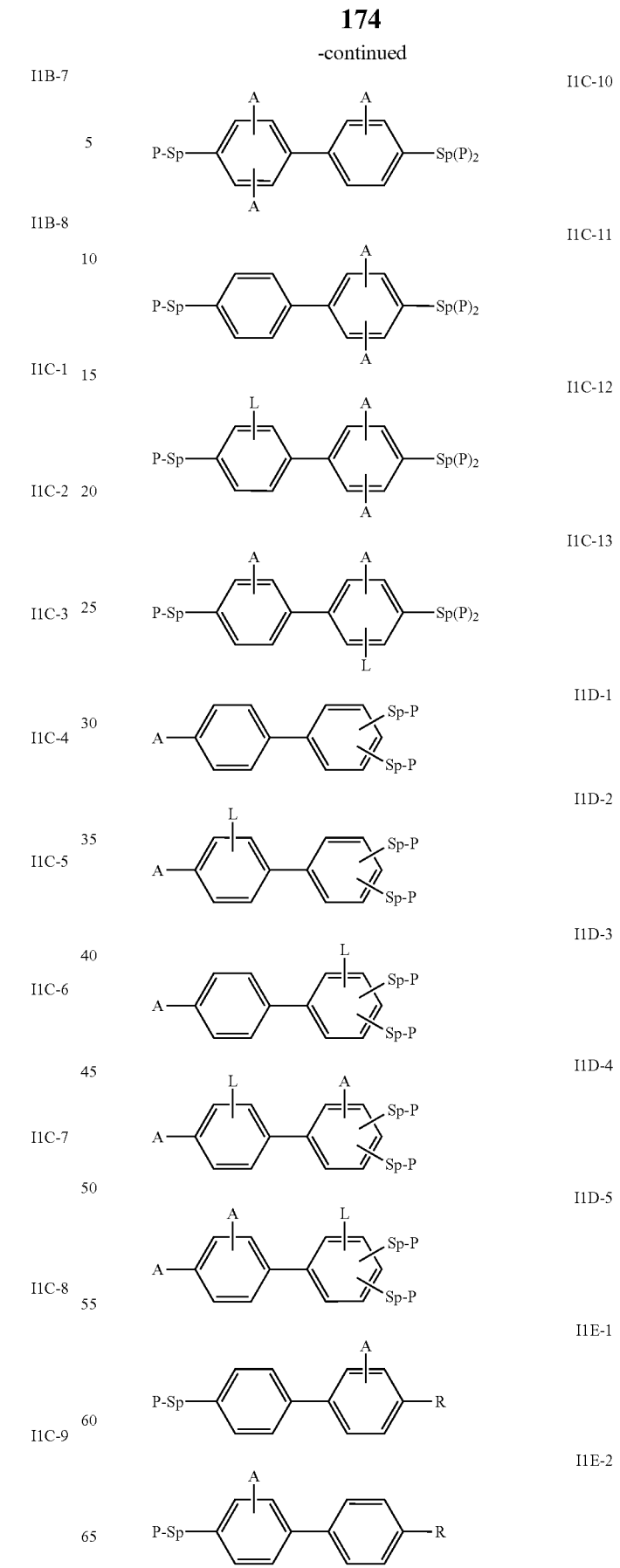

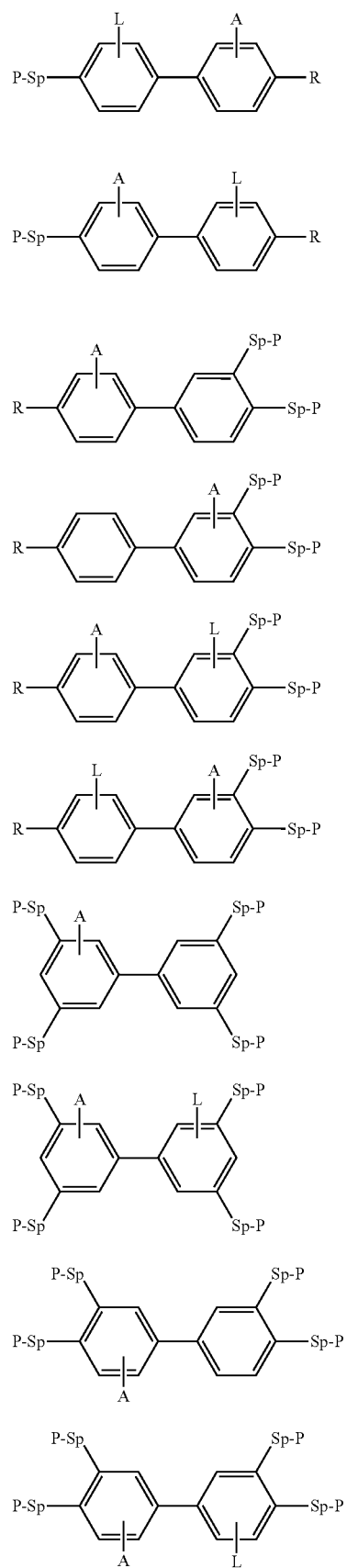
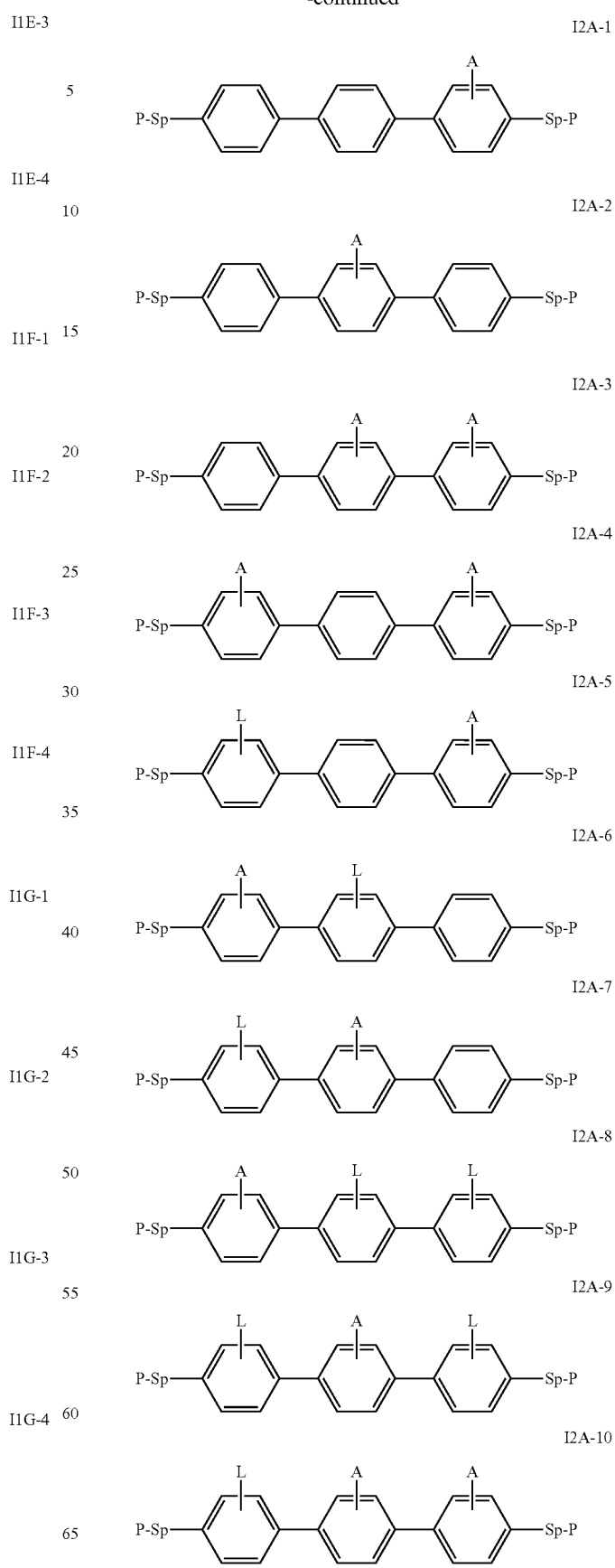

I2A-11
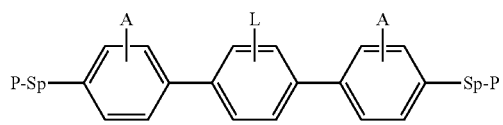
I2A-12
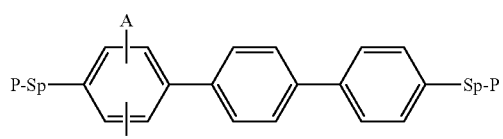
I2A-13
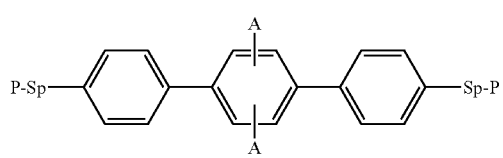
I2A-14
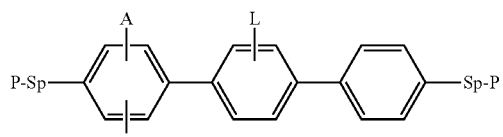
I2A-15
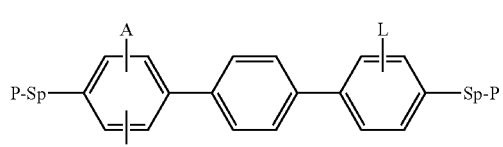
I2A-16
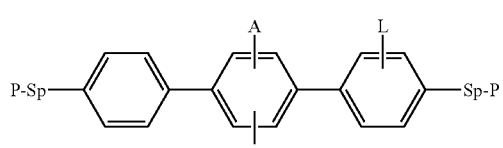
I2A-17
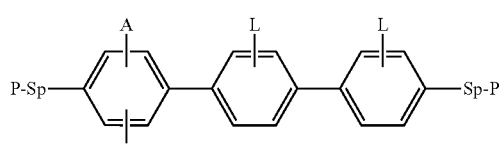
I2A-18
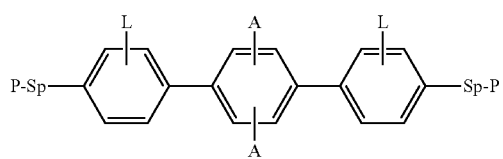
I2B-1
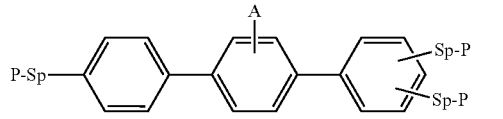
I2B-2
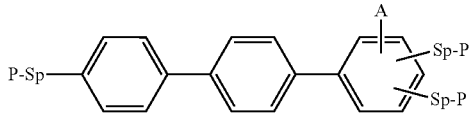
I2B-3
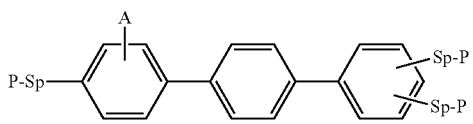
I2B-4
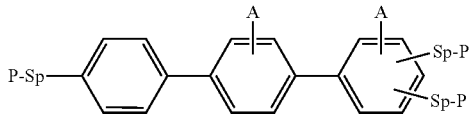
I2B-5
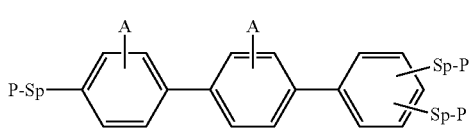
I2B-6
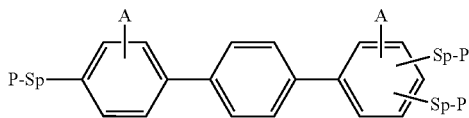
I2B-7
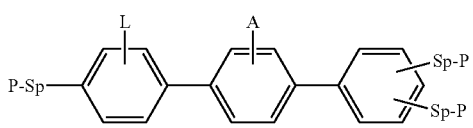
I2B-8
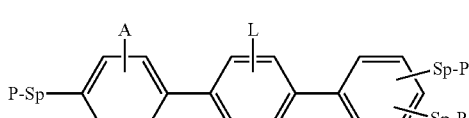
I2B-9
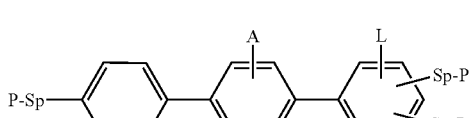
I2B-10
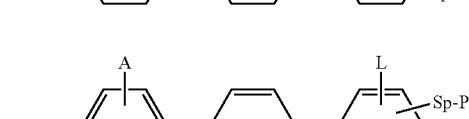
I2B-11
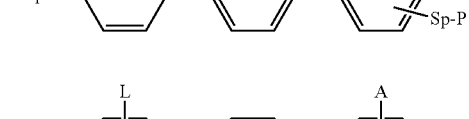
I2B-12
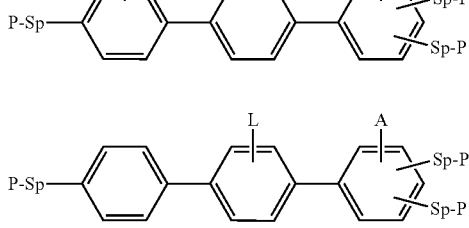

I2B-13
I2B-14
I2B-15
I2B-16
I2B-16'
I2B-17
I2B-18
I2B-19
I2B-20
I2B-21
I2B-22
I2B-23
I2C-1
I2C-2
I2C-3
I2C-4
I2C-5

-continued
I2C-6
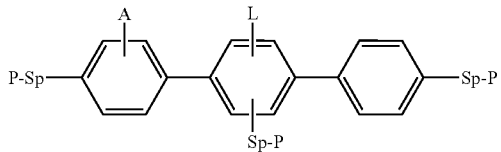
I2C-7
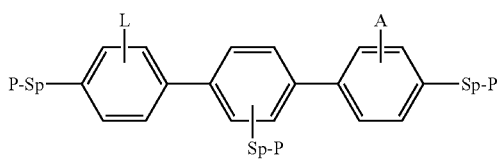
I2C-8
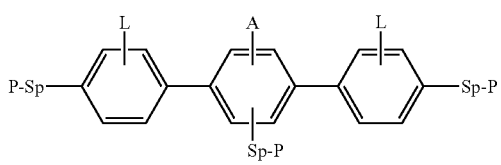
I2C-9
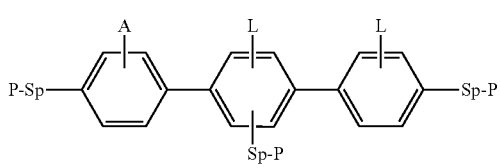
I2C-10
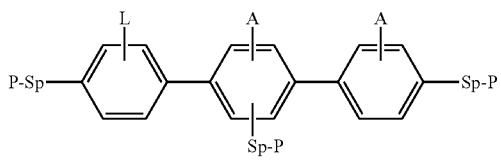
I2C-11
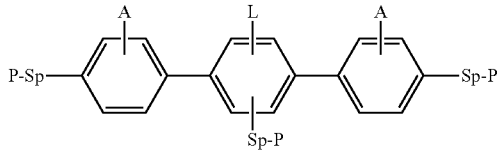
I2C-12
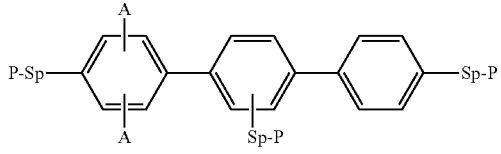
I2C-13
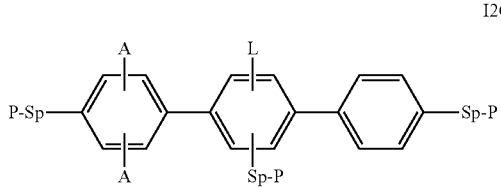
-continued
I2C-14
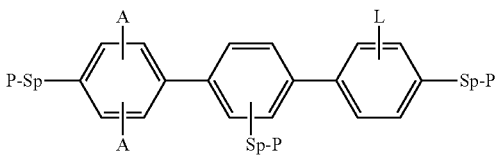
I2C-15
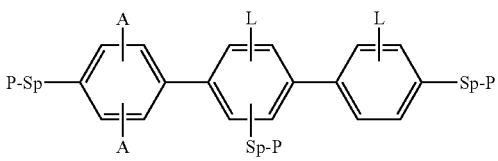
I2D-1
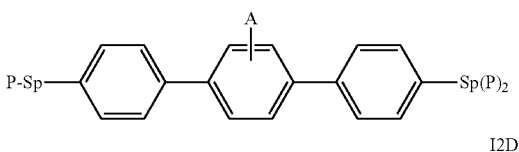
I2D-2
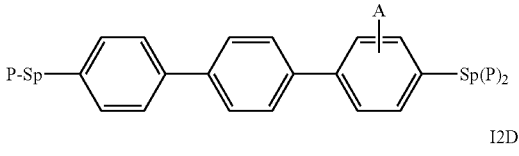
I2D-3
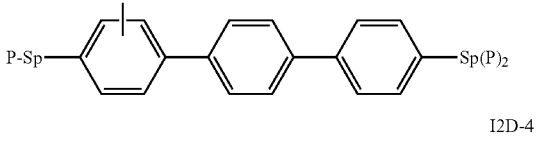
I2D-4
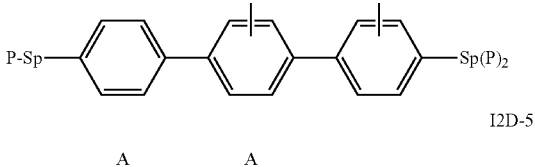
I2D-5
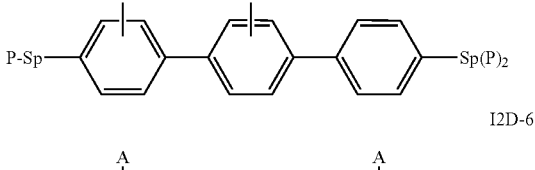
I2D-6
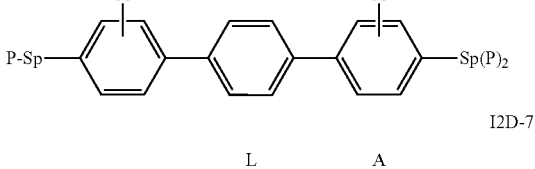
I2D-7
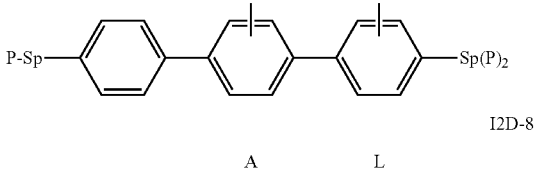
I2D-8

I2D-9
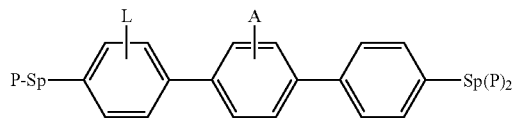
I2D-10
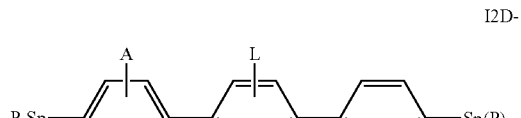
I2D-11
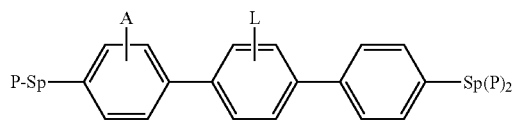
I2D-12
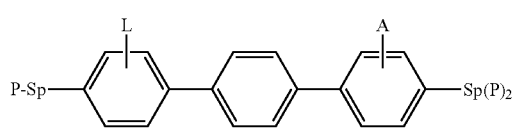
I2D-13
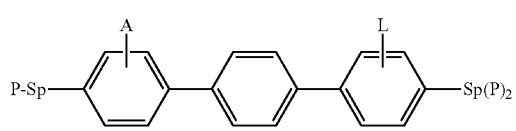
I2D-14
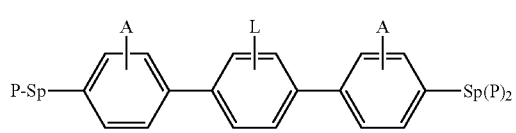
I2D-15
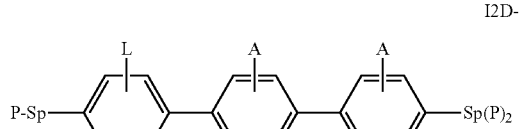
I2D-16
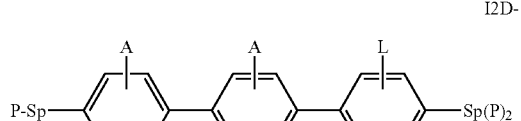
I2D-17
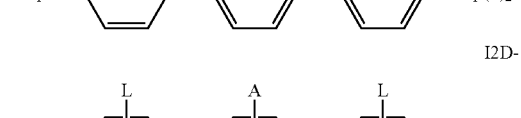
I2D-18
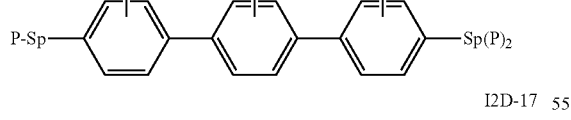
I2D-19
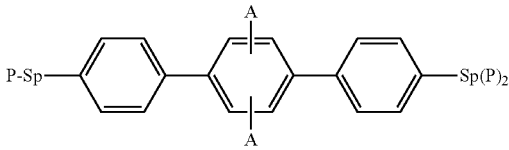
I2D-20
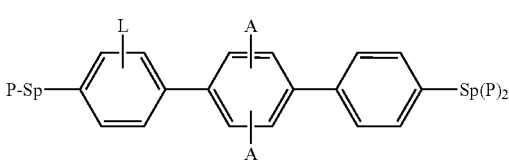
I2D-21
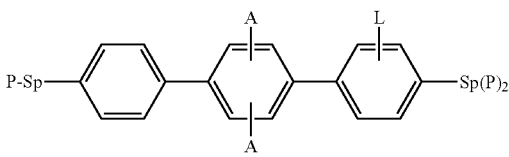
I2D-22
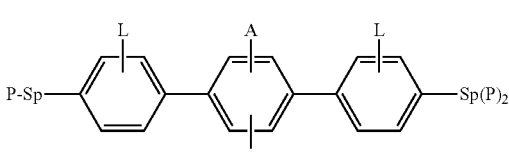
I2D-23
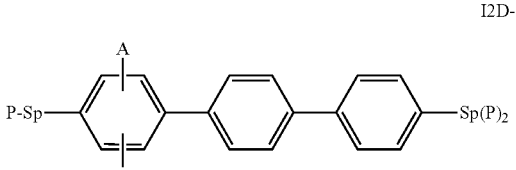
I2D-24
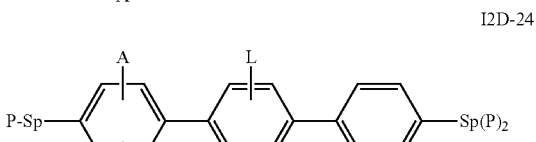
I2D-25
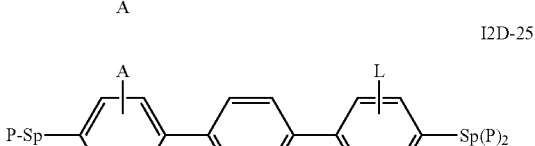
I2D-26
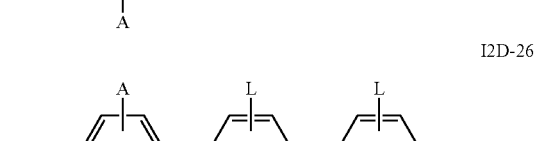
I2D-27
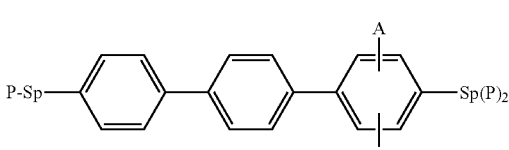

I2D-28
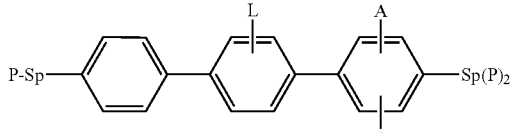

I2D-29
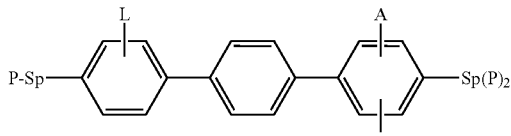

I2D-30
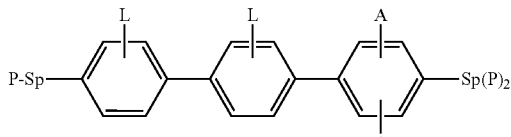

I2E-1
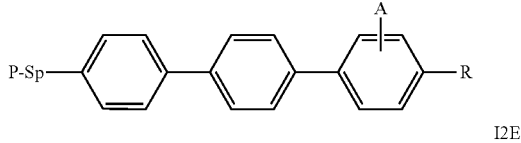

I2E-2
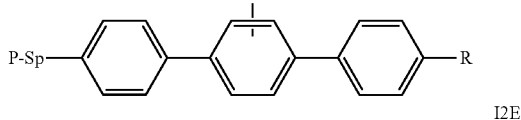

I2E-3
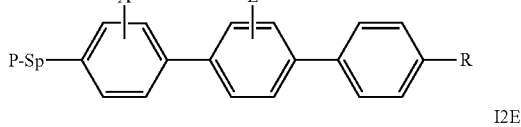

I2E-4
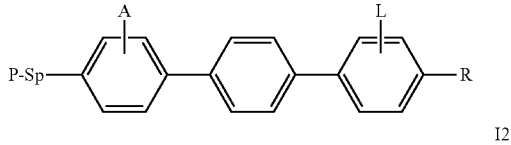

I2F-1
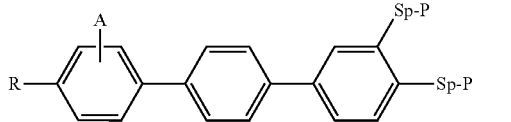

I2F-2
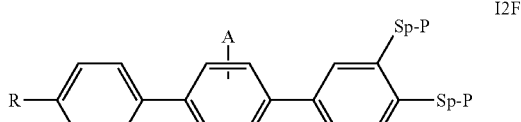

I2F-3
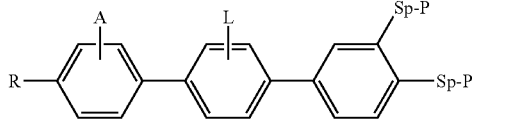

I2F-4
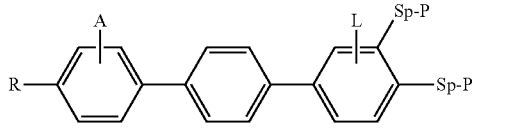

I2G-1
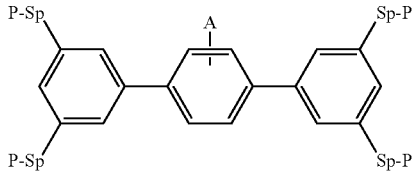

I2G-2
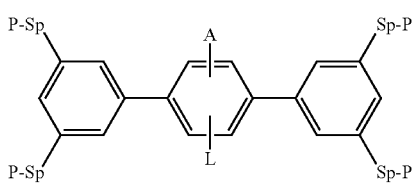

I2G-3
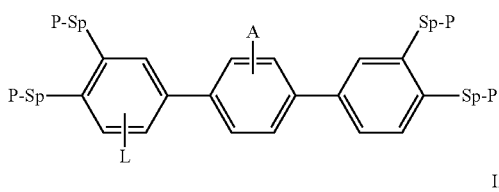

I2G-4
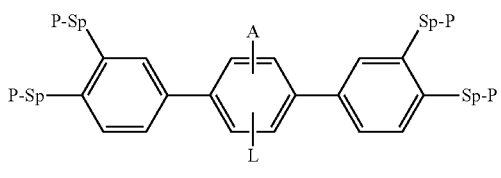

wherein

L is F, Cl, —CN, P-Sp- or a straight chain alkyl having 1 to 25 C atoms or a branched or cyclic alkyl having 3 to 25 C atoms, wherein one or more non-adjacent CH$_2$-groups are optionally replaced by —O—, —S—, —CO—, —CO—O—, —O—CO—, —O—CO—O—, CR$^0$=CR$^{00}$—, —C≡C—,

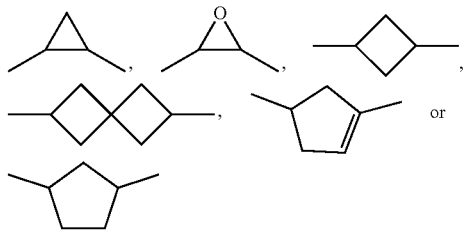

in such a manner that O- and/or S-atoms are not directly connected with each other, and wherein one or more H atoms are each optionally replaced by P-Sp-, F or Cl, R$^0$, R$^{00}$ is, each independently, H or alkyl having 1 to 12 C atoms, P is a polymerizable group, Sp is a spacer group or a single bond, A is —SCH$_3$, —SC$_2$H$_5$ or —SC$_3$H$_7$, and R is F, Cl, —CN, or a straight chain alkyl having 1 to 25 C atoms or a branched or cyclic alkyl having 3 to 25 C atoms, wherein one or more non-adjacent CH$_2$-groups are optionally replaced by —O—, —S—, —CO—, —CO—O—, —O—CO—, —O—CO—O—, CR$^0$=CR$^{00}$—, —C≡C—,

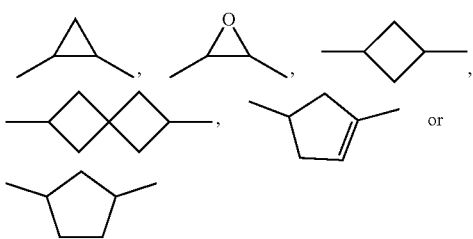

in such a manner that O- and/or S-atoms are not directly connected with each other, and wherein one or more H atoms are each optionally replaced by F or Cl or P-Sp-.

3. The compound according to claim 1, wherein A denotes —$SCH_3$.

4. The compound according to claim 3, wherein P is selected from the group consisting of vinyloxy, acrylate, methacrylate, fluoroacrylate, chloroacrylate, oxetane and epoxide.

5. The compound according to claim 3, wherein Sp, when being different from a single bond, are selected from the group consisting of —$(CH_2)_{p1}$—, —O—$(CH_2)_{p1}$—, —O—CO—$(CH_2)_{p1}$, and —CO—O—$(CH_2)_{p1}$, wherein p1 is 2, 3, 4, 5 or 6, and, if Sp is —O—$(CH_2)_{p1}$—, —O—CO—$(CH_2)_{p1}$ or —CO—O—$(CH_2)_{p1}$ the O-atom or CO-group, respectively, is linked to the benzene ring.

6. A compound, which is selected from the following compounds:

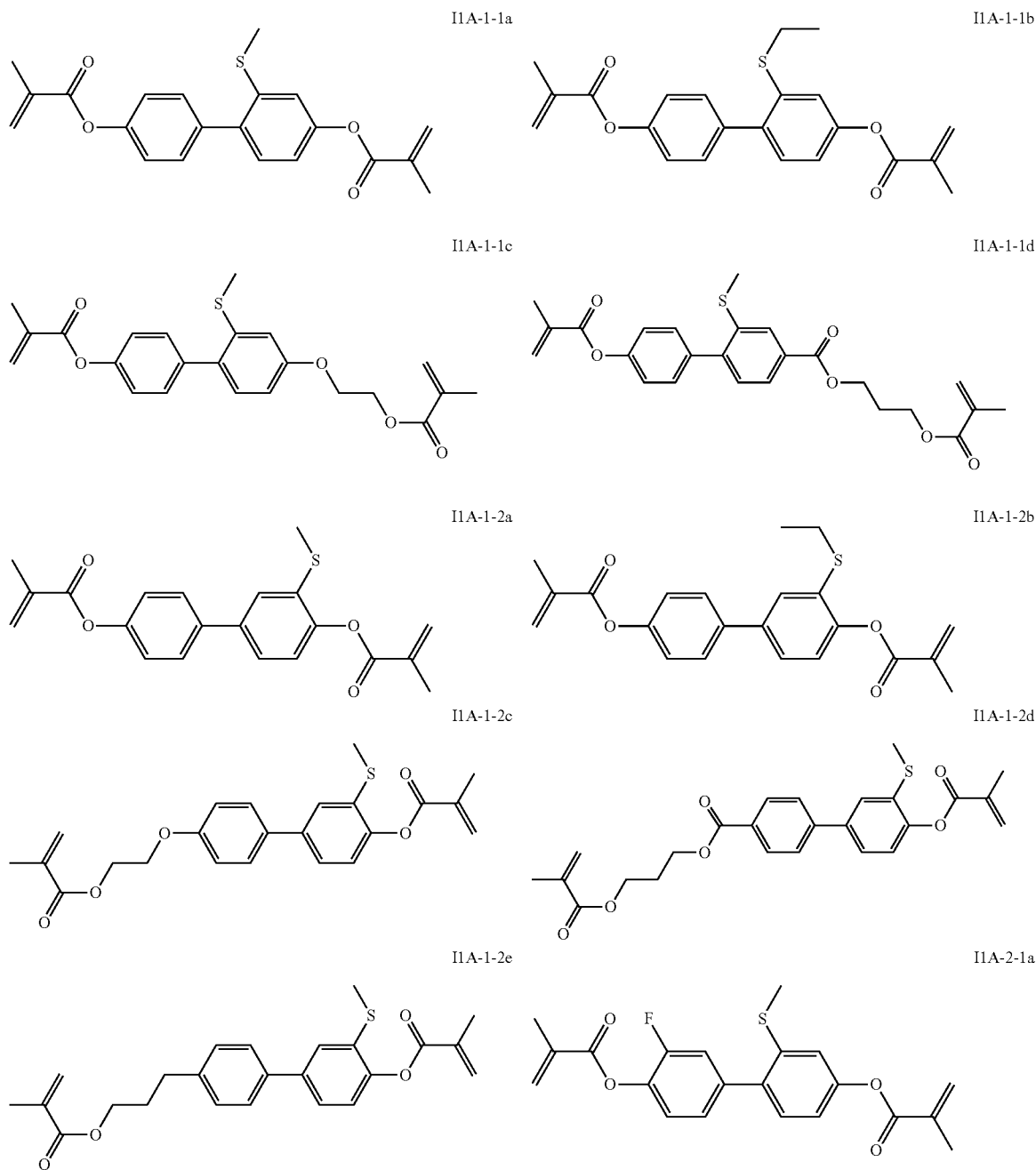

-continued
I1A-2-1b
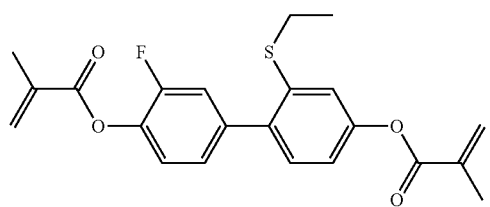
I1A-2-2a
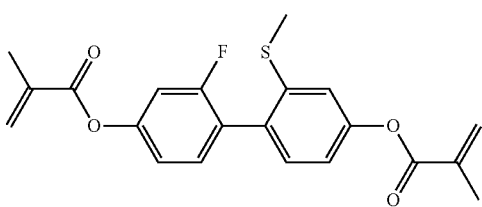
I1A-2-2b
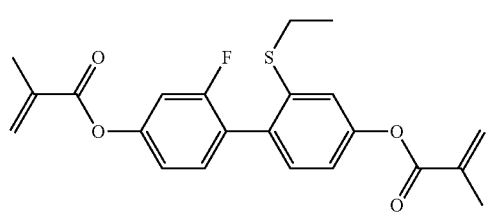
I1A-2-3a
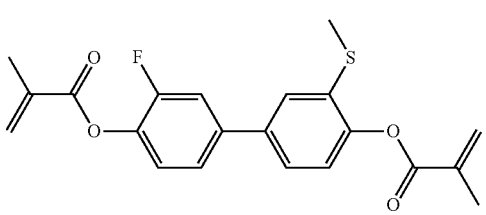
I1A-2-3b
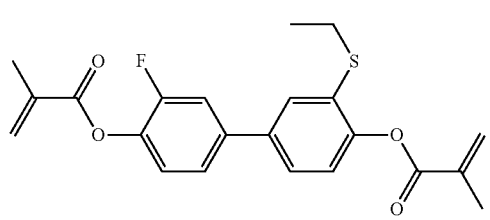
I1A-2-4a
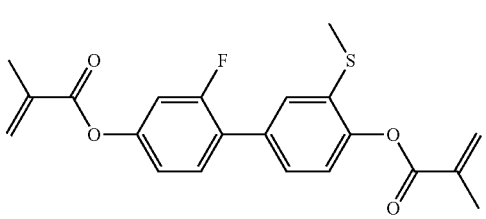
I1A-2-4b
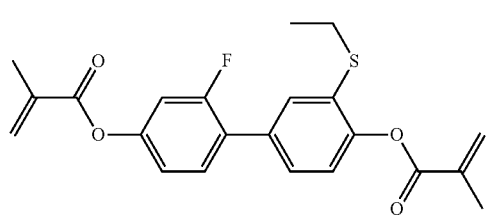
I1A-4-1a
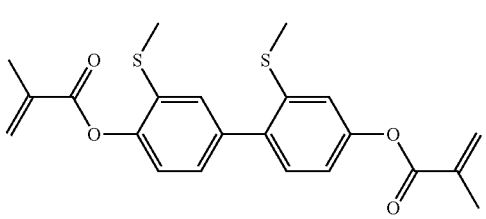
I1A-4-1b
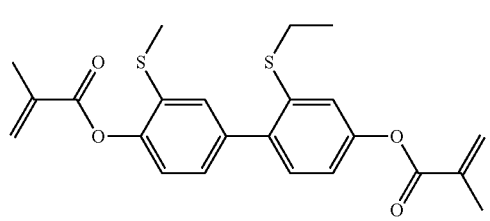
I1A-4-1c
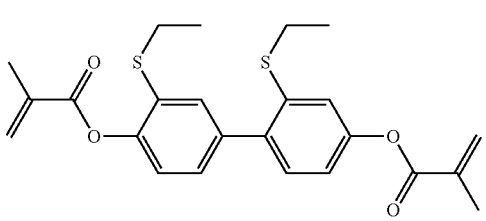
I1A-4-2a
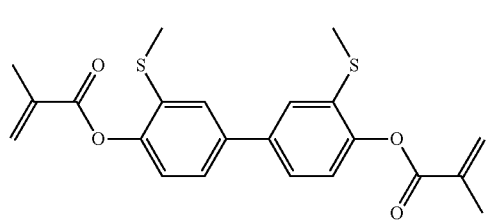
I1A-4-2b
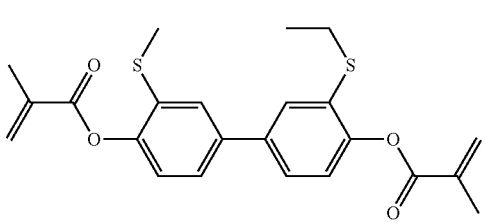
I1A-4-2c
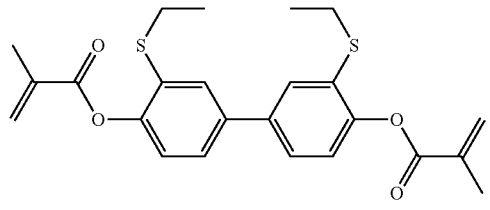
I1A-4-3a
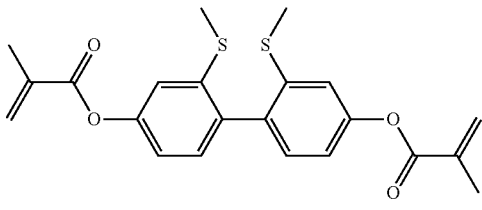

-continued
I1A-4-3b
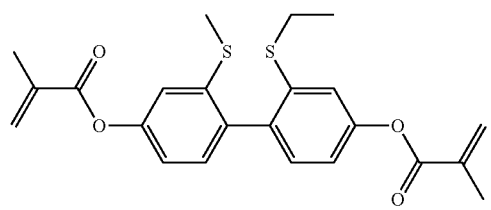
I1A-4-3c
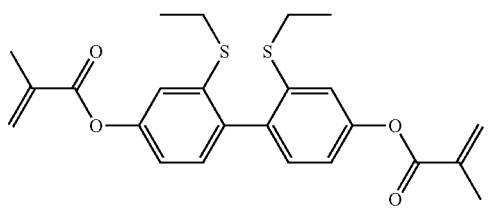
I1B-1-1a
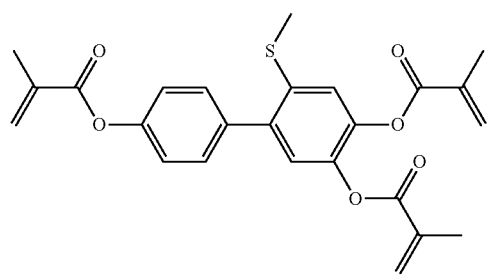
I1B-2-1a
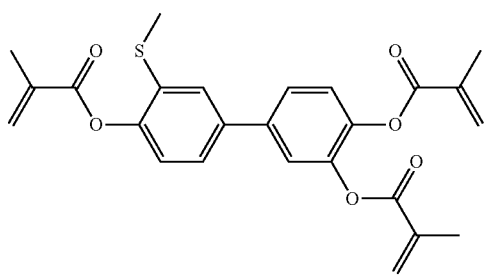
I1B-2-1b
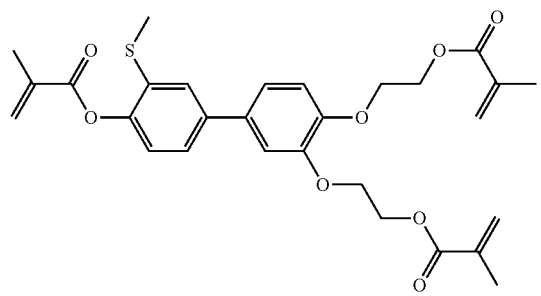
I1B-2-1c
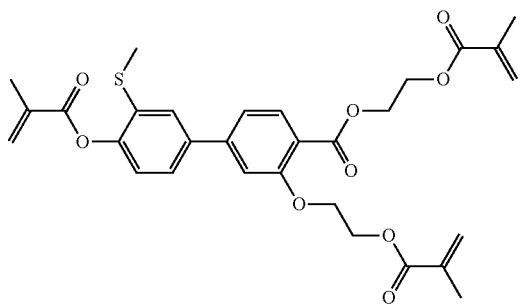
I1B-2-2a
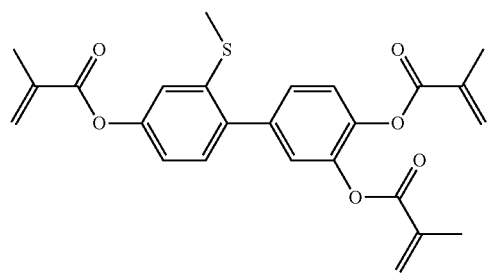
I1B-2-3a
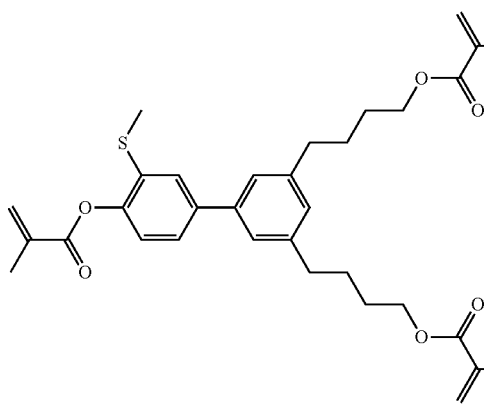
I1B-2-3b
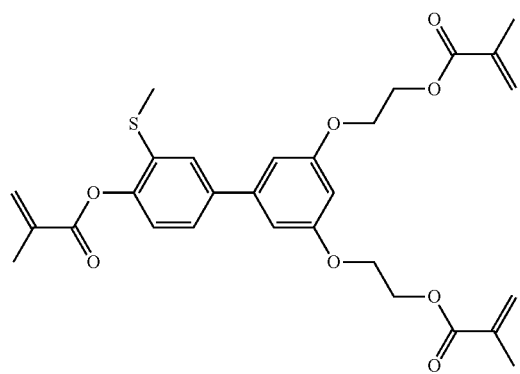
I1B-2-5a
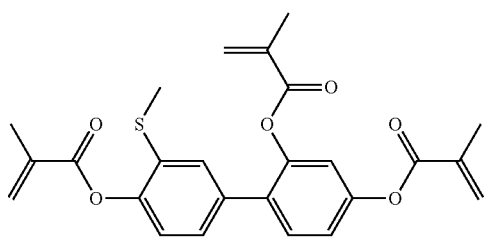

-continued
I1B-2-5b
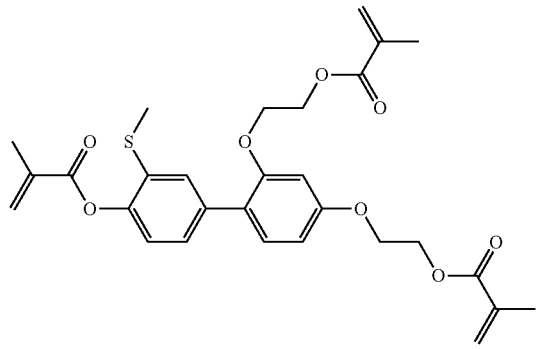
I2A-1-1a
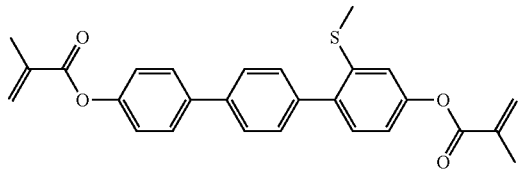
I2A-1-1b
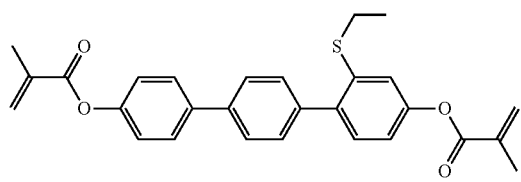
I2A-1-1c
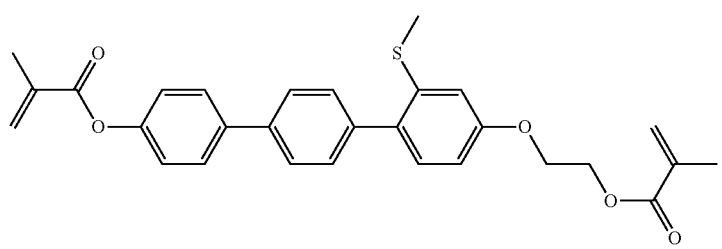
I2A-1-1d
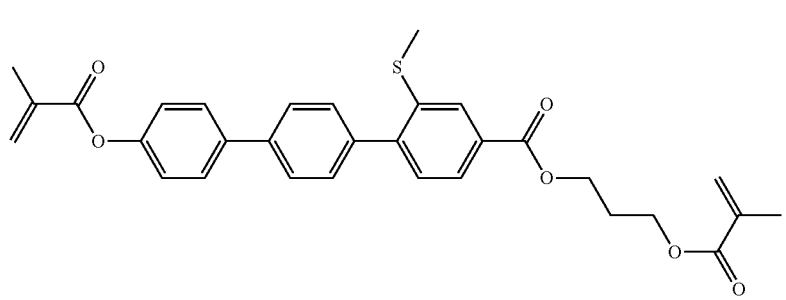
I2A-2-1A
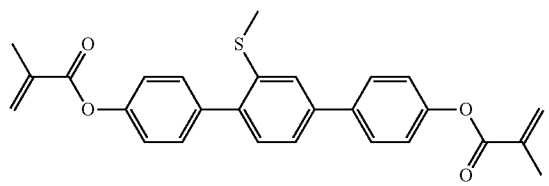
I2A-2-2a
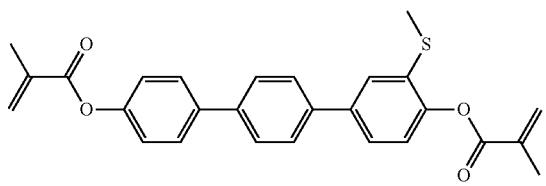
I2A-2-2b
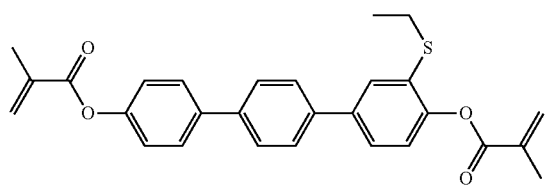
I2A-3-1a
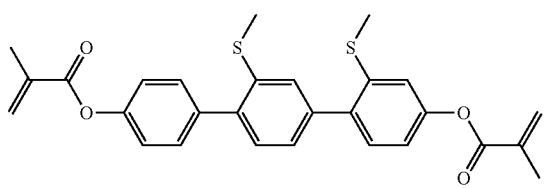

-continued
I2A-3-3a
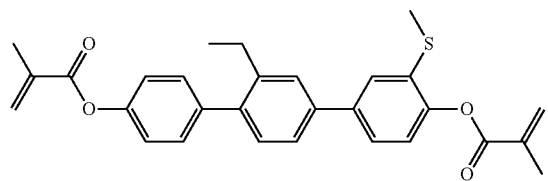
I2A-5-3a
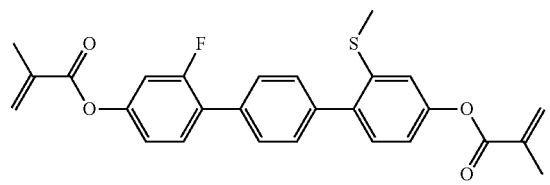
I2B-1-1a
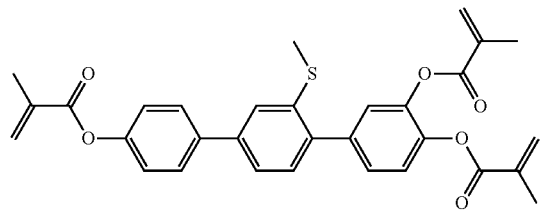
I2B-1-1b
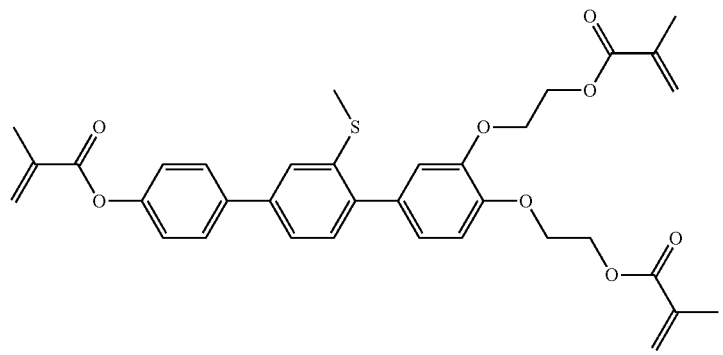
I2B-1-6a
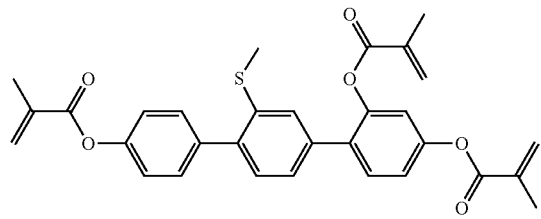
I2B-1-6b
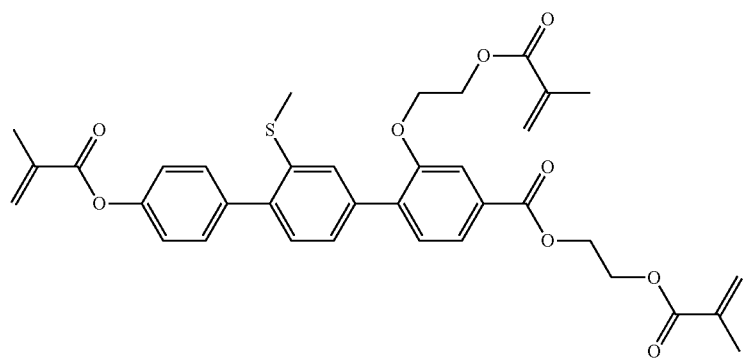

7. A composition comprising one or more compounds of claim 3.

8. A polymer obtained by polymerizing a compound of claim 3, optionally by UV photopolymerization.

9. A method comprising incorporating a compound according to claim 3 into a liquid crystalline media for a protective, decorative or optoelectronic application.

10. A method of preparing a polymer, comprising polymerizing a compound according to claim 3.

11. The compound according to claim 6, which is the following compound

I1A-I-2a

12. The compound according to claim 6, which is the following compound

I1A-1-1a

I1A-1-1b

I1A-1-1c

I1A-1-1d

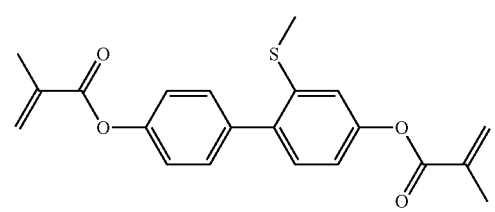

-continued

I1A-1-2a

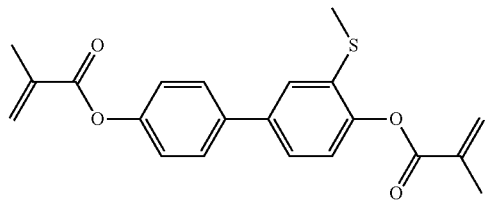

I1A-1-2b

I1A-1-2c

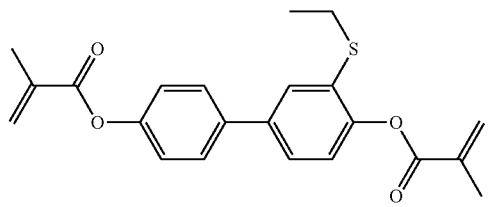

I1A-1-2d

I1A-1-2e

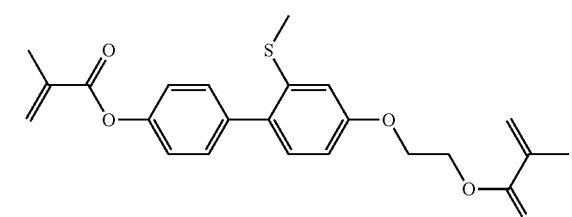

I1A-2-1a

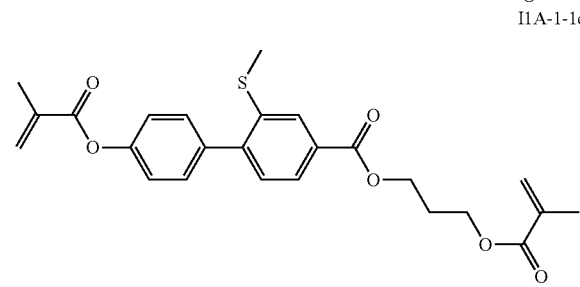

I1A-2-1b
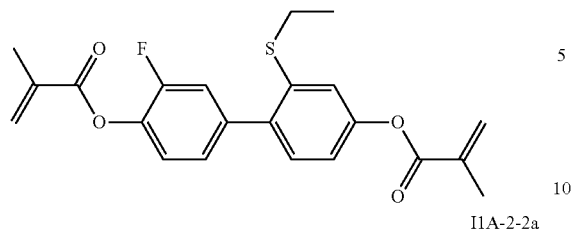
I1A-2-2a
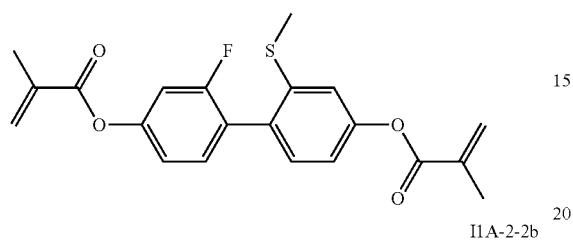
I1A-2-2b
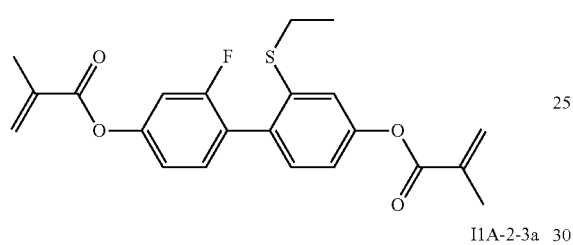
I1A-2-3a
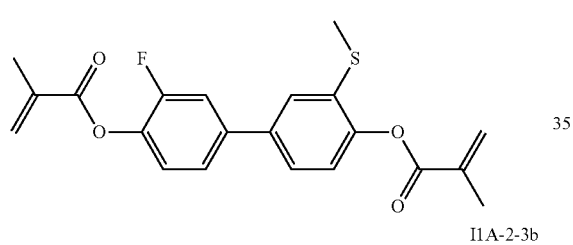
I1A-2-3b
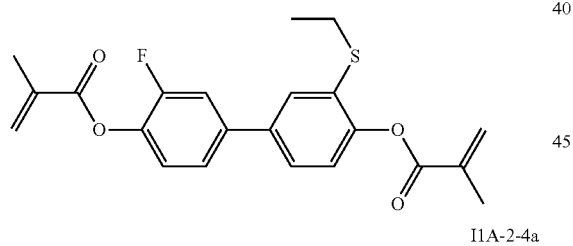
I1A-2-4a
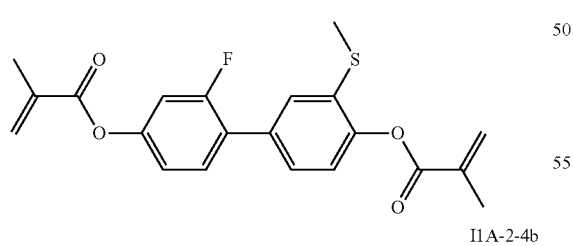
I1A-2-4b
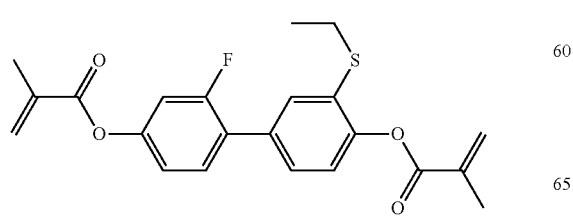
I1A-4-1a
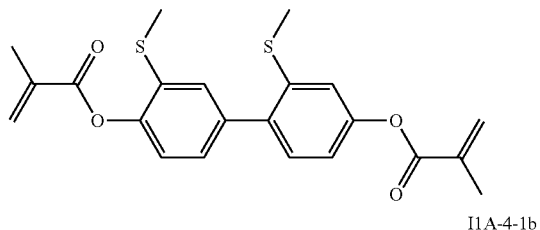
I1A-4-1b
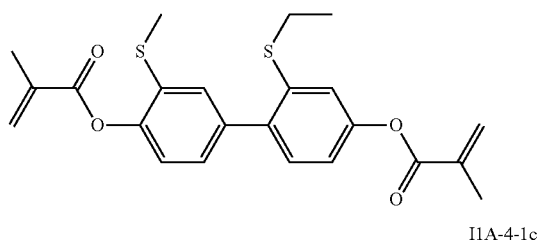
I1A-4-1c
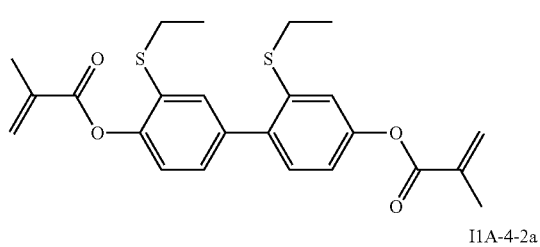
I1A-4-2a
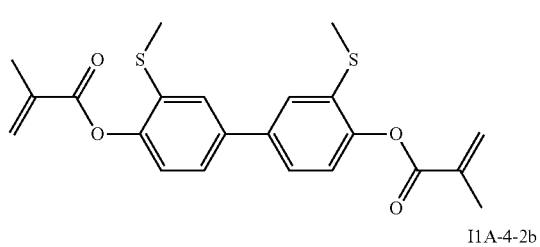
I1A-4-2b
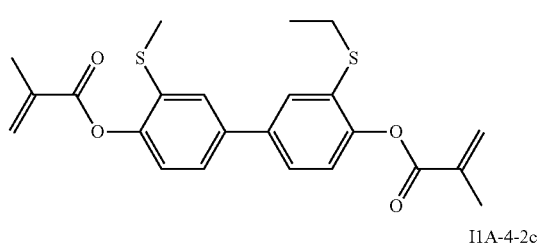
I1A-4-2c
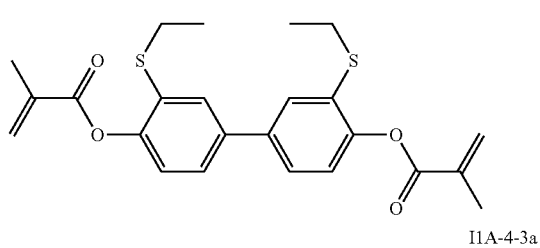
I1A-4-3a
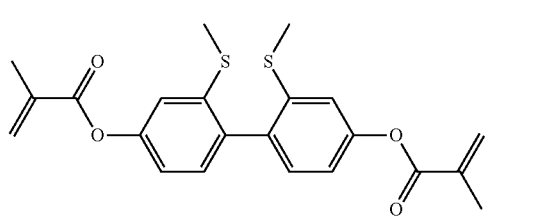

-continued
I1A-4-3b
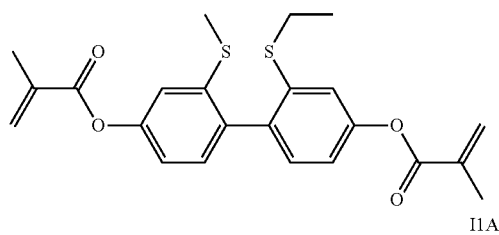
I1A-4-3c
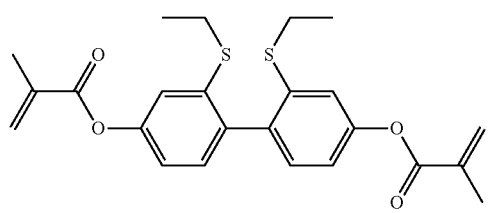
I1B-1-1a
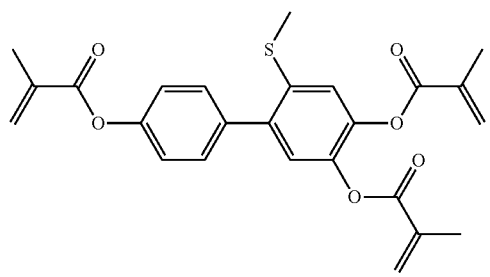
I1B-2-1a
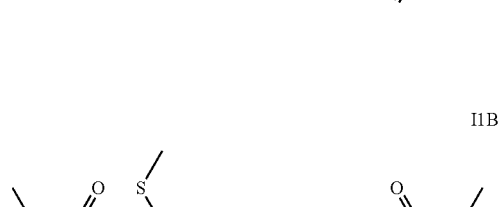
I1B-2-1b
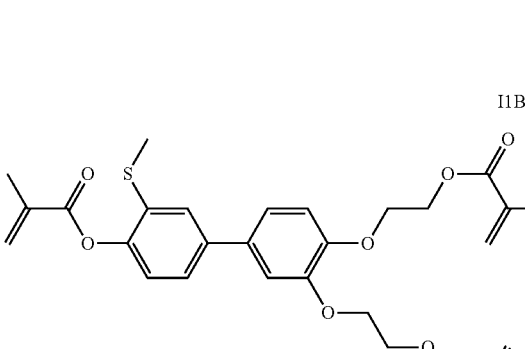
-continued
I1B-2-1c
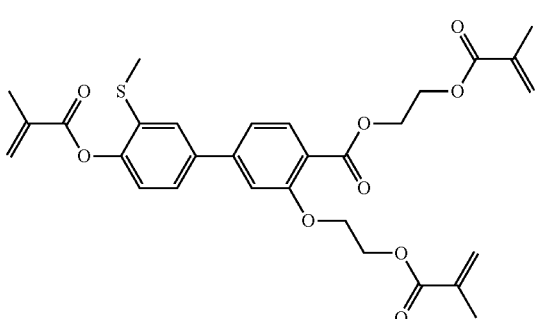
I1B-2-2a
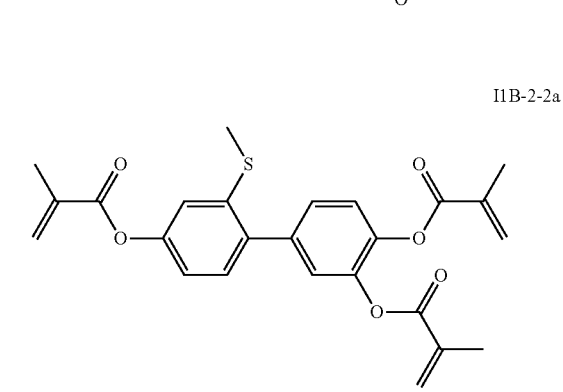
I1B-2-3a
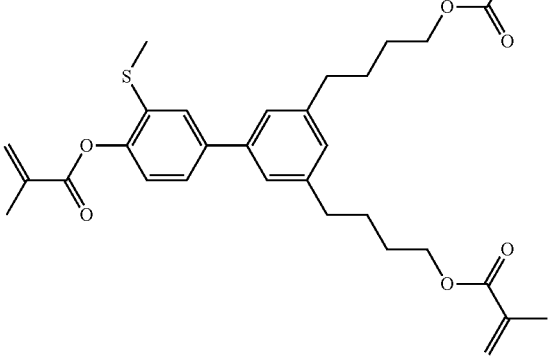
I1B-2-3b
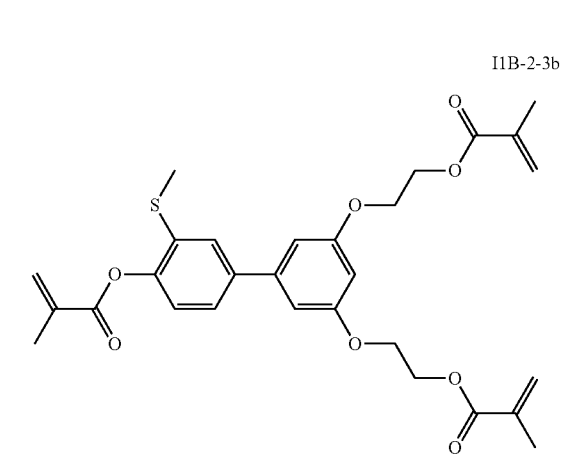

-continued
I1B-2-5a
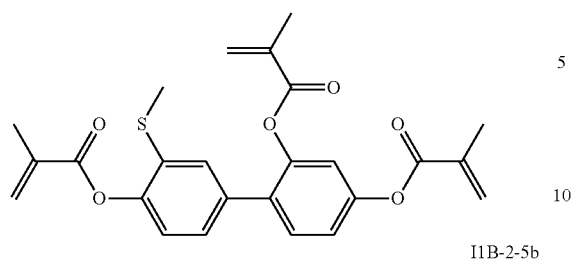
I1B-2-5b
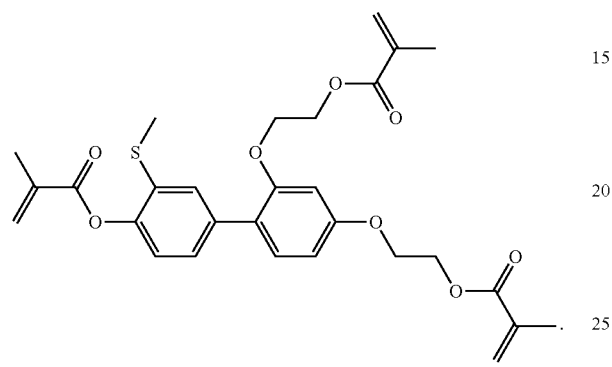
* * * * *